US010300142B2

(12) United States Patent
Yum et al.

(10) Patent No.: US 10,300,142 B2
(45) Date of Patent: *May 28, 2019

(54) COMPOSITIONS WITH A RHEOLOGICAL MODIFIER TO REDUCE DISSOLUTION VARIABILITY

(71) Applicant: Durect Corporation, Cupertino, CA (US)

(72) Inventors: Su Il Yum, Los Altos, CA (US); Wendy Chao, San Jose, CA (US); Huey-Ching Su, San Jose, CA (US); Roger Fu, Saratoga, CA (US); Michael S. Zamloot, Austin, TX (US); Karl Bratin, Groton, CT (US); Ravi M. Shanker, Groton, CT (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,226

(22) Filed: Nov. 29, 2017

(65) Prior Publication Data
US 2018/0339049 A1    Nov. 29, 2018

Related U.S. Application Data

(63) Continuation of application No. 15/398,426, filed on Jan. 4, 2017, now Pat. No. 9,855,333, which is a continuation of application No. 14/776,585, filed as application No. PCT/US2014/029607 on Mar. 14, 2014, now Pat. No. 9,572,885.

(60) Provisional application No. 61/801,110, filed on Mar. 15, 2013.

(51) Int. Cl.
A61K 9/48      (2006.01)
A61K 47/02     (2006.01)
A61K 47/14     (2017.01)
A61K 47/26     (2006.01)
A61K 47/38     (2006.01)
A61K 31/485    (2006.01)

(52) U.S. Cl.
CPC .............. *A61K 47/02* (2013.01); *A61K 9/485* (2013.01); *A61K 9/4816* (2013.01); *A61K 31/485* (2013.01); *A61K 47/14* (2013.01); *A61K 47/26* (2013.01); *A61K 47/38* (2013.01)

(58) Field of Classification Search
CPC ........ A61K 47/02; A61K 47/38; A61K 47/26; A61K 47/14; A61K 9/485; A61K 9/4816; A61K 31/485
See application file for complete search history.

(56) References Cited

U.S. PATENT DOCUMENTS

| 2,799,241 | A | 7/1957 | Wurster |
| 2,931,802 | A | 4/1960 | Toney et al. |
| 3,339,546 | A | 9/1967 | Chen |
| 3,743,398 | A | 7/1973 | Johnson et al. |
| 3,845,770 | A | 11/1974 | Theeuwes et al. |
| 3,853,837 | A | 12/1974 | Fujino et al. |
| 3,916,889 | A | 11/1975 | Russell |
| 3,916,899 | A | 11/1975 | Theeuwes et al. |
| 3,952,741 | A | 4/1976 | Baker |
| 3,992,365 | A | 11/1976 | Beddell et al. |
| 3,995,631 | A | 12/1976 | Higuchi et al. |
| 4,008,719 | A | 2/1977 | Theeuwes et al. |
| 4,014,334 | A | 3/1977 | Theeuwes et al. |
| 4,016,880 | A | 4/1977 | Theeuwes et al. |
| 4,024,248 | A | 5/1977 | Konig et al. |
| 4,063,064 | A | 12/1977 | Saunders et al. |
| 4,088,864 | A | 5/1978 | Theeuwes et al. |
| 4,100,274 | A | 7/1978 | Dutta et al. |
| 4,111,202 | A | 9/1978 | Theeuwes |
| 4,160,020 | A | 7/1979 | Ayer et al. |
| 4,327,725 | A | 5/1982 | Cortese et al. |
| 4,360,019 | A | 11/1982 | Portner et al. |
| 4,395,405 | A | 7/1983 | Noda et al. |
| 4,395,495 | A | 7/1983 | Cummings |
| 4,411,890 | A | 10/1983 | Momany |
| 4,487,603 | A | 12/1984 | Harris |
| 4,530,840 | A | 7/1985 | Tice et al. |
| 4,578,075 | A | 3/1986 | Urquhart et al. |
| 4,622,219 | A | 11/1986 | Haynes |
| 4,681,583 | A | 7/1987 | Urquhart et al. |
| 4,681,765 | A | 7/1987 | Guley |
| 4,689,222 | A | 8/1987 | McMichael |

(Continued)

FOREIGN PATENT DOCUMENTS

| AU | 8374575 | 8/1975 |
| CA | 2222567 | 1/2002 |

(Continued)

OTHER PUBLICATIONS

U.S. Appl. No. 15/839,428, filed Dec. 12, 2017, Yum, et al.
U.S. Appl. No. 15/872,855, filed Jan. 16, 2018, Yum, et al.
U.S. Appl. No. 15/887,797, filed Feb. 2, 2018, Yum, et al.
"New Drugs/Programs"; *Current Drug Discovery*; Nov. 2004; pp. 7-10.
"Ritalin product monograph"; *CPS Compendium of Pharmaceuticals and Specialties*, 34th ed.; Gillis, M., Ed. Canadian Pharmacists Association: Ottawa, (1999); pp. 1573-1574.

(Continued)

*Primary Examiner* — Robert A Wax
*Assistant Examiner* — Quanglong N Truong
(74) *Attorney, Agent, or Firm* — Michael B. Rubin; Bozicevic, Field & Francis LLP

(57) ABSTRACT

The present disclosure provides compositions (e.g., extended release compositions) which exhibit a desirable pharmacokinetic profile of an active agent while providing reduced dissolution sample variability, e.g., in the form of reduced inter-capsule variability and/or a reduction in storage-time dependent change in mean release of the active agent from the composition. Related methods of making and administering the disclosed compositions are also provided.

20 Claims, 52 Drawing Sheets

(56) References Cited

U.S. PATENT DOCUMENTS

| | | |
|---|---|---|
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |
| 4,938,763 A | 7/1990 | Dunn et al. |
| 4,957,681 A | 9/1990 | Klimesch et al. |
| 4,957,744 A | 9/1990 | della Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,280 A | 4/1998 | Mooney, III et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Haefield et al. |
| 5,908,850 A | 6/1999 | Zeitlin et al. |
| 5,919,473 A | 7/1999 | Elkhoury |
| 5,932,597 A | 8/1999 | Brown |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |
| 6,245,351 B1 | 6/2001 | Nara et al. |
| 6,291,013 B1 | 9/2001 | Gibson et al. |
| 6,294,195 B1 | 9/2001 | Oshlack et al. |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,921,541 B2 | 7/2005 | Chasin et al. |
| 6,919,373 B1 | 8/2005 | Lam et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 | 11/2010 | Gibson et al. |
| 7,838,522 B2 | 11/2010 | Esposito et al. |
| 8,124,123 B2 | 2/2012 | Pillai et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,163,798 B2 | 4/2012 | Gupta et al. |
| 8,168,217 B2 | 5/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,945,614 B2 | 2/2015 | Yum et al. |
| 8,951,556 B2 | 2/2015 | Yum et al. |
| 8,974,821 B2 | 3/2015 | Yum et al. |
| 9,233,160 B2 | 1/2016 | Yum et al. |
| 9,517,271 B2 | 12/2016 | Yum et al. |
| 9,555,113 B2 | 1/2017 | Yum et al. |

(56) References Cited

U.S. PATENT DOCUMENTS

| | | |
|---|---|---|
| 9,572,885 B2 | 2/2017 | Yum et al. |
| 9,592,204 B2 | 3/2017 | Yum et al. |
| 9,616,055 B2 | 4/2017 | Yum et al. |
| 9,655,861 B2 | 5/2017 | Yum et al. |
| 9,855,333 B2 | 1/2018 | Yum et al. |
| 9,884,056 B2 | 2/2018 | Scicinski et al. |
| 2001/0000522 A1 | 4/2001 | Dyer et al. |
| 2001/0029257 A1 | 10/2001 | Murdock et al. |
| 2001/0047005 A1 | 11/2001 | Farrar et al. |
| 2001/0055613 A1 | 12/2001 | Burnside et al. |
| 2002/0086878 A1 | 7/2002 | Dobrozsi et al. |
| 2002/0114835 A1 | 8/2002 | Sackler et al. |
| 2002/0143065 A1 | 10/2002 | Liu et al. |
| 2003/0004177 A1 | 1/2003 | Kao et al. |
| 2003/0045454 A1 | 3/2003 | Okumu et al. |
| 2003/0152637 A1 | 8/2003 | Chasin et al. |
| 2003/0157168 A1 | 8/2003 | Breder et al. |
| 2003/0165562 A1 | 9/2003 | Gutierrez-Rocca et al. |
| 2003/0185873 A1 | 10/2003 | Chasin et al. |
| 2003/0191147 A1 | 10/2003 | Sherman et al. |
| 2004/0001889 A1 | 1/2004 | Chen et al. |
| 2004/0024021 A1 | 2/2004 | Sudo et al. |
| 2004/0052336 A1 | 3/2004 | Langlet et al. |
| 2004/0101557 A1 | 5/2004 | Gibson et al. |
| 2004/0109893 A1 | 6/2004 | Chen et al. |
| 2004/0138237 A1 | 7/2004 | Shah |
| 2004/0146562 A1 | 7/2004 | Shah |
| 2004/0161382 A1 | 8/2004 | Yum et al. |
| 2004/0224020 A1 | 11/2004 | Schoenhard |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0158382 A1 | 7/2005 | Cruz et al. |
| 2005/0171052 A1 | 8/2005 | Cook et al. |
| 2005/0208132 A1 | 9/2005 | Sathyan et al. |
| 2005/0232876 A1 | 10/2005 | Minga et al. |
| 2005/0244489 A1 | 11/2005 | Paris |
| 2005/0260264 A1 | 11/2005 | Edgren et al. |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0104909 A1 | 5/2006 | Vaghefi et al. |
| 2006/0115527 A1 | 6/2006 | Hassan et al. |
| 2006/0165800 A1 | 7/2006 | Chen et al. |
| 2006/0210599 A1 | 9/2006 | Gibson et al. |
| 2007/0027105 A1 | 2/2007 | Junnarkar et al. |
| 2007/0031502 A1 | 2/2007 | Pettersson et al. |
| 2007/0104763 A1 | 5/2007 | Jobdevairakkam et al. |
| 2007/0259033 A1 | 11/2007 | Cruz |
| 2008/0023261 A1 | 1/2008 | Kaneko et al. |
| 2008/0026052 A1 | 1/2008 | Schoenhard |
| 2008/0145419 A1 | 6/2008 | Gibson et al. |
| 2008/0152708 A1 | 6/2008 | Gibson et al. |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0164240 A1 | 6/2009 | Friedmann et al. |
| 2009/0165578 A1 | 7/2009 | Zamloot et al. |
| 2009/0169631 A1 | 7/2009 | Zamloot et al. |
| 2009/0215808 A1 | 8/2009 | Yum et al. |
| 2009/0298862 A1 | 12/2009 | Yum et al. |
| 2010/0260844 A1 | 10/2010 | Scicinski et al. |
| 2011/0287093 A1 | 11/2011 | Schoenhard |
| 2012/0135072 A1 | 5/2012 | Yum et al. |
| 2012/0135073 A1 | 5/2012 | Yum et al. |
| 2012/0165358 A1 | 6/2012 | Cruz et al. |
| 2013/0281480 A1 | 10/2013 | Yum et al. |
| 2013/0287845 A1 | 10/2013 | Yum et al. |
| 2013/0295168 A1 | 11/2013 | Yum et al. |
| 2013/0309176 A1 | 11/2013 | Port et al. |
| 2013/0317049 A1 | 11/2013 | Yum et al. |
| 2013/0337059 A1 | 12/2013 | Yum et al. |
| 2013/0337060 A1 | 12/2013 | Yum et al. |
| 2016/0038479 A1 | 2/2016 | Yum et al. |
| 2016/0136102 A1 | 5/2016 | Yum et al. |
| 2017/0165255 A1 | 6/2017 | Yum et al. |
| 2017/0196978 A1 | 7/2017 | Yum et al. |
| 2017/0319501 A1 | 11/2017 | Yum et al. |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0635531 | 2/1995 |
| EP | 0640336 | 3/1995 |
| EP | 0711548 | 5/1996 |
| EP | 0773034 | 5/1997 |
| EP | 0778768 | 6/1997 |
| EP | 0537559 | 1/1998 |
| EP | 1010436 | 6/2000 |
| EP | 0782569 | 3/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 2003508449 | 3/2003 |
| WO | WO 1990003768 | 4/1990 |
| WO | WO 1990003809 | 4/1990 |
| WO | WO 1991018016 | 11/1991 |
| WO | WO 199214466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 2000000120 | 1/2000 |
| WO | WO 200016750 | 3/2000 |
| WO | WO 2000078335 | 12/2000 |

(56) References Cited

FOREIGN PATENT DOCUMENTS

| WO | WO 2001008661 | 2/2001 |
| WO | WO 2001015734 | 3/2001 |
| WO | WO 2001051024 | 7/2001 |
| WO | WO 2001076599 | 10/2001 |
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004054542 | 7/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | WO 2006134018 | 12/2006 |
| WO | WO 2007058923 | 5/2007 |
| WO | WO 2006134018 | 6/2007 |
| WO | WO 2007135193 | 11/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2009088414 | 7/2009 |
| WO | WO 2013142279 | 9/2013 |
| WO | WO 2014144984 | 3/2014 |
| WO | WO 2014144975 | 9/2014 |

OTHER PUBLICATIONS

3M, "3M DDS Announces Development of New HFA-Compatible Exipients: Novel Oligomeric Acids as MDI Suspension Aid and Solubilizers" *3M Delivery Newsletter*, vol. 15, 3M Drug Delivery Systems; Jun. 2000, pp. 9-11.

Abdul-Fattah, Ahmad M., et al; "Preparation and In Vitro Evaluation of Solid Dispersions of Halofantrine."; *International Journal of Pharmaceutics 235*; (2002); pp. 17-33.

Adams, Edgar G, et al.; "A comparison of the abuse liability of tramadol, NSAIDS, and hydrocodone in patients with chronic pain"; *Journal of Pain and Symptom Management. 31(5)*; (2006); pp. 465-476.

Ajayaghosh, A., et al., "Solid-Phase Synthesis of N-Methyl- and N-Ethylamides of Peptides Using Photolytically Detachable ((3-Nitro-4-((alkylamino)methyl)benzamido)methyl)polystyrene Resin"; *J. Org. Chem. 55*; (1990); pp. 2826-2829.

Allahham Allahham, et al; "Flow and injection characteristics of pharmaceutical parenteral formulations using a micro-capillary rheometer"; *International Journal of Pharmaceutics. 270*; (2004); pp. 139-148.

Ansel, H.C. et al.; *Pharmaceutical Dosage Forms and Drug Delivery System, sixth ed.*, (1995); 20 pages.

Ash Michael and Ash Irene; "Handbook of Pharmaceutical Additives: An International Guide to More Than 6000 Products by Trade Name, Chemical, Function, and Manufacturer" ; *Gower* (1995); 3 pages.

Aungst, B.J., et al; "Improved Oral Bioavailability of an HIV Protease Inhibitor Using Gelucire 44/14 and Labrasol Vehicles"; *Bulletin Technique Gattefosse*, No. 87; (1994); pp. 49-54.

Aungst, B.J., et al; "Amphiphilic vehicles improve the oral bioavailability of a poorly soluble HIV Protease inhibitor at high doses."; *International Journal of Pharmaceutics*, vol. 156; (1997); pp. 79-88.

Bansal, Tripta, et al; "Solid Self Nanoemulsifying Delivery Systems as a Platform Technology for Formulation of Poorly Soluble Drugs"; *Critical Reviews™ in Therapeutic Drug Carrier Systems*, 25(1); (2008); pp. 63-116.

Barakat, N.S.; "Etodolac-Liquid-Filled Dispersion into Hard Gelatin Capsules: An Approach to Improve Dissolution and Stability of Etodolac Formulation"; *Drug Development and Indisfrial Pharmacy. 32*; (2006); pp. 865-876.

Barb, R., et al.; "Evaluation of the SABER Delivery System for the Controlled Release of Deslorelin: Effect of Dose in Estrogen Primed Ovarectomized Gilts"; *Proceed. Int'l, Symp. Control. Rel. Bioact. Mater.*; (1999) Controlled Release Society, Inc.; pp. 1170-1171.

Barker, S.A., et al. "An investigation into the structure and bioavailability of α-tocopherol dispersions in Gelucire 44/14"; *Journal of Controlled Release 91*; (2003); pp. 477-488.

Becker & Johnson "Effects of Gonadotropin-Releasing Hormone Infused in a Pulsatile or Continuous Fashion Serum Gonadotropin Concentrations and Ovulation in the Mare"; *J. Anim. Sci.* vol. 70; (1992);. pp. 1208-1215.

Bekersky I, et al.; "Effect of low- and high-fat meals on tacrolimus absorption following 5 mg single oral doses to healthy human subjects"; *J Clin Pharmacol*; 41; (2001); pp. 176-182.

Berge et al. "Pharmaceutical salts" *J Pharm. Sci. 66(1)*; Jan. 1977; pp. 1-19.

Betschart, R., et al.; "Evaluation of the Saber™ Delivery System for the Controlled Release of the GnRH Analogue Deslorelin for Advancing Ovulation in Mares: Effect of Gamma Radiation"; *Proceed. Int'l. Symp. Control. Rel. Bioact. Mater.*, 25, Controlled Release Society, Inc.; (1998); pp. 655-656.

Blachez, P., et al; "Development of immediate release pellets of poorly soluble compounds using Gelucire® 44/14 using melt pelletization"; Poster, Conference "*AAPS Annual Meeting & Exposition*"; Salt Lake City, Utah, United States; Oct. 26, 2003; 2 pages.

Blažková, A. et al; "Viscosity properties of aqueous solutions of hydroxyethylcellulose"; *Chem Papers 44(3)*; (1990); pp. 289-301.

Brevard J, et al. "Pain and opioid abuse in a population of substance abuse patients: data from the Navippro™ system." *Conference paper presented at the 42nd American Pain Society (APS) Annual Scientific Meeting*, Washington D.C.; (2007); 1 page.

Bühler, K.; GnRH Agonists and Safety, In GnRH Analagoues The State of the Art 1993, A Summary of the 3rd International Symposium on GnRH Analogues in Cancer and Human Reproduction, Geneva, Feb. 1993; pp. 139-146.

Burns, P. et al.; "Pharmacodynamic Evaluation of the Saber™ Delivery System for the Controlled Release of the GnRH Analogue Deslorelin Acetate for Advancing Ovulation in Cyclic Mares"; *Proceed. Int'l. Symp. Control. Rel. Bioact. Mater.*, 24; Controlled Release Society, Inc. (1997); 4 pages.

"CAB-O-SIL®, Untreated Fumed Silica: Properties & Functions"; *Cabot Corporation, Cab-O-Sil Division*; (1993); pp. 1-34.

Carraway, et al.; "Drug Delivery From a Controlled Release Aerosol: Effects of Formulation Variables"; *AAPS J Abstract. Southern BioSystems, Inc.*, Birmingham AL, USA; (2000); 1 page.

Carraway, et al.; "Drug Release from a Novel Controlled Release Aerosol Based on Sucrose Acetate Isobutyrate" *AAPS Midwest Regional Meeting Chicago, IL*; May 22, 2000; 2 pages.

Cellulose Acetate Butyrate. In: European pharmacopoeia. 4 edn. Strasbourg Cedex, France: Council of Europe; (2001); pp. 853-854.

Chambin, O.; et al; "Interest of Multifunctional Lipid Excipients: Case of Gelucire® 44/14"; *Drug Development and Industrial Pharmacy*, 31; (2005); pp. 527-534.

Chambin, O., et al; "Influence of drug polarity upon the solid-state structure and release properties of self-emulsifying drug delivery systems in relation with water affinity"; *Colloids and Surfaces B: Biointerfaces 71*; (2009); pp. 73-78.

Chauhan, Bhaskar, et al; "Preparation and Characterization of Etoricoxib Solid Dispersions Using Lipid Carriers by Spray Drying Technique"; *AAPS PharmSciTech 6(3)*, Article 50; (http://www.aapspharmscitech.org); (2005); pp. E405-E412.

(56) References Cited

OTHER PUBLICATIONS

Chauhan, B., et al; "Preparation and evaluation of glibenclamide-polyglycolized glycerides solid dispersions with silicon dioxide by spray drying technique"; *European J. Pharm. Sci. 26(2)*; (2005); pp. 219-230.

Chen, X. Q., et al; "Evaluation of Lipid-Based Formulations in Dogs and Monkeys for a Highly Lipophilic Compound"; *Conference "Annual Meeting of AAPS"*; (2007); San Diego, CA; poster abstract; 1 page.

Coy, et al.; "Solid Phase Synthesis of Lutenizing Hormone-Releasing Hormone and Its Analogs"; *Methods Enzymol. 37*; (1975); pp. 416-424.

Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences*, vol. 97, No. 2; Feb. 2008; pp. 995-1012; article first published online Dec. 6, 2007.

Damian, Festo, et al; "Physicochemical characterization of solid dispersions of the antiviral agent UC-781 with polyethylene glycol 6000 and Gelucire 44/14"; *European Journal of Pharmaceutical Sciences 10*; (2000); pp. 311-322.

Darling, et al. (2000) "Extended Release of Human Growth Hormone Suspended in Saber™ Formulation Design and in Vitro Assessment" Genentech, Inc., South San Francisco, CA USA and Southern BioSystems, Inc. Birmingham AL, USA. Poster; 1 page.

DataBase WPI Section Ch, Week 198532 Derwent Publications Ltd., London GB; Class B07, AN 1985-193549 XP002284488 & JP 60120811 A (Sealer, R P KK) Jun. 28, 1985 (Abstract).

Desai et al.; "Surface Modification of Polymeric Biomaterials for Reduced Thrombogenicity"; *Polym. Mater. Sci. Eng.*, 62; Jun. 1990;. pp. 731-735.

Dodson, K.M., et al. "Oral Controlled Release of Antiretrovirals Using the Saber Delivery System Incorporated into Soft Gelatin Capsules", *AAPS Meeting*, (1999), New Orleans, LA.; 2 pages.

Dordunoo, S.K., et al; "Preformulation Studies on Solid Dispersions Containing Triamterene or Temazepam in Polyethylene Glycols or Gelucire 44/14 for Liquid Filling of Hard Gelatin Capsules"; *Drug Development and Indusfrial Pharmacy*, vol. 17, No. 12; (1991); pp. 1685-1713.

Dordunoo, Stephen K., et al; "Solidification studies of polyethylene glycols, Gelucire® 44/14 or their dispersions with Triamterene or Temazepam"; *Journal of Pharm. Pharmacology 48*; (1996); pp. 782-789.

Duan, D.C. et al.; "Novel Dispersing Aids for Hydrofluoroalkane-Based Metered Dose Inhalers"; *1998 Conference of the American Association of Pharmaceutical Scientists*, San Francisco, California; Nov. 1998; 1 page.

Duan, D.C. et al., "Oligomeric Lactic Acids as Solubilizing Aids for HFA-Based Metered Dose Inhalers"; *1998 Conference of the American Association of Pharmaceutical Scientists*, San Francisco, California; Nov. 1998; 1 page.

Dunbar SA, Katz NP; "Chronic opioid therapy for nonmalignant pain in patients with a history of substance abuse: report of 20 cases." *Journal of Pain and Symptom Management. 11(3)*; (1996) pp. 163-171.

Edimo, A., et al; "Capacity of Lipophilic Auxiliary Substances to Give Spheres by Extrusion—Spheronization"; *Drug Development and Industrial Pharmacy*, 19(7); (1993); pp. 827-842.

Eliasen, Helle, et al; "Effects of binder rheology on melt agglomeration in a high shear mixer"; *International Journal of Pharmaceutics 176*; (1998); pp. 73-83.

Fernandez, Sylvie, et al; "Lipolysis of the semi-solid self-emulsifying excipient Gelucire® 44/14 by digestive lipases"; *Biochimica et Biophysica Acta 1781*; (2008); pp. 367-375; available online Jun. 3, 2008.

Final Office Action for U.S. Appl. No. 14/214,057, dated Jul. 12, 2016.

Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season"; *Am. J. Vet. Res.*, vol. 54, No. 10; Oct. 1993; pp. 1746-1751.

Fleury, J., et al., "Evaluation of the Saber Delivery System for the Controlled Release of Deslorelin for Advancing Ovulation in the Mare: Effects of Formulation & Dose", *Proceed. Int'l. Symp. Control. Rel. Bioact. Mater.*, 25; (1998); Controlled Release Society, Inc.; pp. 657-658.

Friedmann N, Klutzaritz V, Webster L.; "Efficacy and safety of an extended-release oxycodone (Remoxy) formulation in patients with moderate to severe osteoarthritic pain"; *J Opioid Manag. 7(3)*; (2011); pp. 193-202.

Friedmann N, Klutzaritz V, Webster L.; "Long-term safety of Remoxy(R) (extended-release oxycodone) in patients with moderate to severe chronic osteoarthritis or low back pain"; *Pain Med. 12(5)*; (2011); pp. 755-760.

Gad, Shayne C., et al; "Nonclinical Vehicle Use in Studies by Multiple Routes in Multiple Species"; *International Journal of Toxicology*, 25; Sep. 20, 2006; pp. 1-23.

Gattefossé Corporation (1989); "To Help With Your Impossible Formulations: A Guide to Gattefosse Liquid Excipients"; 6 pages.

Gattefossé (1998); "Oral Route Excipients"; 8 pages.

Gelucire® 44/14 brochure (1999); "Immediate Release and Enhanced Bioavailability"; pp. 1-16.

Gelucire® Technical Dossier; "Answering the Need for Enhanced Bioavailability"; Oct. 1996; 16 pages.

Gelucire® (1996); "Answering the Need for Enhanced Bioavailability"; 5 pages.

"General Characteristics of Polymers"; Museum of Fine Arts, Boston; (2007); pp. 1-4.

Gibson, et al.; "Effects of Formulation Variables on Controlled Release of Paclitaxel and other Chemotherapeutic Agents from a Novel Delivery System" *AAPS New Orleans, LA*; (1999); Southern BioSystems, Inc. Birmingham AL, USA; 2 pages.

Gibson, et al.; "In Vitro and In Vivo Evaluation of a Novel In Situ-Forming Pareteral Delivery System"; *Meeting of Recent Advances in Drug Delivery Systems*, Salt Lake City, UT; (1999); Southern BioSystems, Inc. Birmingham AL, USA; 2 pages.

Gilderman L., et al; "Remoxy™: A New Opioid Drug With Effective Analgesia and Abuse-Resistance." *American Pain Society Annual Meeting*, San Antonio, TX, May 2006; 1 page.

Ginther, O.J.; "Follicles"; *Ultrasonic Imaging and Reproductive Events in the Mare. EquiServices, Chapter 4*; Cross Plains, WI; (1986); pp. 43-72.

Ginther, O.J., "Effect of a Synthetic Gonadotropin-Releasing Hormone on Plasma Concentrations of Luteinizing Hormone in Ponies", *Am. J. Vet. Res.*, 1 vol. 35, No. x; Jan. 1974; pp. 79-8.

Ginther, O.J., "Reproductive Efficiency", *Reproductive Biology of the Mare Basic and Applied Aspects, Second Ed., Chapter 12*; (1992); pp. 499-509.

Glajchen, M.; "Chronic Pain: Treatment Barriers and Strategies for Clinical Practice."; *J Am Board Fam Pract.*; 14(3); (2001); pp. 212-218.

González et al; "Methylphenidate bioavailability from two extended-release formulations"; *International Journal of Clinical Pharmacology Therapeutics*, vol. 40, No. 4; (2002) pp. 175-184.

Gould, Phillip L.; "Salt selection for basic drugs"; *International Journal of Pharmaceutics*, 33 (1986); pp. 201-217.

Greydanus, D. E.; "Psychopharmacology for ADHD in Adolescents: Quo Vadis?"; *Psychiatric Times* vol. 20, No. 5; May 5, 2003; pp. 1-7.

Handbook of Pharmaceutical Excipients: Sixth Edition; "Medium-chain Triglycerides"; *Pharmaceutical Press and American Pharmacists Association 2009*; pp. 429-431.

Harrison, L.A., et al.; "Comaprison of HCG, Buserelin and Luprostiol for Induction of Ovulation in Cycling Mares"; *Equine Veterinary Science*, vol. 11, No. 3; (1991); pp. 163-166.

Hatakeyama et al.; "Synthesis and physical properties of polyurethanes from saccharide-based polycaprolactones"; *Macromolecular Symposia*, vol. 130; (1998); pp. 127-138.

Hauss, David J., et al; "Lipid-Based Delivery Systems for Improving the Bioavailability and Lymphatic Transport of a Poorly Water-

(56) References Cited

OTHER PUBLICATIONS

Soluble LTB$_4$ Inhibitor"; *Journal of Pharmaceutical Sciences*, vol. 87, No. 2; Feb. 1998; pp. 164-169; published online Jan. 7, 1998.
Hays Lon R.; "A profile of OxyContin addiction"; *Journal of Addictive Diseases 23(4)*; (2004); pp. 1-9.
He Y. et al; "Oral Formulation of a Novel Antiviral Agent, PG301029, in a Mixture of Gelucire 44/14 and DMA (2:1, wt/wt)"; *AAPS Pharm. Sci. Tech. 6(1)*; (2005); pp. E1-E5.
Henry, C.; "Sucrose Acetate Isobutyrate Special Grade for Beverage Applications" *International Food Ingred*; (1995); pp. 47-49.
Hoskin PJ, et al; "The bioavailability and pharmacokinetics of morphine after intravenous, oral and buccal administration in healthy volunteers."; *Br J Clin Pharmacol*; 27 (4); (1989); pp. 499-505.
Hülsmann, S., et al; "Melt extrusion—an alternative method for enhancing the dissolution rate of 17β-estradiol hemihydrate"; *European Journal of Pharmaceutics and Biopharmaceutics 49*; (2000); pp. 237-242.
Hyland, J.H., et al.; "Infusion of Gonadotrophin-releasing hormone (GnRH) Induces Ovulation and Fertile Oestrus in Mares During Seasonal Anoestrus"; *J. Reprod. Fert., Suppl. 35* (1987); pp. 211-220.
Inciardi James A, et al; "Mechanisms of prescription drug diversion among drug-involved club- and street-based populations"; *Pain Medicine. 8(2)*, (2007); pp. 171-183.
Irvine, D.S., et al; "Duration of Oestrus and Time of Ovulation in Mares Treated with Synthetic GnRH (Ay24,031)"; *J. Reprod. Fert. Supp. 23*; (1975); pp. 279-283.
Irvine; "GnRH Clinical Application"; *In Equine Reproduction*, (eds) McKinon, A.O. and Voss, J.L., Chapter 36, Lea & Febiger; (1993); pp. 41-45.
Ishida T, Oguri K, et al; "Isolation and identification of urinary metabolites of oxycodone in rabbits"; *Drug Metab Dispos*; 7(3); (1979); pp. 162-165.
Ishida T, Oguri K, Yoshimura H.; "Determination of oxycodone metabolites in urines and feces of several mammalian species"; *J Pharmacobiodyn*; 5(7); (1982); pp. 521-525.
Itoh, K., et al; "Improvement of physiochemical properties of N-4472 part I formulation design by using self-microemulsifying system"; *Int .J. Pharm.*, 238); (2002); pp. 153-160.
Iwanaga, Kazunori, et al; "Disposition of Lipid-Based Formulation in the Intestinal Tract Affects the Absorption of Poorly Water-Soluble Drugs"; *Biol. Pharm. Bull.* vol. 29, No. 3; (2006); pp. 508-512; published online Dec. 5, 2005.
Iyakuhin Tenkabutsu Kenkyykai Ed.; "Jitsuyo Iyakuhin Tenkabutsu (Practical Medical Additives)"; pub. *Kagaku Kogyo-sha*; Mar. 5, 1974; Tokyo; 6 pages.
Jannin, V., et al; "Systemes auto-emulsionnables et emulsions seches"; *STP Pharma Pratiques*, vol. 15, No. 3; May/Jun. 2005; pp. 246-255.
Jannin, V., et al; "Approaches for the development of solid and semi-solid lipid-based formulations"; *Advanced Drug Delivery Reviews 60*; (2008); pp. 734-746; available online Nov. 4, 2007.
Japanese Office Action for Japanese Application No. 2010-537128, dated Jun. 5, 2013.
Jöchle, W., et al.; "Control of Ovulation in the Mare with Ovuplant a Short-Term Release Implant (STI) Containing the GnRH Analogue Deslorelin Acetate: Studies from 1990 to 1994"; *Journal of Equine Veterinary Science*, vol. 14m No. 12; (1994); pp. 632-644.
Johnson, et al; "Biodegradable Delivery Systems for Estradiol: Comparison Between Poly(DL-Lactide) Microspheres and the Saber Delivery System"; *Proceed. Int'l Symp. Control. Rel. Bioact. Mater.*, 26; Controlled Release Society, Inc.; (1999); 1 page.
Johnson, R.M., et al; "Applications of Continuous Site-Directed Drug Delivery"; *Proc. West Pharmacol Soc.* vol. 45; (2002); pp. 219-222.
Johnston Lloyd D, et al; "Monitoring the future. National results on adolescent drug use: overview of key findings"; (NIH Publication No. 05-5726). Bethesda, MD: National Institute on Drug Abuse; (2004); pp. 1-66.
Kaiko; "Pharmacology of Tablets of Oxycontin the Development Process Thereof"; *Palliative Care Research* 7(1); (2005); pp. 3-13.
Kale, A., et al; "Design and Evaluation of Self-Emulsifying Drug Delivery Systems (SEDDS) of Nimodipine"; *AAPS Pharm. Sci. Tech.*, 9(1); (2008); pp. 191-196.
Kamel S., et al; "Pharmaceutical significance of cellulose: A review"; *eXPRESS Polymer Letters* vol. 2, No. 11; (2008); pp. 758-778.
Kane, Anil, et al; "A Statistical Mixture Design Approach for Formulating Poorly Soluble Compounds in Liquid Filled Hard Shell Capsules"; *Bulletin Technique Gattefosse No 99*; (2006); pp. 43-49.
Karatas, A., et al; "Improved solubility and dissolution rate of piroxicam using gelucire 44/14 and labrasol"; *II Farmaco 60(9)*; (2005); pp. 777-782; available online Aug. 9, 2005.
Katz NP, et al.; "Behavioral monitoring and urine toxicology testing in patients receiving longterm opioid therapy" *Anesth Analg.* 97(4); (2003); pp. 1097-1102.
Katz NP, et al; "Development and preliminary experience with an ease of extractability rating system for prescription opioids"; *Drug Development and Industrial Pharmacy. 32(6)*; (2006); pp. 727-746.
Katz NP, et al; "Prescription monitoring of medical and non-medical Schedule II opioid abuse in Massachusetts: 1996-2005"; *Conference paper presented at the 69th College on Problems of Drug Dependence (CPDD)*, Quebec, Canada; (2007); 1 page.
Katz NP, et al; "Challenges in the development of prescription opioid abuse-deterrent formulations"; *Clin J Pain*,;23(8); (2007); pp. 648-660.
King; "Tablets, Capsules, and Pills" Remington's Pharmaceutical Sciences, Ed. Arthur Osol, Chapter 89, (1980); pp. 1553-1584.
Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics 54*; (2002); pp. 311-318.
Kulkarni, et al., "Polyactic Acid for Surgical Implants," *Arch. Surg.* vol. 93; (1966); pp. 839-843.
Lacoste, D., et al.; "Reversible Inhibition of Testicular Androgen Secretion by 3-, 5- and 6-Month Controlled-Release Microsphere Formulations of the LH-RH Agonist [D-Trp.sup.6, des-Gly-NH.sub.2]LH-RH Ethylamide in the Dog"; *J. Seroid Biochem.* vol. 33, No. 5; (1989); pp. 1007-1011.
Laforet, Jean-Pierre, et al; "The Right Mix"; *Gattefosse*, vol. 7, No. 1; (1995); pp. 1-10.
Lalovic Bojan, et al; "Pharmacokinetics and pharmacodynamics of oral oxycodone in healthy human subjects: role of circulating active metabolites"; *Clin Pharmacol Ther 79(5)*; (2006); pp. 461-479.
Larsen, A., et al; "In vitro evaluation of Pharmaceutical surfactants fate during lipolysis and its effects on solubilization of a poorly soluble model compound: Danazol"; *Conference on When Poor Solubility Becomes an Issue: From Early Stage to Proof of Principles*; (2006); Verona (Italy); 2 pages.
Larsen, Anne, et al; "Pharmaceutical Surfactants in Biorelevant Media: Impact on Lipolysis and Solubility of a Poorly Soluble Compound; Danazol"; *Conference, 5th World Meeting on Pharmaceutics Biopharmaceutics and Pharmaceutical Technology*, Geneva, Switzerland; (2006); 2 pages.
Lopez et a;. "Comparative efficacy of two once daily methylphenidate formulations (Ritalin LA and Concerta) and placebo in children with attention deficit hyperactivity disorder across the school day"; *Pediatr Drugs 5(8)*; (2003); pp. 545-555.
Lowden, K.; "Filling hard gelatin capsules: experience in a new environment"; *Pharmaceutical Manufacturing Review*, vol. 10, No. 5; (1998); pp. 27-29.
Loy, R.G., et al; "The Effects of Human Chorionic Gonadotrophin on Ovulation, Length of Estrus, and Fertility in the Mare"; University of California, Davis, California, Jan. 30, 1965; pp. 41-50.
Malhotra Bimal K. et al; . "The pharmacokinetics of oxycodone and its metabolites following single oral doses of Remoxy®, an abuse-deterrent formulation of extended-release oxycodone, in patients with hepatic or renal impairment"; *Journal of Opioid Management 11:2*; Mar./Apr. 2015; pp. 157-169.
Markowitz et al; "Advances in the pharmacotherapy of attention-deficit-hyperactivity disorder: focus on methylphenidate formulations"; *Pharmacotherapy 23(10)*; (2003); pp. 1281-1299.

(56) References Cited

OTHER PUBLICATIONS

Markowitz et al; "Pharmacokinetics of methylphenidate after oral administration of two modified-release formulations in healthy adults"; *Clin Pharmacokinet 42(4)*; (2003); pp. 393-401.

Material Safety Data Sheet "Eastman. Cellulose Acetate Butyrate CAB-381-2 BP CAB381-20 BP: Coating Chemicals" Eastman Chemical Company, Publication E-296B, Aug. 1994.

Material Safety Data Sheet "Eastman: Cellulose Esters for Pharmaceutical Drug Delivery" Eastman Chemical Company, Publication PCI-105B, Jun. 2004.

Material Safety Data Sheet of Eastman Chemical Products, "SAIB" Sucrose Acetate Isobutyrate, pp. 1-24. Publication GN-311F (Jun. 2004).

Material Safety Data Sheet of Eastman Fine Chemical Pharmaceutical Ingredients, Sucrose Acetate Isobutyrate Special Grade (SAIB-SG), Publication No. EFC-211, (May 1991).

Material Safety Data Sheet of Eastman Products for the Food Industry, "Sucrose Acetate Isbutyrate (SAIB-SB) for Use in Fruit-Flavored Beverages," Publication No. ZM-90, (Sep. 1989); pp. 2-7.

McCabe SE, et al; "Motives, diversion and routes of administration associated with nonmedical use of prescription opioids"; *Addictive Behaviors. 32*; (2007); pp. 562-575.

McCarthy, P.F., et al.; "Management of Stallions on Large Breeding Farms"; *Veterinary Clinics of North America: Equine Practice*, vol. 8, No. 1; Apr. 1992; pp. 219-235.

McKinnon, A.O., et al.; "Effect of GnRH Analogue (Ovuplant), hCG and Dexamethasone on Time to Ovulation in Cycling Mares"; *World Equine Veterinary Review*, vol. 2: No. 3; (1997); pp. 16-18.

McKinnon, A.O., et al.; "Repeated Use of a GnRH Analogue Deslorelin (Ovuplant) for Hastening Ovulation in the Transitional Mare"; *Equine Veterinary Journal 29 (2)*; (1996); pp. 153-155.

McLellan AT, et al; An improved diagnostic instrument for substance abuse patients—The Addiction Severity Index: *The Journal of Nervous and Mental Disease*. vol. 168, No. 1; (1980); pp. 26-33.

Mearns, D.; "Changing Seasons"; *The Blood-Horse*; Sep. 28, 1996; pp. 4794-4765.

Meehan, E., et al; "Monitoring the stability of excipients used in lipid matrix formulations"; (Poster Abstract), Conference "*33rd Annual Meeting of the Controlled Release Society*", Vienna, Austria. Jul. 22, 2006; 2 pages.

Mehuys, E., et al; "Human bioavailability of propranolol from a matrix-in-cylinder system with a HPMC-Gelucire® core"; *Journal of Controlled Release 107*; (2005); pp. 523-536; available online Aug. 1, 2005.

Merrifield, Bruce; "Solid Phase Synthesis"; *Science*, vol. 232; Apr. 18, 1986; pp. 341-347.

Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005; pp. 1-4.

Montovan, S.M., et al; "The Effect of a Potent GnRH Agonist on Gonadal and Sexual Activity in the Horse"; *Theriogenology*, vol. 33 No. 6; Jun. 1990; pp. 1305-1321.

Mumford, E.L.; "Use of Deslorelin Short-Term Implants to Induce Ovulation in Cycling Mares During Three Consecutive Estrous Cycles"; *Animal Reproduction Science*, vol. 39; (1995); pp. 129-140.

Murray Sally, et al; "Alcohol-associated rapid release of a long-acting opioid"; *CMAJ*;173(7); Sep. 27, 2005; pp. 756.

Nabors, et al; "Controlled Release of Diclofenac-Na from Cellulose Ester Microspheres"; *PDD Presentation 7481 at the 1994 Ninth Annual AAPS Meeting in San Diego, CA*; Nov. 6-10, 1994; 2 pages.

Nakagaki, Arita; "Seizai Butsuri Kagaku (Physical Chemistry of Medical Preparations)", pub. *Asakura Shoten*; Nov. 5, 1968; Tokyo; 6 pages.

Nally, J., et al.; "Induction of Mucosal IgA Specific for SeMF3 for *Streptococcus equi* with Intranasal Vaccination Using a Sucrose Acetate Isobutyrate Based Delivery System", *Proceed. Int'l. Symp. Control. Rel. Bioact. Mater.*, 26; (1999); Controlled Release Society, Inc. 2 pages.

"Natrosol® Hydroxyethylcellulose A Nonionic Water-Soluble Polymer"; *Hercules Incorporated, Aqualon Division*; (1999); pp. 1-24.

Nett, T.M., et al.; "Further Studies on the Radioimmunoassay of Gonadotropin-releasing Hormone: Effect of Radioiodination, Antiserum and Unextracted Serum on Levels of Immunoreactivity in Serum"; *Endocrinology* vol. 101, No. 4, (1977); pp. 1135-1144.

O'Driscoll, Caitriona. M.; "Lipid-based formulations for intestinal lymphatic delivery"; *European Journal of Pharmaceutical Sciences 15*; (2002); pp. 405-415.

Office Action for U.S. Appl. No. 14/214,057, dated Oct. 5, 2015.

Okumu, et al; "Evaluation of Saber™ as a Local Delivery System for rhVEGF-Formulation Design and In Vitro Assessment" Genentech, Inc., South San Francisco, CA USA and Southern BioSystems, Inc. Birmingham AL, USA; (2000); 1 page.

Okumu, et al; "Evaluation of Saber as a Local Delivery System for rhVEGF-Formulation Design and In Vitro Assessment" Genentech, Inc., South San Francisco, CA USA and Southern BioSystems, Inc. Birmingham AL, USA. Poster; (2001); 1 page.

Patel, Pranav, et al; "Preparation, Evaluation and Comparison of Lipid Based Drug Delivery Systems of Tacrolimus"; *International Journal of Pharmacy and Pharmaceutical Sciences*, vol. 6 Suppl 2; (2014); pp. 588-591.

Patrick et al; "New methylphenidate formulations for the treatment of attention-deficit/hyperactivity disorder" *Expert Opin Drug Deliv 2(1)*; (2005); pp. 121-143.

Pelham et al; "Once-a-day Concerta methylphenidate versus three-times-daily methylphenidate in laboratory and natural settings"; *Pediatrics* vol. 107, No. 6; Jun. 6, 2001; pp. 1-15.

Perissutti, B.; et al; "Solid dispersions of carbamazepine with Gelucire 44/14 and 50/13"; *S.T.P. Pharma Sciences 10(6)*; (2000); pp. 479-484.

Pozzi, Franco, et al; "Formulations of Ubidecarenone with Improved Bioavailability"; *Eur. J. Pharm. Biopharm*, vol. 37, No. 4; (1991); pp. 243-246.

Pulido et al.; "Enzymatic Regioselective Acylation of Hexoses and Pentoses Using Oxime Esters"; *J. Chem. Soc. Perkin Trans. 1, (21)*; (1992); pp. 2891-2898.

Rabb et al.; "Effects of Active Immunication Against GnRH on LH, FSH and Prolactin Storage, Sectretion and Response to Their Secretagogues in Pony Geldings"; *J. Anim. Sci.*, 68; (1990); pp. 3322-3329.

Ren, Shan, et al.; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.

Reynolds, R.C. et al.; "Sucrose acetate isobutyrate (SAIB): historical aspects of its use in beverages and a review of toxicity studies prior to 1988"; *Food Chem. Toxicol.36(2)*, (1998); pp. 81-93.

Reynolds, R.C.; "Metabolism and pharmacokinetics of sucrose acetate isobutyrate (SAIB) and sucrose octaisobutyrate (SOIB) in rats, dogs, monkeys or humans. a review"; *Food Chem. Toxicol.*, 36(2); (1998); pp. 95-99.

Robinson; "Coating of Pharmaceutical Dosage Forms" *Remington's Pharmaceutical Sciences*, Ed. Arthur Osol, Chapter 90; (1980); pp. 1585-1593.

Roser, J.J., et al.; "The Development of Antibodies to Human Chorionic Gonadotrpins Following its Repeated Injection in the Cyclic Mare"; *J. Reprod. Fert Suppl.*, (1979); pp. 173-179.

Roussin, P. et al; "Gelucire® 44/14; A High-Performance System to Enhance Bioavailability of Poorly Water Soluble Drugs"; *Bulletin Technique Gattefosse*, No. 90; (1997); pp. 51-58.

Sachs-Barrable, K., et al; "Lipid Excipients Peceol and Gelucire 44/14 decrease P-glycoprotein mediated efflux of Rhodamine 123 partially due to modifying P-glycoprotein expression within Caco-2 Cells."; *J. Pharm. Pharm. Sci.*, 10(3); (2007); pp. 319-331.

Saeio, Kiattisak, et al; "Factors Influencing Drug Dissolution Characteristic From Hydrophilic Polymer Matrix Tablet"; *Scientia Pharmaceutica (Sci. Pharm) 75*; (2007); pp. 147-163.

Saeki; "Progress of Orally Opiate Analgesics and Non-Steroidal Anti-Flammatory Agent" *Drug Deliv Syst* 20(5); (2005) pp. 521-529.

Santus et al.; "Osmotic Drug Delivery: A Review of the Patent Liter" *J Control Release 35(1)*; (1995); pp. 1-21.

(56) References Cited

OTHER PUBLICATIONS

Schamp, Karen, et al; "Development of an in vitro/in vivo correlation for lipid formulations of EMD 50733, a poorly soluble, lipophilic drug substance"; *European Journal of Pharmaceutics and Biopharmaceutics 62*; (2006); pp. 227-234; available online Oct. 24, 2005.
Selimovic, Seila, and Hu Yue; "Aging Effects in Suspensions of Silica Particles"; *Mat. Res. Soc. Symp. Proc.*, vol. 790 Materials Research Society; (2004) pp. P7.11.1-P7.11.6.
Serajuddin, Abu T.M., et al; "Effect of Vehicle Amphiphilicity on the Dissolution and Bioavailability of a Poorly Water-Soluble Drug from Solid Dispersions"; *Journal of Pharmaceutical Sciences*, vol. 77, No. 5, May 1988; pp. 414-417.
Serajuddin, Abu T.M., et al; "Water Migration from Soft Gelatin Capsule Shell to Fill Material and Its Effect on Drug Solubility"; *Journal of Pharmaceutical Sciences*, vol. 75, No. 1; Jan. 1986; pp. 62-64.
Sethia, Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences*, vol. 91, No. 9; Sep. 2002; pp. 1948-1957.
Sethia, Sundeep, et al; "In Vitro-In Vivo Evaluation of Supercritical Processed Solid Dispersions: Permeability and Viability Assessment in Caco-2 Cells"; *Journal of Pharmaceutical Sciences*, vol. 93, No. 12; Dec. 2004; pp. 2985-2993; published online Oct. 1, 2004.
Setnik B, Roland CL, Cleveland JM, Webster L.; "The abuse potential of Remoxy((R)), an extended-release formulation of oxycodone, compared with immediate- and extended-release oxycodone"; *Pain Med. 12(4)*; (2011); pp. 618-631.
Shah, N. H; et al; "Self-Emulsifying Drug Delivery Systems (SEDDS) for Improving In Vitro Dissolution and Oral Absorption of Lipophilic Drugs"; *Bulletin Technique. GattefosséReport*, No. 85; (1992/93); pp. 45-54.
Sheen, Pai-Chang, et al; "Bioavailability of a Poorly Water-Soluble Drug from Tablet and Solid Dispersion in Humans"; *Journal of Pharmaceutical Sciences*, vol. 80, No. 7; Jul. 1991; pp. 712-714.
Shimpi, Shyam, et al; "Preparation and Evaluation of Diltiazem Hydrochloride-Gelucire 43/01 Floating Granules Prepared by Melt Granulation"; *AAPS PharmSciTech 5(3)*, Article 43, (http://www.aapspharmscitech.org); (2004); pp. 1-6; published online Jul. 12, 2004.
Smith & Tipton; "A Novel Parental Delivery System" *AAPS Presentation DD 7270*, Seattle, WA; (1996) Annual Meeting; 2 pages.
Soliman, M. S., et al; "Preparation and in vitro characterization of a semi-solid dispersion of flurbiprofen with Gelucire 44/14 and Labrasol"; *Pharmazie 60(4)*; (2005); pp. 288-293.
Srinivas et al.; "Enantioselective pharmacokinetics and pharmacodynamics of dl-threo-methylphenidate in children with attention deficit hyperactivity disorder"; *Clin Pharmacal Ther 52(5)*; (1992); pp. 561-568.
Stegemann. S., et al; "When Poor Solubility Becomes an Issue: From Early Stage to Proof of Concept"; *European Journal of Pharmaceutical Sciences 31*; (2007); pp. 249-261.
Strickley, Robert G; "An Overview of Lipid Excipients Currently Available: Strengths, Weaknesses and Opportunity Gaps: The Options for the Formulator"; *Bulletin Technique Gattefosse*, No. 100; (2007); pp. 31-37.
Strickley, Robert G.; "Solubilizing Excipients in Oral and Injectable Formulations"; *Pharmaceutical Research*, vol. 21, No. 2; Feb. 2004; pp. 201-230.
Subramanian, Ramaswamy, et al; "Effect of Lipid Excipients on In Vitro Pancreatic Lipase Activity"; *Drug Development and Industrial Pharmacy*, vol. 29, No. 8; (2003); pp. 885-890.
Sucrose Acetate Isobutyrate, 21 CFR 172.831 (1999).
Sullivan, et al (1997) "Delivery of Taxol® and other Antineoplastic Agents from a Novel System Based on Sucrose Acetate Isobutyrate" *AAPS Boston, MA. Southern BioSystems, Inc.* Birmingham AL, USA 2 pages.
Sullivan, et al. (1998) "Sustained Release of Bupivacaine from the Saber TM Delivery System" *AAPS*, San Francisco, CA. Southern BioSystems, Inc. Birmingham AL, USA.
Sullivan, et al; "Sustained Release of Orally Administered Active Using Saber Delivery System Incorporated into Soft Gelatin Capsules"; *Proceed. Int'l. Control. Rei. Bioact. Mater. Controlled Release Society.* vol. 25; Jun. 1998 Las Vegas NV; pp. 918-919.
Sullivan, et al; "Sustained Release of Progesterone and Estradiol from the Saber™ Delivery System: In Vitro and In Vivo Release Rates" *CRS Las Vegas, NV. Southern BioSystems, Inc.* Birmingham AL, USA; (1998); 2 pages.
Sullivan, et al (1999) "Sustained Release of Lysozyme from the Saber™ Delivery System" *AAPS*, New Orleans, LA. Southern BioSystems, Inc. Birmingham AL, USA; 2 pages.
Sullivan, et al; "Incorporation of Polymer Microparticles Into Sucrose Acetate Isobutyrate Reduces Burst and Extends Release" *Proceed. Int'l Symp. Control. Rel. Bioact. Mater.*, 27, Controlled Release Society, Inc. Paris, France; Jul. 7-13, 2000.
Sullivan, J. J., et al.; "Duration of Estrus and Ovulation Time in Nonlactating Mares Given Human Chorionic Gonadotropin During Three Successive Estrous Periods"; *J.A.V.M.A.*, vol. 162, No. x; May 15, 1973; pp. 895-898.
Svensson, A., et al; "Hydration of an amphiphilic excipient Gelucire® 44/14"; *Int. J. Pharm. 281(1-2)*; (2004); pp. 107-118.
Swanson et al; "Objective and subjective measures of the pharmacodynamic effects of Adderall in the treatment of children with ADHD in a controlled laboratory classroom setting"; *Psychopharmacol Bull 34(1)*; (1998); pp. 55-60.
Swanson et al; "Acute tolerance to methylphenidate in the treatment of attention deficit hyperactivity disorder in children" *Clin Pharmacal Ther 66(3)*; (1999); pp. 295-305.
Swanson et al. Ritalin Theory and Practice. 2nd Edition, Greenhill & Osman Ed., Mary Ann Liebert, Larchmont, NY; (1999) pp. 405-430.
Swanson et al; "Efficacy of a new pattern of delivery of methylphenidate for the treatment of ADHD: effects on activity level in the classroom and on the playground" *J Am Acad Child Adolesc Psychiatry 41(11)*; (2002); pp. 1306-1314.
Swanson et al; "Pharmacokinetic and pharmacodynamic properties of stimulants: implications for the design of new treatments for ADHD"; *Behav Brain Res 130(1-2)*; (2002); pp. 73-78.
Swanson et al; "Development of a new once-a-day formulation of methylphenidate for the treatment of attention-deficit/hyperactivity disorder: proof-of-concept and proof-of-product studies"; *Arch Gen Psychiatry 60(2)*; (2003); pp. 204-211.
Swanson et al; "Serum and brain concentrations of methylphenidate: implications for use and abuse"; *Neurosci Biobehav Rev 27(7)*; (2003); pp. 615-621.
Swanson et al; "A comparison of once-daily extended-release methylphenidate formulations in children with attention-deficit/hyperactivity disorder in the laboratory school (the Comacs Study)"; *Pediatrics 113(3 Pt. 1)*; (2004); pp. e206-e216.
Swiderski et al.; "Application of 14C Isotope in Studies on the Lability of Sugar Substituents" *Nukleonika, Supl.*, vol. 10; (1966); pp. 347-352.
Tashtoush, Bassam M., et al; "In Vitro and In Vivo Evaluation of Glibenclamide in Solid Dispersion Systems"; *Drug Development and Industrial Pharmacy*, vol. 30, No. 6; (2004); pp. 601-607.
Thompson, D. L., et al., "Effects of Melatonin and Thyrotropin Releasing Hormone on Mares During the Nonbreeding Season", Journal of Animal Science, vol. 56, No. 3, (1983), pp. 668-677.
Thompson, D. L., et al., "Testosterone Effects on Mares During Synchronization with Altrenogest: FHS, LH, Estrous Duration and Pregnancy Rate"; *Journal of Animal Science*, vol. 56, No. 3; (1983); pp. 678-686.
Tipton; "Peptide Delivery from an In Situ Gelling System Based Ion Sucrose Acetate Isobutyrate" *AAPS J Abstract*. Southern BioSystems, Inc. Birmingham AL, USA; (1999); 1 page.
Tipton, "In Situ Gelling Systems"; Sustained-Release Injectable Products, Ed. Senior & Radomsky, Interpharm Press, Denver, CO; (2000); pp. 258-259.

(56) References Cited

OTHER PUBLICATIONS

Tipton, et al; "Local Delivery from a Novel Biodegradable In Situ Delivery System"; *Sixth World Biomaterials Congress*, Kamuela, HI, Southern BioSystems, Inc. Birmingham AL, USA, May 15-20, 2000; 1 page.

Tran, Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics 72*; (2009); pp. 83-90; available online Dec. 25, 2008.

Trescot AM, et al; "Opioid Guidelines in the Management of Chronic Non-Cancer Pain." *Pain Physician*, vol. 9; (2006), pp. 1-40.

U.S. Department of Health and Human Services "Guidance for Industry: Food-Effect Bioavailability and Fed Bioequivalence Studies" FDA, Center for Drug Evaluation and Research (CDER), Dec. 2002.

U.S. Appl. No. 12/754,486, filed Apr. 5, 2010, 103 pages; with Preliminary Amendment filed Nov. 23, 2010, 13 pages.

U.S. Appl. No. 60/434,839, filed Dec. 18, 2002, 111 pages.

Vega-Rios Aracelly, et al; "Acid-catalyzed hydrolysis of triacylglycerols obeys monoexponential kinetics."; *International Journal of Chemical Kinetics*, vol. 24; (1992); pp. 887-894.

Vankatesan, N. et al; "Gelucire® 44/14 and Labrasol® in Enhancing Oral Absorption of Poorly Absorbable Drugs"; *Bulletin Technique Gattefosse*, No. 99; (2006); pp. 79-88.

Vila Jato, J.L., et al; "Influence of melting point and HLB on the release of amoxicillin from granulates containing Gelucire as excipients"; *S.T.P. Pharma*, vol. 6, No. 5; (1990); pp. 287-292.

Volkow et al; "Relationship between psychostimulant-induced "high" and dopamine transporter occupancy"; *Proc Natl Acad Sci USA 93(19)*; (1996); pp. 10388-10392.

Volkow et al. "Temporal relationships between the pharmacokinetics of methylphenidate in the human brain and its behavioral and cardiovascular effects"; *Psychopharmacology 123*; (1996).

Volkow et al; "Methylphenidate and cocaine have a similar in vivo potency to block dopamine transporters in the human brain"; *Life Sciences* vol. 65, No. 1; (1999); p. L7-p. L12.

Volkow et al; "Relationship between blockade of dopamine transporters by oral methylphenidate and the increases in extracellular dopamine: therapeutic implications"; *Synapse 43(3)*; (2002); pp. 181-187.

Volkow, et al; "Dopamine transporter occupancies in the human brain induced by therapeutic doses of oral methylphenidate"; *Am J Psychiatry 155(10)*; (1998); pp. 1325-1331.

Voss, J.L., et al; "The Effect of HCG on Duration of Oestrus, Ovulation Time and Fertility in Mares"; Journal of Reprod. Fert., Suppl. 23; (1975); pp. 297-301.

Webster LR.; "PTI-821: sustained-release oxycodone using gel-cap technology"; *Expert Opin Investig Drugs. 16(3)*; (2007); pp. 359-366.

Wigal et al; "Reliability and validity of the SKAMP rating scale in a laboratory school setting" *Psychopharmacol Bulletin*, vol. 34, No. 1; (1998); pp. 47-53.

Wigal et al; "Selection of the Optimal Dose Ratio for a Controlled-Delivery Formulation of Methylphenidate"; *The Journal of Applied Research 3*; (2003); pp. 46-63.

Wightman et al; "Transient changes in mesolimbic dopamine and their association with 'reward'"; *Journal of Neurochemistry 82(4)*; (2002); pp. 721-735.

Wolraich et al; "Randomized, controlled trial of oros methylphenidate once a day in children with attention-deficit/hyperactivity disorder"; *Pediatrics 108(4)*; (2001); pp. 883-892.

Yuksel, Niliifer, et al; "Enhanced bioavailability of piroxicam using Gelucire 44/14 and Labrasol: in vitro and in vivo evaluation"; *European Journal of Pharmaceutics and Biopharmaceutics 56*; (2003); pp. 453-459.

Zamloot M, et al.; "Remoxy®: a novel formulation of extended-release oxycodone developed using the Oradur® technology"; *J Appl Res. 10(3)* (2010); pp. 88-96.

M = Months
L.S. = Label strength

Panel A
Loss Module vs. SiO₂ Composition at 50-70°C

Panel B
Damping Factor vs. SiO₂ Composition at 50-70°C

COMPOSITIONS WITH A RHEOLOGICAL MODIFIER TO REDUCE DISSOLUTION VARIABILITY

CROSS-REFERENCE TO RELATED APPLICATIONS

This application is a continuation of U.S. patent application Ser. No. 15/398,426, filed Jan. 4, 2017, now U.S. Pat. No. 9,855,333, which application is a continuation of U.S. patent application Ser. No. 14/776,585, filed Sep. 14, 2015, now U.S. Pat. No. 9,572,885, which application is a national stage entry of International Patent Application No. PCT/US2014/029607, filed Mar. 14, 2014, which application claims the benefit of and expressly incorporates by reference herein the entire disclosure of U.S. Provisional Patent Application No. 61/801,110, filed Mar. 15, 2013.

INTRODUCTION

Extended release pharmaceutical compositions, including extended release oxycodone compositions, may include various pharmaceutically inactive components which contribute to the desired pharmacokinetic parameters of the active agent in the composition. Such compositions may also include pharmaceutically inactive components which contribute to one or more abuse-deterrent characteristics of the composition. In some such cases, extended release pharmaceutical compositions may be provided which are viscoelastic in nature with a combination of hydrophilic and hydrophobic components. In addition to solubility of the active agent in the composition, the release of the active agent may be controlled, at least in part, by balancing the viscoelastic, hydrophilic and/or hydrophobic nature of the composition. However, in some cases, the viscoelastic, hydrophilic, and/or hydrophobic nature of the composition may also contribute to undesirable sample variability during dissolution of the active agent from the composition. This undesirable sample variability may be evidenced by inter-capsule variability at a particular time point and/or as a storage-time dependent change in mean release of the active agent from the composition (aging). The present disclosure addresses these issues and provides related advantages.

SUMMARY

The present disclosure provides compositions (e.g., extended release compositions) which exhibit a desirable pharmacokinetic profile of an active agent while providing reduced dissolution sample variability, e.g., in the form of reduced inter-capsule variability and/or a reduction in storage-time dependent change in mean release of the active agent from the composition. Related methods of making and administering the disclosed compositions are also provided.

DEFINITIONS

Figure 1A:
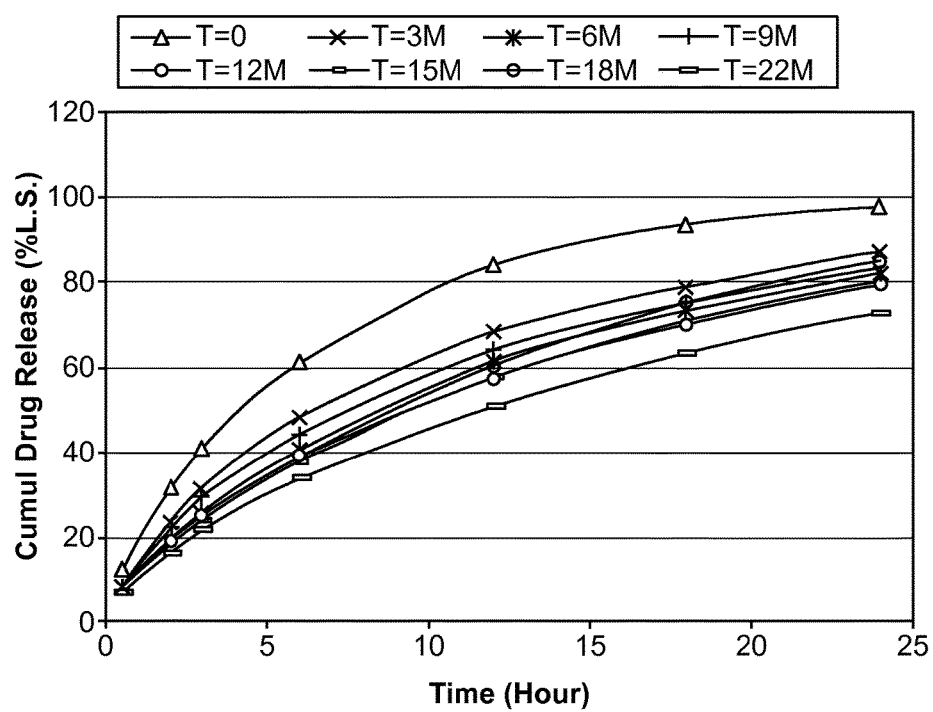
FIG. 1A is a graph showing a storage-time dependent change in the release of oxycodone from a reference composition (Reference Formulation A (with BHT)).

As used interchangeably herein, the terms "active agent", "pharmacologically active agent" and "beneficial agent" refer to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology.

As used herein, the term "high viscosity liquid carrier material (HVLCM)" refers to a non-polymeric, non-water soluble liquid material having a viscosity of at least 5000 cP at 37° C. that does not crystallize neat at 25° C. and 1 atmosphere.

As used herein, the term "rheology modifier" refers to a substance that possesses both a hydrophobic and a hydrophilic moiety. Rheology modifiers suitable for use in the disclosed compositions and methods generally have a logarithm of octanol-water partition coefficient ("Log P") of between about −7 and +15, e.g., between −5 and +10, e.g., between −1 and +7.

As used herein, the term "network former" refers to a material or compound that forms a network structure when introduced into a liquid medium (such as a HVLCM).

As used herein, the term "hydrophilic agent" means a compound or material having a natural affinity for aqueous systems. A material may be regarded as a hydrophilic agent for the purposes of this disclosure if the material displays a water sorption between about 10 to 100% (w/w). Hydrophilic agents will have a low Log P value, for example, a Log P of less than +1.

As used herein, the term "hydrophilic solvent" means a solvent meeting the definition of a hydrophilic agent as described above.

The term "solvent", as used herein, refers to any substance that dissolves another substance (solute).

As used herein, the term "treatment", "treat" and "treating" pain refers to eliminating, reducing, suppressing or ameliorating, either temporarily or permanently, either partially or completely, a clinical symptom, manifestation or progression of pain. In addition, or alternatively, the terms "treatment", "treat" and "treating" as used herein with respect to the methods as described refer to inhibiting, delaying, suppressing, reducing, eliminating or ameliorating, either temporarily or permanently, either partially or completely, pain. In some embodiments the treating is effective to reduce a symptom, sign, and/or condition of pain in a subject by at least about 10% (e.g., 15%, 20%, 25%, 30%, 35%, 40%, 45%, 50%, 55%, 60%, 65%, 70%, 75%, 80%, 85%, 90%, 95%, or 100%) including, as compared to a baseline measurement of the symptom, sign, and/or condition made prior to the treatment. In some embodiments, the treating is effective to improve an assessment used to diagnose pain in a subject including, as compared to a baseline assessment made prior to the treatment. Such treating as provided herein need not be absolute to be useful.

The term "pharmaceutically acceptable salt," as used herein, intends those salts that retain the biological effectiveness and properties of neutral active agents and are not otherwise unacceptable for pharmaceutical use.

As used herein, the term "viscosity enhancing agent" refers to a compound or material that can be added to an extended release composition in order to increase the viscosity of the resulting composition.

As used herein, the term "stabilizer" refers to any substance used to inhibit or reduce degradation (e.g., chemical) of other substances with which the stabilizer is mixed.

The terms "% w/w" and "w %" are used interchangeably herein to refer to percent weight per weight.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a composition" includes a plurality of such compositions and reference to "the capsule" includes reference to one or more capsules and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

To the extent the definition or usage of any term herein conflicts with a definition or usage of a term in an application or reference incorporated by reference herein, the instant application shall control.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

As discussed previously herein, the viscoelastic, hydrophilic and/or hydrophobic nature of a pharmaceutical composition may contribute to undesirable sample variability during dissolution of the active agent from the composition. This undesirable sample variability may be evidenced by inter-capsule variability at a particular time point and/or as a storage-time dependent change in mean release of the active agent from the composition.

The present disclosure provides compositions (e.g., extended release compositions) which exhibit a desirable pharmacokinetic profile of an active agent while providing reduced dissolution sample variability, e.g., in the form of reduced in vitro inter-capsule variability and/or a reduction in storage-time dependent change in mean in vitro release of the active agent from the composition. Related methods of making and administering the disclosed compositions are also provided. The compositions of the present disclosure generally include a pharmacologically active agent, a high viscosity liquid carrier material (HVLCM) and a solvent. In some embodiments, the compositions also include one or more of a rheology modifier, a network former, a hydrophilic agent, a viscosity enhancing agent and a stabilizing agent.

In some embodiments, the inclusion of a viscosity enhancing agent, e.g., a mineral particle such as silicon dioxide, within a specified concentration range in the composition surprisingly provides for decreased variability in the dissolution profile of the active agent from the composition, e.g., as evidenced by a relative decrease in inter-capsule dissolution profile variability, while maintaining an acceptable level of rigidity/or viscosity which does not significantly interfere with the processability of the composition. This unexpected, beneficial balance between dissolution variability and processability may be achieved by including the viscosity enhancing agent, e.g., a mineral particle such as silicon dioxide, at from about 2.4 to about 5.4 percent by weight relative to the total weight of the composition.

As demonstrated by the present disclosure, the concentration of a rheology modifier, such as isopropyl myristate (IPM), in a pharmaceutical composition may also have a significant effect on sample variability, e.g., as evidenced by inter-capsule dissolution profile variability. It is an unexpected discovery of the present disclosure that providing a relatively low concentration range of a rheology modifier such as IPM, e.g., at from about 2% to about 10% by weight based on the total weight of the composition, contributes to a desirable pharmacokinetic profile while reducing inter-capsule dissolution profile variability.

The present disclosure also provides improved compositions which exhibit a reduction in a storage-time dependent change in mean in vitro release of the active agent from the composition. Without intending to be bound by any particular theory, it is believed that reducing the amount of water available to the compositions of the present disclosure may minimize these effects. For example, by utilizing HPMC capsules (~2-6% w/w water, e.g., ~4-6% w/w water) instead of gelatin capsules (~13-16% w/w water) the amount of water available to the compositions may be reduced. Accordingly, in some embodiments, the compositions of the present disclosure are specifically encapsulated within capsules having lower water content than gelatin capsules. Thus, in some embodiments a composition according to the present disclosure is one which has relatively low water content. For example, in some embodiments, a composition according to the present disclosure does not include more than about 5% water by weight, based on total weight of the composition.

In addition, the present disclosure demonstrates that a specified ratio range of the amount of an HVLCM such as sucrose acetate isobutyrate (SAIB), to a solvent such as triacetin, to a rheology modifier such as IPM in a composition contributes to an improved level of sample variability, e.g., as evidenced by a reduced time-dependent change in an in vitro release profile of a composition. Accordingly, in some embodiments the compositions of the present disclosure specifically include an HVLCM, a solvent, and a rheology modifier, wherein the HVLCM, the solvent and the rheology modifier are present in the composition at a ratio of about 1.3:1.0:0.3 to about 1.0:1.0:0.05.

Pharmacologically Active Agent

The pharmacologically active agents that may be included in the compositions of the present disclosure may include any type of biologically active compound or composition of matter which, when administered to an organism (human or animal subject) induces a desired pharmacologic and/or physiologic effect by local and/or systemic action.

Examples of such biologically active compounds or compositions of matter useful in the disclosed compositions include, but are not limited to, opioids, CNS depressants and stimulants.

Opioids are a class of potent narcotics that includes, for example, morphine, codeine, oxycodone and fentanyl and related drugs. Morphine is often used to alleviate severe pain. Codeine is used for milder pain. Other examples of opioids that can be prescribed to alleviate pain include oxycodone (e.g. OxyContin®-an oral, controlled release form of the drug); propoxyphene (e.g. Darvon™); hydrocodone (e.g. Vicodin™); hydromorphone (e.g. Dilaudid™); and meperidine (e.g. Demerol™).

In addition to relieving pain, opioids can also produce a sensation of euphoria, and when taken in large doses, can cause severe respiratory depression which can be fatal.

CNS depressants slow down normal brain function by increasing GABA activity, thereby producing a drowsy or calming effect. In higher doses, some CNS depressants can become general anesthetics, and in very high doses may cause respiratory failure and death. CNS depressants are frequently abused, and often the abuse of CNS depressants occurs in conjunction with the abuse of another substance or drug, such as alcohol or cocaine. Many deaths occur yearly through such drug abuse. CNS depressants can be divided into two groups, based on their chemistry and pharmacology: (1) Barbiturates, such as mephobarbital (e.g. Mebaral™) and pentobarbital sodium (e.g. Nembutal™), which are used to treat anxiety, tension, and sleep disorders. (2) Benzodiazepines, such as diazepam (e.g. Valium™), chlordiazepoxide HCl (e.g. Librium™), and alprazolam (e.g. Xanax™), which can be prescribed to treat anxiety, acute stress reactions, and panic attacks. Benzodiazepines that have a more sedating effect, such as triazolam (e.g. Halcion™) and estazolam (e.g. ProSom™) can be prescribed for short-term treatment of sleep disorders.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma. Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system. In addition, the increase in dopamine is associated with a sense of euphoria that can accompany the use of these drugs.

Taking high doses of a stimulant can result in an irregular heartbeat, dangerously high body temperatures, and/or the potential for cardiovascular failure or lethal seizures. Taking high doses of some stimulants repeatedly over a short period of time can lead to hostility or feelings of paranoia in some individuals.

One class of biologically active compounds that may be included in the compositions of the present disclosure is the opioids class, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dextromethorphan, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, levomethorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate (NTII), naltriben (NTB), nor-binaltorphimine (nor-BNI), tapentadol, beta-funaltrexamine (b-FNA), 7-Benzylidenenaltrexone (BNTX), cyprodime, N,N-diallyl-Tyr-Aib-Aib-Phe-Leu (ICI-174,864), 3-[1-(3-hydroxy-3-phenylpropyl)-3,4-dimethylpiperidin-4-yl]phenol (LY117413), [(−)-(1R,5R,9R)-5,9-diethyl-2-(3-furylmethyl)-2'-hydroxy-6,7-benzomorphan] (MR2266), etorphine, [D-Ala$^2$, NMe-Phe$^4$, Gly-ol$^5$]-enkephalin (DAMGO), CTOP (CAS No:103429-31-8), diprenorphine, naloxone benzoylhydrazone, bremazocine, ethylketocyclazocine, (U50,488), (U69,593), spiradoline, [D-Pen$^{2,5}$]Enkephalin (DPDPE), [D-Ala2,Glu4] deltorphin, [D-Ser$^2$, Leu$^5$, Thr$^6$]-enkephalin (DSLET), Met-enkephalin, Leu-enkephalin, β-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

In some embodiments, opioids for use in the compositions of the present disclosure are selected from morphine, hydrocodone, oxycodone, codeine, fentanyl (and its relatives), hydromorphone, meperidine, methadone, oxymorphone, propoxyphene or tramadol, or mixtures thereof. In some embodiments, opioids for use in the compositions of the present disclosure are selected from oxycodone, oxymorphone, hydrocodone and hydromorphone. In some embodiments, the opioids for use in the compositions of the present disclosure may be micronized. With respect to the opioid oxycodone, it may be beneficial to provide compositions that have a reduced level of peroxide degradation products such as alpha beta unsaturated ketones (ABUK). In such cases, the compositions of the present disclosure can be subjected to peroxide contaminant reduction and/or removal techniques in accordance with known methods.

Other pharmacologically active compounds or compositions of matter useful in the disclosed compositions include prochlorperazine edisylate, ferrous sulfate, aminocaproic acid, potassium chloride, mecamylamine, procainamide, amphetamine (all forms including dexamphetamine, dextroamphetamine, d-S-amphetamine, and levoamphetamine), benzphetamine, isoproternol, methamphetamine, dexmethamphetamine, phenmetrazine, bethanechol, metacholine, pilocarpine, atropine, methascopolamine, isopropamide, tridihexethyl, phenformin, methylphenidate (all forms including dexmethylphenidate, d-threo methylphenidate, and dl-threo methylphenidate), oxprenolol, metroprolol, cimetidine, diphenidol, meclizine, prochlorperazine, phenoxybenzamine, thiethylperazine, anisindone, diphenadione erythrityl, digoxin, isofurophate, reserpine, acetazolamide, methazolamide, bendroflumethiazide, chlorpropamide, tolazamide, chlormadinone, phenaglycodol, allopurinol, aluminum aspirin, methotrexate, acetyl sulfisoxazole, erythromycin, progestins, estrogenic progrestational, corticosteroids, hydrocortisone, hydrocorticosterone acetate, cortisone acetate, triamcinolone, methyltesterone, 17 beta-estradiol, ethinyl estradiol, ethinyl estradiol 3-methyl ether, prednisolone, 17-hydroxyprogesterone acetate, 19-nor-progesterone, norgestrel, orethindone, norethiderone, progesterone, norgestrone, norethynodrel, aspirin, indomethacin, naproxen, fenoprofen, sulindac, diclofenac, indoprofen, nitroglycerin, propranolol, metroprolol, sodium valproate, valproic acid, taxanes such as paclitaxel, camptothecins such as 9-aminocamptothecin, oxprenolol, timolol, atenolol, alprenolol, cimetidine, clonidine, imipramine, levodopa, chloropromazine, resperine, methyldopa, dihydroxyphenylalanine, pivaloyloxyethyl ester of α-methyldopa hydrochloride, theophylline, calcium gluconate ferrous lactate, ketoprofen, ibuprofen, cephalexin, haloperiodol, zomepirac, vincamine, diazepam, phenoxybenzamine, β-blocking agents, calcium-channel blocking drugs such as nifedipine, diltiazen, verapamil, lisinopril, captopril, ramipril, fosimopril, benazepril, libenzapril, cilazapril cilazaprilat, perindopril, zofenopril, enalapril, indalapril, qumapril, and the like.

The active agent can be present in the compositions of the present disclosure in a neutral form, as a free base form, or in the form of a pharmaceutically acceptable salt. Pharmaceutically acceptable salts include salts of acidic or basic groups, which groups may be present in the active agents. Those active agents that are basic in nature are capable of forming a wide variety of salts with various inorganic and organic acids. Pharmaceutically acceptable acid addition salts of basic active agents suitable for use herein are those that form acid addition salts, i.e., salts including pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Active agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) *J. Pharm. Sci.* 66:1-19, the disclosure of which is incorporated by reference herein.

In the compositions of the present disclosure, the pharmacologically active agent will be dissolved (fully or partially) in one or more components of the composition or dispersed within one or more components of the composition. The phrase "dissolved or dispersed" is intended to encompass all means of establishing a presence of the active agent in the subject compositions and includes dissolution, dispersion, partial dissolution and dispersion, and/or suspension and the like. In addition, in certain embodiments of the present disclosure wherein the active agent is in a solid particulate form suspended within one or more other components of the composition, the active agent particulate may be pre-treated with a micronization process such as those described in U.S. Application Publication No. 2009/0215808, the disclosure of which is incorporated by reference herein, to provide a particle population having a substantially homogeneous particle size the bulk of which fall within the micron (μm) range.

The pharmacologically active agent, which can include one or more suitable active agent, may be present in the disclosed compositions in an amount of from about 50 to about 0.1 percent by weight relative to the total weight of the composition (wt %), e.g., in an amount of from about 40 to about 0.1 wt %, in an amount of from about 30 to about 0.1 wt %, in an amount of from about 20 to about 0.1 wt %, in an amount of from about 10 to about 0.1 wt %, in an amount of from about 9 to about 0.1 wt %, in an amount of from about 8 to about 0.1 wt %, in an amount of from about 7 to about 0.1 wt %, in an amount of from about 6 to about 0.1 wt %, in an amount of from about 5 to about 0.1 wt %, in an amount of from about 4 to about 0.1 wt %, in an amount of from about 3 to about 0.1 wt %, in an amount of from about 2 to about 0.1 wt %, or in an amount of from about 1 to about 0.1 wt %, depending upon the identity of the active agent, the desired dose required for the dosage form, and the intended use thereof.

In some embodiments, the pharmacologically active agent may be present in the disclosed compositions in an amount from about 0.1 to about 5 w %, in an amount from about 5 to about 10 w %, in an amount from about 10 to about 20 w %, in an amount from about 20 to about 30 w %, in an amount from about 30 to about 40 w %, or in an amount from about 40 to about 50 w %, depending upon the identity of the active agent, the desired dose required for the dosage form, and the intended use thereof.

In some embodiments, the active agent is present in the composition in an amount of about 1 to about 10 wt %, and can thus be loaded into a suitable dosage form to provide single dosages ranging from about 0.01 mg to about 1000 mg, or from about 0.1 mg to about 500 mg, or from about 2 mg to about 250 mg, or from about 2 mg to about 250 mg, or from about 2 mg to about 150 mg, or from about 5 mg to about 100 mg, or from about 5 mg to about 80 mg. For example, in some embodiments, the active agent is present in the composition in an amount of from about 2 wt % to about 9 wt %, from about 3 wt % to about 8 wt %, from about 4 wt % to about 7 wt %, or from about 5 wt % to about 6 wt %. In some embodiments, the active agent is present in the composition in an amount of about 1 wt %, about 2 wt %, about 3 wt %, about 4 wt %, about 5 wt %, about 6 wt %, about 7 wt %, about 8 wt %, about 9 wt %, or about 10 wt %.

For some embodiments that include an opioid active agent, exemplary single dosages include, but are not limited to, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150 and about 160 mg.

In other embodiments that include a CNS depressant or CNS stimulant, exemplary single dosages include, but are not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, and about 100 mg.

In some embodiments, where the active agent includes oxycodone free base, the active agent is present in the composition in an amount of from about 50 to about 0.1 percent by weight relative to the total weight of the composition (wt %), e.g., in an amount of from about 40 to about 0.1 wt %, in an amount of from about 30 to about 0.1 wt %, in an amount of from about 20 to about 0.1 wt %, in an amount of from about 10 to about 0.1 wt %, in an amount of from about 9 to about 0.1 wt %, in an amount of from about 8 to about 0.1 wt %, in an amount of from about 7 to about 0.1 wt %, in an amount of from about 6 to about 0.1 wt %, in an amount of from about 5 to about 0.1 wt %, in an amount of from about 4 to about 0.1 wt %, in an amount of from about 3 to about 0.1 wt %, in an amount of from about 2 to about 0.1 wt %, or in an amount of from about 1 to about 0.1 wt %.

In some embodiments, where the active agent includes oxycodone free base, the active agent may be present in the disclosed compositions in an amount from about 0.1 to about 5 w %, in an amount from about 5 to about 10 w %, in an amount from about 10 to about 20 w %, in an amount from about 20 to about 30 w %, in an amount from about 30 to about 40 w %, or in an amount from about 40 to about 50 w %.

In some embodiments, where the active agent comprises oxycodone free base, the active agent is present in the composition in an amount of about 1 to about 10 wt %, and can thus be loaded into a suitable dosage form to provide single dosages ranging from about 0.01 mg to about 1000 mg, or from about 0.1 mg to about 500 mg, or from about 2 mg to about 250 mg, or from about 2 mg to about 250 mg, or from about 2 mg to about 150 mg, or from about 5 mg to about 100 mg, or from about 5 mg to about 80 mg. For example, in some embodiments, where the active agent comprises oxycodone free base, the active agent is present in the composition in an amount of from about 2 wt % to about 9 wt %, from about 3 wt % to about 8 wt %, from about 4 wt % to about 7 wt %, or from about 5 wt % to about 6 wt %. In some embodiments, where the active agent comprises oxycodone free base, the active agent is present in the composition in an amount of about 1 wt %, about 2 wt %, about 3 wt %, about 4 wt %, about 5 wt %, about 6 wt %, about 7 wt %, about 8 wt %, about 9 wt %, or about 10 wt %.

For some embodiments, where the active agent comprises oxycodone free base, exemplary single dosages include, but are not limited to, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, and about 160 mg.

In some embodiments, where the active agent is oxycodone free base, the active agent is present in the composition in an amount of about 1 to about 10 wt %, and can thus be loaded into a suitable dosage form to provide single dosages ranging from about 0.01 mg to 1000 mg, or from about 0.1 mg to 500 mg, or from about 2 mg to 250 mg, or from about 2 mg to 250 mg, or from about 2 mg to 150 mg, or from about 5 mg to 100 mg, or from about 5 mg to 80 mg. For example, in some embodiments, the oxycodone free base is present in the composition in an amount of from about 2 wt % to about 9 wt %, from about 3 wt % to about 8 wt %, from about 4 wt % to about 7 wt %, or from about 5 wt % to about 6 wt %.

In some embodiments, the oxycodone free base is present in the composition in an amount of about 1 wt %, about 2 wt %, about 3 wt %, about 4 wt %, about 5 wt %, about 6 wt %, about 7 wt %, about 8 wt %, about 9 wt %, or about 10 wt %.

The precise amount of active agent desired can be determined by routine methods well known to pharmacological arts, and will depend on the type of agent, and the pharmacokinetics and pharmacodynamics of that agent.

High Viscosity Liquid Carrier Material (HVLCM)

An HVLCM is a non-polymeric, non-water soluble liquid material having a viscosity of at least 5000 cP at 37° C. that does not crystallize neat at 25° C. and 1 atmosphere. The term "non-water soluble" refers to a material that is soluble in water to a degree of less than one percent by weight at 25° C. and 1 atmosphere. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "non-polymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein. HVLCMs may be carbohydrate-based, and may include one or more cyclic carbohydrates chemically combined with one or more carboxylic acids. HVLCMs also include non-polymeric esters or mixed esters of one or more carboxylic acids, having a viscosity of at least 5,000 cP at 37° C., that do not crystallize neat at 25° C. and 1 atmosphere, wherein when the ester contains an alcohol moiety (e.g., glycerol). The ester may, for example include from about 2 to about 20 hydroxy acid moieties. Various HVLCMs, which may be used be included in disclosed compositions are described in U.S. Pat. Nos. 5,747,058; 5,968,542; and 6,413,536; the disclosures of each of which are incorporated by reference herein. The presently disclosed compositions may employ any HVLCM described in these patents but is not limited to any specifically described materials.

The HVLCM may be present in the composition at from about 35% by weight to about 45% by weight, based on total weight of the composition. For example, the HVLCM may be present in the composition at from about 36% by weight to about 45% by weight, from about 37% by weight to about 45% by weight, from about 38% by weight to about 45% by weight, from about 39% by weight to about 45% by weight, from about 40% by weight to about 45% by weight, from about 41% by weight to about 45% by weight, from about 42% by weight to about 45% by weight, from about 43% by weight to about 45% by weight, or from about 44% by weight to about 45% by weight relative to the total weight of the composition. In some embodiments, the HVLCM may be present in the composition at from about 35% by weight to about 37% by weight, from about 37% by weight to about 39% by weight, from about 39% by weight to about 41% by weight, from about 41% by weight to about 43% by weight, or from about 43% by weight to about 45% by weight relative to the total weight of the composition. In some embodiments, the HVLCM may be present in the composition at about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

In some embodiments, the amount of the HVLCM present in the composition is provided relative to the amount of the solvent present in the composition. For example, the HVLCM and the solvent may be provided in the composition at a ratio of about 1.3:1 to about 1:1, e.g., about 1.20:1 to about 1:1, about 1.15:1 to about 1:1, about 1.10:1 to about 1:1, or about 1:1. For example, in some embodiments, the HVLCM and the solvent may be provided in the composition at a ratio of about 1.30:1.0, about 1.25:1.0, about 1.20:1.0, about 1.15:1.0, or about 1.0:1.0. In some embodiments, the HVLCM and the solvent may be provided in the composition at a ratio of about 0.6:1 to about 1.6:1, e.g., about 0.8:1 to about 1.5:1, or about 0.9:1 to about 1.5:1. For example, in some embodiments, the HVLCM and the solvent (e.g., triacetin) may be provided in the composition at a ratio of about 0.6:1.0, about 0.7:1.0, about 0.8:1.0, about 0.9:1.0, about 1.0:1.0, about 1.1:1.0, about 1.2:1.0, about 1.3:1.0, about 1.4:1.0, about 1.5:1.0, or about 1.6:1.0.

In some embodiments, Sucrose Acetate Isobutyrate ("SAIB") may be included in the composition as the HVLCM or the HVLCM may include SAIB. SAIB is a non-polymeric highly viscous liquid at temperatures ranging from −80° C. to over 100° C., it is a fully esterified sucrose derivative, at a nominal ratio of six isobutyrates to two acetates. The chemical structure of SAIB is provided in U.S. Application Publication No. 2009/0215808, the disclosure of which is incorporated by reference herein. The SAIB material is available from a variety of commercial sources including Eastman Chemical Company, where it is available as a mixed ester that does not crystallize but exists as a very highly viscous liquid. It is a hydrophobic, non-crystalline, low molecular weight molecule that is water insoluble and has a viscosity that varies with temperature. For example, pure SAIB exhibits a viscosity of approximately 2,000,000 centipoise (cP) at ambient temperature (RT) and approximately 600 cP at 80° C. The SAIB material has unique solution-viscosity relationship in that a SAIB solution established in a number of organic solvents has a significantly lower viscosity value than the pure SAIB material, and therefore the SAIB-organic solvent solutions render themselves capable of processing using conventional equipment such as mixers, liquid pumps and capsule production machines. SAIB also has applications in drug formulation and delivery, for example as described in U.S. Pat. Nos. 5,747,058; 5,968,542; 6,413,536; and 6,498,153, the disclosure of which are incorporated by reference herein.

In the compositions of the present disclosure, SAIB may be used as the HVLCM or the HVLCM may include SAIB at from about 35% by weight to about 45% by weight, based on total weight of the composition. For example, the SAIB may be present in the composition at from about 36% by weight to about 45% by weight, from about 37% by weight to about 45% by weight, from about 38% by weight to about 45% by weight, from about 39% by weight to about 45% by weight, from about 40% by weight to about 45% by weight, from about 41% by weight to about 45% by weight, from about 42% by weight to about 45% by weight, from about 43% by weight to about 45% by weight, or from about 44% by weight to about 45% by weight relative to the total weight of the composition. In some embodiments, the SAIB may be present in the composition at from about 35% by weight to about 37% by weight, from about 37% by weight to about 39% by weight, from about 39% by weight to about 41% by weight, from about 41% by weight to about 43% by weight, or from about 43% by weight to about 45% by weight relative to the total weight of the composition. In some embodiments, the SAIB may be present in the composition at about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

In some embodiments, the amount of SAIB present in the composition is provided relative to the amount of the solvent (e.g., triacetin) present in the composition. For example, the SAIB and the solvent may be provided in the composition at a ratio of about 1.3:1 to about 1:1, e.g., about 1.20:1 to about 1:1, about 1.15:1 to about 1:1, about 1.10:1 to about 1:1, or about 1:1. For example, in some embodiments, the SAIB and the solvent may be provided in the composition at a ratio of about 1.30:1.0, about 1.25:1.0, about 1.20:1.0, about 1.15:1.0, or about 1.0:1.0. In some embodiments, the SAIB and the solvent may be provided in the composition at a ratio of about 0.6:1 to about 1.6:1, e.g., about 0.8:1 to about 1.5:1, or about 0.9:1 to about 1.5:1. For example, in some embodiments, the SAIB and the solvent (e.g., triacetin) may be provided in the composition at a ratio of about 0.6:1.0, about 0.7:1.0, about 0.8:1.0, about 0.9:1.0, about 1.0:1.0, about 1.1:1.0, about 1.2:1.0, about 1.3:1.0, about 1.4:1.0, about 1.5:1.0, or about 1.6:1.0.

In some embodiments, it may be beneficial to provide a SAIB carrier material having a lower peroxide level to avoid peroxide-based degradation of various components of the composition and/or active agent. See, e.g., U.S. Patent Application Publication Number US 2007/0027105, "Peroxide Removal From Drug Delivery Vehicle", the disclosure of which is incorporated by reference herein.

Solvents

Solvents may be used in the compositions of the present disclosure to dissolve one or more of the following constituents: HVCLMs; active agents; network formers; rheology modifiers; viscosity enhancing agents; hydrophilic agents; and stabilizing agents. In some embodiments, the solvent can dissolve both the HVLCM and the network former. In some embodiments of the compositions of the present disclosure, a composition may include both a hydrophilic solvent and a hydrophobic solvent. Organic solvents suitable for use with the compositions of the present disclosure include, but are not limited to: substituted heterocyclic compounds such as N-methyl-2-pyrrolidone (NMP) and 2-pyrrolidone (2-pyrol); triacetin; esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as benzyl alcohol, ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof.

In some embodiments, the solvent includes or is selected from triacetin, N-methyl-2-pyrrolidone, 2-pyrrolidone, dimethylsulfoxide, ethyl lactate, propylene carbonate, and glycofurol. In some embodiments, the solvent is triacetin which is a hydrophilic solvent. In some embodiments, the hydrophilic triacetin solvent can be combined with a hydrophobic solvent to provide a hydrophobic/hydrophilic solvent system within the composition.

The solvent, which can include one or more suitable solvent materials, can be present in the compositions at from about 31% by weight to about 45% by weight, based on total weight of the composition. For example, the solvent may be present in the composition at from about 32% by weight to about 45% by weight, at from about 33% by weight to about 45% by weight, at from about 34% by weight to about 45% by weight, at from about 35% by weight to about 45% by weight, at from about 36% by weight to about 45% by weight, at from about 37% by weight to about 45% by weight, at from about 38% by weight to about 45% by weight, at from about 39% by weight to about 45% by weight, at from about 40% by weight to about 45% by weight, at from about 41% by weight to about 45% by weight, at from about 42% by weight to about 45% by weight, at from about 43% by weight to about 45% by weight, or at from about 44% by weight to about 45% by weight relative to the total weight of the composition. In some embodiments, the solvent may be present in the composition at from about 31% by weight to about 33% by weight, at from about 33% by weight to about 35% by weight, at from about 35% by weight to about 37% by weight, at from about 37% by weight to about 39% by weight, at from about 39% by weight to about 41% by weight, at from about 41% by weight to about 43% by weight, or at from about 43% by weight to about 45% by weight relative to the total weight of the composition. In some embodiments, the solvent may be present in the composition at about 31% by weight, about 32% by weight, about 33% by weight, about 34% by weight about 35% by weight, about 36% by weight, about 37% by weight, about 38% by weight, about 39% by weight, about 40% by weight, about 41% by weight, about 42% by weight, about 43% by weight, about 44% by weight, or about 45% by weight relative to the total weight of the composition.

Rheology Modifier

Rheology refers to the property of deformation and/or flow of a liquid, and rheology modifiers are used to modify viscosity and flow of a liquid composition. Rheology modifiers, which may be used in the compositions of the present disclosure include, for example, caprylic/capric triglyceride (e.g., Miglyol® 810 or Miglyol® 812), isopropyl myristate (IM or IPM), ethyl oleate, triethyl citrate, dimethyl phthalate, and benzyl benzoate.

In some embodiments, the rheology modifier is or includes IPM. The rheology modifier, which can include one or more suitable rheology modifier materials, can be present in the compositions at from about 2 to about 10 percent by weight relative to the total weight of the composition (wt %), e.g., at from about 2 to about 8 wt %, at from about 2 to about 6 wt %, or at from about 2 to about 4 wt %. In some embodiments, the rheology modifier is preset in the compositions at from about 2 to about 4 wt %, at from about 4 to about 6 wt %, at from about 6 to about 8 wt %, or at from about 8 to about 10 wt %. For example, in some embodiments, the rheology modifier, e.g., IPM, is present in the composition at about 2 wt %, about 3 wt %, about 4 wt %, about 5 wt %, about 6 wt %, about 7 wt %, about 8 wt %, about 9 wt %, or about 10 wt %.

In some embodiments, the rheology modifier is present in the compositions of the present disclosure in an amount relative to the amount of solvent in the compositions. For example, in some embodiments the solvent and the rheology modifier are present in the compositions at a ratio of about 1:0.3 to about 1.0:0.05, e.g., about 1:0.2 to about 1:0.06, about 1:0.1 to about 1:0.07, or about 1:0.09 to about 1:0.08. For example, in some embodiments, the solvent and the rheology modifier are present in the compositions at a ratio of about 1.0:0.3, about 1.0:0.2, about 1.0:0.1, about 1.0:0.09, about 1.0:0.08, about 1.0:0.07, about 1.0:0.06, or about 1.0:0.05. In some embodiments, where the solvent is triacetin and the rheology modifier is IPM, the solvent and the rheology modifier are present in the compositions at a ratio of about 1.0:0.3, about 1.0:0.2, about 1.0:0.1, about 1.0:0.09, about 1.0:0.08, about 1.0:0.07, about 1.0:0.06, or about 1.0:0.05.

Network Former

Network formers may be added to a composition such that, upon exposure to an aqueous environment, they form a three dimensional network within the composition. While not intending to be bound by any particular theory, it is believed that the network former allows the formation of a micro-network within the composition upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the composition and the aqueous environment of the GI tract, as well as the formation of a three-dimensional micro-network of precipitated network former within the composition. The network former is selected so as to have good solubility in the selected solvent used in the compositions, for example a solubility of between about 0.1 and 20 wt %. Additionally, good network formers will typically have a Log P between about −1 to 7. Suitable network formers include, for example, cellulose acetate butyrate ("CAB"), carbohydrate polymers, organic acids of carbohydrate polymers and other polymers, hydrogels, cellulose acetate phthalate, ethyl cellulose, Pluronic® (nonionic triblock copolymer), Eudragit® (polymethacrylate), Carbomer™ (polyacrylic acid), hydroxyl propyl methyl cellulose, other cellulose acetates such as cellulose triacetate, Poly(methyl methacrylate) (PMMA), as well as any other material capable of associating, aligning or congealing to form three-dimensional networks in an aqueous environment.

In some embodiments, the network former used in the compositions of the present disclosure is or includes a CAB having a number average molecular weight ranging from about 50,000 Daltons to about 100,000 Daltons, e.g., from about 60,000 Daltons to about 100,000 Daltons, from about 70,000 Daltons to about 100,000 Daltons, from about 80,000 Daltons to about 100,000 Daltons, or from about 90,000 Daltons to about 100,000 Daltons. In some embodiments, the network former used in the compositions of the present disclosure is or includes a CAB having a number average molecular weight ranging from about 60,000 Daltons to about 90,000 Daltons, or from about 70,000 Daltons to about 80,000 Daltons. In some embodiments, the network former used in the compositions of the present disclosure is or includes a CAB having a number average molecular weight of about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 95,000 Daltons, or about 100,000 Daltons.

In some embodiments, the network former used in the compositions of the present disclosure is or includes a CAB having at least one feature selected from a butyryl content ranging from about 17% to about 41%, an acetyl content ranging from about 13% to about 30%, and a hydroxyl content ranging from about 0.5% to about 1.7%. In some further embodiments, the network former used in the compositions of the present disclosure is or includes a CAB comprising at least two of a butyryl content ranging from about 17% to about 41%, an acetyl content ranging from about 13% to about 30%, and a hydroxyl content ranging from about 0.5% to about 1.7%. In still further embodiments, the network former used in the compositions of the present disclosure is or includes a CAB comprising all three of a butyryl content ranging from about 17% to about 41%, an acetyl content ranging from about 13% to about 30%, and a hydroxyl content ranging from about 0.5% to about 1.7%.

Accordingly, in some embodiments, the network former used in the compositions of the present disclosure is or includes a CAB having a butyryl content ranging from about 17% to about 41%. In some embodiments, the network former used in the compositions of the present disclosure is or includes a CAB having an acetyl content ranging from about 13% to about 30%. In some embodiments, the network former used in the compositions of the present disclosure is or includes a CAB having a hydroxyl content ranging from about 0.5% to about 1.7%. In some embodiments, the network former used in the compositions of the present disclosure is or includes a CAB having a butyryl content ranging from about 17% to about 41% and an acetyl content ranging from about 13% to about 30%. In some embodiments, the network former used in the compositions of the present disclosure is or includes a CAB having a butyryl content ranging from about 17% to about 41% and a hydroxyl content ranging from about 0.5% to about 1.7%. In some embodiments, the network former used in the compositions of the present disclosure is or includes a CAB having an acetyl content ranging from about 13% to about 30% and a hydroxyl content ranging from about 0.5% to about 1.7%. In still other embodiments, the network former used in the compositions of the present disclosure is or includes a CAB having a butyryl content ranging from about 17% to about 41%, an acetyl content ranging from about 13% to about 30%, and a hydroxyl content ranging from about 0.5% to about 1.7%. In further embodiments, in addition to one of the above features of butyryl content, acetyl content and/or hydroxyl content, the CAB also has a number average molecular weight ranging from about 50,000 Daltons to about 100,000 Daltons, e.g., from about 60,000 Daltons to about 100,000 Daltons, from about 70,000 Daltons to about 100,000 Daltons, from about 80,000 Daltons to about 100,000 Daltons, or from about 90,000 Daltons to about 100,000 Daltons. In further embodiments, in addition to one of the above features of butyryl content, acetyl content and/or hydroxyl content, the CAB also has a number average molecular weight ranging from about 60,000 Daltons to about 90,000 Daltons, or from about 70,000 Daltons to about 80,000 Daltons. In further embodiments, in addition to one of the above features of butyryl content, acetyl content and/or hydroxyl content, the CAB also has a number average molecular weight of about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 95,000 Daltons, or about 100,000 Daltons.

In some embodiments, the network former used in the compositions of the present disclosure is or includes cellulose acetate butyrate grade 381-20BP ("CAB 381-20BP" available from Eastman Chemicals). In some embodiments, the network former used in the compositions of the present disclosure is or includes a CAB, wherein the CAB is a non-biodegradable polymer material that has the following chemical and physical characteristics: butyryl content of about 36 wt %, acetyl content of about 15.5 wt %, hydroxyl content of about 0.8%, a melting point of from about 185-196° C., a glass transition temperature of about 128° C., and a number average of from about 66,000 to 83,000, e.g., about 70,000. In some embodiments, if a CAB material is used in the composition, it may be subjected to an ethanol washing step (and subsequent drying step) prior to addition to the composition in order to remove potential contaminants therefrom.

In some embodiments, the network former of the present disclosure specifically excludes a network former having an acetyl content of about 2.0%, a butyryl content of about 46.0%, a hydroxyl content of 4.8%, a melting point of from about 150-160° C., a glass transition temperature of about 136° C., and a number average molecular weight of about 20,000, e.g., CAB-553-0.4 available from Eastman Chemicals).

In some embodiments, the network former of the present disclosure specifically excludes a network former, e.g, a CAB, which is soluble in ethanol.

The network former, which can include one or more suitable network former materials, can be present in the compositions at from about 0.1 to about 20 percent by weight relative to the total weight of the composition (wt %), e.g., at from about 1 to about 18 wt %, from about 2 to about 10 wt %, from about 4 to about 6 wt %, or at about 5 wt %. In some embodiments, a network former is present in the compositions of the present disclosure at from about 0.1 to about 1 wt %, about 1 to about 5 wt %, about 5 to about 10 wt %, about 10 to about 15 wt %, or about 15 to about 20 wt %. In some embodiments, a network former is present in the compositions of the present disclosure at about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, or about 20 wt %.

Hydrophilic Agent

Materials that can be used as "hydrophilic agents" in the compositions of the present disclosure include those that have natural affinity for aqueous systems. A material may be regarded as a hydrophilic agent for the purposes of this disclosure if the material displays a water sorption between about 10 to about 100% (w/w). Hydrophilic agents will have a low Log P value, for example, a Log P of less than +1. As discussed herein above, there are a number of constituents which may be used to produce the compositions of the present disclosure that can be classed as a hydrophilic material (e.g., a hydrophilic solvent), or at least a material having a hydrophilic portion (e.g., a rheology modifier). Since the HVLCM material used in the compositions is hydrophobic, it may be useful to include other materials in the composition that are hydrophilic in order to provide a carrier system that is balanced to have both hydrophobic and hydrophilic characteristics. For example, it is believed that the inclusion of one or more hydrophilic agents in the compositions of the present disclosure may participate in the control of active agent diffusion from the compositions. Accordingly, suitable hydrophilic agents include, but are not limited to, sugars such as sorbitol, lactose, mannitol, fructose, sucrose and dextrose, salts such as sodium chloride and sodium carbonate, starches, hyaluronic acid, glycine, fibrin, collagen, polymers such as hydroxylpropylcellulose ("HPC"), carboxymethylcellulose, hydroxyethyl cellulose ("HEC"); polyethylene glycol and polyvinylpyrrolidone, and the like. In some embodiments, a controlled release carrier system is provided that includes HEC as a hydrophilic agent or a component of a hydrophilic agent.

The hydrophilic agent, which can include one or more suitable hydrophilic agent materials, e.g., HEC, can be present in the compositions at from about 0.1 to about 10 percent by weight relative to the total weight of the composition (wt %), e.g., from about 1 to about 8 wt %, from about 2 to about 7 wt %, from about 3 to about 6 wt %, or from about 4 to about 5 wt %. In some embodiments, a hydrophilic agent is present in the compositions of the present disclosure at about 0.1 wt % to about 0.5 wt %, about 0.5 wt % to about 1 wt %, about 1 wt % to about 5 wt %, or about 5 wt % to about 10 wt %. In some embodiments, a hydrophilic agent is present in the compositions of the present disclosure at about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, or about 10 wt %.

Viscosity Enhancing Agent

Viscosity enhancing agents can be selected to have good hydrogen bonding capability, such as a bonding capability greater than or equal to one per molecule. In certain cases, the viscosity enhancing agent has very low to no significant solubility in the composition. If the agent is soluble, then, in some embodiments, the solubility is less than 50 wt %. For inorganic or mineral viscosity enhancing agents, it is preferable if the material has a specific surface area greater than or equal to about 100 m$^2$/g. Suitable viscosity enhancing agents include biodegradable and non-biodegradable polymer materials. Non-limiting examples of suitable biodegradable polymers and oligomers include: poly(lactide), poly (lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly (malic acid), chitin, chitosan, and copolymers, terpolymers, oxidized cellulose, hydroxyethyl cellulose, or combinations or mixtures of the above materials. Suitable non-biodegradable polymers include: polyacrylates, ethylene-vinyl acetate polymers, cellulose and cellulose derivatives, acyl substituted cellulose acetates and derivatives thereof including cellulose acetate butyrate (CAB), which is also used herein as a network former, non-erodible polyurethanes, polystyrenes, polyvinyl chloride, polyvinyl fluoride, polyvinyl (imidazole), chlorosulphonated polyolefins, polyethylene oxide, and polyethylene.

Other suitable viscosity enhancing materials include mineral particles such as clay compounds, including, talc, bentonite and kaolin; metal oxides including silicon dioxide, zinc oxide, magnesium oxide, titanium oxide, and calcium oxide; and fumed silica, reagent grade sand, precipitated silica, amorphous silica, colloidal silicon dioxide, fused silica, silica gel, and quartz. In some embodiments of the present disclosure, a colloidal silicon dioxide, e.g., Cab-O-Sil® M-5P (untreated fumed silica that complies with the pharmacopeia monograph "Colloidal Silicon Dioxide" in the U.S. Pharmacopeia/National Formulary), is used in the compositions as a viscosity enhancing agent.

The viscosity enhancing agent, e.g., mineral particle, which can include one or more suitable viscosity enhancing materials, can be present in the compositions at from about 2.4 to about 6.0 percent by weight relative to the total weight of the composition (wt %), e.g., at from about 2.5 to about 6.0 wt %, at from about 2.6 to about 6.0 wt %, at from about 2.7 to about 6.0 wt %, at from about 2.8 to about 6.0 wt %, at from about 2.9 to about 6.0 wt %, at from about 3.0 to about 6.0 wt %, at from about 3.1 to about 6.0 wt %, at from about 3.2 to about 6.0 wt %, at from about 3.3 to about 6.0 wt %, at from about 3.4 to about 6.0 wt %, at from about 3.5 to about 6.0 wt %, at from about 3.6 to about 6.0 wt %, at from about 3.7 to about 6.0 wt %, at from about 3.8 to about 6.0 wt %, at from about 3.9 to about 6.0 wt %, at from about 4.0 to about 6.0 wt %, at from about 4.1 to about 6.0 wt %, at from about 4.2 to about 6.0 wt %, at from about 4.3 to about 6.0 wt %, at from about 4.4 to about 6.0 wt %, at from about 4.5 to about 6.0 wt %, at from about 4.6 to about 6.0 wt %, at from about 4.7 to about 6.0 wt %, at from about 4.8 to about 6.0 wt %, at from about 4.9 to about 6.0 wt %, at from about 5.0 to about 6.0 wt %, at from about 5.1 to about 6.0 wt %, at from about 5.2 to about 6.0 wt %, at from about 5.3 to about 6.0 wt %, at from about 5.4 to about 6.0 wt %, at from about 5.5 to about 6.0 wt %, at from about 5.6 to about 6.0 wt %, at from about 5.7 to about 6.0 wt %, at from about 5.8 to about 6.0 wt %, or at from about 5.9 to about 6.0 wt %.

In some embodiments, a composition according to the present disclosure includes a viscosity enhancing agent, e.g., mineral particle, at from about 2.4 to about 2.6 wt %, at from about 2.6 wt % to about 2.8 wt %, at from about 2.8 wt % to about 3.0 wt %, at from about 3.0 wt % to about 3.2 wt %, at from about 3.2 wt % to about 3.4 wt %, at from about 3.4 wt % to about 3.6 wt %, at from about 3.6 wt % to about 3.8 wt %, at from about 3.8 wt % to about 4.0 wt %, at from about 4.0 wt % to about 4.2 wt %, at from about 4.2 wt % to about 4.4 wt %, at from about 4.4 wt % to about 4.6 wt %, at from about 4.6 wt % to about 4.8 wt %, at from about 4.8 wt % to about 5.0 wt %, at from about 5.0 wt % to about 5.2 wt %, at from about 5.2 wt % to about 5.4 wt %, at from about 5.4 wt % to about 5.6 wt %, at from about 5.6 wt % to about 5.8 wt %, or at from about 5.8 wt % to about 6.0 wt %.

In some embodiments, a composition according to the present disclosure includes a viscosity enhancing agent, e.g., mineral particle (e.g., silicon dioxide) at about 2.4 wt %, about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, 4.1 wt %, 4.2 wt %, 4.3 wt %, 4.4 wt %, 4.5 wt %, 4.6 wt %, 4.7 wt %, 4.8 wt %, 4.9 wt %, 5.0 wt %, 5.1 wt %, 5.2 wt %, 5.3 wt %, 5.4 wt %, 5.5 wt %, 5.6 wt %, 5.7 wt %, 5.8 wt %, 5.9 wt %, or 6.0 wt %.

As discussed in the Examples below, providing a viscosity enhancing agent, e.g., a mineral particle such as silicon dioxide, in an amount outside of one or more of the ranges specified above may result in undesirable composition characteristics. For example, variability in a dissolution profile of the active agent from the composition, e.g., as evidenced by increased inter-capsule variability, may be seen at relatively low silicon dioxide levels. On the other hand, reduced processability may be seen at relatively high silicon dioxide levels due to an increase in the rigidity and/or viscosity of the composition. Accordingly, in some embodiments, the compositions of the present disclosure specifically exclude viscosity enhancing agents, e.g., mineral particles, in an amount outside of one or more of the ranges specified above.

In some embodiments an unexpected, beneficial balance between dissolution variability and processability may be achieved by including the viscosity enhancing agent, e.g., mineral particle such as silicon dioxide, at from about 2.4 to about 5.4 percent by weight relative to the total weight of the composition (wt %), e.g., at from about 2.4 to about 2.6 wt %, at from about 2.6 to about 2.8 wt %, at from about 2.8 to about 3.0 wt %, at from about 3.0 to about 3.2 wt %, at from about 3.2 to about 3.4 wt %, at from about 3.4 to about 3.6 wt %, at from about 3.6 to about 3.8 wt %, at from about 3.8 to about 4.0 wt %, at from about 4.0 to about 4.2 wt %, at from about 4.2 to about 4.4 wt %, at from about 4.4 to about 4.6 wt %, at from about 4.6 to about 4.8 wt %, at from about 4.8 to about 5.0 wt %, at from about 5.0 to about 5.2 wt %, or at from about 5.2 to about 5.4 wt %. Similarly, a beneficial balance between dissolution variability and processability may be achieved by including the viscosity enhancing agent, e.g., mineral particle such as silicon dioxide, at from about 2.6 to about 5.4 wt %, e.g., at from about 2.8 to about 5.4 wt %, at from about 3.0 to about 5.4 wt %, at from about 3.2 to about 5.4 wt %, at from about 3.4 to about 5.4 wt %, at from about 3.6 to about 5.4 wt %, at from about 3.8 to about 5.4 wt %, at from about 4.0 to about 5.4 wt %, at from about 4.2 to about 5.4 wt %, at from about 4.4 to about 5.4 wt %, at from about 4.6 to about 5.4 wt %, at from about 4.8 to about 5.4 wt %, at from about 5.0 to about 5.4 wt %, or at from about 5.2 to about 5.4 wt %.

As discussed above, a viscosity enhancing agent, e.g., mineral particle, such as silicon dioxide, when included at specific concentration ranges in the compositions of the present disclosure, may reduce dissolution variability of the composition, e.g., inter-capsule dissolution variability as determined using a USP Apparatus 2 dissolution tester and method as described below in the Examples. See also, *USP-NF, Dissolution* <711>. Rockville, Md.: US Pharmacopeial Convention; 2008, the disclosure of which is incorporated by reference herein.

Stabilizing Agent

Materials that can be used as stabilizing agents in the compositions of the present disclosure include any material or substance that can inhibit or reduce degradation (e.g., by chemical reactions) of other substances or substances in the composition with which the stabilizer is mixed. Exemplary stabilizers typically are antioxidants that prevent oxidative damage and degradation, e.g., sodium citrate, ascorbyl palmitate, vitamin A, and propyl gallate and/or reducing agents. Other examples include ascorbic acid, vitamin E, sodium bisulfite, butylhydroxyl toluene (BHT), BHA, acetylcysteine, monothioglycerol, phenyl-alpha-nathylamine, lecithin, and EDTA. These stabilizing materials, which can include one or more of such suitable materials, can be present in the compositions at from about 0.001 to about 2 percent by weight relative to the total weight of the composition (wt %), e.g., at from about 0.01 to about 0.1 wt %, or at from about 0.01 to about 0.02 wt %. In some embodiments, the compositions of the present disclosure specifically exclude a stabilizing agent, such as those listed above.

Surfactants

In some embodiments, a composition according to the present disclosure may include one or more surfactants. Materials that can be used as surfactants in the practice of the present disclosure include neutral and/or anionic/cationic excipients. Accordingly, suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof; ampiphilic surfactants (glycerides, etc.); Gelucire®s (saturated polyglycolized glyceride (e.g., Gattefosse brand)); and like materials. Surfactants, which can include one or more suitable surfactant material, can be present in the compositions of the present disclosure at from about 0.01 to about 5 percent by weight relative to the total weight of the composition (wt %), e.g., at from about 0.1 to about 5 wt %, or at from about 0.1 to about 3 wt %. In some embodiments, a surfactant is present in the compositions of the present disclosure at about 0.1 wt %, about 0.5 wt %, about 1 wt %, about 2 wt %, about 3 wt %, about 4 wt %, or about 5 wt %.

In some embodiments, a suitable surfactant for incorporation into the compositions of the present disclosure includes one or more Gelucire®s (saturated polyglycolized glycerides). Suitable Gelucire®s include, e.g., Gelucire® 44/14 (lauroyl polyoxylglycerides) and Gelucire® 50/13 (stearoyl polyoxylglycerides). Accordingly, in some embodiments, a Gelucire®, e.g., Gelucire® 44/14, Gelucire® 50/13, or a combination thereof, is present the compositions of the present disclosure at from about 0.01 to about 5 percent by weight relative to the total weight of the composition (wt %), e.g., at from about 0.1 to about 5 wt %, or at from about 0.1 to about 3 wt %. In some embodiments, a Gelucire®, e.g., Gelucire® 44/14, Gelucire® 50/13, or a combination thereof, is present in the compositions of the present disclosure at about 0.1 wt %, about 0.5 wt %, about 1 wt %, about 2 wt %, about 3 wt %, about 4 wt %, or about 5 wt %.

Exemplary Compositions

With reference to the various components discussed above, exemplary compositions are now described.

In some embodiments a composition is provided which includes a pharmacologically active agent; about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere; about 31% by weight to about 45% by weight, based on total weight of the composition, of a solvent; about 2% by weight to about 10% by weight, based on total weight of the composition, of a rheology modifier; and a cellulose acetate butyrate. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes a pharmacologically active agent; about 35% by weight to about 45% by weight, based on total weight of the composition, of sucrose acetate isobutyrate (SAIB); about 31% by weight to about 45% by weight, based on total weight of the composition, of triacetin; about 2% by weight to about 10% by weight, based on total weight of the composition, of isopropyl myristate (IPM); and about 4% to about 6% of a cellulose acetate butyrate (CAB), based on total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; about 2% by weight to about 10% by weight, based on total weight of the composition, of a rheology modifier; and a cellulose acetate butyrate (CAB), wherein the HVLCM and the solvent are present in the composition at a ratio of about 1.3:1 to about 1:1. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio of about 1.3:1.0:0.3 to about 1.0:1.0:0.05. Optionally, the composition may be provided within a capsule having a water content of less than about 10% by weight, e.g., an HPMC capsule having a water content of less than about 10% by weight, e.g., less than about 5% by weight.

In some embodiments, compositions are provided which provide specific advantages relative to a reference composition, e.g., Reference Formulation A as described in Example 1 below. Accordingly, in some embodiments a composition is provided which includes a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, an increase in the reproducibility of release may refer to a reduction or decrease in a storage time-dependent change in an in vitro release profile of a composition. In such embodiments, the reproducibility of release for the composition may be determined relative to Reference Formulation A, which exhibits more than 10% mean drug release decline, a similarity factor ($f_2$) of less than 50, when stored at 40° C./75% RH for a one month period of time relative to its initial release profile.

"Similarity factor" ($f_2$) as used herein refers to a logarithmic reciprocal square root transformation of one plus the mean squared (the average sum of squares) differences of drug percent dissolved between the test and the reference products. In other words, the similarity factor ($f_2$) is a logarithmic transformation of the sum-squared error of differences between the test $T_t$ and reference products $R_t$ over all time points. It represents the closeness of two comparative compositions. Generally similarity factor in the range of 50-100 is acceptable according to the US FDA. $f_2$ may be calculated as follows: $f_2=50*\log\{[1+(1/n)\Sigma_{t=1}*n (R_t-T_t)^2]^{-0.5}*100\}$, where $R_t$ and $T_t$ are the cumulative percentage dissolved at each of the selected n time points of the reference and test product respectively.

In some embodiments, an increase in the reproducibility of release may refer to a reduction or decrease in inter-capsule variability at a particular time point. In such embodiments, a decrease in inter-capsule variability may be evidenced by a % RSD of less than about 15%, e.g., less than about 10%, or less than about 5% at the particular time point, e.g., t=2 hr or t=3 hr. % RSD may be calculated as follows: % RSD=((SD/mean)×100). In some embodiments, a decrease in inter-capsule variability may be evidenced by a % RSD of from about 15% to about 1%, e.g., from about 10% to about 1%, or from about 5% to about 1%.

Suitable in vitro dissolution test conditions for determining a time-dependent change in an in vitro release profile of a composition or inter-capsule variability of a composition, e.g., an oxycodone or hydrocodone containing composition are as follows: a USP Apparatus 2 dissolution tester modified to include a 20 mesh screen hanging basket to hold the test article is utilized with dissolution medium containing 1000 ml 0.1 N HCl with 0.5% (w/w) SDS. The dissolution medium is maintained at 37° C. with stirring with 100 rpm paddle speed over the course of a 24 hour dissolution test. Standard sampling time points of 0.5, 2, 3, 6, 12 and 24 hours are utilized. A 1 mL sample is taken at each time point and assayed using reverse-phase HPLC at 240 nm wavelength with a mobile phase including 0.35% (w/v) SDS/ 0.7% (v/v) acetic acid/44% (v/v) acetonitrile in water. Where the dissolution test is used to determining a time-dependent change in an in vitro release profile of a composition, the composition may be stored for a suitable period of time prior to testing, e.g., the composition may be stored at 25° C./60% relative humidity (RH) for from 1 to 6 months or at 40° C./75% RH for from 1 to 6 months. A suitable number of capsules per composition tested may be, e.g., 12 capsules.

For compositions including amphetamine, the following dissolution testing protocol may be utilized: 2-phase dissolution medium is utilized in a USP Apparatus 2. Capsules are placed in stainless steel (316SS) wire spiral capsule sinkers for dissolution testing. The dissolution parameters are as follows: Dissolution medium: 750 ml 0.1N HCl for the first 2 hours, with the addition of 200 ml 0.19M phosphate buffer to achieve a final pH of 6.0; Paddle speed: 50 rpm; Vessel temperature: 37° C. Sampling time points: 0.25, 0.5, 1, 1.5, 2, 3, 6, 9, 12 and 24 hours. Sampling volume: 1 mL. Suitable HPLC parameters are as follows: Mobile phase A: 5 mM 1-Decanesulfonic acid, sodium salt, 5 mM sodium phosphate monobasic, pH 2.5; Mobile phase B: 100% acetonitrile; Mobile phase: 67% Mobile phase A and 33% Mobile phase B; 210 nm wavelength. A suitable number of capsules per composition tested may be, e.g., 6 capsules.

For compositions including methylphenidate, the following dissolution testing protocol may be utilized: 2-phase dissolution medium is utilized in a USP Apparatus 2. Capsules are placed in stainless steel (316SS) wire spiral capsule sinkers for dissolution testing. The dissolution parameters are as follows: Dissolution medium: 750 ml 0.1N HCl for the first 2 hours, with the addition of 200 ml 0.19M phosphate buffer to achieve a final pH of 6.0; Paddle speed: 50 rpm; Vessel temperature: 37° C. Sampling time points: 0.25, 0.5, 1, 1.5, 2, 3, 6, 9, 12 and 24 hours. Sampling volume: 1 mL. Suitable HPLC parameters are as follows: Mobile phase A: 5 mM 1-Decanesulfonic acid, sodium salt, 5 mM sodium phosphate monobasic, pH 2.5; Mobile phase B: 100% acetonitrile; Mobile phase: 71% Mobile phase A and 29% Mobile phase B; 210 nm wavelength.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate, wherein the composition is encapsulated within a hydroxypropylmethylcellulose capsule, and wherein the composition within the capsule includes less than 5% water by weight, based on total weight of the composition within the capsule.

In some embodiments, a composition is provided which includes: a pharmacologically active agent; and means for reducing a storage time-dependent change in an in vitro release profile of a composition relative to Reference Formulation A. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; and means for reducing a storage time-dependent change in an in vitro release profile of the composition Relative to Ref. Formulation A. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the mineral particle is present in the composition in an amount from about 2.4% by weight to about 5.4% by weight relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: an opioid; sucrose acetate isobutyrate (SAIB); triacetin; isopropyl myristate (IPM); cellulose acetate butyrate (CAB); hydroxyethyl cellulose (HEC); and silicon dioxide, wherein the silicon dioxide is present in the composition in an amount from about 2.4% by weight to about 5.4% by weight relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone; about 35% by weight to about 45% sucrose acetate isobutyrate (SAIB) relative to the total weight of the composition; about 31% by weight to about 45% of triacetin relative to the total weight of the composition; about 2% by weight to about 10% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.4% by weight to about 5.4% by weight of silicon dioxide relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: about 5% by weight of oxycodone relative to the total weight of the composition; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide at about 2.9% by weight relative to the total weight of the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide at about 2.9% by weight relative to the total weight of the composition, wherein the composition is encapsulated within a hydroxypropylmethylcellulose (HPMC) capsule.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to reduce a storage time-dependent change in an in vitro release profile of a composition relative to Reference Formulation A. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to reduce inter-capsule variability in an in vitro release profile of the composition relative to Reference Formulation A, when assayed in a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; a high viscosity liquid carrier material (HVLCM) having a viscosity of at least 5000 cP at 37° C. that does not crystallize neat at 25° C. and 1 atmosphere; a solvent; a network former; and a mineral particle, wherein the HVLCM, the solvent, the network former, and the mineral particle are present in a ratio sufficient to provide an in vitro release profile characterized by an inter-capsule variability having a % RSD of less than or equal to 10% at t=2 hr as determined by an in vitro dissolution assay using a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce a storage time-dependent change in an in vitro release profile of the composition relative to Reference Formulation A. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce inter-capsule variability relative to Formulation A when assayed in a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: oxycodone at about 5% by weight relative to the total weight of the composition; sucrose acetate isobutyrate (SAIB); triacetin; isopropyl myristate (IPM); cellulose acetate butyrate (CAB); hydroxyethyl cellulose (HEC); and silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; and combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to inter-capsule variability relative to Reference Formulation A when assayed in a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; and combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

In some embodiments, a composition is provided which includes: a pharmacologically active agent; and combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to storage time relative to Reference Formulation A when assayed in a USP Apparatus 2 dissolution tester modified to have a 20-mesh basket for containing the composition. Optionally, the composition may be provided within a capsule having a water content of less than about 10% by weight, e.g., an HPMC capsule having a water content of less than about 10% by weight, e.g., less than about 5% by weight.

Methods of Making, Encapsulating and Administering

Once constituents have been selected to produce a composition (e.g., an extended release composition) in accordance with the present disclosure, a liquid pharmaceutical composition can be prepared by simply mixing, for example a HVLCM, a rheology modifier, a network former, the active agent, a solvent and any additional additives. The compositions of the present disclosure are produced as liquid mixtures, and have a number of excipient ingredients that are in solution, suspension, or in partial solution within the final composition. Suitable methods for compounding or manufacturing the compositions make use of typical pharmaceutical/chemical mixing and handling apparatus and techniques. Since the liquid compositions of the present disclosure are formed from a number of highly viscous liquids and solids, they may have high final viscosities. Accordingly, the specific equipment and techniques employed in the manufacture of such compositions may be selected so as to accommodate such material demands. In particular, various excipients, such as network formers, may be added to the composition mixture in the solid or semi-solid state, and as such they may be screened or otherwise size-reduced prior to addition to a composition mixing apparatus. Other solid excipients may require melting prior to addition to the liquid mixture. The HVLCM materials are very high viscosity liquid materials, however they tend to exhibit a dramatic reduction in viscosity with increases in heat, and as such the mixing apparatus may be heated to accommodate the addition of the HVLCM material or other similar materials. However, the mixing and processing conditions should take into account the final integrity of the composition and accordingly the mixing conditions may be selected so as to have a low-sheer effect on the composition, and/or to avoid any extended or pronounced excursions into high or low heat conditions. Once the composition has been properly combined, an appropriate amount of the resulting liquid mixture can be placed into a suitable capsule, such as a gelatin or HPMC capsule to provide an oral pharmaceutical dosage form. Alternative liquid compositions may include emulsifying the mixture in water, and introducing this emulsion into a capsule.

Figure 2:
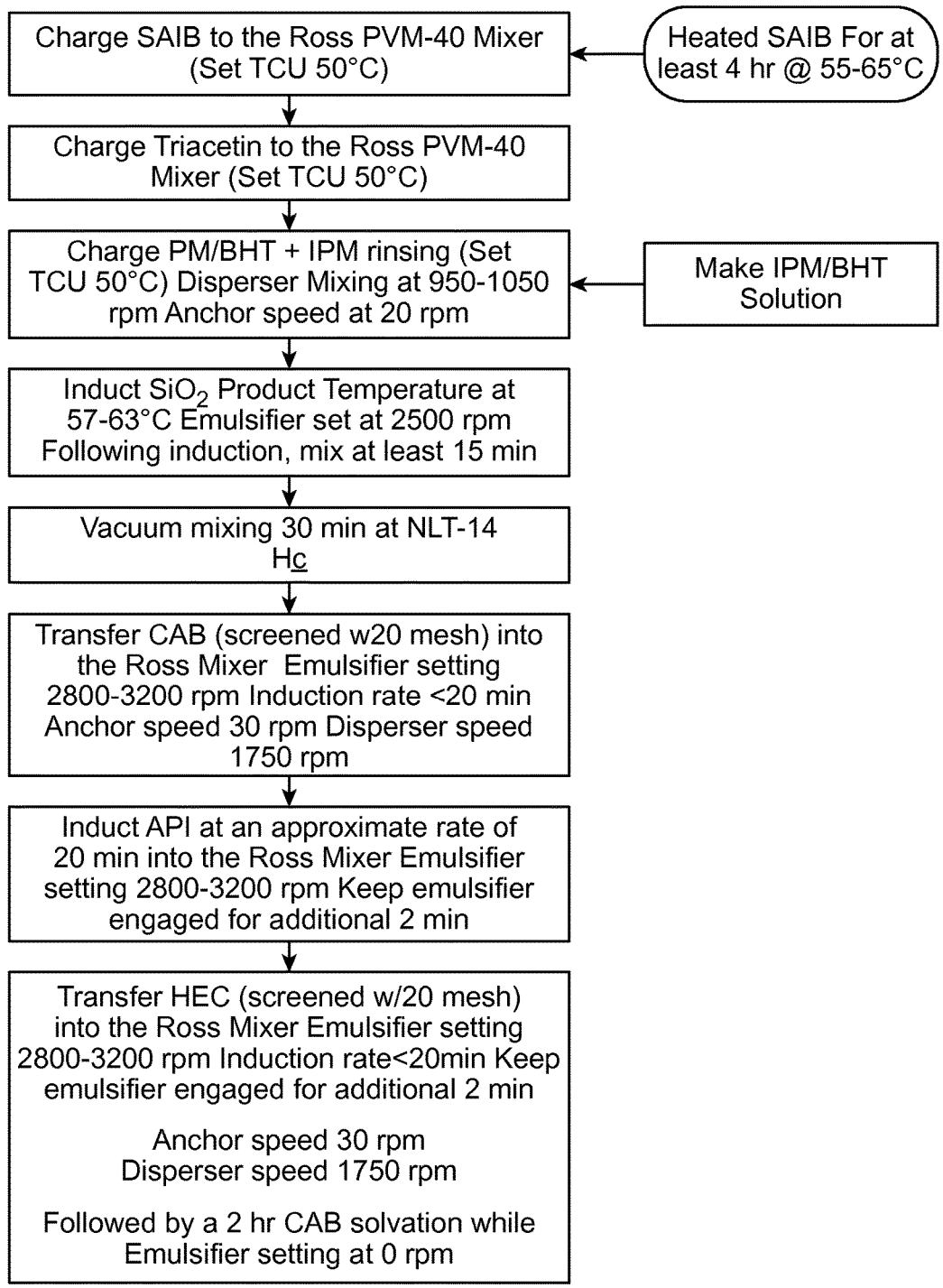
FIG. 2 shows a flow diagram of an exemplary composition preparation and encapsulation method.
Figure 2:
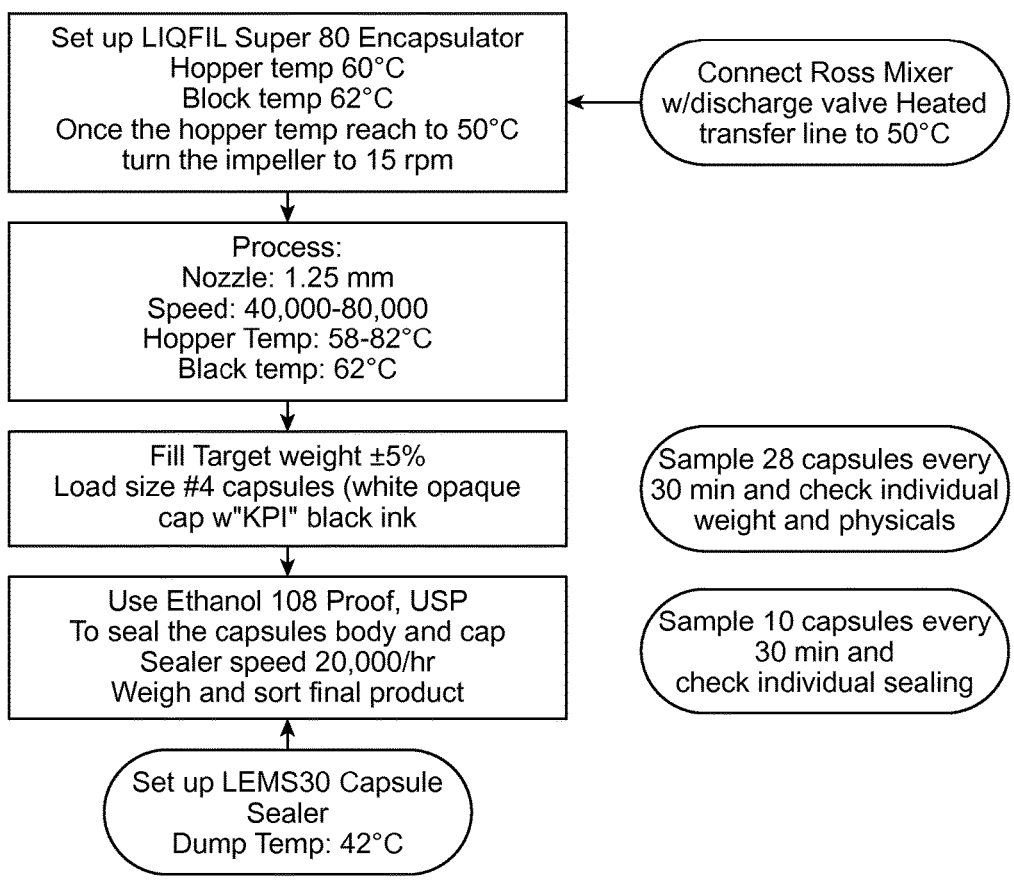

An additional, exemplary composition preparation and encapsulation scheme is provided in FIG. 2.

In some embodiments, an oral dosage form is provided which is composed of a liquid composition containing the active agent and any additional components within an enclosure or capsule, e.g., a biodegradable enclosure or capsule, such as a capsule or a gelatin capsule ("gelcap"), wherein the capsule is made of a substance that degrades or otherwise dissociates when exposed to conditions present in the gastrointestinal tract of a mammal. Capsules and gelcaps are well known in drug delivery technology and one of skill could select such a capsule as appropriate for delivery of a particular active agent. Once the capsule has dissolved or dissociated from the composition, the disclosed compositions generally remains intact, especially for hydrophobic compositions, and passes through the GI tract without emulsification or fragmentation.

Suitable capsules which may be utilized in connection with the disclosed compositions include, but are not limited to hard-shelled capsules, soft-shelled capsules, and interlocking capsules.

In some embodiments a suitable capsule includes gelatin or synthetic polymers such as hydroxyl ethyl cellulose and/or hydroxyl propylmethyl cellulose. Gelcaps can be of the hard or soft variety, including, for example, polysaccharide or hypromellose acetate succinate based caps (e.g., Vegicaps brand, available from Catalent). The capsule can also be coated with an enteric coating material such as AQIAT (Shin-Etsu) to delay release.

As discussed in the Examples below, certain time-dependent changes in drug release performance have been observed for Reference Formulation A. Without intending to be bound by any particular theory, it is believed that reducing the amount of water available to the compositions of the present disclosure may minimize these effects. For example, by utilizing HPMC capsules (~2-6% w/w water, e.g., 4-6% w/w water) instead of gelatin capsules (~13-16% w/w water) the amount of water available to the compositions may be reduced. Accordingly, in some embodiments, the compositions of the present disclosure are specifically encapsulated within capsules having lower water content than gelatin capsules, e.g., water content of less than about 15% w/w, less than about 14% w/w, less than about 13% w/w, less than about 12% w/w, less than about 11% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, or less than about 1% w/w. In some embodiments, the compositions of the present disclosure are encapsulated within capsules having a water content of from about 1% w/w to about 10% w/w, e.g., from about 1% w/w to about 9% w/w, from about 1% w/w to about 8% w/w, from about 1% w/w to about 7% w/w, from about 1% w/w to about 6% w/w, from about 1% w/w to about 5% w/w, from about 1% w/w to about 4% w/w, from about 1% w/w to about 3% w/w, or from about 1% w/w to about 2% w/w. In some embodiments, the compositions of the present disclosure are encapsulated in capsules having a water content less than about 1% w/w including, for example, from about 0.1% w/w to about 1% w/w, from about 0.2% w/w to about 0.8% w/w, from about 0.4% w/w to about 0.8% w/w, or from about 0.6% w/w to about 0.8% w/w. Suitable HPMC capsules may include, for example, V-Caps™, V-caps Plus™, Quali-V™, VegiCaps™, Embo Caps-Vg™, and HMPC capsules provided by Baotou Capstech Co., Ltd, and Zhejiang LinFeng Capsules Co. Ltd.

The water content of a capsule, composition, or composition in combination with a capsule, when provided within a capsule as described in the present disclosure, may be determined by Karl Fischer titration method as set forth in USP <921> Method 1C. In some embodiments, an AquaStar C3000 Karl Fischer Coulometric Titrator may be used in connection with the disclosed titration method.

In some embodiments, a composition according to the present disclosure is one which has relatively low water content. For example, in some embodiments, a composition according to the present disclosure does not include more than about 5% water by weight, based on total weight of the composition. For example, the composition may include water at less than about 5% by weight, less than about 4% by weight, less than about 3% by weight, or less than about 2% by weight, based on the total weight of the composition. In some embodiments, a composition according to the present disclosure includes water at from about 1.0 to about 5.0% by weight, based on total weight of the composition, e.g., at from about 1.0 to about 4.5% by weight, at from about 1.0 to about 3.0% by weight, at from about 1.0 to about 2.5% by weight, at from about 1.0 to about 2.0% by weight, or at from about 1.0 to about 1.5% by weight, based on total weight of the composition. In some embodiments, a composition according to the present disclosure includes water at about 1.0% by weight, about 1.5% by weight, about 2% by weight, about 2.5% by weight, about 3% by weight, about 3.5% by weight, about 4% by weight, about 4.5% by weight, or about 5% by weight, based on the total weight of the composition. In the above embodiments, each of the above compositions may be a composition which has been encapsulated within a capsule having a water content of less than about 15% w/w (e.g., less than about 10% w/w or less than about 5% w/w), e.g., an HPMC capsule, and stored for a period of time, e.g., 1, 2, 3, 4, 5, 6, 7, 8, 9, 10, 11 or 12 months, at 25° C. and 60% relative humidity (RH), 30° C. and 65% RH, or 40° C. and 75% RH.

The water content of a composition as described in the present disclosure may be determined by Karl Fischer titration method as set forth in USP <921> Method 1C. In some embodiments, an AquaStar C3000 Karl Fischer Coulometric Titrator may be used in connection with the disclosed titration method.

In some embodiments, the water content of the composition and the capsule combined is less than about 5% by weight based on the total weight of the composition and the capsule combined, e.g., less than about 4% by weight, less than about 3% by weight, or less than about 2% by weight based on the total weight of the composition and the capsule combined. In some embodiments, the water content of the composition and the capsule combined is from about 5% by weight to about 4% by weight, from about 4% by weight to about 3% by weight, from about 3% by weight to about 2% by weight, or from about 2% by weight to about 1% by weight based on the total weight of the composition and the capsule combined. In some embodiments, the water content of the composition and the capsule combined is about 1.0% by weight, about 1.5% by weight, about 2% by weight, about 2.5% by weight, about 3% by weight, about 3.5% by weight, about 4% by weight, about 4.5% by weight, or about 5% by weight, based on the total weight of the composition and the capsule combined. The water content of a composition and capsule combined as described in the present disclosure may be determined by Karl Fischer titration method as set forth in USP <921> Method 1C. In some embodiments, an AquaStar C3000 Karl Fischer Coulometric Titrator may be used in connection with the disclosed titration method.

The time-dependent change in release performance may also be addressed by formulating the various components of the composition in specific concentration ranges and/or at specific ratios for oral dosage forms. Accordingly, the present disclosure provides a method of orally administering a composition, including: reducing a time-dependent change in an in vitro release profile of a composition by formulating the composition to include, in addition to a pharmacologically active agent, about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere, about 31% by weight to about 45% by weight, based on total weight of the composition, of a solvent, about 2% by weight to about 10% by weight, based on total weight of the composition, of a rheology modifier, and a cellulose acetate butyrate; and orally administering the composition. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of reducing a time-dependent change in an in vitro release profile of a pharmacologically active agent from a composition, wherein the method includes formulating the pharmacologically active agent with (a) a high viscosity liquid carrier material (HVLCM) having a viscosity of at least 5000 cP at 37 C that does not crystallize neat at 25 C and 1 atmosphere, (b) a solvent, (c) a rheology modifier and (d) cellulose acetate butyrate, such that the composition includes about 35% by weight to about 45% by weight, based on total weight of the composition, of the high viscosity liquid carrier material (HVLCM) having a viscosity of at least 5000 cP at 37 C that does not crystallize neat at 25 C and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a use of (a) a high viscosity liquid carrier material (HVLCM) having a viscosity of at least 5000 cP at 37 C that does not crystallize neat at 25 C and 1 atmosphere, (b) a solvent, (c) a rheology modifier and (d) cellulose acetate butyrate, for reducing a time-dependent change in an in vitro release profile of a pharmacologically active agent from a composition, wherein the use includes formulating the pharmacologically active agent with (a) the high viscosity liquid carrier material (HVLCM) having a viscosity of at least 5000 cP at 37 C that does not crystallize neat at 25 C and 1 atmosphere, (b) the solvent, (c) the rheology modifier and (d) cellulose acetate butyrate, thereby providing a composition that includes about 35% by weight to about 45% by weight, based on total weight of the composition, of the high viscosity liquid carrier material (HVLCM) having a viscosity of at least 5000 cP at 37 C that does not crystallize neat at 25 C and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere, a solvent; about 2% by weight to about 10% by weight, based on total weight of the composition, of a rheology modifier, and a cellulose acetate butyrate (CAB), wherein the HVLCM and the solvent are present in the composition at a ratio of about 1.3:1.0 to about 1.0:1.0; and orally administering the composition. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio of about 1.3:1.0:0.3 to about 1.0:1.0:0.05; and orally administering the composition. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere; a solvent; a rheology modifier; and a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition; and orally administering the composition. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: reducing a storage time-dependent change in a release profile of a composition by formulating the composition to include, in addition to a pharmacologically active agent, means for the reducing a storage time-dependent change in a release profile of the composition relative to Reference Formulation A. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including an opioid; a high viscosity liquid carrier material (HVLCM) having a viscosity of at least 5000 cP at 37° C. that does not crystallize neat at 25° C. and 1 atmosphere; a solvent; a network former; and silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including an opioid; sucrose acetate isobutyrate (SAIB); triacetin; isopropyl myristate (IPM); cellulose acetate butyrate (CAB); hydroxyethyl cellulose (HEC); and silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including oxycodone; about 35% by weight to about 45% sucrose acetate isobutyrate (SAIB) relative to the total weight of the composition; about 31% by weight to about 45% of triacetin relative to the total weight of the composition; about 2% by weight to about 10% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.4% by weight to about 5.4% by weight of silicon dioxide relative to the total weight of the composition, wherein one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including oxycodone; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition, wherein one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including about 5% by weight of oxycodone relative to the total weight of the composition; about 39% by weight to about 41% sucrose acetate isobutyrate (SAIB) relative to the total weight of the composition; about 38% by weight to about 41% of triacetin relative to the total weight of the composition; about 2% by weight to about 3% by weight of isopropyl myristate (IPM) relative to the total weight of the composition; about 4% to about 6% by weight of cellulose acetate butyrate (CAB) relative to the total weight of the composition; about 5% by weight to about 6% by weight of hydroxyethyl cellulose (HEC) relative to the total weight of the composition; and about 2.5% by weight to about 3.2% by weight of silicon dioxide relative to the total weight of the composition, wherein one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method for treating pain in a subject, the method including: orally administering to the subject a composition including oxycodone at about 5% by weight relative to the total weight of the composition; sucrose acetate isobutyrate (SAIB) at about 40% by weight relative to the total weight of the composition; triacetin at about 39% by weight relative to the total weight of the composition; isopropyl myristate (IPM) at about 2.5% by weight relative to the total weight of the composition; cellulose acetate butyrate (CAB) at about 4.5% by weight relative to the total weight of the composition; hydroxyethyl cellulose (HEC) at about 5.5% by weight relative to the total weight of the composition; and silicon dioxide, wherein the silicon dioxide is present in the composition at about 2.9% by weight relative to the total weight of the composition, wherein the composition is formulated for oral administration, and one or more symptoms or signs associated with the subject's pain is alleviated. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: improving reproducibility of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and orally administering the composition. Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering a composition, including: decreasing the variability of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and orally administering the composition.

Optionally, the composition may be provided within a capsule having a water content of less than about 10% by weight, e.g., an HPMC capsule having a water content of less than about 10% by weight, e.g., less than about 5% by weight.

In some embodiments, the present disclosure provides a method of orally administering an encapsulated composition, including: forming a composition including: a pharmacologically active agent, a high viscosity liquid carrier material (HVLCM) having a viscosity of at least 5000 cP at 37° C. that does not crystallize neat at 25° C. and 1 atmosphere, a solvent, a network former, and a mineral particle, wherein the mineral particle is present in the composition in an amount from about 2.4% by weight to about 5.4% by weight relative to the total weight of the composition; improving an in vitro release profile of the composition by encapsulating the composition within a capsule including hydroxypropyl methylcellulose to form an encapsulated composition; and orally administering the encapsulated composition.

In some embodiments, the present disclosure provides a method of orally administering an encapsulated composition, including: forming a composition including: a pharmacologically active agent, a high viscosity liquid carrier material (HVLCM) having a viscosity of at least 5000 cP at 37° C. that does not crystallize neat at 25° C. and 1 atmosphere, a solvent, a network former, and a mineral particle, wherein the mineral particle is present in the composition in an amount from about 2.4% by weight to about 5.4% by weight relative to the total weight of the composition; reducing exposure of the composition to water by encapsulating the composition within a capsule including hydroxypropyl methylcellulose to form an encapsulated composition; and orally administering the encapsulated composition.

In certain embodiments, the compositions of the present disclosure may be formulated so as to produce particular controlled plasma levels of an active agent over a particular period, e.g., to maintain a plasma level within an appropriate therapeutic range. An appropriate therapeutic range will vary depending on the active agent, but can range from femtogram/mL levels up to above microgram/mL levels for a desired period of time. For example, a single dose of a composition disclosed herein may result in maintenance of plasma levels of greater than 5 ng/mL for a period of greater than 8 hours. In other embodiments, the plasma level achieved using a single dose may be greater than about 5 ng/mL for a period of greater than about 10 hours, greater than about 12 hours, greater than about 14 hours, greater than about 16 hours, greater than about 18 hours, or greater than about 20 hours. In yet other embodiments, the plasma level achieved using a single dose may be greater than about 5 ng/mL, greater than about 10 ng/mL, greater than about 15 ng/mL, greater than about 20 ng/mL, greater than about 30 ng/mL, greater than about 40 ng/mL, or greater than about 50 ng/mL for a period of about 4, about 8, about 10, about 12, about 14, about 16, about 18, about 20 or about 24 hours. The maximum plasma concentration of an active agent may be reached at a time following administration from between about 0.1 hr to about 24 hr, or from about 0.25 hr to about 10 hr, or from about 0.25 hr to about 8 hr, or from about 0.5 hr to about 6 hr, or from about 0.5 hr to about 4 hr, or from about 0.5 hr to about 2 hr, or from about 0.5 hr to about 1 hr. The time to maximum plasma concentration may be adjusted by adjusting various components of the controlled release carrier system as taught herein.

The plasma levels obtained may be adjusted by adjusting the dose of the active agent, and/or by adjusting the components of the composition, and desirable plasma levels will depend on the therapeutic range or its index for any particular active agent. It is readily within the skill of one in the art to determine the desired therapeutic index.

The rate of active agent release from the composition may be varied depending on the agent used and the dosage required. Release rates may be different in different parts of the GI tract, and release rates may be averaged over the time of transit through the GI tract (approximately 8-24 hrs). Typical average release rates may vary substantially. For many active agents, they may range from about 0.01 to about 500 mg/hr, e.g., from about 0.5 to about 250 mg/hr, from about 0.75 to about 100 mg/hr, from about 1 to about 100 mg/hr, from about 2 to about 100 mg/hr, from about 5 to about 100 mg/hr, from about 10 to about 100 mg/hr, from about 10 to about 80 mg/hr, from about 20 to about 50 mg/hr, or from about 20 to about 40 mg/hr.

Dosage regimens for a particular active agent of interest may be determined by the physician in accordance with standard practices. Once per day (QD) or twice per day (BID) dosing may be used to maintain a sufficient clinical effect, e.g., to maintain pain relief.

Exemplary Non-Limiting Aspects of the Disclosure

The present disclosure includes a composition comprising: an opioid (e.g., about 2% by weight to about 50% by weight, relative to the total weight of the composition, of an opioid selected from oxycodone, oxymorphone, hydrocodone, and hydromorphone, either in the free base form or a pharmaceutically acceptable salt form thereof); sucrose acetate isobutyrate (SAIB); triacetin; isopropyl myristate (IPM); cellulose acetate butyrate (CAB), wherein the CAB has a number average molecular weight ranging from 66,000 Daltons to 83,000 Daltons, and wherein the CAB has at least one feature selected from a butyryl content ranging from about 17% to about 38%, an acetyl content ranging from about 13% to about 30%, and a hydroxyl content ranging from about 0.8% to about 1.7%; hydroxyethyl cellulose (HEC); and silicon dioxide, wherein the silicon dioxide is present in the composition in an amount from about 2.5% by weight to about 3.0% by weight relative to the total weight of the composition. In some embodiments, the composition does not comprise more than 5% water by weight, based on total weight of the composition. For instance, the composition may comprise water at from about 1.0 to about 2.5% by weight (e.g., from about 1.0 to about 2.0% by weight), based on total weight of the composition. In some embodiments, the composition is contained within a capsule (e.g., a hydroxymethylcellulose capsule).

Aspects, including embodiments, of the present subject matter described above may be beneficial alone or in combination, with one or more other aspects or embodiments. Without limiting the foregoing description, certain non-limiting aspects of the disclosure numbered 1-604 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A composition comprising:
   a pharmacologically active agent;
   about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere;
about 31% by weight to about 45% by weight, based on total weight of the composition, of a solvent;
about 2% by weight to about 10% by weight, based on total weight of the composition, of a rheology modifier; and
a cellulose acetate butyrate.

2. The composition of 1, wherein the HVLCM is sucrose acetate isobutyrate (SAIB).

3. The composition of 1 or 2, wherein the composition is in a capsule having a water content of less than 10%.

4. The composition of any one of 1 to 3, wherein the solvent is a hydrophilic solvent.

5. The composition of any one of 1 to 4, wherein the composition is within a hydroxypropylmethylcellulose (HPMC) capsule.

6. The composition of any one of 1 to 5, wherein the HVLCM is sucrose acetate isobutyrate (SAIB), the solvent is triacetin, and the rheology modifier is isopropyl myristate (IPM).

7. The composition of any one of 1 to 6, comprising a mineral particle.

8. The composition of 7, wherein the mineral particle is selected from talc, bentonite and kaolin.

9. The composition of 7, wherein the mineral particle is selected from silicon dioxide, zinc oxide, magnesium oxide, titanium oxide, and calcium oxide.

10. The composition of 7, wherein the mineral particle comprises silicon dioxide.

11. The composition of any one of 1 to 10, wherein the pharmacologically active agent is selected from opioid, stimulant, and depressant.

12. The composition of 11, wherein the pharmacologically active agent is an opioid.

13. The composition of 11, wherein the pharmacologically active agent is selected from oxycodone, oxymorphone, hydrocodone, and hydromorphone, either in the free base form or a pharmaceutically acceptable salt form thereof.

14. The composition of 11, wherein the pharmacologically active agent is oxycodone.

15. The composition of any one of 1 to 14, comprising a surfactant.

16. The composition of 15, wherein the surfactant is saturated polyglycolized glyceride.

17. The composition of any one of 1 to 16, wherein the composition does not comprise more than 5% water by weight, based on total weight of the composition.

18. The composition of 17, wherein the composition does not comprise more than 2.5% water by weight, based on total weight of the composition.

19. The composition of 17, wherein the composition does not comprise more than 2.0% water by weight, based on total weight of the composition.

20. The composition of any one of 1 to 15, wherein the composition comprises water at from about 1.0 to about 2.5% by weight, based on total weight of the composition.

21. The composition of 20, wherein the composition comprises water at from about 1.0 to about 2.0% by weight, based on total weight of the composition.

22. The composition of 21, wherein the composition comprises water at from about 1.0 to about 1.5% by weight, based on total weight of the composition.

23. A composition comprising:
a pharmacologically active agent;
about 35% by weight to about 45% by weight, based on total weight of the composition, of sucrose acetate isobutyrate (SAIB);
about 31% by weight to about 45% by weight, based on total weight of the composition, of triacetin;
about 2% by weight to about 10% by weight, based on total weight of the composition, of isopropyl myristate (IPM); and
about 4% to about 6% of a cellulose acetate butyrate (CAB), based on total weight of the composition.

24. The composition of 23, wherein the cellulose acetate butyrate comprises CAB having a number average molecular weight ranging from 50,000 Daltons to 100,000 Daltons.

25. The composition of 23 or 24, wherein the cellulose acetate butyrate comprises CAB having at least one feature selected from a butyryl content ranging from about 17% to about 41%, an acetyl content ranging from about 13% to about 30%, and a hydroxyl content ranging from about 0.5% to about 1.7%.

26. A composition comprising:
a pharmacologically active agent;
at least 35% by weight of a high viscosity liquid carrier material (HVLCM) having a viscosity of at least 5000 cP at 37° C. that does not crystallize neat at 25° C. and 1 atmosphere, based on the total weight of the composition;
a solvent;
about 2% by weight to about 10% by weight, based on total weight of the composition, of a rheology modifier; and
a cellulose acetate butyrate (CAB), wherein the HVLCM and the solvent are present in the composition at a ratio of about 1.3:1 to about 1:1.

27. The composition of 26, wherein the HVLCM is sucrose acetate isobutyrate (SAIB).

28. The composition of 26 or 27, wherein the composition is in a capsule having a water content of less than 10%.

29. The composition of any one of 26 to 28, wherein the solvent is a hydrophilic solvent.

30. The composition of any one of 26 to 29, wherein the composition is within a hydroxypropylmethylcellulose (HPMC) capsule.

31. The composition of any one of 26 to 30, wherein the HVLCM is sucrose acetate isobutyrate (SAIB), the solvent is triacetin, and the rheology modifier is isopropyl myristate (IPM).

32. The composition of any one of 26 to 31, comprising a mineral particle.

33. The composition of 32, wherein the mineral particle is selected from talc, bentonite and kaolin.

34. The composition of 32, wherein the mineral particle is selected from silicon dioxide, zinc oxide, magnesium oxide, titanium oxide, and calcium oxide.

35. The composition of 32, wherein the mineral particle comprises silicon dioxide.

36. The composition of any one of 26 to 35, wherein the pharmacologically active agent is selected from opioid, stimulant, and depressant.

37. The composition of 36, wherein the pharmacologically active agent is an opioid.

38. The composition of 36, wherein the pharmacologically active agent is selected from oxycodone, oxymorphone, hydrocodone, and hydromorphone, either in the free base form or a pharmaceutically acceptable salt form thereof.

39. The composition of 36, wherein the pharmacologically active agent is oxycodone.
40. The composition of any one of 26 to 39, comprising a surfactant.
41. The composition of 40, wherein the surfactant is saturated polyglycolized glyceride.
42. The composition of any one of 26 to 41, wherein the composition does not comprise more than 5% water by weight, based on total weight of the composition.
43. The composition of 42, wherein the composition does not comprise more than 2.5% water by weight, based on total weight of the composition.
44. The composition of 42, wherein the composition does not comprise more than 2.0% water by weight, based on total weight of the composition.
45. The composition of any one of 26 to 41, wherein the composition comprises water at from about 1.0 to about 2.5% by weight, based on total weight of the composition.
46. The composition of 45, wherein the composition comprises water at from about 1.0 to about 2.0% by weight, based on total weight of the composition.
47. The composition of 45, wherein the composition comprises water at from about 1.0 to about 1.5% by weight, based on total weight of the composition.
48. A composition comprising:
a pharmacologically active agent;
at least 35% by weight of a high viscosity liquid carrier material (HVLCM) having a viscosity of at least 5000 cP at 37° C. that does not crystallize neat at 25° C. and 1 atmosphere, based on the total weight of the composition;
a solvent;
a rheology modifier; and
a cellulose acetate butyrate (CAB), wherein the HVLCM, the solvent and the rheology modifier are present in the composition at a ratio of about 1.3:1.0:0.3 to about 1.0:1.0:0.05.
49. The composition of 48, wherein the HVLCM is sucrose acetate isobutyrate (SAIB).
50. The composition of 48 or 49, wherein the composition is in a capsule having a water content of less than 10%.
51. The composition of any one of 48 to 50, wherein the solvent is a hydrophilic solvent.
52. The composition of any one of 48 to 51, wherein the composition is within a hydroxypropylmethylcellulose (HPMC) capsule.
53. The composition of any one of 48 to 52, wherein the HVLCM is sucrose acetate isobutyrate (SAIB), the solvent is triacetin, and the rheology modifier is isopropyl myristate (IPM).
54. The composition of any one of 48 to 53, comprising a mineral particle.
55. The composition of 54, wherein the mineral particle is selected from talc, bentonite and kaolin.
56. The composition of 54, wherein the mineral particle is selected from silicon dioxide, zinc oxide, magnesium oxide, titanium oxide, and calcium oxide.
57. The composition of 54, wherein the mineral particle comprises silicon dioxide.
58. The composition of any one of 48 to 57, wherein the pharmacologically active agent is selected from opioid, stimulant, and depressant.
59. The composition of 58, wherein the pharmacologically active agent is an opioid.
60. The composition of 58, wherein the pharmacologically active agent is selected from oxycodone, oxymorphone, hydrocodone, and hydromorphone, either in the free base form or a pharmaceutically acceptable salt form thereof.
61. The composition of 58, wherein the pharmacologically active agent is oxycodone.
62. The composition of any one of 48 to 61, comprising a surfactant.
63. The composition of 62, wherein the surfactant is saturated polyglycolized glyceride.
64. The composition of any one of 48 to 63, wherein the composition does not comprise more than 5% water by weight, based on total weight of the composition.
65. The composition of 64, wherein the composition does not comprise more than 2.5% water by weight, based on total weight of the composition.
66. The composition of 64, wherein the composition does not comprise more than 2.0% water by weight, based on total weight of the composition.
67. The composition of any one of 48 to 63, wherein the composition comprises water at from about 1.0 to about 2.5% by weight, based on total weight of the composition.
68. The composition of 67, wherein the composition comprises water at from about 1.0 to about 2.0% by weight, based on total weight of the composition.
69. The composition of 68, wherein the composition comprises water at from about 1.0 to about 1.5% by weight, based on total weight of the composition.
70. A composition comprising:
a pharmacologically active agent;
a high viscosity liquid carrier material (HVLCM) having a viscosity of at least 5000 cP at 37° C. that does not crystallize neat at 25° C. and 1 atmosphere;
a solvent;
a rheology modifier; and
a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition.
71. The composition of 70, wherein the HVLCM is sucrose acetate isobutyrate (SAIB).
72. The composition of any one of 70 to 71, wherein the composition is in a capsule having a water content of less than 10%.
73. The composition of any one of 70 to 72, wherein the solvent is a hydrophilic solvent.
74. The composition of any one of 70 to 73, wherein the composition is within a hydroxypropyl methylcellulose (HPMC) capsule.
75. The composition of any one of 70 to 74, wherein the HVLCM is sucrose acetate isobutyrate (SAIB), the solvent is triacetin, and the rheology modifier is isopropyl myristate (IPM).
76. The composition of any one of 70 to 75, comprising a mineral particle.
77. The composition of 76, wherein the mineral particle is selected from talc, bentonite and kaolin.
78. The composition of 76, wherein the mineral particle is selected from silicon dioxide, zinc oxide, magnesium oxide, titanium oxide, and calcium oxide.
79. The composition of 76, wherein the mineral particle comprises silicon dioxide.
80. The composition of any one of 70 to 79, wherein the pharmacologically active agent is selected from opioid, stimulant, and depressant.

81. The composition of 80, wherein the pharmacologically active agent is an opioid.
82. The composition of 80, wherein the pharmacologically active agent is selected from oxycodone, oxymorphone, hydrocodone, and hydromorphone, either in the free base form or a pharmaceutically acceptable salt form thereof.
83. The composition of 80, wherein the pharmacologically active agent is oxycodone.
84. The composition of any one of 70 to 83, comprising a surfactant.
85. The composition of 84, wherein the surfactant is saturated polyglycolized glyceride.
86. The composition of any one of 70 to 85, wherein the composition does not comprise more than 5% water by weight, based on total weight of the composition.
87. The composition of 86, wherein the composition does not comprise more than 2.5% water by weight, based on total weight of the composition.
88. The composition of 86, wherein the composition does not comprise more than 2.0% water by weight, based on total weight of the composition.
89. The composition of any one of 70 to 85, wherein the composition comprises water at from about 1.0 to about 2.5% by weight, based on total weight of the composition.
90. The composition of 89, wherein the composition comprises water at from about 1.0 to about 2.0% by weight, based on total weight of the composition.
91. The composition of 90, wherein the composition comprises water at from about 1.0 to about 1.5% by weight, based on total weight of the composition.
92. A composition comprising:
a pharmacologically active agent;
a high viscosity liquid carrier material (HVLCM) having a viscosity of at least 5000 cP at 37° C. that does not crystallize neat at 25° C. and 1 atmosphere;
a solvent;
a rheology modifier; and
a cellulose acetate butyrate,
wherein the composition is encapsulated within a hydroxypropylmethylcellulose capsule, and
wherein the composition within the capsule comprises less than 5% water by weight, based on total weight of the composition within the capsule.
93. The composition of 92, wherein the composition comprises less than 2% water by weight, based on total weight of the composition.
94. The composition of 92, wherein the HVLCM is sucrose acetate isobutyrate (SAIB).
95. The composition of any one of 92 to 94, wherein the solvent is a hydrophilic solvent.
96. The composition of any one of 92 to 95, wherein the HVLCM is sucrose acetate isobutyrate (SAIB), the solvent is triacetin, and the rheology modifier is isopropyl myristate (IPM).
97. The composition of any one of 92 to 96, comprising a mineral particle.
98. The composition of 97, wherein the mineral particle is selected from talc, bentonite and kaolin.
99. The composition of 97, wherein the mineral particle is selected from silicon dioxide, zinc oxide, magnesium oxide, titanium oxide, and calcium oxide.
100. The composition of 97, wherein the mineral particle comprises silicon dioxide.
101. The composition of any one of 92 to 100, wherein the pharmacologically active agent is selected from opioid, stimulant, and depressant.
102. The composition of 101, wherein the pharmacologically active agent is an opioid.
103. The composition of 101, wherein the pharmacologically active agent is selected from oxycodone, oxymorphone, hydrocodone, and hydromorphone, either in the free base form or a pharmaceutically acceptable salt form thereof.
104. The composition of 101, wherein the pharmacologically active agent is oxycodone.
105. The composition of any one of 92 to 104, comprising a surfactant.
106. The composition of 105, wherein the surfactant is saturated polyglycolized glyceride.
107. A composition comprising:
a pharmacologically active agent; and
means for reducing a storage time-dependent change in an in vitro release profile of a composition relative to Reference Formulation A.
108. The composition of 107, wherein the storage time-dependent change in the release profile occurs following storage for 12 months at 25° C. and 60% RH.
109. The composition of 107, wherein Reference Formulation A exhibits more than 10% mean drug release decline, a similarity factor ($f_2$) of less than 50, when stored at 40° C./75% RH for a one month period of time relative to its initial release profile.
110. A composition comprising:
oxycodone at about 5% by weight to about 10% by weight relative to the total weight of the composition; and
means for reducing a storage time-dependent change in an in vitro release profile of the composition Relative to Ref. Formulation A.
111. The composition of 110, wherein the storage time-dependent change in the release profile occurs following storage for 12 months at 25° C. and 60% RH.
112. The composition of 110, wherein Reference Formulation A exhibits more than 10% mean drug release decline, a similarity factor ($f_2$) of less than 50, when stored at 40° C./75% RH for a one month period of time relative to its initial release profile.
113. A method of orally administering a composition, comprising:
reducing a time-dependent change in an in vitro release profile of a composition by formulating the composition to include, in addition to a pharmacologically active agent,
about 35% by weight to about 45% by weight, based on total weight of the composition, of a high viscosity liquid carrier material (HVLCM) having a viscosity of at least 5000 cP at 37° C. that does not crystallize neat at 25° C. and 1 atmosphere,
about 31% by weight to about 45% by weight, based on total weight of the composition, of a solvent,
about 2% by weight to about 10% by weight, based on total weight of the composition, of a rheology modifier, and
a cellulose acetate butyrate; and
orally administering the composition.
114. The method of 113, wherein the in vitro release profile results remain similar, a similarity factor ($f_2$) of greater than 50, for the composition when stored at 40 C/75% RH for a one month period of time relative to an initial release profile.
115. The method of 113, wherein the in vitro release profile results remain similar, a similarity factor ($f_2$) of greater than 60, for the composition when stored at 40 C/75% RH for a one month period of time relative to an initial release profile.

116. The method of 113, wherein the in vitro release profile results remain similar, a similarity factor ($f_2$) of greater than 70, for the composition when stored at 40 C/75% RH for a one month period of time relative to an initial release profile.

117. The method of 113, wherein the in vitro release profile results remain similar, a similarity factor ($f_2$) of greater than 80, for the composition when stored at 40 C/75% RH for a one month period of time relative to an initial release profile.

118. The method of 113, wherein the in vitro release profile results remain similar, a similarity factor ($f_2$) of greater than 90, for the composition when stored at 40 C/75% RH for a one month period of time relative to an initial release profile.

119. The method of 113, wherein the HVLCM is sucrose acetate isobutyrate (SAIB).

120. The method of 113 or 119, wherein the composition is in a capsule having a water content of less than 10%.

121. The method of any one of 113 to 120, wherein the solvent is a hydrophilic solvent.

122. The method of any one of 113 to 121, wherein the composition is within a hydroxypropyl methylcellulose (HPMC) capsule.

123. The method of any one of 113 to 122, wherein the HVLCM is sucrose acetate isobutyrate (SAIB), the solvent is triacetin, and the rheology modifier is isopropyl myristate (IPM).

124. The method of any one of 113 to 123, wherein the composition comprises a mineral particle.

125. The method of 124, wherein the mineral particle is selected from talc, bentonite and kaolin.

126. The method of 124, wherein the mineral particle is selected from silicon dioxide, zinc oxide, magnesium oxide, titanium oxide, and calcium oxide.

127. The method of 124, wherein the mineral particle comprises silicon dioxide.

128. The method of any one of 113 to 127, wherein the pharmacologically active agent is selected from opioid, stimulant, and depressant.

129. The method of 128, wherein the pharmacologically active agent is an opioid.

130. The method of 128, wherein the pharmacologically active agent is selected from oxycodone, oxymorphone, hydrocodone, and hydromorphone, either in the free base form or a pharmaceutically acceptable salt form thereof.

131. The method of 128, wherein the pharmacologically active agent is oxycodone.

132. The method of any one of 113 to 131, wherein the composition does not comprise more than 5% water by weight, based on total weight of the composition.

133. The method of 132, wherein the composition does not comprise more than 2.5% water by weight, based on total weight of the composition.

134. The method of 132, wherein the composition does not comprise more than 2.0% water by weight, based on total weight of the composition.

135. The method of any one of 113 to 131, wherein the composition comprises water at from about 1.0 to about 2.5% by weight, based on total weight of the composition.

136. The method of 135, wherein the composition comprises water at from about 1.0 to about 2.0% by weight, based on total weight of the composition.

137. The method of 136, wherein the composition comprises water at from about 1.0 to about 1.5% by weight, based on total weight of the composition.

138. A method of reducing a time-dependent change in an in vitro release profile of a pharmacologically active agent from a composition, wherein the method comprises formulating the pharmacologically active agent with (a) a high viscosity liquid carrier material (HVLCM) having a viscosity of at least 5000 cP at 37° C. that does not crystallize neat at 25° C. and 1 atmosphere, (b) a solvent, (c) a rheology modifier and (d) cellulose acetate butyrate, such that the composition comprises about 35% by weight to about 45% by weight, based on total weight of the composition, of the high viscosity liquid carrier material (HVLCM) having a viscosity of at least 5000 cP at 37° C. that does not crystallize neat at 25° C. and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate.

139. The method of 138, wherein the in vitro release profile results remain similar, a similarity factor ($f_2$) of greater than 50, for the composition when stored at 40 C/75% RH for a one month period of time relative to an initial release profile.

140. The method of 138, wherein the in vitro release profile results remain similar, a similarity factor ($f_2$) of greater than 60, for the composition when stored at 40 C/75% RH for a one month period of time relative to an initial release profile.

141. The method of 138, wherein the in vitro release profile results remain similar, a similarity factor ($f_2$) of greater than 70, for the composition when stored at 40 C/75% RH for a one month period of time relative to an initial release profile.

142. The method of 138, wherein the in vitro release profile results remain similar, a similarity factor ($f_2$) of greater than 80, for the composition when stored at 40 C/75% RH for a one month period of time relative to an initial release profile.

143. The method of 138, wherein the in vitro release profile results remain similar, a similarity factor ($f_2$) of greater than 90, for the composition when stored at 40 C/75% RH for a one month period of time relative to an initial release profile.

144. Use of (a) a high viscosity liquid carrier material (HVLCM) having a viscosity of at least 5000 cP at 37 C that does not crystallize neat at 25° C. and 1 atmosphere, (b) a solvent, (c) a rheology modifier and (d) cellulose acetate butyrate, for reducing a time-dependent change in an in vitro release profile of a pharmacologically active agent from a composition, wherein the use comprises formulating the pharmacologically active agent with (a) the high viscosity liquid carrier material (HVLCM) having a viscosity of at least 5000 cP at 37° C. that does not crystallize neat at 25 C and 1 atmosphere, (b) the solvent, (c) the rheology modifier and (d) cellulose acetate butyrate, thereby providing a composition that comprises about 35% by weight to about 45% by weight, based on total weight of the composition, of the high viscosity liquid carrier material (HVLCM) having a viscosity of at least 5000 cP at 37° C. that does not crystallize neat at 25° C. and 1 atmosphere, about 31% by weight to about 45% by weight, based on total weight of the composition, of the solvent, about 2% by weight to about 10% by weight, based on total weight of the composition, of the rheology modifier, and the cellulose acetate butyrate.

145. The use of 144, wherein the in vitro release profile results remain similar, a similarity factor ($f_2$) of greater than 50, for the composition when stored at 40 C/75% RH for a one month period of time relative to an initial release profile.

146. The use of 144, wherein the in vitro release profile results remain similar, a similarity factor ($f_2$) of greater than 60, for the composition when stored at 40 C/75% RH for a one month period of time relative to an initial release profile.

147. The use of 144, wherein the in vitro release profile results remain similar, a similarity factor ($f_2$) of greater than 70, for the composition when stored at 40 C/75% RH for a one month period of time relative to an initial release profile.

148. The use of 144, wherein the in vitro release profile results remain similar, a similarity factor ($f_2$) of greater than 80, for the composition when stored at 40 C/75% RH for a one month period of time relative to an initial release profile.

149. The use of 144, wherein the in vitro release profile results remain similar, a similarity factor ($f_2$) of greater than 90, for the composition when stored at 40 C/75% RH for a one month period of time relative to an initial release profile.

150. A method of orally administering a composition, comprising:
reducing a time-dependent change in an in vitro release profile of a composition by formulating the composition to include, in addition to a pharmacologically active agent,
at least 35% by weight of a high viscosity liquid carrier material (HVLCM) having a viscosity of at least 5000 cP at 37° C. that does not crystallize neat at 25° C. and 1 atmosphere,
a solvent;
about 2% by weight to about 10% by weight, based on total weight of the
composition, of a rheology modifier, and
a cellulose acetate butyrate (CAB), wherein the HVLCM and the solvent are present in the composition at a ratio of about 1.3:1.0 to about 1.0:1.0; and
orally administering the composition.

151. The method of 150, wherein the in vitro release profile results remain similar, a similarity factor ($f_2$) of greater than 50, for the composition when stored at 40 C/75% RH for a one month period of time relative to an initial release profile.

152. The method of 150, wherein the in vitro release profile results remain similar, a similarity factor ($f_2$) of greater than 60, for the composition when stored at 40 C/75% RH for a one month period of time relative to an initial release profile.

153. The method of 150, wherein the in vitro release profile results remain similar, a similarity factor ($f_2$) of greater than 70, for the composition when stored at 40 C/75% RH for a one month period of time relative to an initial release profile.

154. The method of 150, wherein the in vitro release profile results remain similar, a similarity factor ($f_2$) of greater than 80, for the composition when stored at 40 C/75% RH for a one month period of time relative to an initial release profile.

155. The method of 150, wherein the in vitro release profile results remain similar, a similarity factor ($f_2$) of greater than 90, for the composition when stored at 40 C/75% RH for a one month period of time relative to an initial release profile.

156. The method of any one of 150 to 155, wherein the HVLCM is sucrose acetate isobutyrate (SAIB).

157. The method of any one of 150 to 156, wherein the composition is in a capsule having a water content of less than 10%.

158. The method of any one of 150 to 157, wherein the solvent is a hydrophilic solvent.

159. The method of any one of 150 to 158, wherein the composition is within a hydroxypropyl methylcellulose (HPMC) capsule.

160. The method of any one of 150 to 159, wherein the HVLCM is sucrose acetate isobutyrate (SAIB), the solvent is triacetin, and the rheology modifier is isopropyl myristate (IPM).

161. The method of any one of 150 to 160, wherein the composition comprises a mineral particle.

162. The method of 161, wherein the mineral particle is selected from talc, bentonite and kaolin.

163. The method of 161, wherein the mineral particle is selected from silicon dioxide, zinc oxide, magnesium oxide, titanium oxide, and calcium oxide.

164. The method of 161, wherein the mineral particle comprises silicon dioxide.

165. The method of any one of 150 to 164, wherein the pharmacologically active agent is selected from opioid, stimulant, and depressant.

166. The method of 165, wherein the pharmacologically active agent is an opioid.

167. The method of 165, wherein the pharmacologically active agent is selected from oxycodone, oxymorphone, hydrocodone, and hydromorphone, either in the free base form or a pharmaceutically acceptable salt form thereof.

168. The method of 165, wherein the pharmacologically active agent is oxycodone.

169. The method of any one of 150 to 168, wherein the composition does not comprise more than 5% water by weight, based on total weight of the composition.

170. The method of 169, wherein the composition does not comprise more than 2.5% water by weight, based on total weight of the composition.

171. The method of 169, wherein the composition does not comprise more than 2.0% water by weight, based on total weight of the composition.

172. The method of any one of 150 to 168, wherein the composition comprises water at from about 1.0 to about 2.5% by weight, based on total weight of the composition.

173. The method of 172, wherein the composition comprises water at from about 1.0 to about 2.0% by weight, based on total weight of the composition.

174. The method of 173, wherein the composition comprises water at from about 1.0 to about 1.5% by weight, based on total weight of the composition.

175. A method of orally administering a composition, comprising:
reducing a time-dependent change in an in vitro release profile of a composition by formulating the composition to include, in addition to a pharmacologically active agent,
at least 35% by weight of a high viscosity liquid carrier material (HVLCM) having a viscosity of at least 5000 cP at 37° C. that does not crystallize neat at 25° C. and 1 atmosphere;
a solvent;
a rheology modifier; and a cellulose acetate butyrate (CAB), wherein the HVLCM, the solvent and the rheology modifier are present in the composition at a ratio of about 1.3:1.0:0.3 to about 1.0:1.0:0.05; and orally administering the composition.

176. The method of 175, wherein the in vitro release profile results remain similar, a similarity factor ($f_2$) of greater than 50, for the composition when stored at 40 C/75% RH for a one month period of time relative to an initial release profile.

177. The method of 175, wherein the in vitro release profile results remain similar, a similarity factor ($f_2$) of greater than 60, for the composition when stored at 40 C/75% RH for a one month period of time relative to an initial release profile.

178. The method of 175, wherein the in vitro release profile results remain similar, a similarity factor ($f_2$) of greater than 70, for the composition when stored at 40 C/75% RH for a one month period of time relative to an initial release profile.

179. The method of 175, wherein the in vitro release profile results remain similar, a similarity factor ($f_2$) of greater than 80, for the composition when stored at 40 C/75% RH for a one month period of time relative to an initial release profile.

180. The method of 175, wherein the in vitro release profile results remain similar, a similarity factor ($f_2$) of greater than 90, for the composition when stored at 40 C/75% RH for a one month period of time relative to an initial release profile.

181. The method of any one of 175 to 180, wherein the HVLCM is sucrose acetate isobutyrate (SAIB).

182. The method of any one of 175 to 181, wherein the composition is in a capsule having a water content of less than 10%.

183. The method of any one of 175 to 182, wherein the solvent is a hydrophilic solvent.

184. The method of any one of 175 to 183, wherein the composition is within a hydroxypropyl methylcellulose (HPMC) capsule.

185. The method of any one of 175 to 184, wherein the HVLCM is sucrose acetate isobutyrate (SAIB), the solvent is triacetin, and the rheology modifier is isopropyl myristate (IPM).

186. The method of any one of 175 to 185, wherein the composition comprises a mineral particle.

187. The method of 186, wherein the mineral particle is selected from talc, bentonite and kaolin.

188. The method of 186, wherein the mineral particle is selected from silicon dioxide, zinc oxide, magnesium oxide, titanium oxide, and calcium oxide.

189. The method of 186, wherein the mineral particle comprises silicon dioxide.

190. The method of any one of 175 to 189, wherein the pharmacologically active agent is selected from opioid, stimulant, and depressant.

191. The method of 190, wherein the pharmacologically active agent is an opioid.

192. The method of 190, wherein the pharmacologically active agent is selected from oxycodone, oxymorphone, hydrocodone, and hydromorphone, either in the free base form or a pharmaceutically acceptable salt form thereof.

193. The method of 190, wherein the pharmacologically active agent is oxycodone.

194. The method of any one of 175 to 193, wherein the composition does not comprise more than 5% water by weight, based on total weight of the composition.

195. The method of 194, wherein the composition does not comprise more than 2.5% water by weight, based on total weight of the composition.

196. The method of 194, wherein the composition does not comprise more than 2.0% water by weight, based on total weight of the composition.

197. The method of any one of 175 to 193, wherein the composition comprises water at from about 1.0 to about 2.5% by weight, based on total weight of the composition.

198. The method of 197, wherein the composition comprises water at from about 1.0 to about 2.0% by weight, based on total weight of the composition.

199. The method of 198, wherein the composition comprises water at from about 1.0 to about 1.5% by weight, based on total weight of the composition.

200. A method of orally administering a composition, comprising:

reducing a time-dependent change in an in vitro release profile of a composition by formulating the composition to include, in addition to a pharmacologically active agent, a high viscosity liquid carrier material (HVLCM) having a viscosity of at least 5000 cP at 37° C. that does not crystallize neat at 25° C. and 1 atmosphere;

a solvent;

a rheology modifier; and a cellulose acetate butyrate (CAB), wherein the HVLCM, the solvent and the rheology modifier are present in the composition at a ratio sufficient to increase reproducibility of release relative to Reference Formulation A when assayed in a USP Apparatus 2 dissolution tester modified to have a 20-mesh basket for containing the composition; and orally administering the composition.

201. The method of 200, wherein the in vitro release profile results remain similar, a similarity factor ($f_2$) of greater than 50, for the composition when stored at 40 C/75% RH for a one month period of time relative to an initial release profile.

202. The method of 200, wherein the in vitro release profile results remain similar, a similarity factor ($f_2$) of greater than 60, for the composition when stored at 40 C/75% RH for a one month period of time relative to an initial release profile.

203. The method of 200, wherein the in vitro release profile results remain similar, a similarity factor ($f_2$) of greater than 70, for the composition when stored at 40 C/75% RH for a one month period of time relative to an initial release profile.

204. The method of 200, wherein the in vitro release profile results remain similar, a similarity factor ($f_2$) of greater than 80, for the composition when stored at 40 C/75% RH for a one month period of time relative to an initial release profile.

205. The method of 200, wherein the in vitro release profile results remain similar, a similarity factor ($f_2$) of greater than 90, for the composition when stored at 40 C/75% RH for a one month period of time relative to an initial release profile.

206. The method of any one of 200 to 205, wherein the HVLCM is sucrose acetate isobutyrate (SAIB).

207. The method of any one of 200 to 206, wherein the composition is in a capsule having a water content of less than 10%.

208. The method of any one of 200 to 207, wherein the solvent is a hydrophilic solvent.

209. The method of any one of 200 to 208, wherein the composition is within a hydroxypropyl methylcellulose (HPMC) capsule.
210. The method of any one of 200 to 209, wherein the HVLCM is sucrose acetate isobutyrate (SAIB), the solvent is triacetin, and the rheology modifier is isopropyl myristate (IPM).
211. The method of any one of 200 to 210, wherein the composition comprises a mineral particle.
212. The method of 211, wherein the mineral particle is selected from talc, bentonite and kaolin.
213. The method of 211, wherein the mineral particle is selected from silicon dioxide, zinc oxide, magnesium oxide, titanium oxide, and calcium oxide.
214. The method of 211, wherein the mineral particle comprises silicon dioxide.
215. The method of any one of 200 to 214, wherein the pharmacologically active agent is selected from opioid, stimulant, and depressant.
216. The method of 215, wherein the pharmacologically active agent is an opioid.
217. The method of 200, wherein the pharmacologically active agent is selected from oxycodone, oxymorphone, hydrocodone, and hydromorphone, either in the free base form or a pharmaceutically acceptable salt form thereof.
218. The method of 200, wherein the pharmacologically active agent is oxycodone.
219. The method of any one of 200 to 218, wherein the composition does not comprise more than 5% water by weight, based on total weight of the composition.
220. The method of 219, wherein the composition does not comprise more than 2.5% water by weight, based on total weight of the composition.
221. The method of 219, wherein the composition does not comprise more than 2.0% water by weight, based on total weight of the composition.
222. The method of any one of 200 to 218, wherein the composition comprises water at from about 1.0 to about 2.5% by weight, based on total weight of the composition.
223. The method of 222, wherein the composition comprises water at from about 1.0 to about 2.0% by weight, based on total weight of the composition.
224. The method of 223, wherein the composition comprises water at from about 1.0 to about 1.5% by weight, based on total weight of the composition.
225. A method of orally administering a composition, comprising:
reducing a storage time-dependent change in a release profile of a composition by formulating the composition to include, in addition to a pharmacologically active agent, means for the reducing a storage time-dependent change in a release profile of the composition relative to Reference Formulation A.
226. The method of 225, wherein the storage time-dependent change in the release profile occurs following storage for 12 months at 25° C. and 60% RH.
227. The method of 225, wherein Reference Formulation A exhibits more than 10% mean drug release decline, a similarity factor ($f_2$) of less than 50, when stored at 40° C./75% RH for a one month period of time relative to its initial release profile.
228. A composition comprising:
a pharmacologically active agent;
a high viscosity liquid carrier material (HVLCM) having a viscosity of at least 5000 cP at 37° C. that does not crystallize neat at 25° C. and 1 atmosphere;
a solvent;
a network former; and
a mineral particle, wherein the mineral particle is present in the composition in an amount from about 2.4% by weight to about 5.4% by weight relative to the total weight of the composition.
229. The composition of 228, wherein the mineral particle is selected from talc, bentonite and kaolin.
230. The composition of 228, wherein the mineral particle is selected from silicon dioxide, zinc oxide, magnesium oxide, titanium oxide, and calcium oxide.
231. The composition of 228, wherein the mineral particle comprises silicon dioxide.
232. The composition of 228, wherein the pharmacologically active agent is selected from opioid, stimulant, and depressant.
233. The composition of 228, wherein the pharmacologically active agent is an opioid.
234. The composition of 228, wherein the pharmacologically active agent is selected from oxycodone, oxymorphone, hydrocodone, and hydromorphone, either in the free base form or a pharmaceutically acceptable salt form thereof.
235. The composition of 228, wherein the pharmacologically active agent is oxycodone.
236. The composition of any one of 228 to 235, wherein the HVLCM is sucrose acetate isobutyrate (SAIB).
237. The composition of any one of 228 to 236, comprising about 35% by weight to about 45% by weight of the HVLCM relative to the total weight of the composition.
238. The composition of any one of 228 to 237, wherein the solvent is selected from triacetin, N-methyl-2-pyrrolidone, 2-pyrrolidone, dimethylsulfoxide, ethyl lactate, propylene carbonate and glycofurol.
239. The composition of any one of 228 to 238, wherein the solvent comprises triacetin.
240. The composition of any one of 228 to 238, wherein the solvent comprises N-methyl-2-pyrrolidone.
241. The composition of any one of 228 to 238, wherein the solvent comprises 2-pyrrolidone.
242. The composition of any one of 228 to 238, wherein the solvent comprises dimethylsulfoxide.
243. The composition of any one of 228 to 238, wherein the solvent comprises ethyl lactate.
244. The composition of any one of 228 to 238, wherein the solvent comprises propylene carbonate.
245. The composition of any one of 228 to 238, wherein the solvent comprises glycofurol.
246. The composition of any one of 228 to 245, comprising about 31% by weight to about 45% by weight of the solvent relative to the total weight of the composition.
247. The composition of 246, comprising about 38% by weight to about 41% by weight of the solvent relative to the total weight of the composition.
248. The composition of any one of 228 to 247, further comprising a rheology modifier.
249. The composition of 248, wherein the rheology modifier is selected from isopropyl myristate (IPM), caprylic/capric triglyceride, ethyl oleate, triethyl citrate, dimethyl phthalate and benzyl benzoate.
250. The composition of 248, wherein the rheology modifier is IPM.
251. The composition of 248, wherein the rheology modifier is caprylic/capric triglyceride.
252. The composition of 248, wherein the rheology modifier is ethyl oleate.
253. The composition of 248, wherein the rheology modifier is triethyl citrate.

254. The composition of 248, wherein the rheology modifier is dimethyl phthalate.

255. The composition of 248, wherein the rheology modifier is benzyl benzoate.

256. The composition of any one of 248 to 255, comprising about 2% by weight to about 10% by weight of the rheology modifier relative to the total weight of the composition.

257. The composition of any one of 228 to 256, wherein the network former is selected from cellulose acetate butyrate (CAB), cellulose acetate phthalate, ethyl cellulose, hydroxypropylmethyl cellulose and cellulose triacetate.

258. The composition of any one of 228 to 257, wherein the network former comprises cellulose acetate butyrate (CAB).

259. The composition of any one of 228 to 258, wherein the network former comprises CAB having a number average molecular weight ranging from 50,000 Daltons to 100,000 Daltons.

260. The composition of any one of 228 to 259, wherein the network former comprises CAB having at least one feature selected from a butyryl content ranging from about 17% to about 41%, an acetyl content ranging from about 13% to about 30%, and a hydroxyl content ranging from about 0.5% to about 1.7%.

261. The composition of any one of 228 to 260, further comprising a hydrophilic agent.

262. The composition of 261, wherein the hydrophilic agent is selected from hydroxyethyl cellulose (HEC), hydroxypropyl cellulose, caboxymethyl cellulose, polyethylene glycol and polyvinylpyrrolidone.

263. The composition of 261, wherein the hydrophilic agent comprises HEC.

264. The composition of any one of 228 to 263, wherein the mineral particle is present in the composition in an amount from about 2.5% by weight to about 4.0% by weight relative to the total weight of the composition.

265. The composition of any one of 228 to 264, wherein the mineral particle is present in the composition in an amount from about 2.5% by weight to about 3.5% by weight relative to the total weight of the composition.

266. The composition of any one of 228 to 265, wherein the mineral particle is present in the composition in an amount from about 2.5% by weight to about 3.2% by weight relative to the total weight of the composition.

267. The composition of any one of 228 to 266, wherein the mineral particle is present in the composition in an amount from about 2.5% by weight to about 3.0% by weight relative to the total weight of the composition.

268. The composition of any one of 228 to 267, wherein the mineral particle is present in the composition at from about 2.5% by weight to about 2.9% by weight relative to the total weight of the composition.

269. The composition of any one of 228 to 268, wherein the composition has a complex viscosity of from about 100 Pa·s to about 300 Pa·s, wherein the complex viscosity is determined at a constant strain of 0.5%, a frequency of 1 Hz and a temperature of 25° C.

270. The composition of any one of 228 to 269, wherein the composition has a complex viscosity of from about 120 Pa·s to about 250 Pa·s, wherein the complex viscosity is determined at a constant strain of 0.5%, a frequency of 1 Hz and a temperature of 25° C.

271. The composition of any one of 228 to 270, wherein the composition has a complex viscosity of from about 140 Pa·s to about 200 Pa·s, wherein the complex viscosity is determined at a constant strain of 0.5%, a frequency of 1 Hz and a temperature of 25° C.

272. The composition of any one of 228 to 271, wherein the ratio of the HVLCM to the solvent in the composition is about 0.6:1 to 1.6:1.

273. The composition of 272, wherein the ratio of the HVLCM to the solvent in the composition is about 0.8:1 to 1.5:1.

274. The composition of 273, wherein the ratio of the HVLCM to the solvent in the composition is about 0.9:1 to 1.5:1.

275. The composition of any one of 228 to 272, wherein the composition comprises:
about 35% by weight to about 45% by weight of the HVLCM relative to the total weight of the composition,
about 31% by weight to about 45% by weight of the solvent relative to the total weight of the composition, and
about 2% by weight to about 10% by weight of the network former relative to the total weight of the composition.

276. The composition of 275, comprising about 0.1% by weight to about 8% by weight of a rheology modifier relative to the total weight of the composition.

277. The composition of 275 to 276, comprising about 2% by weight to about 10% by weight of a hydrophilic agent.

278. The composition of any one of 228 to 277, wherein the composition comprises:
about 39% by weight to about 41% by weight of the HVLCM relative to the total weight of the composition,
about 38% by weight to about 40% by weight of the solvent relative to the total weight of the composition, and
about 4% by weight to about 6% by weight of the network former relative to the total weight of the composition.

279. The composition of any one of 228 to 278, comprising about 2% by weight to about 3% by weight of a rheology modifier relative to the total weight of the composition.

280. The composition of any one of 228 to 279, comprising about 5% by weight to about 6% by weight of a hydrophilic agent relative to the total weight of the composition.

281. The composition of any one of 228 to 280, wherein the HVLCM is SAIB, the solvent is triacetin, and the network former is CAB.

282. The composition of 281, comprising IPM.

283. The composition of 281 or 282, comprising HEC.

284. The composition of any one of 228 to 283, wherein the pharmacologically active agent is present in the composition at about 2% by weight to about 50% by weight relative to the total weight of the composition.

285. The composition of any one of 228 to 284, wherein the composition is contained within a capsule.

286. The composition of any one of 228 to 285, wherein the composition is contained within a capsule comprising hydroxypropyl methylcellulose.

287. The composition of any one of 228 to 286, wherein the composition is contained within a hard capsule comprising hydroxypropyl methylcellulose.

288. The composition of any one of 228 to 287, comprising a surfactant.

289. The composition of 288, wherein the surfactant is saturated polyglycolized glyceride.

290. The composition of any one of 228 to 289, wherein the composition does not comprise more than 5% water by weight, based on total weight of the composition.

291. The composition of 290, wherein the composition does not comprise more than 2.5% water by weight, based on total weight of the composition.
292. The composition of 290, wherein the composition does not comprise more than 2.0% water by weight, based on total weight of the composition.
293. The composition of any one of 228 to 289, wherein the composition comprises water at from about 1.0 to about 2.5% by weight, based on total weight of the composition.
294. The composition of 293, wherein the composition comprises water at from about 1.0 to about 2.0% by weight, based on total weight of the composition.
295. The composition of 294, wherein the composition comprises water at from about 1.0 to about 1.5% by weight, based on total weight of the composition.
296. A composition comprising:
    an opioid;
    sucrose acetate isobutyrate (SAIB);
    triacetin;
    isopropyl myristate (IPM);
    cellulose acetate butyrate (CAB);
    hydroxyethyl cellulose (HEC); and
    silicon dioxide, wherein the silicon dioxide is present in the composition in an amount from about 2.4% by weight to about 5.4% by weight relative to the total weight of the composition.
297. The composition of 296, wherein the SAIB is present in the composition in an amount from about 35% by weight to about 45% by weight relative to the total weight of the composition, the triacetin is present in the composition in an amount from about 31% by weight to about 45% by weight relative to the total weight of the composition, the IPM is present in the composition in an amount from about 2% by weight to about 10% by weight relative to the total weight of the composition, the CAB is present in the composition at about 4% to about 6% by weight relative to the total weight of the composition, and the HEC is present in the composition in an amount from about 5% by weight to about 6% by weight relative to the total weight of the composition.
298. The composition of 296 or 297, comprising about 38% by weight to about 41% by weight of the triacetin relative to the total weight of the composition.
299. The composition of any one of 296 to 298, comprising about 2% by weight to about 3% by weight of the IPM relative to the total weight of the composition.
300. The composition of any one of 296 to 299, wherein the CAB has a number average molecular weight ranging from 66,000 Daltons to 83,000 Daltons.
301. The composition of any one of 296 to 300, wherein the CAB has at least one feature selected from a butyryl content ranging from about 17% to about 38%, an acetyl content ranging from about 13% to about 30%, and a hydroxyl content ranging from about 0.8% to about 1.7%.
302. The composition of any one of 296 to 301, wherein the silicon dioxide is present in the composition in an amount from about 2.5% by weight to about 3.5% by weight relative to the total weight of the composition.
303. The composition of any one of 296 to 302, wherein the silicon dioxide is present in the composition in an amount from about 2.5% by weight to about 3.2% by weight relative to the total weight of the composition.
304. The composition of any one of 296 to 303, wherein the silicon dioxide is present in the composition in an amount from about 2.5% by weight to about 3.0% by weight relative to the total weight of the composition.
305. The composition of any one of 296 to 304, wherein the silicon dioxide is present in the composition in an amount from about 2.5% by weight to about 2.9% by weight relative to the total weight of the composition.
306. The composition of any one of 296 to 305, wherein the composition has a complex viscosity of from about 100 Pa·s to about 300 Pa·s, wherein the complex viscosity is determined at a constant strain of 0.5% and a frequency of 1 Hz and a temperature of 25° C.
307. The composition of any one of 296 to 306, wherein the composition has a complex viscosity of from about 120 Pa·s to about 250 Pa·s, wherein the complex viscosity is determined at a constant strain of 0.5% and a frequency of 1 Hz and a temperature of 25° C.
308. The composition of any one of 296 to 307, wherein the composition has a complex viscosity of from about 140 Pa·s to about 200 Pa·s, wherein the complex viscosity is determined at a constant strain of 0.5% and a frequency of 1 Hz and a temperature of 25° C.
309. The composition of any one of 296 to 308, wherein the opioid is selected from oxycodone, oxymorphone, hydrocodone, and hydromorphone, either in the free base form or a pharmaceutically acceptable salt form thereof.
310. The composition of any one of 296 to 309, wherein the opioid is oxycodone.
311. The composition of any one of 296 to 310, wherein the opioid is present in the composition at about 5% by weight relative to the total weight of the composition.
312. The composition of any one of 296 to 311, wherein the composition does not comprise more than 5% water by weight, based on total weight of the composition.
313. The composition of 312, wherein the composition does not comprise more than 2.5% water by weight, based on total weight of the composition.
314. The composition of 312, wherein the composition does not comprise more than 2.0% water by weight, based on total weight of the composition.
315. The composition of any one of 296 to 311, wherein the composition comprises water at from about 1.0 to about 2.5% by weight, based on total weight of the composition.
316. The composition of 315, wherein the composition comprises water at from about 1.0 to about 2.0% by weight, based on total weight of the composition.
317. The composition of 316, wherein the composition comprises water at from about 1.0 to about 1.5% by weight, based on total weight of the composition.
318. A composition comprising:
    oxycodone;
    about 35% by weight to about 45% sucrose acetate isobutyrate (SAIB) relative to the total weight of the composition;
    about 31% by weight to about 45% of triacetin relative to the total weight of the composition;
    about 2% by weight to about 10% by weight of isopropyl myristate (IPM) relative to the total weight of the composition;
    about 4% to about 6% by weight of cellulose acetate butyrate (CAB) relative to the total weight of the composition;
    about 5% by weight to about 6% by weight of hydroxyethyl cellulose (HEC) relative to the total weight of the composition; and
    about 2.4% by weight to about 5.4% by weight of silicon dioxide relative to the total weight of the composition.

319. A composition comprising:
oxycodone;
about 39% by weight to about 41% sucrose acetate isobutyrate (SAIB) relative to the total weight of the composition;
about 38% by weight to about 41% of triacetin relative to the total weight of the composition;
about 2% by weight to about 3% by weight of isopropyl myristate (IPM) relative to the total weight of the composition;
about 4% to about 6% by weight of cellulose acetate butyrate (CAB) relative to the total weight of the composition;
about 5% by weight to about 6% by weight of hydroxyethyl cellulose (HEC) relative to the total weight of the composition; and
about 2.5% by weight to about 3.2% by weight of silicon dioxide relative to the total weight of the composition.

320. A composition comprising:
about 5% by weight of oxycodone relative to the total weight of the composition;
about 39% by weight to about 41% sucrose acetate isobutyrate (SAIB) relative to the total weight of the composition;
about 38% by weight to about 41% of triacetin relative to the total weight of the composition;
about 2% by weight to about 3% by weight of isopropyl myristate (IPM) relative to the total weight of the composition;
about 4% to about 6% by weight of cellulose acetate butyrate (CAB) relative to the total weight of the composition;
about 5% by weight to about 6% by weight of hydroxyethyl cellulose (HEC) relative to the total weight of the composition; and
about 2.5% by weight to about 3.2% by weight of silicon dioxide relative to the total weight of the composition.

321. A composition comprising:
oxycodone at about 5% by weight relative to the total weight of the composition;
sucrose acetate isobutyrate (SAIB) at about 40% by weight relative to the total weight of the composition;
triacetin at about 39% by weight relative to the total weight of the composition;
isopropyl myristate (IPM) at about 2.5% by weight relative to the total weight of the composition;
cellulose acetate butyrate (CAB) at about 4.5% by weight relative to the total weight of the composition;
hydroxyethyl cellulose (HEC) at about 5.5% by weight relative to the total weight of the composition; and
silicon dioxide at about 2.9% by weight relative to the total weight of the composition.

322. A composition comprising:
oxycodone at about 5% by weight relative to the total weight of the composition;
sucrose acetate isobutyrate (SAIB) at about 40% by weight relative to the total weight of the composition;
triacetin at about 39% by weight relative to the total weight of the composition;
isopropyl myristate (IPM) at about 2.5% by weight relative to the total weight of the composition;
cellulose acetate butyrate (CAB) at about 4.5% by weight relative to the total weight of the composition;
hydroxyethyl cellulose (HEC) at about 5.5% by weight relative to the total weight of the composition; and
silicon dioxide at about 2.9% by weight relative to the total weight of the composition, wherein the composition is encapsulated in a hydroxypropylmethylcellulose (HPMC) capsule.

323. A composition comprising:
a pharmacologically active agent;
a high viscosity liquid carrier material (HVLCM) having a viscosity of at least 5000 cP at 37° C. that does not crystallize neat at 25° C. and 1 atmosphere;
a solvent;
a network former; and
a mineral particle, wherein the HVLCM, the solvent, the network former, and the mineral particle are present in a ratio sufficient to reduce a storage time-dependent change in an in vitro release profile of a composition relative to Reference Formulation A.

324. The composition of 323, wherein Reference Formulation A exhibits more than 10% mean drug release decline, a similarity factor ($f_2$) of less than 50, when stored at 40° C./75% RH for a one month period of time relative to its initial release profile.

325. The composition of 323, wherein the mineral particle is selected from talc, bentonite and kaolin.

326. The composition of 323, wherein the mineral particle is selected from silicon dioxide, zinc oxide, magnesium oxide, titanium oxide, and calcium oxide.

327. The composition of 323, wherein the mineral particle comprises silicon dioxide.

328. The composition of 323, wherein the pharmacologically active agent is selected from opioid, stimulant, and depressant.

329. The composition of 323, wherein the pharmacologically active agent is an opioid.

330. The composition of 323, wherein the pharmacologically active agent is selected from oxycodone, oxymorphone, hydrocodone, and hydromorphone, either in the free base form or a pharmaceutically acceptable salt form thereof.

331. The composition of 323, wherein the pharmacologically active agent is oxycodone.

332. The composition of any one of 323 to 331, wherein the HVLCM is sucrose acetate isobutyrate (SAIB).

333. The composition of any one of 323 to 332, comprising about 35% by weight to about 45% by weight of the HVLCM relative to the total weight of the composition.

334. The composition of any one of 323 to 333, wherein the solvent is selected from triacetin, N-methyl-2-pyrrolidone, 2-pyrrolidone, dimethylsulfoxide, ethyl lactate, propylene carbonate and glycofurol.

335. The composition of any one of 323 to 334, wherein the solvent comprises triacetin.

336. The composition of any one of 323 to 334, wherein the solvent comprises N-methyl-2-pyrrolidone.

337. The composition of any one of 323 to 334, wherein the solvent comprises 2-pyrrolidone.

338. The composition of any one of 323 to 334, wherein the solvent comprises dimethylsulfoxide.

339. The composition of any one of 323 to 334, wherein the solvent comprises ethyl lactate.

340. The composition of any one of 323 to 334, wherein the solvent comprises propylene carbonate.

341. The composition of any one of 323 to 334, wherein the solvent comprises glycofurol.

342. The composition of any one of 323 to 341, comprising about 31% by weight to about 45% by weight of the solvent relative to the total weight of the composition.

343. The composition of 342, comprising about 38% by weight to about 41% by weight of the solvent relative to the total weight of the composition.
344. The composition of any one of 323 to 343, further comprising a rheology modifier.
345. The composition of 344, wherein the rheology modifier is selected from isopropyl myristate (IPM), caprylic/capric triglyceride, ethyl oleate, triethyl citrate, dimethyl phthalate and benzyl benzoate.
346. The composition of 344, wherein the rheology modifier is IPM.
347. The composition of 344, wherein the rheology modifier is caprylic/capric triglyceride.
348. The composition of 344, wherein the rheology modifier is ethyl oleate.
349. The composition of 344, wherein the rheology modifier is triethyl citrate.
350. The composition of 344, wherein the rheology modifier is dimethyl phthalate.
351. The composition of 344, wherein the rheology modifier is benzyl benzoate.
352. The composition of any one of 344-351, comprising about 2% by weight to about 10% by weight of the rheology modifier relative to the total weight of the composition.
353. The composition of any one of 323 to 351, wherein the network former is selected from cellulose acetate butyrate (CAB), cellulose acetate phthalate, ethyl cellulose, hydroxypropyl methylcellulose and cellulose triacetate.
354. The composition of any one of 323 to 353, wherein the network former comprises cellulose acetate butyrate (CAB).
355. The composition of any one of 323 to 354, wherein the network former comprises CAB having a number average molecular weight ranging from 50,000 Daltons to 100,000 Daltons.
356. The composition of any one of 323 to 355, wherein the network former comprises CAB having at least one feature selected from a butyryl content ranging from about 17% to about 41%, an acetyl content ranging from about 13% to about 30%, and a hydroxyl content ranging from about 0.5% to about 1.7%.
357. The composition of any one of 323 to 356, further comprising a hydrophilic agent.
358. The composition of 357, wherein the hydrophilic agent is selected from hydroxyethyl cellulose (HEC), hydroxypropyl cellulose, caboxymethyl cellulose, polyethylene glycol and polyvinylpyrrolidone.
359. The composition of 357, wherein the hydrophilic agent comprises HEC.
360. The composition of any one of 323 to 359, wherein the mineral particle is present in the composition in an amount from about 2.5% by weight to about 4.0% by weight relative to the total weight of the composition.
361. The composition of any one of 323 to 360, wherein the mineral particle is present in the composition in an amount from about 2.5% by weight to about 3.5% by weight relative to the total weight of the composition.
362. The composition of any one of 323 to 361, wherein the mineral particle is present in the composition in an amount from about 2.5% by weight to about 3.2% by weight relative to the total weight of the composition.
363. The composition of any one of 323 to 362, wherein the mineral particle is present in the composition in an amount from about 2.5% by weight to about 3.0% by weight relative to the total weight of the composition.
364. The composition of any one of 323 to 363, wherein the mineral particle is present in the composition at from about 2.5% by weight to about 2.9% by weight relative to the total weight of the composition.
365. The composition of any one of 323 to 364, wherein the composition has a complex viscosity of from about 100 Pa·s to about 300 Pa·s, wherein the complex viscosity is determined at a constant strain of 0.5% and a frequency of 1 Hz and a temperature of 25° C.
366. The composition of any one of 323 to 365, wherein the composition has a complex viscosity of from about 120 Pa·s to about 250 Pa·s, wherein the complex viscosity is determined at a constant strain of 0.5% and a frequency of 1 Hz and a temperature of 25° C.
367. The composition of any one of 323 to 366, wherein the composition has a complex viscosity of from about 140 Pa·s to about 200 Pa·s, wherein the complex viscosity is determined at a constant strain of 0.5% and a frequency of 1 Hz and a temperature of 25° C.
368. The composition of any one of 323 to 367, wherein the ratio of the HVLCM to the solvent in the composition is about 0.6:1 to 1.6:1.
369. The composition of 368, wherein the ratio of the HVLCM to the solvent in the composition is about 0.8:1 to 1.5:1.
370. The composition of 369, wherein the ratio of the HVLCM to the solvent in the composition is about 0.9:1 to 1.5:1.
371. The composition of any one of 323 to 370, wherein the composition comprises:
   about 35% by weight to about 45% by weight of the HVLCM relative to the total weight of the composition,
   about 31% by weight to about 45% by weight of the solvent relative to the total weight of the composition, and
   about 2% by weight to about 10% by weight of the network former relative to the total weight of the composition.
372. The composition of 371, comprising about 0.1% by weight to about 8% by weight of a rheology modifier relative to the total weight of the composition.
373. The composition of 371 or 372, comprising about 2% by weight to about 10% by weight of a hydrophilic agent.
374. The composition of any one of 323 to 373, wherein the composition comprises:
   about 39% by weight to about 41% by weight of the HVLCM relative to the total weight of the composition,
   about 38% by weight to about 40% by weight of the solvent relative to the total weight of the composition, and
   about 4% by weight to about 6% by weight of the network former relative to the total weight of the composition.
375. The composition of any one of 323-374, comprising about 2% by weight to about 3% by weight of a rheology modifier relative to the total weight of the composition.
376. The composition of any one of 323-375, comprising about 5% by weight to about 6% by weight of a hydrophilic agent relative to the total weight of the composition.
377. The composition of any one of 323 to 376, wherein the HVLCM is SAIB, the solvent is triacetin, and the network former is CAB.
378. The composition of 377, comprising IPM.
379. The composition of 377 or 378, comprising HEC.
380. The composition of any one of 323 to 379, wherein the pharmacologically active agent is present in the composition at about 2% by weight to about 50% by weight relative to the total weight of the composition.

381. The composition of any one of 323 to 380, wherein the composition is contained within a capsule.
382. The composition of any one of 323 to 381, wherein the composition is contained within a capsule comprising hydroxypropylmethylcellulose.
383. The composition of any one of 323 to 382, wherein the composition is contained within a hard capsule comprising hydroxypropylmethylcellulose.
384. The composition of any one of 296-310, wherein the opioid is present in the composition at about 5% by weight relative to the total weight of the composition.
385. The composition of any one of 396-311, wherein the composition does not comprise more than 5% water by weight, based on total weight of the composition.
386. The composition of 312, wherein the composition does not comprise more than 2.5% water by weight, based on total weight of the composition.
387. The composition of 312, wherein the composition does not comprise more than 2.0% water by weight, based on total weight of the composition.
388. The composition of any one of 296-311, wherein the composition comprises water at from about 1.0 to about 2.5% by weight, based on total weight of the composition.
389. The composition of 315, wherein the composition comprises water at from about 1.0 to about 2.0% by weight, based on total weight of the composition.
390. The composition of 316, wherein the composition comprises water at from about 1.0 to about 1.5% by weight, based on total weight of the composition.
391. A composition comprising:
 a pharmacologically active agent;
 a high viscosity liquid carrier material (HVLCM) having a viscosity of at least 5000 cP at 37° C. that does not crystallize neat at 25° C. and 1 atmosphere;
 a solvent;
 a network former; and
 a mineral particle, wherein the HVLCM, the solvent, the network former, and the mineral particle are present in a ratio sufficient to reduce inter-capsule variability in an in vitro release profile of the composition relative to Reference Formulation A, when assayed in a USP Apparatus 2 dissolution tester modified to have a 20-mesh basket for containing the composition.
392. The composition of 391, wherein the reduction in inter-capsule variability is evidenced by a % RSD of less than 10% at t=2 hr.
393. The composition of 391, wherein the reduction in inter-capsule variability is evidenced by a % RSD of less than 10% at t=6 hr.
394. The composition of 391, wherein the mineral particle is selected from talc, bentonite and kaolin.
395. The composition of 391, wherein the mineral particle is selected from silicon dioxide, zinc oxide, magnesium oxide, titanium oxide, and calcium oxide.
396. The composition of 391, wherein the mineral particle comprises silicon dioxide.
397. The composition of 391, wherein the pharmacologically active agent is selected from opioid, stimulant, and depressant.
398. The composition of 391, wherein the pharmacologically active agent is an opioid.
399. The composition of 391, wherein the pharmacologically active agent is selected from oxycodone, oxymorphone, hydrocodone, and hydromorphone, either in the free base form or a pharmaceutically acceptable salt form thereof.
400. The composition of 391, wherein the pharmacologically active agent is oxycodone.
401. The composition of any one of 391 to 400, wherein the HVLCM is sucrose acetate isobutyrate (SAIB).
402. The composition of any one of 391 to 401, comprising about 35% by weight to about 45% by weight of the HVLCM relative to the total weight of the composition.
403. The composition of any one of 391 to 402, wherein the solvent is selected from triacetin, N-methyl-2-pyrrolidone, 2-pyrrolidone, dimethylsulfoxide, ethyl lactate, propylene carbonate and glycofurol.
404. The composition of any one of 391 to 403, wherein the solvent comprises triacetin.
405. The composition of any one of 391 to 403, wherein the solvent comprises N-methyl-2-pyrrolidone.
406. The composition of any one of 391 to 403, wherein the solvent comprises 2-pyrrolidone.
407. The composition of any one of 391 to 403, wherein the solvent comprises dimethylsulfoxide.
408. The composition of any one of 391 to 403, wherein the solvent comprises ethyl lactate.
409. The composition of any one of 391 to 403, wherein the solvent comprises propylene carbonate.
410. The composition of any one of 391 to 403, wherein the solvent comprises glycofurol.
411. The composition of any one of 391 to 410, comprising about 31% by weight to about 45% by weight of the solvent relative to the total weight of the composition.
412. The composition of 411, comprising about 38% by weight to about 41% by weight of the solvent relative to the total weight of the composition.
413. The composition of any one of 391 to 412, further comprising a rheology modifier.
414. The composition of 413, wherein the rheology modifier is selected from isopropyl myristate (IPM), caprylic/capric triglyceride, ethyl oleate, triethyl citrate, dimethyl phthalate and benzyl benzoate.
415. The composition of 413, wherein the rheology modifier is IPM.
416. The composition of 413, wherein the rheology modifier is caprylic/capric triglyceride.
417. The composition of 413, wherein the rheology modifier is ethyl oleate.
418. The composition of 413, wherein the rheology modifier is triethyl citrate.
419. The composition of 413, wherein the rheology modifier is dimethyl phthalate.
420. The composition of 413, wherein the rheology modifier is benzyl benzoate.
421. The composition of any one of 413-420, comprising about 2% by weight to about 10% by weight of the rheology modifier relative to the total weight of the composition.
422. The composition of any one of 391 to 420, wherein the network former is selected from cellulose acetate butyrate (CAB), cellulose acetate phthalate, ethyl cellulose, hydroxypropylmethyl cellulose and cellulose triacetate.
423. The composition of any one of 391 to 422, wherein the network former comprises cellulose acetate butyrate (CAB).
424. The composition of any one of 391 to 423, wherein the network former comprises CAB having a number average molecular weight ranging from 50,000 Daltons to 100,000 Daltons.
425. The composition of any one of 391 to 424, wherein the network former comprises CAB having at least one feature selected from a butyryl content ranging from about 17% to about 41%, an acetyl content ranging from about 13% to about 30%, and a hydroxyl content ranging from about 0.5% to about 1.7%.

426. The composition of any one of 391 to 425, further comprising a hydrophilic agent.

427. The composition of 426, wherein the hydrophilic agent is selected from hydroxyethyl cellulose (HEC), hydroxypropyl cellulose, caboxymethyl cellulose, polyethylene glycol and polyvinylpyrrolidone.

428. The composition of 426, wherein the hydrophilic agent comprises HEC.

429. The composition of any one of 391 to 428, wherein the mineral particle is present in the composition in an amount from about 2.5% by weight to about 4.0% by weight relative to the total weight of the composition.

430. The composition of any one of 391 to 429, wherein the mineral particle is present in the composition in an amount from about 2.5% by weight to about 3.5% by weight relative to the total weight of the composition.

431. The composition of any one of 391 to 430, wherein the mineral particle is present in the composition in an amount from about 2.5% by weight to about 3.2% by weight relative to the total weight of the composition.

432. The composition of any one of 391 to 431, wherein the mineral particle is present in the composition in an amount from about 2.5% by weight to about 3.0% by weight relative to the total weight of the composition.

433. The composition of any one of 391 to 432, wherein the mineral particle is present in the composition at from about 2.5% by weight to about 2.9% by weight relative to the total weight of the composition.

434. The composition of any one of 391 to 433, wherein the composition has a complex viscosity of from about 100 Pa·s to about 300 Pa·s, wherein the complex viscosity is determined at a constant strain of 0.5% and a frequency of 1 Hz and a temperature of 25° C.

435. The composition of any one of 391 to 434, wherein the composition has a complex viscosity of from about 120 Pa·s to about 250 Pa·s, wherein the complex viscosity is determined at a constant strain of 0.5% and a frequency of 1 Hz and a temperature of 25° C.

436. The composition of any one of 391 to 435, wherein the composition has a complex viscosity of from about 140 Pa·s to about 200 Pa·s, wherein the complex viscosity is determined at a constant strain of 0.5% and a frequency of 1 Hz and a temperature of 25° C.

437. The composition of any one of 391 to 436, wherein the ratio of the HVLCM to the solvent in the composition is about 0.6:1 to 1.6:1.

438. The composition of 437, wherein the ratio of the HVLCM to the solvent in the composition is about 0.8:1 to 1.5:1.

439. The composition of 438, wherein the ratio of the HVLCM to the solvent in the composition is about 0.9:1 to 1.5:1.

440. The composition of any one of 391 to 439, wherein the composition comprises:
about 35% by weight to about 45% by weight of the HVLCM relative to the total weight of the composition,
about 31% by weight to about 45% by weight of the solvent relative to the total weight of the composition, and
about 2% by weight to about 10% by weight of the network former relative to the total weight of the composition.

441. The composition of 440, comprising about 0.1% by weight to about 8% by weight of a rheology modifier relative to the total weight of the composition.

442. The composition of 440 or 441, comprising about 2% by weight to about 10% by weight of a hydrophilic agent.

443. The composition of any one of 391 to 442, wherein the composition comprises:
about 39% by weight to about 41% by weight of the HVLCM relative to the total weight of the composition,
about 38% by weight to about 40% by weight of the solvent relative to the total weight of the composition, and
about 4% by weight to about 6% by weight of the network former relative to the total weight of the composition.

444. The composition of any one of 391-443, comprising about 2% by weight to about 3% by weight of a rheology modifier relative to the total weight of the composition.

445. The composition of any one of 391-444, comprising about 5% by weight to about 6% by weight of a hydrophilic agent relative to the total weight of the composition.

446. The composition of any one of 391 to 445, wherein the HVLCM is SAIB, the solvent is triacetin, and the network former is CAB.

447. The composition of 446, comprising IPM.

448. The composition of 446 or 447, comprising HEC.

449. The composition of any one of 391 to 448, wherein the pharmacologically active agent is present in the composition at about 2% by weight to about 50% by weight relative to the total weight of the composition.

450. The composition of any one of 391 to 449, wherein the composition is contained within a capsule.

451. The composition of any one of 391 to 450, wherein the composition is contained within a capsule comprising hydroxypropyl methylcellulose.

452. The composition of any one of 391 to 451, wherein the composition is contained within a hard capsule comprising hydroxypropyl methylcellulose.

453. The composition of any one of 391-452, wherein the composition does not comprise more than 5% water by weight, based on total weight of the composition.

454. The composition of 453, wherein the composition does not comprise more than 2.5% water by weight, based on total weight of the composition.

455. The composition of 453, wherein the composition does not comprise more than 2.0% water by weight, based on total weight of the composition.

456. The composition of any one of 391-452, wherein the composition comprises water at from about 1.0 to about 2.5% by weight, based on total weight of the composition.

457. The composition of 456, wherein the composition comprises water at from about 1.0 to about 2.0% by weight, based on total weight of the composition.

458. The composition of 457, wherein the composition comprises water at from about 1.0 to about 1.5% by weight, based on total weight of the composition.

459. A composition comprising:
a pharmacologically active agent;
a high viscosity liquid carrier material (HVLCM) having a viscosity of at least 5000 cP at 37° C. that does not crystallize neat at 25° C. and 1 atmosphere;
a solvent;
a network former; and
a mineral particle, wherein the HVLCM, the solvent, the network former, and the mineral particle are present in a ratio sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

460. A composition comprising:
oxycodone at about 5% by weight to about 10% by weight relative to the total weight of the composition;
sucrose acetate isobutyrate (SAIB);
triacetin;
isopropyl myristate (IPM);
cellulose acetate butyrate (CAB);
hydroxyethyl cellulose (HEC); and
silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce a storage time-dependent change in an in vitro release profile of the composition relative to Reference Formulation A.

461. The composition of 460, wherein Reference Formulation A exhibits more than 10% mean drug release decline, a similarity factor ($f_2$) of less than 50, when stored at 40° C./75% RH for a one month period of time relative to its initial release profile.

462. A composition comprising:
oxycodone at about 5% by weight to about 10% by weight relative to the total weight of the composition;
sucrose acetate isobutyrate (SAIB);
triacetin;
isopropyl myristate (IPM);
cellulose acetate butyrate (CAB);
hydroxyethyl cellulose (HEC); and
silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to reduce inter-capsule variability relative to Formulation A when assayed in a USP Apparatus 2 dissolution tester modified to have a 20-mesh basket for containing the composition.

463. The composition of 462, wherein the reduction in inter-capsule variability is evidenced by a % RSD of less than 10% at t=2 hr.

464. The composition of 462, wherein the reduction in inter-capsule variability is evidenced by a % RSD of less than 10% at t=6 hr.

465. A composition comprising:
oxycodone at about 5% by weight to about 10% by weight relative to the total weight of the composition;
sucrose acetate isobutyrate (SAIB);
triacetin;
isopropyl myristate (IPM);
cellulose acetate butyrate (CAB);
hydroxyethyl cellulose (HEC); and
silicon dioxide, wherein the sucrose acetate isobutyrate (SAIB), triacetin, isopropyl myristate (IPM), cellulose acetate butyrate (CAB), hydroxyethyl cellulose (HEC), and silicon dioxide, are present in a ratio sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

466. A composition comprising:
a pharmacologically active agent; and
combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to inter-capsule variability relative to Reference Formulation A when assayed in a USP Apparatus 2 dissolution tester modified to have a 20-mesh basket for containing the composition.

467. The composition of 466, wherein the increase in reproducibility of release is evidenced by a % RSD of less than 10% at t=2 hr.

468. The composition of 466, wherein the increase in reproducibility of release is evidenced by a % RSD of less than 10% at t=6 hr.

469. A composition comprising:
a pharmacologically active agent; and
combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to provide an in vitro release profile characterized by an inter-capsule variability having a % RSD of less than 10% at t=2 hr as determined by an in vitro dissolution assay using a USP Apparatus 2 dissolution tester modified to have a 20-mesh basket for containing the composition.

470. A composition comprising:
a pharmacologically active agent; and
combined amounts of a high viscosity liquid carrier material (HVLCM) having a viscosity of at least 5000 cP at 37° C. that does not crystallize neat at 25° C. and 1 atmosphere, a solvent, a rheology modifier, silicon dioxide, and a cellulose acetate butyrate, wherein the combined amounts are sufficient to increase reproducibility of release with respect to storage time relative to Reference Formulation A when assayed in a USP Apparatus 2 dissolution tester modified to have a 20-mesh basket for containing the composition.

471. The composition of 470, wherein Reference Formulation A exhibits more than 10% mean drug release decline, a similarity factor ($f_2$) of less than 50, when stored at 40° C./75% RH for a one month period of time relative to its initial release profile.

472. A method for treating pain in a subject, the method comprising:
orally administering to the subject a composition comprising an opioid;
a high viscosity liquid carrier material (HVLCM) having a viscosity of at least 5000 cP at 37° C. that does not crystallize neat at 25° C. and 1 atmosphere;
a solvent;
a network former; and
silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated.

473. The method of 472, wherein the opioid is selected from oxycodone, oxymorphone, hydrocodone, and hydromorphone, either in the free base form or a pharmaceutically acceptable salt form thereof.

474. The method of 472 or 473, wherein the opioid is oxycodone.

475. The method of any one of 472-474, wherein the HVLCM is sucrose acetate isobutyrate (SAIB).
476. The method of any one of 472 to 475, wherein the composition comprises about 35% by weight to about 45% by weight of the HVLCM relative to the total weight of the composition.
477. The method of any one of 472-475, wherein the solvent is selected from triacetin, N-methyl-2-pyrrolidone, 2-pyrrolidone, dimethylsulfoxide, ethyl lactate, propylene carbonate and glycofurol.
478. The method of any one of 472-477, wherein the solvent comprises triacetin.
479. The method of any one of 472 to 478, wherein the composition comprises about 31% by weight to about 45% by weight of the solvent relative to the total weight of the composition.
480. The method of 479, wherein the composition comprises about 38% by weight to about 41% by weight of the solvent relative to the total weight of the composition.
481. The method of any one of 472 to 480, wherein the composition further comprises a rheology modifier.
482. The method of 481, wherein the rheology modifier is selected from isopropyl myristate (IPM), caprylic/capric triglyceride, ethyl oleate, triethyl citrate, dimethyl phthalate and benzyl benzoate.
483. The method of any one of 472-480, wherein the composition further comprises IPM.
484. The method of 483, wherein the composition comprises about 2% by weight to about 10% by weight of the IPM relative to the total weight of the composition.
485. The method of any one of 472-482, wherein the network former is selected from cellulose acetate butyrate (CAB), cellulose acetate phthalate, ethyl cellulose, hydroxypropylmethyl cellulose and cellulose triacetate.
486. The method of any one of 472 to 485, wherein the network former comprises CAB.
487. The method of any one of 472 to 486, wherein the network former comprises CAB having a number average molecular weight ranging from 66,000 Daltons to 83,000 Daltons.
488. The method of any one of 472 to 487, wherein the network former comprises CAB having at least one feature selected from a butyryl content ranging from about 17% to about 38%, an acetyl content ranging from about 13% to about 30%, and a hydroxyl content ranging from about 0.8% to about 1.7%.
489. The method of any one of 472-488, wherein the composition comprises a hydrophilic agent.
490. The method of 489, wherein the hydrophilic agent is selected from hydroxyethyl cellulose (HEC), hydroxypropyl cellulose, caboxymethyl cellulose, polyethylene glycol and polyvinylpyrrolidone.
491. The method of any one of 472-490, wherein the silicon dioxide is present in the composition in an amount from about 2.5% by weight to about 3.5% by weight relative to the total weight of the composition.
492. The method of any one of 472-491, wherein the silicon dioxide is present in the composition in an amount from about 2.5% by weight to about 3.2% by weight relative to the total weight of the composition.
493. The method of any one of 472-492, wherein the silicon dioxide is present in the composition in an amount from about 2.5% by weight to about 3.0% by weight relative to the total weight of the composition.

494. The method of any one of 472-493, wherein the silicon dioxide is present in the composition at about 2.5% by weight to about 2.9% by weight relative to the total weight of the composition.
495. The method of any one of 472 to 494, wherein the composition has a complex viscosity of from about 100 Pa·s to about 300 Pa·s, wherein the complex viscosity is determined at a constant strain of 0.5% and a frequency of 1 Hz and a temperature of 25° C.
496. The method of any one of 472 to 495, wherein the composition has a complex viscosity of from about 120 Pa·s to about 250 Pa·s, wherein the complex viscosity is determined at a constant strain of 0.5% and a frequency of 1 Hz and a temperature of 25° C.
497. The method of any one of 472 to 496, wherein the composition has a complex viscosity of from about 140 Pa·s to about 200 Pa·s, wherein the complex viscosity is determined at a constant strain of 0.5% and a frequency of 1 Hz and a temperature of 25° C.
498. The method of any one of 472 to 497, wherein the ratio of the HVLCM to the solvent in the composition is about 0.6:1 to 1.6:1.
499. The method of 498, wherein the ratio of the HVLCM to the solvent in the composition is about 0.8:1 to 1.5:1.
500. The method of 499, wherein the ratio of the HVLCM to the solvent in the composition is about 0.9:1 to 1.5:1.
501. The method of any one of 472-500, wherein the composition comprises:
about 35% by weight to about 45% by weight of the HVLCM relative to the total weight of the composition,
about 31% by weight to about 45% by weight of the solvent relative to the total weight of the composition, and
about 2% by weight to about 10% by weight of the network former relative to the total weight of the composition.
502. The method of 501, comprising about 0.1% by weight to about 8% by weight of a rheology modifier relative to the total weight of the composition.
503. The method of 501 or 502, comprising about 2% by weight to about 10% by weight of a hydrophilic agent.
504. The method of any one of 472 to 503, wherein the composition comprises:
about 39% by weight to about 41% by weight of the HVLCM relative to the total weight of the composition,
about 38% by weight to about 40% by weight of the solvent relative to the total weight of the composition, and
about 4% by weight to about 6% by weight of the network former relative to the total weight of the composition.
505. The method of any one of 472-504, comprising about 2% by weight to about 3% by weight of a rheology modifier relative to the total weight of the composition.
506. The method of any one of 472-505, wherein the composition comprises about 5% by weight to about 6% by weight of a hydrophilic agent relative to the total weight of the composition.
507. The method of any one of 472-506, wherein the HVLCM is SAIB, the solvent is triacetin, and the network former is CAB.
508. The method of 507, wherein the composition comprises IPM.
509. The method of 507 or 508, wherein the composition comprises HEC.
510. The method of any one of 472 to 509, wherein the pharmacologically active agent is present in the composition at about 2% by weight to about 50% by weight relative to the total weight of the composition.

511. The method of any one of 472 to 510, wherein the composition is contained within a capsule.

512. The method of any one of 472 to 511, wherein the composition is contained within a capsule comprising hydroxypropyl methylcellulose.

513. The method of any one of 472 to 512, wherein the composition is contained within a hard capsule comprising hydroxypropyl methylcellulose.

514. The method of any one of 472-513, wherein the composition is administered no more than twice in a 24-hour period.

515. The method of any one of 472-514, wherein the composition does not comprise more than 5% water by weight, based on total weight of the composition.

516. The method of 515, wherein the composition does not comprise more than 2.5% water by weight, based on total weight of the composition.

517. The method of 515, wherein the composition does not comprise more than 2.0% water by weight, based on total weight of the composition.

518. The method of any one of 472-514, wherein the composition comprises water at from about 1.0 to about 2.5% by weight, based on total weight of the composition.

519. The method of 518, wherein the composition comprises water at from about 1.0 to about 2.0% by weight, based on total weight of the composition.

520. The method of 519, wherein the composition comprises water at from about 1.0 to about 1.5% by weight, based on total weight of the composition.

521. A method for treating pain in a subject, the method comprising:
orally administering to the subject a composition comprising
an opioid;
sucrose acetate isobutyrate (SAIB);
triacetin;
isopropyl myristate (IPM);
cellulose acetate butyrate (CAB);
hydroxyethyl cellulose (HEC); and
silicon dioxide, wherein the silicon dioxide is present in the composition in an amount from about 2.4% by weight to about 5.4% by weight relative to the total weight of the composition, wherein the composition is formulated for oral administration, and one or more symptoms or signs associated with the subject's pain is alleviated.

522. The method of 521, wherein the SAIB is present in the composition in an amount from about 35% by weight to about 45% by weight relative to the total weight of the composition, the triacetin is present in the composition in an amount from about 31% by weight to about 45% by weight relative to the total weight of the composition, the IPM is present in the composition in an amount from about 2% by weight to about 10% by weight relative to the total weight of the composition, the CAB is present in the composition at about 4% by weight to about 6% by weight relative to the total weight of the composition, and the HEC is present in the composition in an amount from about 5% by weight to about 6% by weight relative to the total weight of the composition.

523. The method of 521 or 522, wherein the composition comprises about 38% by weight to about 41% by weight of the triacetin relative to the total weight of the composition.

524. The method of any one of 521 to 523, wherein the composition comprises about 2% by weight to about 3% by weight of the IPM relative to the total weight of the composition.

525. The method of any one of 521 to 524, wherein the CAB has a number average molecular weight ranging from 66,000 Daltons to 83,000 Daltons.

526. The method of any one of 521 to 525, wherein the network former comprises CAB having at least one feature selected from a butyryl content ranging from about 17% to about 38%, an acetyl content ranging from about 13% to about 30%, and a hydroxyl content ranging from about 0.8% to about 1.7%.

527. The method of any one of 521-526, wherein the silicon dioxide is present in the composition in an amount from about 2.5% by weight to about 3.2% by weight relative to the total weight of the composition.

528. The method of any one of 521-527, wherein the silicon dioxide is present in the composition in an amount from about 2.5% by weight to about 3.0% by weight relative to the total weight of the composition.

529. The method of any one of 521-528, wherein the silicon dioxide is present in the composition in an amount from about 2.5% by weight to about 3.0% by weight relative to the total weight of the composition.

530. The method of any one of 521-529, wherein the silicon dioxide is present in the composition in an amount from about 2.5% by weight to about 2.9% by weight relative to the total weight of the composition.

531. The method of any one of 105 to 530, wherein the composition has a complex viscosity of from about 100 Pa·s to about 300 Pa·s, wherein the complex viscosity is determined at a constant strain of 0.5% and a frequency of 1 Hz and a temperature of 25° C.

532. The method of any one of 105 to 531, wherein the composition has a complex viscosity of from about 120 Pa·s to about 250 Pa·s, wherein the complex viscosity is determined at a constant strain of 0.5% and a frequency of 1 Hz and a temperature of 25° C.

533. The method of any one of 105 to 532, wherein the composition has a complex viscosity of from about 140 Pa·s to about 200 Pa·s, wherein the complex viscosity is determined at a constant strain of 0.5% and a frequency of 1 Hz and a temperature of 25° C.

534. The method of any one of 521-533, wherein the opioid is selected from oxycodone, oxymorphone, hydrocodone, and hydromorphone, either in the free base form or a pharmaceutically acceptable salt form thereof.

535. The method of any one of 521-534, wherein the opioid is oxycodone.

536. The method of any one of 521-535, wherein the opioid is present in the composition at about 5% by weight relative to the total weight of the composition.

537. The method of any one of 521-536, wherein the composition is encapsulated for oral administration.

538. The method of any one of 521 to 537, wherein the composition is contained within a capsule.

539. The method of any one of 521 to 538, wherein the composition is contained within a capsule comprising hydroxypropyl methylcellulose.

540. The method of any one of 521 to 539, wherein the composition is contained within a hard capsule comprising hydroxypropyl methylcellulose.

541. The method of any one of 521-537, wherein the composition is administered no more than twice in a 24-hour period.

542. The method of any one of 521-541, wherein the composition does not comprise more than 5% water by weight, based on total weight of the composition.

543. The method of 542, wherein the composition does not comprise more than 2.5% water by weight, based on total weight of the composition.

544. The method of 542, wherein the composition does not comprise more than 2.0% water by weight, based on total weight of the composition.

545. The method of any one of 521-541, wherein the composition comprises water at from about 1.0 to about 2.5% by weight, based on total weight of the composition.

546. The method of 545, wherein the composition comprises water at from about 1.0 to about 2.0% by weight, based on total weight of the composition.

547. The method of 546, wherein the composition comprises water at from about 1.0 to about 1.5% by weight, based on total weight of the composition.

548. A method for treating pain in a subject, the method comprising:
orally administering to the subject a composition comprising oxycodone;
about 35% by weight to about 45% sucrose acetate isobutyrate (SAIB) relative to the total weight of the composition;
about 31% by weight to about 45% of triacetin relative to the total weight of the composition;
about 2% by weight to about 10% by weight of isopropyl myristate (IPM) relative to the total weight of the composition;
about 4% to about 6% by weight of cellulose acetate butyrate (CAB) relative to the total weight of the composition;
about 5% by weight to about 6% by weight of hydroxyethyl cellulose (HEC) relative to the total weight of the composition; and
about 2.4% by weight to about 5.4% by weight of silicon dioxide relative to the total weight of the composition, wherein one or more symptoms or signs associated with the subject's pain is alleviated.

549. A method for treating pain in a subject, the method comprising:
orally administering to the subject a composition comprising oxycodone;
about 39% by weight to about 41% sucrose acetate isobutyrate (SAIB) relative to the total weight of the composition;
about 38% by weight to about 41% of triacetin relative to the total weight of the composition;
about 2% by weight to about 3% by weight of isopropyl myristate (IPM) relative to the total weight of the composition;
about 4% to about 6% by weight of cellulose acetate butyrate (CAB) relative to the total weight of the composition;
about 5% by weight to about 6% by weight of hydroxyethyl cellulose (HEC) relative to the total weight of the composition; and
about 2.5% by weight to about 3.2% by weight of silicon dioxide relative to the total weight of the composition, wherein one or more symptoms or signs associated with the subject's pain is alleviated.

550. A method for treating pain in a subject, the method comprising:
orally administering to the subject a composition comprising about 5% by weight of oxycodone relative to the total weight of the composition;
about 39% by weight to about 41% sucrose acetate isobutyrate (SAIB) relative to the total weight of the composition;
about 38% by weight to about 41% of triacetin relative to the total weight of the composition;
about 2% by weight to about 3% by weight of isopropyl myristate (IPM) relative to the total weight of the composition;
about 4% to about 6% by weight of cellulose acetate butyrate (CAB) relative to the total weight of the composition;
about 5% by weight to about 6% by weight of hydroxyethyl cellulose (HEC) relative to the total weight of the composition; and
about 2.5% by weight to about 3.2% by weight of silicon dioxide relative to the total weight of the composition, wherein one or more symptoms or signs associated with the subject's pain is alleviated.

551. A method for treating pain in a subject, the method comprising:
orally administering to the subject a composition comprising oxycodone at about 5% by weight relative to the total weight of the composition;
sucrose acetate isobutyrate (SAIB) at about 40% by weight relative to the total weight of the composition;
triacetin at about 39% by weight relative to the total weight of the composition;
isopropyl myristate (IPM) at about 2.5% by weight relative to the total weight of the composition;
cellulose acetate butyrate (CAB) at about 4.5% by weight or 4.7% by weight relative to the total weight of the composition;
hydroxyethyl cellulose (HEC) at about 5.5% by weight relative to the total weight of the composition; and
silicon dioxide, wherein the silicon dioxide is present in the composition at about 2.9% by weight relative to the total weight of the composition, wherein the composition is formulated for oral administration, wherein one or more symptoms or signs associated with the subject's pain is alleviated.

552. The method of 550, wherein the composition is contained within a capsule.

553. The method of 550 or 552, wherein the composition is contained within a capsule comprising hydroxypropyl methylcellulose.

554. The method of any one of 550 to 553, wherein the composition is contained within a hard capsule comprising hydroxypropyl methylcellulose.

555. The method any one of 550-554, wherein the composition is administered no more than twice in a 24-hour period.

556. A method of orally administering a composition, comprising:
improving reproducibility of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and
orally administering the composition.

557. A method of orally administering a composition, comprising:
decreasing the variability of an in vitro release profile of a composition by including about 2.4% by weight to about 5.4% by weight, relative to the total weight of the composition, of mineral particle in the composition, wherein the composition also includes a pharmacologically active agent, a high viscosity liquid carrier material (HVLCM) having a viscosity of at least 5000 cP at 37° C. that does not crystallize neat at 25° C. and 1 atmosphere, a solvent, and a network former; and orally administering the composition.

558. A method of orally administering an encapsulated composition, comprising:
forming a composition comprising:
a pharmacologically active agent,
a high viscosity liquid carrier material (HVLCM) having a viscosity of at least 5000 cP at 37° C. that does not crystallize neat at 25° C. and 1 atmosphere,
a solvent,
a network former, and
a mineral particle, wherein the mineral particle is present in the composition in an amount from about 2.4% by weight to about 5.4% by weight relative to the total weight of the composition;
improving an in vitro release profile of the composition by encapsulating the composition in a capsule comprising hydroxypropyl methylcellulose to form an encapsulated composition; and
orally administering the encapsulated composition.

559. A method of orally administering an encapsulated composition, comprising:
forming a composition comprising:
a pharmacologically active agent,
a high viscosity liquid carrier material (HVLCM) having a viscosity of at least 5000 cP at 37° C. that does not crystallize neat at 25° C. and 1 atmosphere,
a solvent,
a network former, and
a mineral particle, wherein the mineral particle is present in the composition in an amount from about 2.4% by weight to about 5.4% by weight relative to the total weight of the composition;
reducing exposure of the composition to water by encapsulating the composition in a capsule comprising hydroxypropyl methylcellulose to form an encapsulated composition; and
orally administering the encapsulated composition.

560. The composition of any one of 1-112 and 228-471, wherein the solvent is selected from triacetin, N-methyl-2-pyrrolidone, 2-pyrrolidone, dimethylsulfoxide, ethyl lactate, propylene carbonate and glycofurol and mixtures thereof 561. The composition of 560, wherein the solvent comprises triacetin.

562. The composition of 561, wherein the solvent is triacetin.

563. The composition of any one of 1-112, 228-471 and 560-562, wherein the rheology modifier is selected from isopropyl myristate (IPM), caprylic/capric triglyceride, ethyl oleate, triethyl citrate, dimethyl phthalate and benzyl benzoate.

564. The composition of 563, wherein the rheology modifier is isopropyl myristate (IPM).

565. The composition of any one of 1-112, 228-471 and 560-564, wherein the cellulose acetate butyrate is a CAB having a number average molecular weight ranging from 50,000 Daltons to 100,000 Daltons.

566. The composition of any one of 1-112, 228-471 and 560-565, wherein the cellulose acetate butyrate is a CAB having at least one feature selected from a butyryl content ranging from about 17% to about 41%, an acetyl content ranging from about 13% to about 30%, and a hydroxyl content ranging from about 0.5% to about 1.7%.

567. The composition of any one of 1-112, 228-471 and 560-566, comprising a surfactant.

568. The composition of 567, wherein the surfactant is saturated polyglycolized glyceride.

569. The composition of any one of 1-112, 228-471 and 560-568, comprising a hydrophilic agent.

570. The composition of 569, wherein the hydrophilic agent is selected from hydroxyethyl cellulose (HEC), hydroxypropyl cellulose, caboxymethyl cellulose, polyethylene glycol and polyvinylpyrrolidone.

571. The composition of any one of 569-570, wherein the hydrophilic agent comprises HEC.

572. The composition of any one of 1-112, 228-471 and 560-571, wherein the composition has a complex viscosity of from about 100 Pa·s to about 300 Pa·s, wherein the complex viscosity is determined at a constant strain of 0.5% and a frequency of 1 Hz and a temperature of 25° C.

573. The composition of any one of 1-112, 228-471 and 560-572, wherein the composition has a complex viscosity of from about 120 Pa·s to about 250 Pa·s, wherein the complex viscosity is determined at a constant strain of 0.5% and a frequency of 1 Hz and a temperature of 25° C.

574. The composition of any one of 1-112, 228-471 and 560-573, wherein the composition has a complex viscosity of from about 140 Pa·s to about 200 Pa·s, wherein the complex viscosity is determined at a constant strain of 0.5% and a frequency of 1 Hz and a temperature of 25° C.

575. The composition of any one of 1-112, 228-471 and 560-574, wherein the pharmacologically active agent is present in the composition in an amount from about 0.1% by weight to about 30% by weight relative to the total weight of the composition.

576. The composition of 575, wherein the pharmacologically active agent is present in the composition in an amount from about 1% by weight to about 10% by weight relative to the total weight of the composition.

577. The composition of any one of 1-112, 228-471 and 560-576, wherein the mineral particle is present in the composition in an amount from about 2.4% by weight to about 5.4% by weight relative to the total weight of the composition.

578. The composition of 577, wherein the mineral particle is present in the composition in an amount from about 2.5% by weight to about 4.0% by weight relative to the total weight of the composition.

579. The composition of 577, wherein the mineral particle is present in the composition in an amount from about 2.5% by weight to about 3.5% by weight relative to the total weight of the composition.

580. The composition of 577, wherein the mineral particle is present in the composition in an amount from about 2.5% by weight to about 3.2% by weight relative to the total weight of the composition.

581. The composition of 577, wherein the mineral particle is present in the composition in an amount from about 2.5% by weight to about 3.0% by weight relative to the total weight of the composition.

582. The composition of 577, wherein the mineral particle is present in the composition at from about 2.5% by weight to about 2.9% by weight relative to the total weight of the composition.

583. A composition as defined in any one of 1-112, 228-471 and 560-582, for use as a medicament.
584. A composition as defined in any one of 1-112, 228-471 and 560-582, for use in a method of treating pain, wherein the composition comprises an opioid.
585. Use of a composition as defined in any one of 1-112, 228-471 and 560-582 for the manufacture of a medicament for treating pain, wherein the composition comprises an opioid.
586. A method for treating pain in a subject, the method comprising administering to the subject a composition as defined in any one of 1-112, 228-471 and 560-582, wherein the composition comprises an opioid and wherein one or more symptoms or signs associated with the subject's pain is alleviated.
587. A composition comprising:
a pharmacologically active agent;
a high viscosity liquid carrier material (HVLCM) having a viscosity of at least 5000 cP at 37° C. that does not crystallize neat at 25° C. and 1 atmosphere; and
a cellulose acetate butyrate,
wherein the composition is encapsulated within a hydroxypropylmethylcellulose capsule, and
wherein the composition within the capsule comprises less than 5% water by weight, based on total weight of the composition within the capsule.
588. A composition comprising:
a pharmacologically active agent;
a high viscosity liquid carrier material (HVLCM) having a viscosity of at least 5000 cP at 37° C. that does not crystallize neat at 25° C. and 1 atmosphere;
a network former; and
a mineral particle, wherein the mineral particle is present in the composition in an amount from about 2.5% by weight to about 3.0% by weight relative to the total weight of the composition.
589. A composition comprising:
an opioid;
sucrose acetate isobutyrate (SAIB);
triacetin;
isopropyl myristate (IPM);
cellulose acetate butyrate (CAB), wherein the CAB has a number average molecular weight ranging from 66,000 Daltons to 83,000 Daltons, and wherein the CAB has at least one feature selected from a butyryl content ranging from about 17% to about 38%, an acetyl content ranging from about 13% to about 30%, and a hydroxyl content ranging from about 0.8% to about 1.7%;
hydroxyethyl cellulose (HEC); and
silicon dioxide, wherein the silicon dioxide is present in the composition in an amount from about 2.5% by weight to about 3.0% by weight relative to the total weight of the composition.
590. The composition of 589, wherein the SAIB is present in the composition in an amount from about 35% by weight to about 45% by weight relative to the total weight of the composition, the triacetin is present in the composition in an amount from about 31% by weight to about 45% by weight relative to the total weight of the composition, the IPM is present in the composition in an amount from about 2% by weight to about 10% by weight relative to the total weight of the composition, the CAB is present in the composition at about 4% to about 6% by weight relative to the total weight of the composition, and the HEC is present in the composition in an amount from about 5% by weight to about 6% by weight relative to the total weight of the composition.
591. The composition of 589 or 590, comprising about 38% by weight to about 41% by weight of the triacetin relative to the total weight of the composition.
592. The composition of any one of 589 to 591, comprising about 2% by weight to about 3% by weight of the IPM relative to the total weight of the composition.
593. The composition of any one of 589 to 592, wherein the composition has a complex viscosity of from about 100 Pa·s to about 300 Pa·s, wherein the complex viscosity is determined at a constant strain of 0.5% and a frequency of 1 Hz and a temperature of 25° C.
594. The composition of any one of 589 to 593, wherein the composition has a complex viscosity of from about 120 Pa·s to about 250 Pa·s, wherein the complex viscosity is determined at a constant strain of 0.5% and a frequency of 1 Hz and a temperature of 25° C.
595. The composition of any one of 589 to 594, wherein the composition has a complex viscosity of from about 140 Pa·s to about 200 Pa·s, wherein the complex viscosity is determined at a constant strain of 0.5% and a frequency of 1 Hz and a temperature of 25° C.
596. The composition of any one of 589 to 595, wherein the opioid is selected from oxycodone, oxymorphone, hydrocodone, and hydromorphone, either in the free base form or a pharmaceutically acceptable salt form thereof.
597. The composition of any one of 589 to 596, wherein the opioid is oxycodone.
598. The composition of any one of 589 to 597, wherein the opioid is present in the composition at about 5% by weight relative to the total weight of the composition.
599. The composition of any one of 589 to 598, wherein the composition does not comprise more than 5% water by weight, based on total weight of the composition.
600. The composition of 599, wherein the composition does not comprise more than 2.5% water by weight, based on total weight of the composition.
601. The composition of 599, wherein the composition does not comprise more than 2.0% water by weight, based on total weight of the composition.
602. The composition of any one of 589 to 601, wherein the composition comprises water at from about 1.0 to about 2.5% by weight, based on total weight of the composition.
603. The composition of 602, wherein the composition comprises water at from about 1.0 to about 2.0% by weight, based on total weight of the composition.
604. The composition of 603, wherein the composition comprises water at from about 1.0 to about 1.5% by weight, based on total weight of the composition.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near one atmosphere. Standard abbreviations may be used, e.g., s or sec, second(s); min, minute(s); h or hr, hour(s); and the like.

Example 1: Time-Dependent Changes in Drug Release Performance of Reference Formulation Reference Formulation A is a capsule product that provides extended release of oral oxycodone. The product is formulated to resist tampering and abuse. Although the product is a semi-solid matrix, the composition is manufactured by a standard liquid-fill manufacturing process. A common viscous composition of the active pharmaceutical ingredient (API), colloidal silicon dioxide (CSD) and hydroxyethyl cellulose (HEC) suspended in a cellulose acetate butyrate (CAB)/sucrose acetate isobutyrate (SAIB)/triacetin (TA)/isopropyl myristate (IPM)/Butylated hydroxytoluene (BHT) solution is filled into a range of capsule sizes to accommodate various dosage strengths.

The composition of Reference Formulation A is as provided below in Table 1A.

TABLE 1A

| Component | Function | % w/w |
|---|---|---|
| Micronized oxycodone base | Active Pharmaceutical Ingredient | 5.13 |
| Sucrose acetate isobutyrate (SAIB) | An esterified sucrose derivative, that is a high viscosity, hydrophobic carrier molecule, which is the base component in the extended release matrix | 40.98 |
| Triacetin (TA) | Hydrophilic solvent that participates in the dissolution or suspension of other components in the extended release matrix | 27.32 |
| Isopropyl Myristate (IPM) | Rheology modifier that participates in the control of drug diffusion from the extended release matrix | 14.23 |
| Cellulose acetate butyrate (CAB) | Polymer additive for abuse deterrence and extended release | 4.74 |
| Hydroxyethyl cellulose (HEC) | Non-ionic, water soluble polymer that participates in the control of drug diffusion from the extended release matrix | 5.69 |
| Colloidal silicon dioxide (CSD) | Suspending agent, viscosity modifier | 1.90 |
| Butylated hydroxytoluene (BHT) | Antioxidant | 0.02 |
| Hard shell capsule | Dosage form encapsulation | Gelatin |

In vitro analysis of Reference Formulation A has shown that it may exhibit time-dependent changes in drug release performance. This is shown, for example, in FIG. 1A, wherein Reference Formulation A (with BHT) stored at 25° C./60% RH for a 22 months period exhibited a decrease in the mean release profile for oxycodone.

Example 2A: Gelatin Vs. HPMC Capsules

It was hypothesized that phase immiscibility could be responsible for the time dependent changes in drug release performance observed for Reference Formulation A. It was further hypothesized that reducing the amount of available water by changing the capsule shell from gelatin (~13-16% w/w water) to HPMC (~4-6% w/w water) could minimize these effects.

Materials and Methods

Figure 1B:
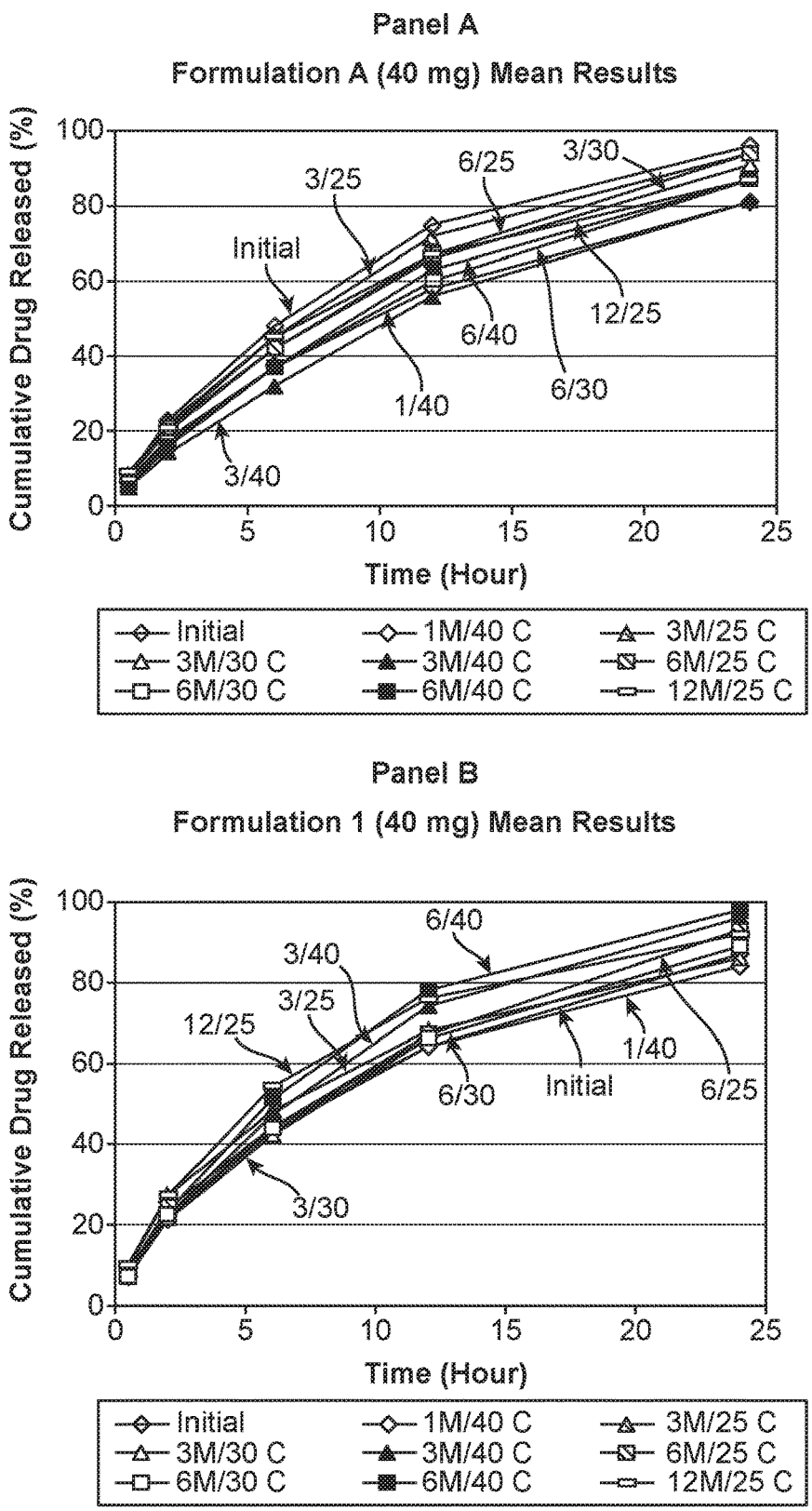
FIG. 1B provides graphs showing the effect of formulating Reference Formulation A in gelatin (Panel A) vs. HPMC (Panel B) capsules.

Dissolution data utilizing the Apparatus 2 method (described below) for Reference Formulation A (without BHT) in gelatin or HPMC capsules stored up to 12 months at 25° C./60% RH, 30° C./65% RH and 40° C./75% RH are shown in FIG. 1B, Panels A and B.

Twelve capsules from each formulation were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Separately, the total water content of a freshly prepared Reference Formulation A formulation in gelatin vs. HPMC capsules was determined. Two preparations were tested for each formulation. The % water (or moisture) was determined by Karl Fischer Coulometric Apparatus and each preparation utilized 5 capsules.

Results

The results for the dissolution experiments are provided in FIG. 1B, Panels A and B. As shown in Panel A, Reference Formulation A in gelatin capsules exhibits a decrease in the mean release profile following storage for 12 months at 25° C., 6 months at 30° C., 6 months at 40° C. and 3 months at 40° C. relative to the initial release profile. In contrast, Reference Formulation A in HPMC capsules exhibited a more stable dissolution profile following storage under the above conditions, with the exception of the 40° C. storage conditions. Inter-capsule dissolution variability was not significantly reduced for Formulation A in HPMC relative to Formulation A in gelatin under the above testing conditions.

The total average water content of Reference Formulation A in gelatin vs. HPMC capsules was found to be 2.2% w/w vs. 1.4% w/w respectively.

Example 2B: Gelatin vs. HPMC Capsules

This study compared two lots of Formulation A (40 mg) prepared without BHT and with the same bulk mass filled into size 00 Licaps® (gelatin) (Lot #1) and Vcaps® Plus (HPMC) capsules (Lot #2). The lots were tested for in vitro dissolution and viscoelastic parameters. In addition, the capsule shells were evaluated by Karl Fischer titration for its potential property change.

Materials and Methods

Dissolution Testing

Two separate tests of the two lots were performed after storage of the lots for approximately 12 months at 25° C./60% RH. The release rate of oxycodone base was determined using a USP Apparatus 3 dissolution tester. Dissolution medium containing 250 ml 0.1 N HCl with 0.02% (w/w) SDS was maintained at 37° C. with 45 dpm (dips per minute) over the course of the 24 hour dissolution test. An glass inner sample tube with two ends covered with 20 mesh SS316 was incorporated to hold the test article. The standard sampling time points were 0.5, 2, 3, 6, 12 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

The results of the dissolution testing experiment are provided in Tables 1B-1D below and FIGS. 1C and 1D.

Rheology Testing

The rheology test was carried out in parallel plates (PP25) at 25° C. using an Anton Paar MCR301 rheometer. The sample was exposed to a constant angular frequency ($10\ s^{-1}$) of increasing dynamic strain (0.1 to 100%).

Water Content by Karl Fischer Titration

Water content of the capsule shell of the two lots was evaluated by Karl Fischer titration using an AquaStar C3000 Karl Fischer Coulometric Titrator. In this experiment, the formulation was completely exuded from the capsule. The capsule shell was cut into small pieces and placed inside a clear sample vial. The vial was crimped with a metal seal cap. In a second vial, which was used as a blank sample, a sufficient amount of anhydrous methanol was transferred to the vial, and the vial was crimped with a metal seal cap. Approximately 1.2 mL of anhydrous methanol from the second vial was added to the sample vial and the weight of methanol introduced was recorded. The sample vial was placed in a mechanical shaker mixing at 300 rpm for about 60 minutes. The percentage water content in the sample was determined by weight gained and calculated against methanol standards.

Results

Dissolution Testing Results

The results of the dissolution testing are provided in Tables 1B-1D below and in FIGS. 1C and 1D.

TABLE 1B

| Time point (hour) | 0.5 | 2 | 3 | 6 | 12 | 24 |
|---|---|---|---|---|---|---|
| Test 1 Dissolution Results, Lot # 1 (n = 6) in gelatin capsules | | | | | | |
| 1 | 21 | 39 | 46 | 62 | 76 | 85 |
| 2 | 29 | 52 | 59 | 72 | 83 | 89 |
| 3 | 23 | 45 | 53 | 69 | 81 | 86 |
| 4 | 21 | 40 | 48 | 65 | 83 | 88 |
| 5 | 19 | 36 | 43 | 57 | 76 | 85 |
| 6 | 19 | 43 | 54 | 70 | 81 | 85 |
| Mean | 22 | 43 | 51 | 66 | 80 | 86 |
| SD | 4 | 6 | 6 | 6 | 3 | 2 |
| % RSD | 18 | 14 | 12 | 9 | 4 | 2 |
| Test 2 Dissolution Results, Lot # 1 (n = 12) in gelatin capsules | | | | | | |
| 1 | 27 | 49 | 57 | 72 | 84 | 88 |
| 2 | 29 | 51 | 60 | 74 | 86 | 91 |
| 3 | 24 | 45 | 52 | 68 | 78 | 84 |
| 4 | 22 | 39 | 45 | 60 | 75 | 85 |
| 5 | 24 | 41 | 49 | 63 | 81 | 89 |
| 6 | 24 | 43 | 50 | 65 | 82 | 90 |
| 7 | 22 | 46 | 53 | 66 | 78 | 85 |
| 8 | 21 | 38 | 43 | 56 | 70 | 83 |
| 9 | 31 | 54 | 62 | 74 | 85 | 89 |
| 10 | 30 | 51 | 58 | 72 | 85 | 91 |
| 11 | 24 | 50 | 58 | 70 | 82 | 89 |
| 12 | 22 | 39 | 45 | 58 | 74 | 88 |
| Mean | 25 | 45 | 53 | 66 | 80 | 88 |
| SD | 4 | 6 | 6 | 6 | 5 | 3 |
| % RSD | 16 | 13 | 13 | 9 | 6 | 3 |

TABLE 1C

| Time point (hour) | 0.5 | 2 | 3 | 6 | 12 | 24 |
|---|---|---|---|---|---|---|
| Test 1 Dissolution Results, Lot # 2 (n = 6) in HPMC capsules | | | | | | |
| 1 | 17 | 45 | 55 | 73 | 85 | 88 |
| 2 | 18 | 53 | 65 | 82 | 90 | 90 |
| 3 | 20 | 35 | 41 | 53 | 70 | 83 |
| 4 | 14 | 34 | 45 | 63 | 78 | 85 |
| 5 | 18 | 38 | 46 | 63 | 80 | 86 |
| 6 | 19 | 45 | 53 | 67 | 81 | 88 |
| Mean | 18 | 42 | 51 | 67 | 81 | 87 |
| SD | 2 | 7 | 9 | 10 | 7 | 3 |
| % RSD | 11 | 17 | 18 | 15 | 9 | 3 |

TABLE 1D

| Time point (hour) | 0.5 | 2 | 3 | 6 | 12 | 24 |
|---|---|---|---|---|---|---|
| Test 2, Dissolution Results, Lot # 2 (n = 12) in HPMC capsules | | | | | | |
| 1 | 18 | 48 | 61 | 80 | 88 | 91 |
| 2 | 18 | 30 | 34 | 43 | 60 | 78 |
| 3 | 10 | 29 | 37 | 54 | 73 | 87 |
| 4 | 18 | 42 | 51 | 69 | 84 | 90 |
| 5 | 18 | 33 | 43 | 60 | 81 | 88 |
| 6 | 16 | 37 | 47 | 68 | 83 | 89 |
| 7 | 21 | 45 | 55 | 77 | 90 | 94 |
| 8 | 20 | 42 | 53 | 73 | 86 | 91 |
| 9 | 19 | 39 | 49 | 71 | 88 | 92 |
| 10 | 20 | 50 | 60 | 74 | 84 | 89 |
| 11 | 22 | 58 | 70 | 85 | 93 | 93 |
| 12 | 29 | 54 | 65 | 79 | 90 | 93 |
| Mean | 19 | 42 | 52 | 69 | 83 | 90 |
| SD | 4 | 9 | 11 | 12 | 9 | 4 |
| % RSD | 21 | 21 | 21 | 17 | 11 | 4 |

Figure 1C:
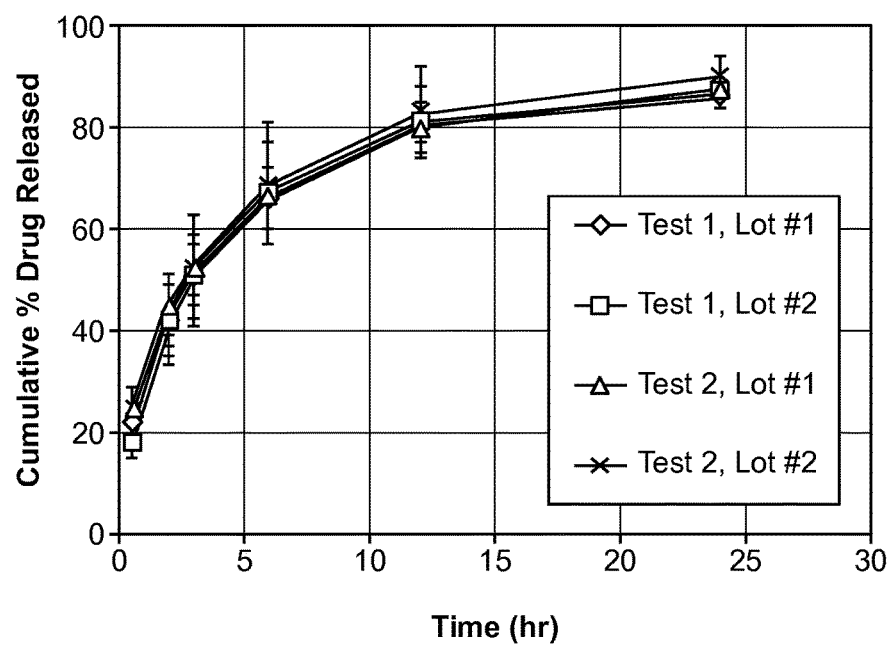
FIG. 1C provides a graph showing comparative plots of Formulation A (without BHT) in gelatin and HPMC capsules. The results of two separate tests are shown.
Figure 1D:
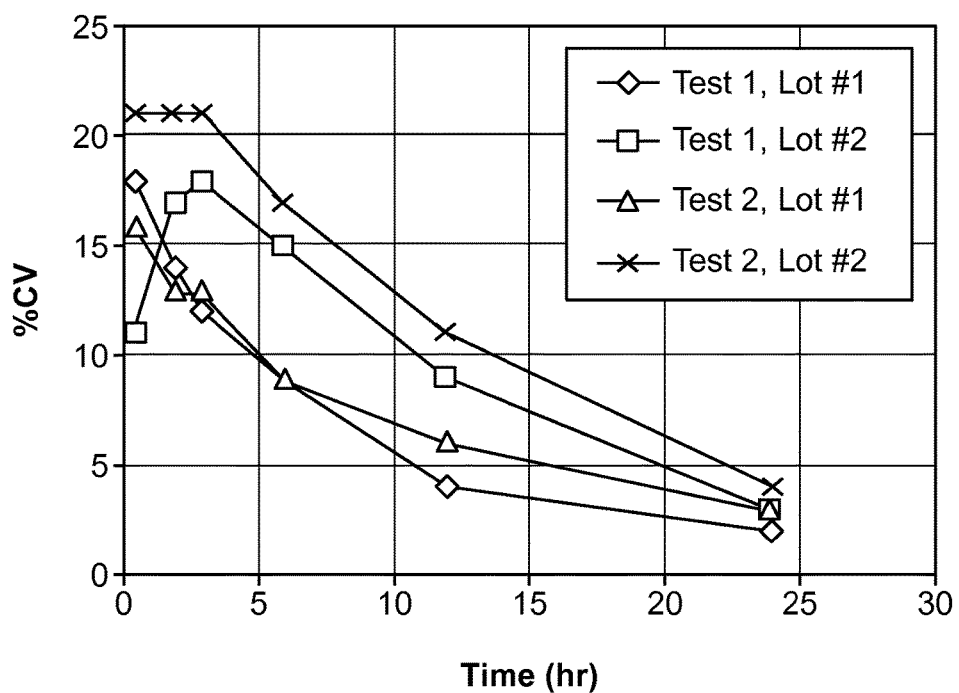
FIG. 1D provides a graph showing the variation of gelatin and HPMC lots using Type 3 dissolution. The results of two separate tests are shown.

FIG. 1C illustrates the dissolution profiles for the data provided in Tables 1B and 1C. The dissolution profiles for both the gelatin and HPMC lots were very similar between the two tests. However, the variation was higher in general for the HPMC lot (FIG. 1D). During the first test, visual observations and photographic evidences were taken at 30 minutes and 20 hours. At 30 minutes, the HPMC lot remained in one single piece while the gelatin lot broke into fragments. However, at the later time (20 hours) the HPMC lot was seen in more small sized pieces. Without intending to be bound by any particular theory, presumably the HPMC lot was more prone to fragmentation after being exposed to the aqueous medium and the fragmentation rate might be more variable than the gelatin capsules.

Rheology Testing Results

Table 1E summarizes the viscoelastic outputs of lots 1 and 2 at the linear viscoelastic (LVE) range. The absolute differences of viscosity $\eta^*$, storage modulus G', and loss modulus G" were 7 Pa·s, 43 Pa, and 56 Pa, respectively lower for the HPMC lot than the gelatin lot. The viscosity differences between the type of capsules are greater than the analytical method variation, which has an estimated standard deviation of approximately ±2 Pa·s, 8 Pa and 14 Pa for $\eta^*$, G' and G", respectively. Although the Formulation A (without BHT) stored in gelatin capsules had a higher viscosity value than the formulation stored in HPMC capsules, this difference did not appear to influence their dissolution profiles.

TABLE 1E

| | all values at LVE range | | | | |
|---|---|---|---|---|---|
| Sample | Complex viscosity $\eta^*$ (Pa·s) | Storage modulus G' (Pa) | Loss modulus G" (Pa) | Damping factor tanδ | Yield Stress[1] (Pa) |
| Lot #1 (Licaps) | 63 | 308 | 553 | 1.80 | 55.3 |
| Lot #2 (Vcaps Plus) | 56 | 265 | 497 | 1.87 | 58.7 |

TABLE 1E-continued

| | all values at LVE range | | | | |
|---|---|---|---|---|---|
| Sample | Complex viscosity η* (Pa · s) | Storage modulus G' (Pa) | Loss modulus G" (Pa) | Damping factor tanδ | Yield Stress[1] (Pa) |
| Absolute difference | 7 | 43 | 56 | −0.07 | −3.4 |

[1]at 5% tolerance of storage modulus G'

Water Content Results

The results of the Karl Fischer Titration are summarized in Tables 1F and 1G below. The water content for the intact non-used capsule shells was found to be as anticipated, i.e. 15% for the gelatin shell and 5.9% for the HPMC shell. The water contents for the Formulation A (without BHT) exposed capsule shells were 3.5% lower for the gelatin lot (11.5%) and 1.6% lower for the HPMC lot (4.3%), compared to the respective intact capsules. The Formulation A (without BHT) gelatin capsule shells lost more water than the Formulation A (without BHT) HPMC capsule shells. Without intending to be bound by any particular theory, the greater water content reduction for the gelatin lot may have occurred between the shell and the bulk mass.

TABLE 1F

Water Content of Lot #1 (gelatin) by Karl Fischer Titration

| Sample ID | Weight of the Capsule (g) | Water content (%) | Change (%) |
|---|---|---|---|
| Intact empty Licaps | 0.120 | 15.0 | — |
| #1 (Licaps) | 0.098 | 11.2 | −3.8 |
| #2 (Licaps) | 0.116 | 11.3 | −3.7 |
| #3 (Licaps) | 0.118 | 12.0 | −3.0 |
| Average | 0.111 | 11.5 | −3.5 |
| Standard deviation | 0.011 | 0.4 | 0.4 |
| % CV | 9.5 | 3.7 | −12.2 |

TABLE 1G

Water Content of Lot #2 (HPMC) by Karl Fischer Titration

| Sample ID | Weight of the Capsule (g) | Water content (%) | Change (%) |
|---|---|---|---|
| Intact empty Vcaps Plus | 0.119 | 5.9 | — |
| #1 (Vcaps Plus) | 0.115 | 4.2 | −1.7 |
| #2 (Vcaps Plus) | 0.126 | 4.4 | −1.6 |
| #3 (Vcaps Plus) | 0.129 | 4.3 | −1.6 |
| Average | 0.123 | 4.3 | −1.6 |
| Standard deviation | 0.007 | 0.1 | 0.1 |
| % CV | 6.1 | 1.8 | −4.8 |

Example 3: Preparation of Extended Release Oxycodone Compositions for PK and BA Analysis Compositions were prepared, for example, as follows to provide the compositions indicated in Table 2 (below). Sucrose Acetate Isobutyrate (SAIB) was transferred into a Ross mixer at an elevated temperature (50° C.) and dissolved in triacetin (TA) and isopropyl myristate (IPM) and uniformly mixed. When present in the composition, butylated hydroxytoluene (BHT) was added prior to uniformly mixing with TA and IPM. Colloidal silicon dioxide (CSD) particles were added into the SAIB solution in the Ross mixer and were dispersed uniformly. Cellulose acetate butyrate (CAB) particles were sieved and fed into the Ross mixer and dispersed and dissolved in the content of the mixer at the elevated temperature. The oxycodone particles were introduced into the Ross mixer and dispersed in the content of the mixer, keeping the same process temperature. Hydroxyethyl cellulose (HEC) was then added into the Ross mixer and dispersed. In order to assure complete dispersion of all particles (oxycodone, $SiO_2$, HEC), high shear mixers (dispenser and emulsifier) may be used for pre-set time periods after the introduction of these solid particles into the Ross mixer.

For the capsule filling operation, the compositions were transferred from the Ross mixer via a temperature controlled (or insulated) (at 50-60° C.) pump and hoses to the capsule filling equipment. The temperature of the compositions was maintained at 50-60° C. during the capsule filling operations.

Individual compositions were encapsulated within size 4 (5 mg dose) or size 00 (40 mg dose) gelatin or HPMC capsules. Encapsulation was achieved using a Capsugel CFS 1000™ apparatus. It was observed that increasing the temperature of the composition and the filling pump, e.g., from about 60° C. to about 75° C., reduced the stringiness of the composition, thereby facilitating the separation of the composition from the nozzle into the capsule shell and allowing clean movement to the next capsule station. The reduced stringiness of the composition also allowed the motor speed setting (fill rate) to be increased, e.g., to a motor speed set point range of about 50% to about 60% (500-600 capsules per hour). Size 00 capsules were successfully filled using, e.g., a 1.8 mm filling nozzle. Size 4 capsules were successfully filled using, e.g., a 2.0-2.2 mm nozzle. An exemplary composition preparation and encapsulation method is depicted graphically in FIG. 2.

The compositions indicated in Table 2 (below) were prepared for use in Examples 4-6 below. Composition components were blended and individual compositions were encapsulated within gelatin or HPMC capsules as described above.

TABLE 2

| | % w/w of component of each formulation Formulation Identification | | | | | | | | | |
|---|---|---|---|---|---|---|---|---|---|---|
| Composition | Reference Formulation A in Gelatin without BHT) | 1 (Reference Formulation A in HPMC without BHT) | 2 | 3 | 4 | 5 | 6 | 7 | 8 | 9 |
| Micronized oxycodone base | 5.13 | 5.13 | 5.13 | 5.13 | 5.13 | 5.13 | 5.13 | 5.13 | 5.13 | 5.13 |
| Sucrose acetate isobutyrate (SAIB) | 40.99 | 40.99 | 46.69 | 48.11 | 40.98 | 40.98 | 36.74 | 38.98 | 40.38 | 39.98 |

TABLE 2-continued

| Composition | Reference Formulation A in Gelatin without BHT) | 1 (Reference Formulation A in HPMC without BHT) | 2 | 3 | 4 | 5 | 6 | 7 | 8 | 9 |
|---|---|---|---|---|---|---|---|---|---|---|
| Triacetin (TA) | 27.32 | 27.32 | 27.32 | 27.31 | 32.55 | 39.08 | 37.56 | 39.08 | 39.08 | 39.08 |
| Isopropyl Myristate (IPM) | 14.23 | 14.23 | 14.23 | 7.12 | 9.00 | 2.48 | 8.25 | 2.48 | 2.48 | 2.48 |
| Cellulose acetate butyrate (CAB) | 4.74 | 4.74 | 4.74 | 4.74 | 4.74 | 4.74 | 4.74 | 4.74 | 4.74 | 4.74 |
| Hydroxyethyl cellulose (HEC) | 5.69 | 5.69 | 0.00 | 5.69 | 5.69 | 5.69 | 5.69 | 5.69 | 5.69 | 5.69 |
| Colloidal silicon dioxide (CSD) | 1.90 | 1.90 | 1.90 | 1.90 | 1.90 | 1.90 | 1.90 | 3.90 | 2.50 | 2.90 |
| Capsule Shell | Gelatin | HPMC | HPMC | HPMC | HPMC | HPMC | HPMC | HPMC | HPMC | HPMC |

% w/w of component of each formulation / Formulation Identification

Example 4: PK Analysis of Extended Release Oxycodone Compositions (Ref. Formulation A and Formulations 2, 3 and 4)

Materials and Methods

This study was an open-label, single-dose, randomized, crossover study of the pharmacokinetics and bioavailability of oxycodone after administration of 40 mg doses of four extended release oxycodone compositions and oxycodone in solution in fed state to healthy volunteers.

The study was intended to evaluate the in vivo performance of several variants of Reference Formulation A (primarily HEC, IPM, and SAIB) and the effect of changing the capsule shell from gelatin to hydroxylpropyl methylcellulose (HPMC).

The study was conducted as an open-label, single-dose, 5-way crossover study in 16 healthy adult volunteers. The treatments (Reference Formulation A, three modified oxycodone compositions Formulation 1 (Reference Formulation A in HPMC), Formulation 2 and Formulation 3, and an oral oxycodone solution; see Table 3) were administered under naltrexone blockade and following ingestion of an intermediate-size breakfast (~450 calories). The primary objective was to estimate the pharmacokinetics and bioavailability of oxycodone following single oral 40 mg doses of three modified compositions relative to the Reference Formulation A. The oral solution was included for the purpose of exploratory in vitro in vivo correlation analysis.

TABLE 3

| Reference Formulation A (without BHT) | Gelatin capsule shell, 40 mg oxycodone | Reference |
|---|---|---|
| Formulation 1 (Reference Formulation A in HPMC) | HPMC capsule shell, 40 mg oxycodone | Test |
| Formulation 2 | HPMC capsule shell without HEC, 40 mg oxycodone | Test |
| Formulation 3 | HPMC capsule shell with 50% reduced IPM content and increase in SAIB, 40 mg oxycodone | Test |
| Oral solution | Oral solution of oxycodone 40 mg | Oral solution |

Results

Figure 3:
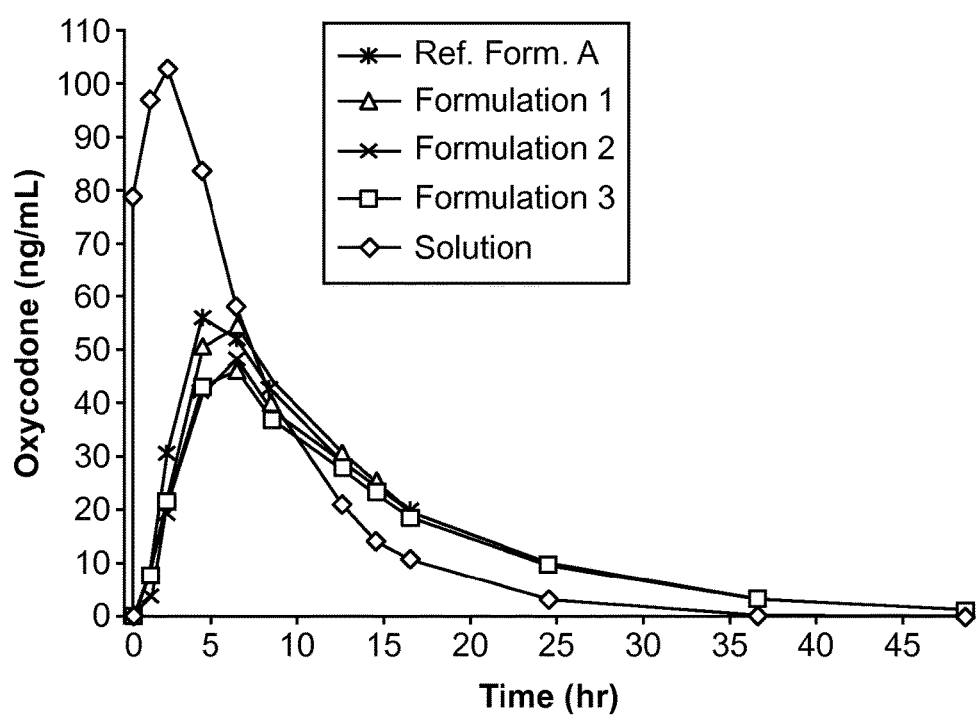
FIG. 3 is a graph showing mean plasma oxycodone concentration profiles following administration of Reference Formulation A (without BHT) and Formulations 1-3.

The mean plasma oxycodone concentration profiles are shown in FIG. 3. The mean (CV %) values for the oxycodone PK parameters are summarized in Table 4, below, along with the geometric mean ratios and 90% confidence intervals for each test composition relative to the Reference Formulation A. Compared with the rapid oral absorption characteristics of the oral solution, Reference Formulation A and the 3 modified oxycodone compositions demonstrated drug delivery characteristics consistent with extended release of the Reference Formulation A. The results demonstrated that changing the capsule shell from gelatin to HPMC did not significantly affect the controlled-release characteristics of the composition based on the geometric mean ratios for C. and AUC. In contrast, the C. and AUC values for the test Formulations 2 and 3, which involved significant changes in excipients—either a removal of HEC (Formulation 2) or a 50% reduction in IPM and corresponding increase in SAIB—the key hydrophobic constituent of Reference Formulation A—(Formulation 3), were generally slightly lower on $C_{max}$ (by approx. 15-20%) than those for Reference Formulation A even though their controlled-release characteristics were retained as compared with the oral solution (Table 4). However, AUC point estimates were similar to the Reference Formulation A (within approx. 90-100% of Reference Formulation A).

TABLE 4

PK Summary

| Parameter (Units) | Reference Formulation A (without BHT) (N = 14) | Formulation 1 (N = 16) | Formulation 2 (N = 14) | Formulation 3 (N = 13) | Oral Solution (N = 14) |
|---|---|---|---|---|---|
| $C_{max}$ (ng/mL) | 62.8 (34) | 58.5 (26) | 51.1 (26) | 55.0 (36) | 116 (20) |
| $T_{max}$ (hr) | 5.0 (2.0-6.0) | 6.0 (2.0-6.0) | 6.0 (4.0-6.1) | 4.0 (2.0-8.0) | 2.0 (0.5-6.0) |
| $AUC_{last}$ (ng*hr/mL) | 752 (12) | 745 (21) | 691 (27) | 676 (24) | 817 (17) |

TABLE 4-continued

| | | | | | |
|---|---|---|---|---|---|
| $AUC_{inf}$ (ng*hr/mL) | 772 (13) | 764 (22) | 712 (28) | 708 (23) | 818 (17) |
| $t_{1/2}$ (hr) | 7.88 (3.01) | 8.01 (3.03) | 8.56 (2.66) | 9.72 (3.86) | 5.83 (0.58) |

BA Assessment

Bioavailability (%) Relative to Formulation A
[90% Confidence Interval]

| Parameter | Formulation 1 | Formulation 2 | Formulation 3 |
|---|---|---|---|
| $C_{max}$ | 92.8 | 80.1 | 87.5 |
| | [77.5, 111.0] | [66.5, 96.4] | [72.5, 105.6] |
| $AUC_{inf}$ | 100.5 | 92.1 | 91.6 |
| | [91.4, 110.5] | [83.5, 101.5] | [83.0, 101.1] |

Geometric mean (% CV) for AUC, $C_{max}$; median (range) for $T_{max}$; arithmetic mean (±SD) for $t_{1/2}$.

Example 5: PK and BA Analysis of Extended Release Oxycodone Compositions (Ref. Formulation A and Formulations 4, 5, 6, 7 and $5^A$)

Materials and Methods

This study was intended to evaluate the in vivo performance of several variants of Reference Formulation A (primarily changes in the relative amounts of TA and IPM). In addition, Formulation 7—a slight variant of Formulation 5, differing only with respect to silicon dioxide (CSD) content—was evaluated as an add-on treatment arm to complete the study. Likewise, the pharmacokinetics and dose proportionality of a 5 mg dose of the 40 mg test Formulation 5 after the initial 4-way crossover portion of the study with Reference Formulation A, 4, 5, and 6 was completed. HPMC capsule shells were used in each modified oxycodone composition, while gelatin capsule shells were used for Reference Formulation A.

This was an open-label, single-dose, randomized, crossover study in healthy adult (18-55 years) male and female volunteers. Twenty (N=20) subjects who met study eligibility criteria were enrolled. The study occurred in three parts. In Part I, three modified oxycodone compositions (Formulations 4, 5, and 6) were compared with Reference Formulation A using a standard single-dose, 4-period, crossover study design, with at least a one-week washout period between doses. Following the completion of Part I, the pharmacokinetic results were reviewed and the test composition that had the PK profile closest to that of Reference Formulation A was selected for Part II (Period 5) to evaluate dose proportionality of the 5 mg strength. After completion of Part II, the protocol was amended to estimate the relative bioavailability of an additional composition (Formulation 7), as part of an add-on, fixed-sequence study design (Part III, Period 6), in the same study population.

All compositions were administered under naltrexone blockade and following ingestion of an intermediate-size breakfast (~450 calories).

Results

Figure 4:
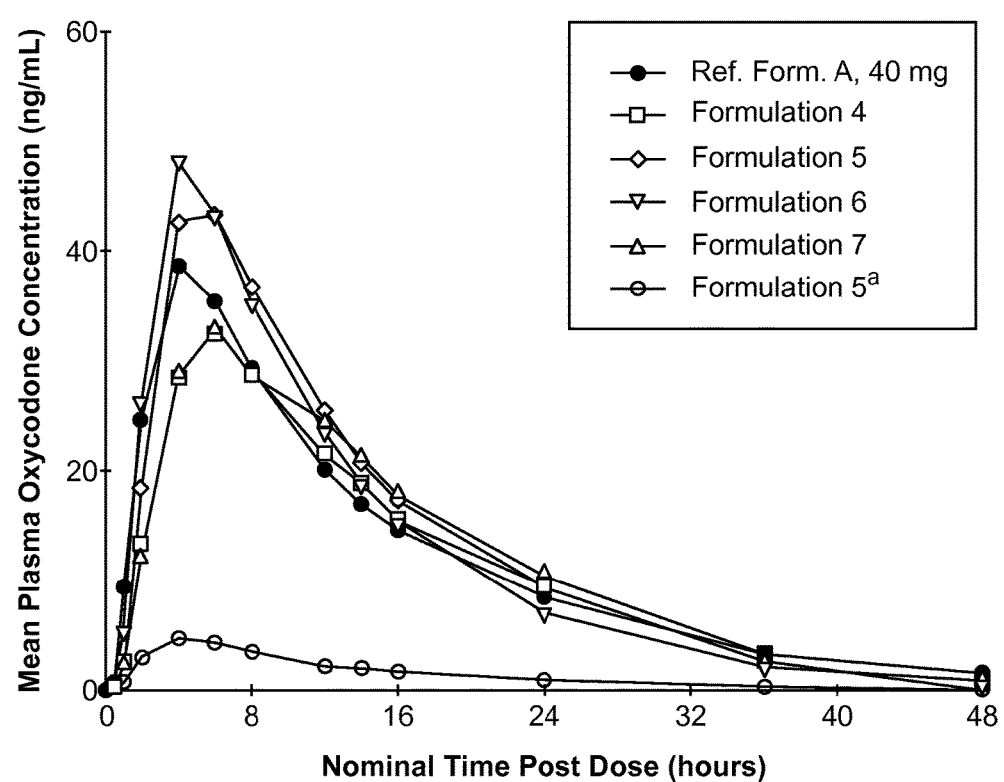
FIG. 4 is a graph showing mean plasma oxycodone concentration profiles following administration of Reference Formulation A (without BHT) and Formulations 4-7 and Formulation $5^a$.

The mean plasma oxycodone concentration profiles and summary statistics for oxycodone PK parameters following single oral doses of each composition tested in this study are shown in FIG. 4 and Table 5, respectively. The initial study results indicated that Formulation 5 had the oxycodone PK and BA characteristics closest to Reference Formulation A with respect to in vivo performance. Therefore, Formulation 5 was selected to establish the dose-proportionality relationship between the 5 mg and 40 mg dosage strengths. The statistical analysis results for relative bioavailability of Formulations 4, 5, 6, and 7 vs. Reference Formulation A, and for the dose proportionality relationship with the 5 mg dosage form (Formulation 5) are also shown in Table 5.

TABLE 5

PK Summary

| Parameter (Units) | Reference Formulation A (without BHT) (N = 19) | Formulation 4 (N = 20) | Formulation 5 (N = 20) | Formulation 6 (N = 20) | Formulation 7 (N = 18) | Formulation $5^a$ (N = 19) |
|---|---|---|---|---|---|---|
| Dose | 40 mg | 40 mg | 40 mg | 40 mg | 40 mg | 5 mg |
| $C_{max}$ (ng/mL) | 41.3 (41) | 32.6 (29) | 46.4 (39) | 52.1 (35) | 35.5 (37) | 4.88 (29) |
| $T_{max}$ (hr) | 4.0 (2.0-8.0) | 6.0 (4.0-12.0) | 6.0 (4.0-8.0) | 4.0 (2.0-12.0) | 6.0 (4.0-14.0) | 4.0 (2.0-8.0) |
| $AUC_{last}$ (ng*hr/mL) | 581 (23) | 523 (25) | 592 (22) | 587 (19) | 571 (19) | 62.8 (27) |
| $AUC_{inf}$ (ng*hr/mL) | 605 (23) | 544 (24) | 600 (22) | 596 (19) | 580 (19) | 66.4 (26) |
| $t_{1/2}$ (hr) | 9.20 + 2.91 | 8.95 + 2.83 | 6.70 + 1.14 | 7.07 + 1.81 | 6.36 + 1.74 | 8.65 + 2.74 |

TABLE 5-continued

BA Assessment

| Parameter | Bioavailability (%) Relative to Formulation A [90% Confidence Interval] | | | | |
|---|---|---|---|---|---|
| Formulation | 4 | 5 | 6 | 7 | 5[b] |
| Dose | 40 mg | 40 mg | 40 mg | 40 mg | 5 mg |
| $C_{max}$ | 79.5 [68.6, 92.1] | 113.3 [97.7, 131.3] | 127.2 [109.7, 147.3] | 85.1 [73.4, 98.6] | 84.1 [72.0, 98.2] |
| $AUC_{inf}$ | 89.2 [84.4, 94.2] | 98.4 [93.1, 104.0] | 97.8 [92.6, 103.3] | 93.5 [87.2, 100.2] | 88.7 [81.1, 97.1] |

Geometric mean (% CV) for AUC, $C_{max}$; median (range) for $T_{max}$; arithmetic mean (±SD) for $t_{1/2}$.
[a]similar in composition to Formulation 5 except for drug content (5 mg)
[b]dose-normalized comparison relative to Formulation 5

The above results indicate that each modified composition tested behaved like a controlled-release composition similar to the Reference Formulation A, with median $T_{max}$ values ranging between 4 and 6 hours (compared with 1-hour when oxycodone is administered as an immediate-release composition; data not shown). The study also revealed that changing the ratio of certain excipients in the Reference Formulation A can result in varying degrees of changes in oxycodone $C_{max}$ (approx. −21% to +27%), with similar extent of bioavailability.

Of the three compositions tested, Formulation 5, with a $C_{max}$ ratio of approximately 113% and 90% CI of 97.7-131.3%, was considered closest to the Reference Formulation A and, therefore, was selected for evaluation at the 5 mg dose in Part II to assess the dose proportionality relationship. In general, there was a dose-related increase in oxycodone $C_{max}$ (4.9 ng/mL vs. 46.4 ng/mL) and $AUC_{inf}$ (66.4 ng·h/mL vs. 600 ng·h/mL) as shown in Table 5.

After completing the PK evaluations for Reference Formulation A and Formulations 4, 5, and 6, an additional treatment arm was added to the study to determine the bioavailability of Formulation 7 (a slight variant of Formulation 5 with increased CSD content). The results of this study suggest that increasing CSD in the composition from 1.9% to 3.9% can potentially decrease $C_{max}$ by approximately 15% relative to Reference Formulation A, without substantially impacting the extent of absorption.

Example 6: PK Analysis of Extended Release Oxycodone Compositions (Ref. Formulation A and Formulations 8 and 9)

Materials and Methods

This study was an open-label, single-dose, randomized crossover study to evaluate the pharmacokinetics and relative bioavailability of oxycodone following oral administration of 40 mg doses.

The test compositions in this study were prepared based on the results from Example 5 above, which suggested that making intermediate adjustments to the CSD content—i.e., relative to the 1.9% CSD content in Formulation 5 and the 3.9% CSD content in Formulation 7—had the potential to provide in vivo drug delivery characteristics of the modified oxycodone composition similar to Reference Formulation A. This study was designed to evaluate the PK and bioavailability of single oral 40 mg doses of modified compositions (Formulations 8 and 9) compared with Reference Formulation A.

This was a randomized, open-label, single-dose, 4-treatment, 4-period, crossover study in healthy volunteers. Eighteen (18) subjects aged 18-55 years who met inclusion and exclusion criteria were enrolled. Two test modified oxycodone compositions (i.e., Formulations 8 and 9,) and the Reference Formulation A were evaluated under fed conditions.

All subjects were to be administered 50 mg of naltrexone HCl by mouth at the following times: 12 hours before, 30 minutes before, and 12 hours after study drug administration to minimize the risk of opioid-related AEs. The results are shown below.

Results

Figure 5:
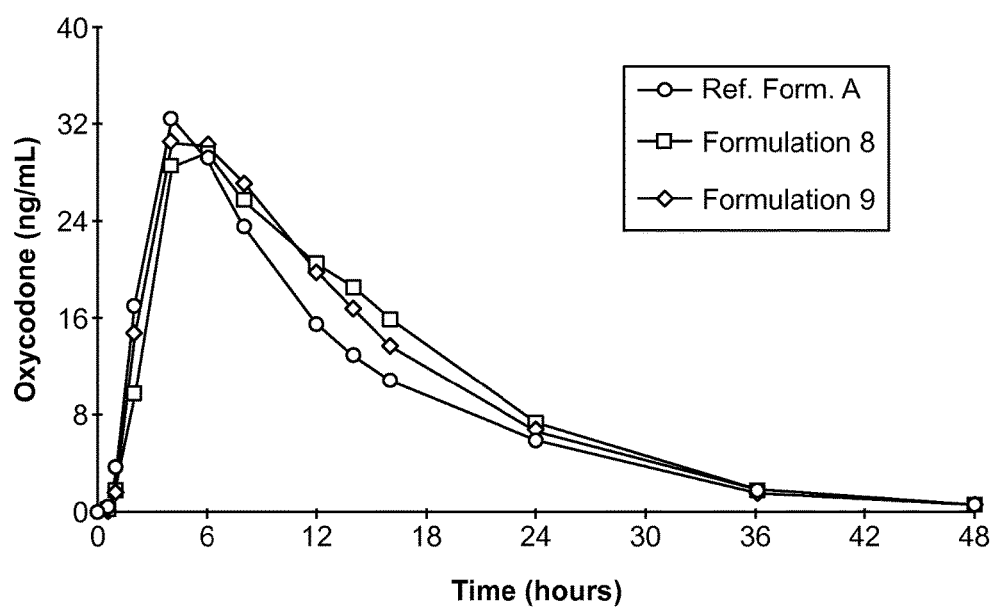
FIG. 5 is a graph showing mean plasma oxycodone concentration profiles following administration of Reference Formulation A (without BHT) and Formulations 8 and 9.

The mean plasma oxycodone concentration profiles for oxycodone PK parameters following single oral doses of each composition tested in the study are shown in FIG. 5. The summary statistics and statistical analysis are given in Table 6, below.

TABLE 6

PK Sumary

| Parameter (Units) | Reference Formulation A (without BHT) | Formulation 8 | Formulation 9 |
|---|---|---|---|
| N | 18 | 18 | 18 |
| $C_{max}$ (ng/mL) | 31.2 (50) | 32.8 (36) | 34.8 (34) |
| $T_{max}$ (hr) | 4.0 (4.0-8.0) | 6.0 (4.0-16.0) | 6.0 (4.0-12.0) |
| $AUC_{last}$ (ng*hr/mL) | 396 (37) | 454 (29) | 447 (28) |
| $AUC_{inf}$ (ng*hr/mL) | 403 (37) | 461 (29) | 453 (28) |
| $t_{1/2}$ (hr) | 7.4 ± 1.7 | 7.1 ± 1.4 | 6.7 ± 1.9 |

TABLE 6-continued

BA Assessment

Bioavailability (%) Relative to Formulation A [90% Confidence Interval]
Formulation

| Parameter | 8 | 9 |
|---|---|---|
| $C_{max}$ | 105.2 [87.6, 126.3] | 111.7 [93.0, 134.1] |
| $AUC_{inf}$ | 114.5 [104.6, 125.4] | 112.4 [102.7, 123.1] |

Geometric mean (% CV) for AUC, Cmax; median (range) for Tmax; arithmetic mean (±SD) for $t_{1/2}$.

The results of the relative BA study indicate that the two modified oxycodone compositions (Formulations 8 and 9) had similar in vivo characteristics with respect to the rate and extent of oxycodone absorption. Each test composition had qualitatively similar PK profiles and bioavailability values, consistent with the desired controlled-release characteristics for a modified oxycodone composition. The $C_{max}$ and AUC ratios for Formulations 8 and 9 were both slightly higher compared to Reference Formulation A, which seemed to underperform slightly with respect to oxycodone exposure parameters (C. and AUC). Nevertheless, there was no apparent difference in oxycodone bioavailability ($C_{max}$ or AUC) with the CSD content used in this study for Formulation 8 (2.5%) and Formulation 9 (2.9%) based on similar point estimates and overlapping 90% confidence intervals of Test/Reference ratios. Overall, the preliminary study results indicated that Formulation 8 and 9 were indistinguishable with respect to PK and bioavailability.

Example 7: Dissolution Performance for Reference Formulation A and Formulations 1-6

Materials and Methods

Dissolution data utilizing the Apparatus 2 method (described below) for Reference Formulation A (without BHT) and Formulations 1 to 3 stored up to 12 months and Formulations 4 to 6 stored up to 6 months at accelerated conditions (40° C./75% RH) and long term storage conditions (25° C./60% RH) are shown in Table 7 and Table 8.

Twelve capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

The results of the in vitro dissolution analysis are shown in Table 7 and Table 8 below.

TABLE 7

| Storage Conditions | Check Point | Ref. Formulation A | | | Formulation 1 | | | Formulation 2 | | | Formulation 3 | | |
|---|---|---|---|---|---|---|---|---|---|---|---|---|---|
| | | Hours | Mean (%) | Range (%) | Hours | Mean (%) | Range (%) | Hours | Mean (%) | Range (%) | Hours | Mean (%) | Range (%) |
| Initial | 0 | 2 | 23 | 20-31 | 2 | 22 | 18-31 | 2 | 24 | 18-30 | 2 | 18 | 15-27 |
| | | 6 | 48 | 42-56 | 6 | 43 | 33-58 | 6 | 38 | 28-48 | 6 | 34 | 28-46 |
| | | 24 | 96 | 86-104 | 24 | 87 | 68-100 | 24 | 59 | 46-74 | 24 | 64 | 50-80 |
| 25° C./ 60% RH | 3 months | 2 | 22 | 17-28 | 2 | 27 | 22-30 | 2 | 18 | 15-21 | 2 | 17 | 12-24 |
| | | 6 | 44 | 37-52 | 6 | 48 | 37-55 | 6 | 31 | 25-37 | 6 | 29 | 23-41 |
| | | 24 | 94 | 85-100 | 24 | 86 | 75-94 | 24 | 56 | 44-69 | 24 | 56 | 42-71 |
| | 6 months | 2 | 21 | 16-28 | 2 | 24 | 19-28 | 2 | 21 | 17-24 | 2 | 18 | 13-25 |
| | | 6 | 42 | 36-54 | 6 | 44 | 36-49 | 6 | 39 | 34-42 | 6 | 32 | 25-43 |
| | | 24 | 94 | 80-101 | 24 | 93 | 90-108 | 24 | 66 | 58-72 | 24 | 60 | 53-72 |
| | 12 months | 2 | 21 | 17-25 | 2 | 27 | 21-30 | 2 | 25 | 19-32 | 2 | 20 | 16-25 |
| | | 6 | 45 | 38-53 | 6 | 54 | 44-63 | 6 | 40 | 30-52 | 6 | 35 | 29-45 |
| | | 24 | 87 | 79-92 | 24 | 92 | 84-97 | 24 | 60 | 45-75 | 24 | 64 | 51-72 |
| 40° C./ 75% RH | 1 month | 2 | 18 | 14-28 | 2 | 21 | 17-25 | Not Evaluated | | | | | |
| | | 6 | 37 | 29-50 | 6 | 44 | 36-52 | | | | | | |
| | | 24 | 81 | 71-92 | 24 | 84 | 78-92 | | | | | | |
| | 3 months | 2 | 14 | 11-16 | 2 | 22 | 19-26 | | | | | | |
| | | 6 | 31 | 27-36 | 6 | 47 | 41-54 | | | | | | |
| | | 24 | 81 | 68-90 | 24 | 96 | 90-102 | | | | | | |
| | 6 months | 2 | 16 | 12-24 | 2 | 23 | 19-30 | | | | | | |
| | | 6 | 37 | 29-48 | 6 | 51 | 45-58 | | | | | | |
| | | 24 | 87 | 75-98 | 24 | 98 | 95-103 | | | | | | |

TABLE 8

| Storage Conditions | Check Point | Formulation 4 | | | Formulation 5 | | | Formulation 6 | | |
|---|---|---|---|---|---|---|---|---|---|---|
| | | Hours | Mean (%) | Range (%) | Hours | Mean (%) | Range (%) | Hours | Mean (%) | Range (%) |
| Initial | 0 | 2 | 25 | 18-31 | 2 | 29 | 23-35 | 2 | 28 | 24-32 |
| | | 6 | 48 | 37-59 | 6 | 61 | 53-74 | 6 | 55 | 50-63 |
| | | 24 | 85 | 72-95 | 24 | 98 | 93-103 | 24 | 95 | 90-102 |
| 25° C./ 60% RH | 3 months | 2 | 24 | 19-33 | 2 | 29 | 24-37 | 2 | 29 | 26-38 |
| | | 6 | 47 | 34-62 | 6 | 63 | 56-74 | 6 | 60 | 53-72 |
| | | 24 | 86 | 57-98 | 24 | 103 | 95-100 | 24 | 103 | 95-106 |
| | 6 months | 2 | 25 | 18-29 | 2 | 28 | 22-34 | 2 | 30 | 26-37 |
| | | 6 | 51 | 36-63 | 6 | 60 | 50-74 | 6 | 60 | 53-71 |
| | | 24 | 85 | 66-97 | 24 | 94 | 90-100 | 24 | 96 | 90-102 |
| 40° C./ 75% RH | 1 month | 2 | 21 | 18-26 | 2 | 22 | 18-28 | 2 | 28 | 26-32 |
| | | 6 | 45 | 34-54 | 6 | 54 | 45-63 | 6 | 57 | 51-65 |
| | | 24 | 89 | 74-99 | 24 | 100 | 95-106 | 24 | 88 | 85-91 |
| | 3 months | 2 | 23 | 18-29 | 2 | 27 | 23-32 | 2 | 32 | 26-37 |
| | | 6 | 45 | 29-58 | 6 | 60 | 52-68 | 6 | 64 | 55-75 |
| | | 24 | 84 | 61-95 | 24 | 100 | 93-106 | 24 | 103 | 99-110 |
| | 6 months | 2 | 25 | 21-32 | 2 | 32 | 28-37 | 2 | 33 | 27-41 |
| | | 6 | 52 | 42-67 | 6 | 63 | 55-69 | 6 | 63 | 46-76 |
| | | 24 | 86 | 74-100 | 24 | 95 | 91-98 | 24 | 98 | 93-102 |

All compositions showed extended release. Formulations 2 and 3 showed incomplete dissolution release relative to the other compositions. No significant change was observed in mean dissolution performance for Formulations 1, 4, 5 and 6 when stored up to 6 months at accelerated or long term storage conditions when compared to initial data. The inter-capsule dissolution variability was not significantly reduced for Formulations 1, 4, 5 and 6 when compared to Reference Formulation A.

The observation that the mean dissolution performance for Formulations 1, 4, 5 and 6 following storage for varying time periods and conditions did not significantly change supports the conclusion that adjusting the composition components as indicated for Formulations 4, 5 and 6 and changing the capsule shell to HPMC may decrease or eliminate the time dependent changes in drug release performance seen for Reference Formulation A.

Example 8: Preparation and Analysis of Extended Release Oxycodone Compositions (Reference Formulation A and Formulations 10-13)

Additional compositions (Formulations 10-13) with varying concentrations of isopropyl myristate (IPM) and silicon dioxide ($SiO_2$) were prepared and compared with Reference Formulation A (with BHT) to determine the effect of these components on inter-capsule dissolution variability and rheology as indicated below.

Materials and Methods

The compositions were prepared as described above for Example 3 to provide the compositions indicated in Table 9 (below).

TABLE 9

| | Vehicle Composition (% w/w) | | | | | | | (mg) Oxy- |
|---|---|---|---|---|---|---|---|---|
| ID | SAIB | TA | IPM | CAB | HEC | $SiO_2$ | BHT | codone |
| Reference Formulation A | 43 | 29 | 15 | 5 | 6 | 2 | 0.02 | 40 |
| Formulation 10 | 47 | 32 | 8 | 5 | 6 | 2 | 0.02 | 40 |
| Formulation 11 | 52 | 35 | 0 | 5 | 6 | 2 | 0.02 | 40 |

TABLE 9-continued

| | Vehicle Composition (% w/w) | | | | | | | (mg) Oxy- |
|---|---|---|---|---|---|---|---|---|
| ID | SAIB | TA | IPM | CAB | HEC | $SiO_2$ | BHT | codone |
| Formulation 12 | 44 | 29 | 15 | 5 | 6 | 1 | 0.02 | 40 |
| Formulation 13 | 44 | 30 | 15 | 5 | 6 | 0 | 0.02 | 40 |

Dissolution Testing

Four capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. over the course of the 24 hour dissolution test. A 20 mesh screen hanging basket was incorporated to hold the test article and the paddle speed was set to 100 rpm. The standard sampling time points were 0.5, 2, 3, 6, 12, 18 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Rheology Testing

Samples of the above compositions (Table 9) were analyzed for rheological properties using an Anton Paar MCR301 Rheometer. The samples were exposed to increasing dynamic strain (0.1 to 100%) at a constant angular frequency (10 $s^{-1}$) at 25° C.

Results

Dissolution Testing Results

Figure 6:
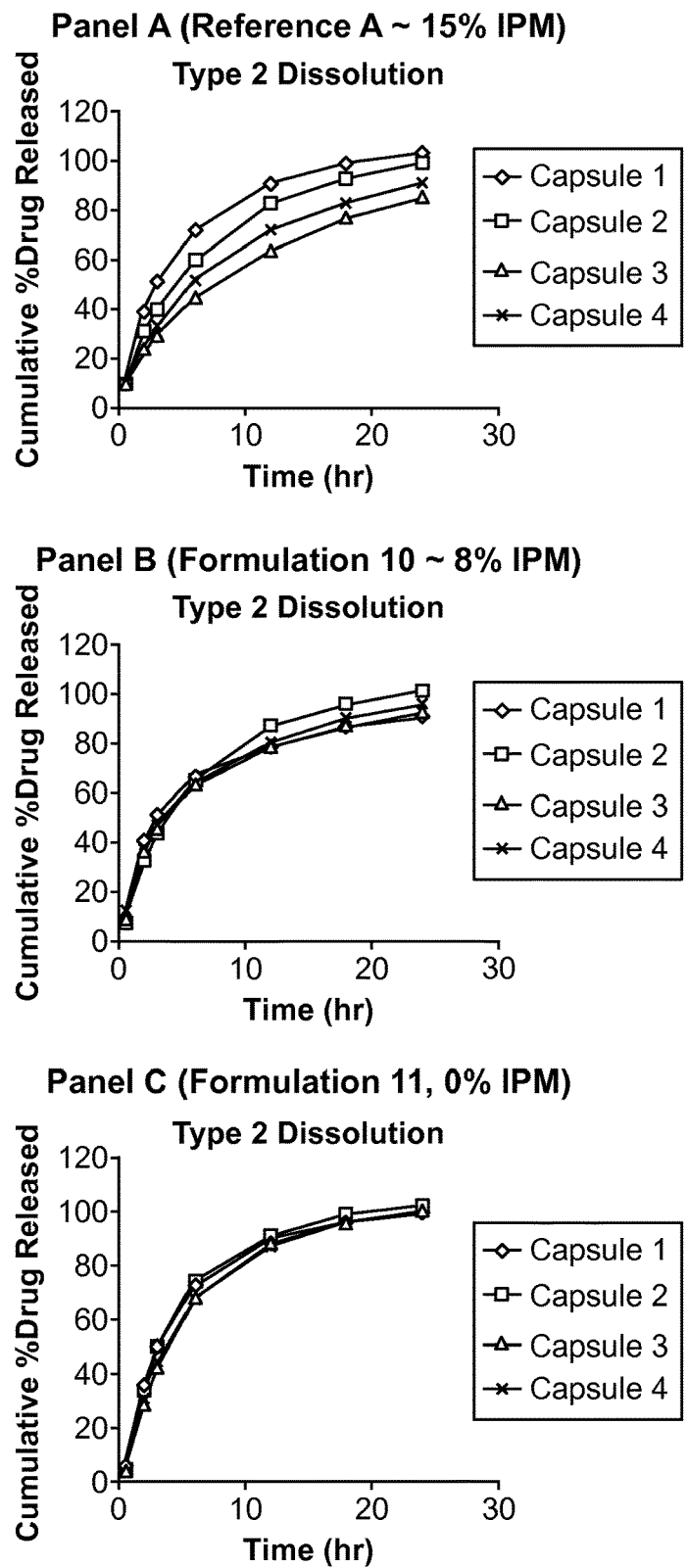
FIG. 6 provides graphs showing the results of in vitro dissolution experiments for Reference Formulation A (with BHT) (Panel A) and Formulations 10 (Panel B) and 11 (Panel C).
Figure 7:
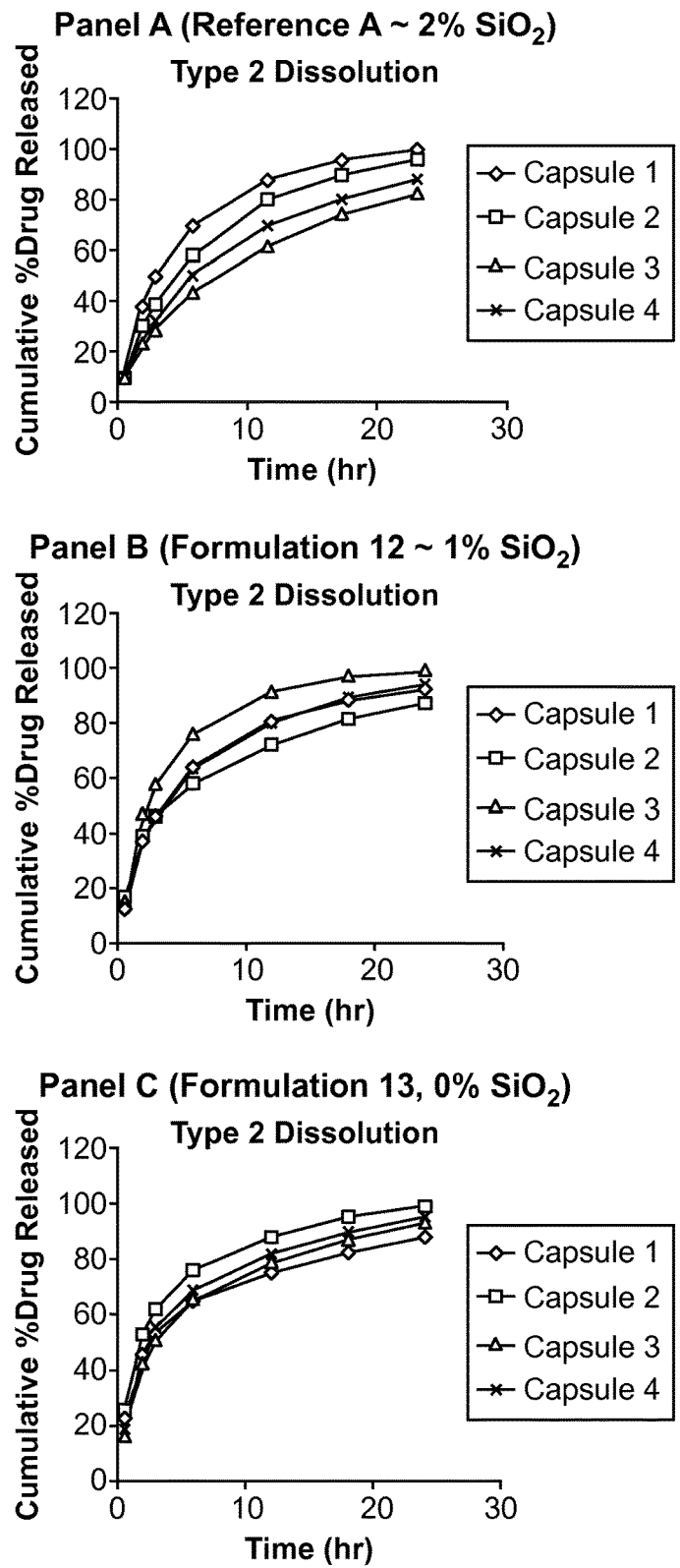
FIG. 7 provides graphs showing the results of in vitro dissolution experiments for Reference Formulation A (with BHT) (Panel A) and Formulations 12 (Panel B) and 13 (Panel C).
Figure 8:
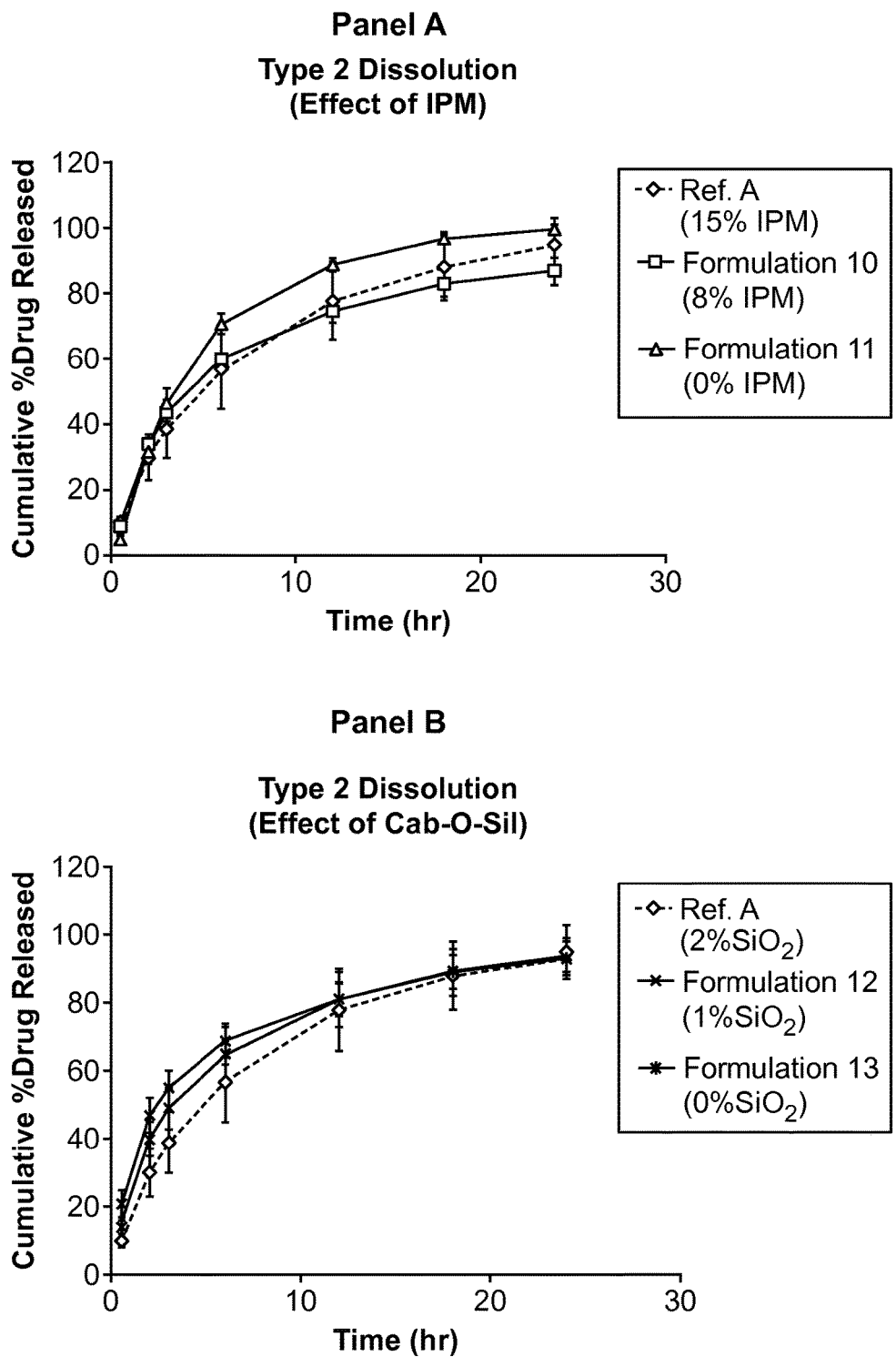
FIG. 8 provides graphs showing the effects of IPM (Panel A) and $SiO_2$ (Panel B) on mean release of oxycodone relative to Reference Formulation A (with BHT).

The results of the dissolution experiments are shown in FIGS. 6 and 7. The in vitro dissolution results showed a reduction in the inter-capsule dissolution variability with a reduction in the concentration of IPM in the composition (see FIG. 6, Panels A-C). Sample variability was significant when the level of $SiO_2$ in the composition was less than 2% as shown in FIG. 7, Panels A-C. The effects of adjusting the concentration of IPM and $SiO_2$ on the dissolution profiles of the compositions are shown in FIG. 8, Panels A and B, respectively, wherein the 0% IPM composition exhibited increased mean release at later time points, and the 0% $SiO_2$ composition exhibited increased mean release at earlier time points.

Rheology Testing Results

Table 10 (below) summarizes the viscoelastic outputs at the linear viscoelastic range for the rheology analysis.

TABLE 10

| ID | Description | Complex Viscosity (Pa · s) | Storage Modulus (G') (Pa) | Loss Modulus (G") (Pa) | Damping Factor (G"/G') |
|---|---|---|---|---|---|
| Reference Formulation A | (15% IPM, 2% $SiO_2$) | 53.3 | 239 | 476 | 1.99 |
| Formulation 10 | (8% IPM) | 90.3 | 473 | 769 | 1.63 |
| Formulation 11 | (0% IPM) | 158 | 993 | 1230 | 1.24 |
| Formulation 12 | (1% $SiO_2$) | 51.8 | 229 | 464 | 2.02 |
| Formulation 13 | (0% $SiO_2$) | 41.1 | 173 | 373 | 2.16 |

Compositions with lower % IPM (as compared to Reference Formulation A) had higher complex viscosity and higher elastic property (higher G' and lower G"/G'). Without intending to be bound by any particular theory, these properties may have resulted in the observed decrease in inter-capsule dissolution variability. Compositions with lower concentrations of $SiO_2$ had lower viscosity and lower elastic property (lower G' and high G"/G') similar to Reference Formulation A. Without intending to be bound by any particular theory, the lower elastic property could relate to an increase in the deformation of the composition structure due to hydrodynamic forces in the dissolution media.

Example 9: Preparation and Analysis of Extended Release Oxycodone Compositions (Formulations 14 and 15)

Additional compositions (Formulations 14 and 15) and Formulation 1 (Reference Formulation A without BHT in HPMC capsule) were prepared and characterized with respect to inter-capsule dissolution variability, rheology and abuse deterrence characteristics as indicated below.

Materials and Methods

The compositions were prepared to provide the compositions indicated in Table 11 (below). Composition components were blended and individual compositions were encapsulated as described above, with the exception that HPMC capsules were used in place of gelatin capsules.

TABLE 11

| Composition (% w/w) | Formulation 1 | Formulation 14 | Formulation 15 |
|---|---|---|---|
| SAIB | 40.99 | 40.42 | 39.85 |
| TA | 27.32 | 26.94 | 26.56 |
| IPM | 14.23 | 14.23 | 14.23 |
| CAB | 4.74 | 4.74 | 4.74 |
| HEC | 5.69 | 5.69 | 5.69 |
| Colloidal $SiO_2$ | 1.90 | 2.85 | 3.79 |

TABLE 11-continued

| Composition (% w/w) | Formulation 1 | Formulation 14 | Formulation 15 |
|---|---|---|---|
| Micronized oxycodone base | 5.13 | 5.13 | 5.13 |
| Capsule shell | HPMC | HPMC | HPMC |

Dissolution Testing

Six capsules from each composition lot were tested according to the testing conditions discussed above to evaluate the effect on mean release and inter-capsule dissolution variability.

Rheology Testing

Triplicate samples for each composition were subjected to rheology testing as discussed above.

Abuse Deterrence

Four capsules from each composition were tested for abuse deterrence characteristics. The release rate of oxycodone base was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5, 1, and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing Results

Figure 9:
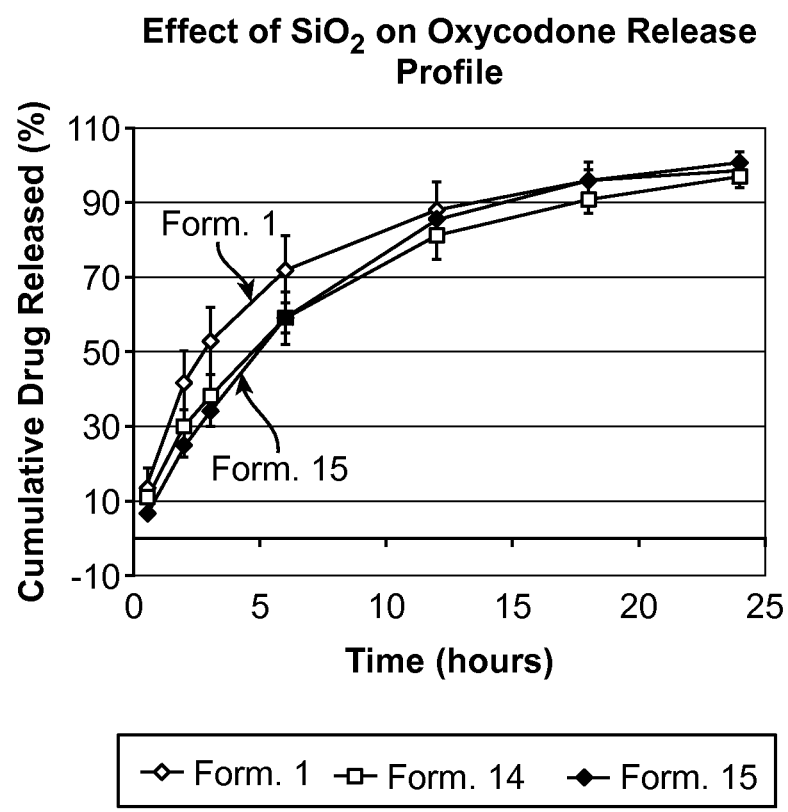
FIG. 9 is a graph showing the effect of $SiO_2$ on an oxycodone mean release profile. Results for Formulation 1, and Formulations 14 and 15 are shown.
Figure 10:
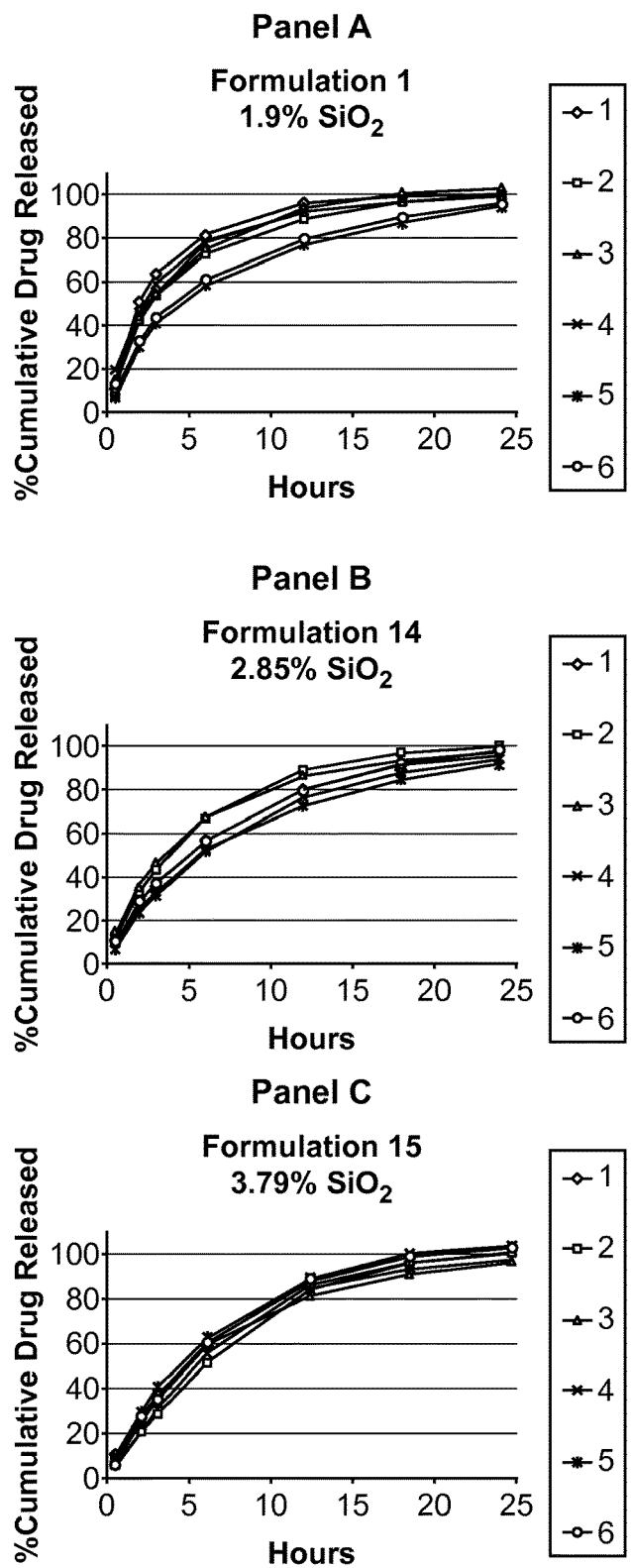
FIG. 10 provides graphs showing the effect of increased amounts of $SiO_2$ on inter-capsule variability during dissolution. Results for Formulation 1 (Panel A), and Formulations 14 (Panel B) and 15 (Panel C) are shown.

The results of the dissolution experiments are provided in FIG. 9; FIG. 10, Panels A-C; and Table 12 (below). The results demonstrate a) a reduction in the mean release prior to 12 hours with increasing $SiO_2$ concentration as shown in FIG. 9, and b) a reduction in the inter-capsule dissolution variability with increasing $SiO_2$ concentration as shown in FIG. 10, Panels A-C, and Table 12.

TABLE 12

| ID | $SiO_2$ (% w/w) | Sample No. | Time Point (hrs) | 0.5 | 2 | 3 | 6 | 12 | 18 | 24 | Sp* |
|---|---|---|---|---|---|---|---|---|---|---|---|
| Formulation 1 | 1.90 | 6 | Mean | 14 | 42 | 53 | 72 | 88 | 96 | 99 | 7 |
| | | | SD | 5 | 8 | 9 | 9 | 8 | 5 | 3 | |
| Formulation 14 | 2.85 | 6 | Mean | 11 | 30 | 38 | 59 | 81 | 91 | 97 | 5 |
| | | | SD | 3 | 5 | 6 | 7 | 6 | 4 | 3 | |

TABLE 12-continued

| ID | SiO$_2$ (% w/w) | Sample No. | Time Point (hrs) | 0.5 | 2 | 3 | 6 | 12 | 18 | 24 | Sp* |
|---|---|---|---|---|---|---|---|---|---|---|---|
| Formulation 15 | 3.79 | 6 | Mean | 7 | 25 | 34 | 59 | 86 | 96 | 101 | 3 |
|  |  |  | SD | 1 | 3 | 4 | 4 | 3 | 3 | 3 |  |

*Sp as used herein = Pooled standard deviation which is calculated as provided below:

$$Sp = \left( \frac{(n_1 - 1)s_1^2 + (n_2 - 1)s_2^2 + \ldots (n_k - 1)s_k^2}{n_1 + n_2 + \ldots n_k - k} \right)^{1/2}$$

wherein, n = sample number and the suffixes 1, 2, ... k refer to the different series of measurements.

Rheology Testing Results

Figure 11:
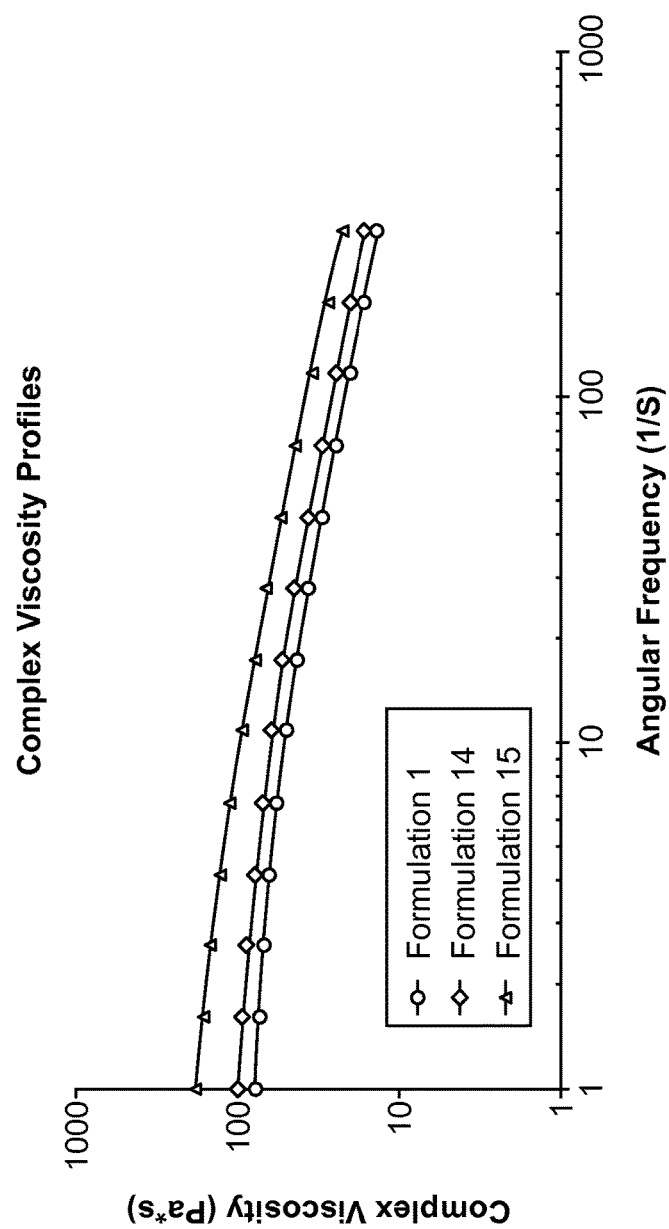
FIG. 11 is a graph showing the complex viscosity profiles for Formulations 1, 14 and 15. Increasing $SiO_2$ concentration above about 2% increases complex viscosity which may lead to decreasing reproducible deformation and therefore low inter-capsule variability during dissolution testing.

Table 13 (below) summarizes the results measured at angular frequency of 10 s$^{-1}$. Complex viscosity profiles with angular frequency sweep are shown in FIG. 11.

TABLE 13

| ID | SAIB (% w/w) | TA (% w/w) | IPM (% w/w) | SiO$_2$ (% w/w) | Complex Viscosity (Pa·s) | Storage Modulus (Pa) (G') | Loss Modulus (Pa) (G") | Damping Factor (G"/G') |
|---|---|---|---|---|---|---|---|---|
| Formulation 1 | 40.98 | 27.32 | 14.23 | 1.90 | 49.53 | 245.00 | 474.33 | 1.93 |
| Formulation 14 | 40.41 | 26.64 | 14.23 | 2.85 | 61.63 | 311.00 | 586.67 | 1.89 |
| Formulation 15 | 39.85 | 26.56 | 14.23 | 3.79 | 95.50 | 540.67 | 874.67 | 1.62 |

As shown, increasing SiO$_2$ concentration above about 2% increases complex viscosity which may lead to decreasing matrix deformation and therefore low inter-capsule variability during dissolution testing. In addition to increase of the Loss Modulus, it is surprising that the extent of increase of Storage Modulus (G') is even higher which results in lower damping factor (G"/G') for Formulations 14 and 15 as compared with Formulation 1 (Reference Formulation A without BHT in HPMC capsule). In other word, increasing of SiO$_2$ does not only increase viscosity but also increase elasticity. Without intending to be bound by any particular theory, a lower damping factor may indicate a more stable microstructure which may lead to more stable dissolution stability.

Abuse Deterrence Results

The % of oxycodone released from each composition at sampling time points 0.5, 1, and 3 hours as determined by reverse-phase HPLC is provided in Table 14 below.

TABLE 14

| ID | SiO$_2$ (%) | Sample # |  | Time point (hrs) |  |  |
|---|---|---|---|---|---|---|
|  |  |  |  | 0.5 | 1 | 3 |
| Formulation 1 | 1.9 | 4 | Mean | 22 | 29 | 46 |
|  |  |  | SD | 3 | 3 | 5 |
| Formulation 14 | 2.85 | 4 | Mean | 18 | 25 | 41 |
|  |  |  | SD | 3 | 4 | 5 |
| Formulation 15 | 3.79 | 4 | Mean | 17 | 23 | 36 |
|  |  |  | SD | 3 | 4 | 7 |

As shown above, the % release of oxycodone decreased at each time point with increased SiO$_2$ concentration, suggesting an improvement in this abuse deterrence characteristic with increased SiO$_2$ in the tested range.

Example 10: One Month Stability Analysis of Extended Release Oxycodone Compositions (Formulations 14 and 15)

Materials and Methods

Formulation 1 (Reference Formulation A without BHT in HPMC capsule) and Formulations 14 and 15 were stored at 25° C./60% RH or 40° C./75% RH for a one-month period of time. Six capsules from each composition lot were tested according to the testing conditions discussed above to evaluate the effect on mean release and inter-capsule dissolution variability.

Results

Figure 12:
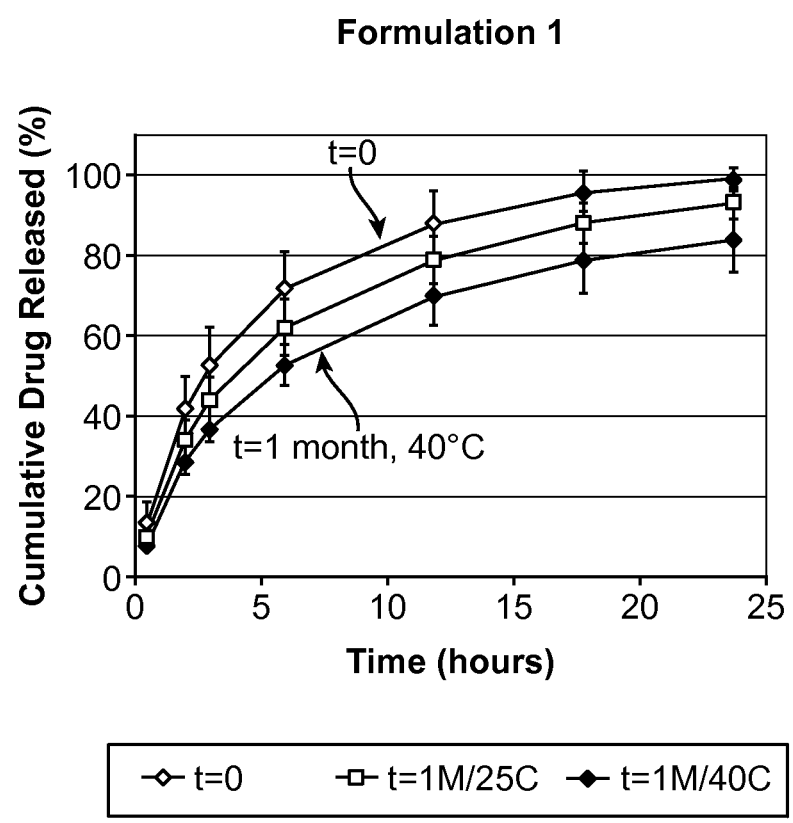
FIG. 12 is a graph showing mean release of oxycodone from Formulation 1 following storage for 1 month at 25° C. or 40° C.
Figure 13:
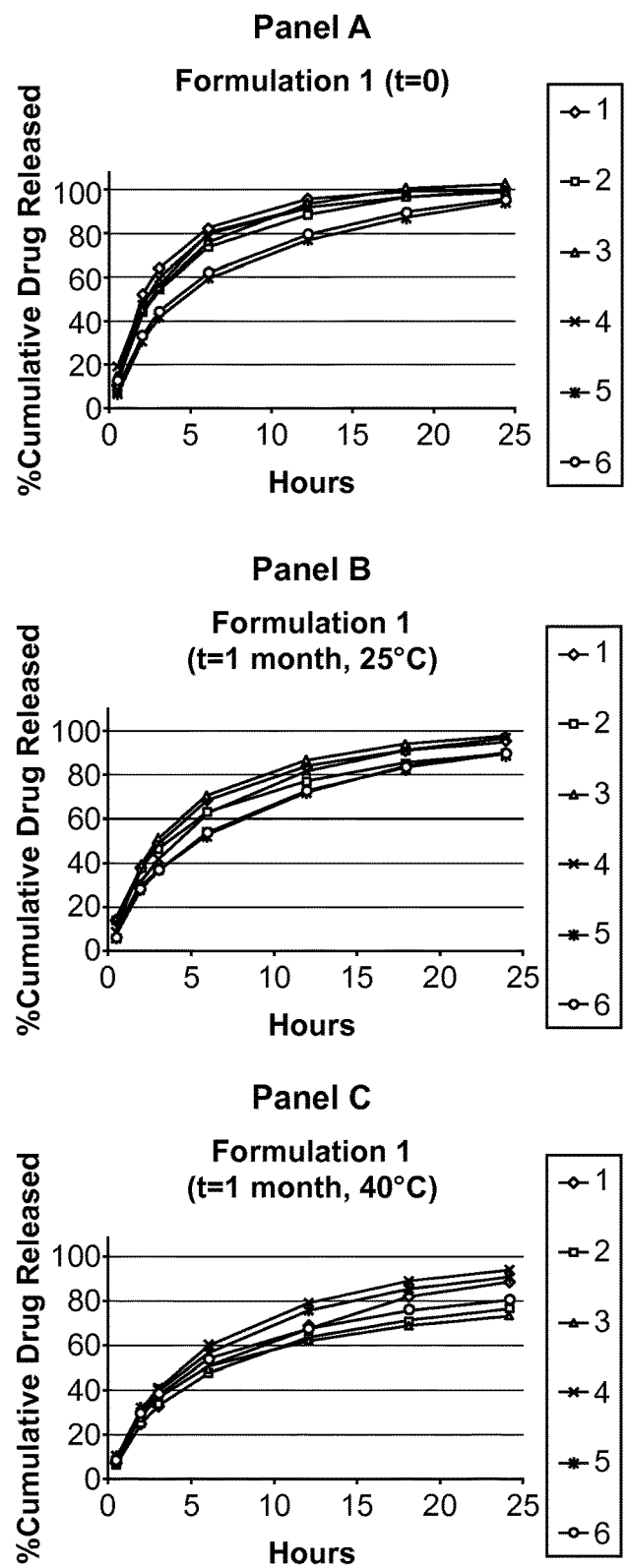
FIG. 13 provides graphs showing inter-capsule variability during dissolution testing of Formulation 1 following storage for 1 month at 25° C. or 40° C.

The results for Formulation 1 are provided in FIG. 12; FIG. 13, Panels A-C; and Table 15 below. Mean release is decreased for the stored Formulation 1 capsule samples relative to the T=0 samples as shown in FIG. 12. Inter-capsule variation was similar for the stored Formulation 1 samples and the T=0 samples as shown in FIG. 13, Panels A-C and Table 15.

TABLE 15

| ID | SiO$_2$ (%) | Time Point (Months) | Storage Condition | Sample No. |  | Time Point (hrs) |  |  |  |  |  |  |  |
|---|---|---|---|---|---|---|---|---|---|---|---|---|---|
|  |  |  |  |  |  | 0.5 | 2 | 3 | 6 | 12 | 18 | 24 | Sp |
| Formulation 1 | 1.90 | 0 | NA | 6 | Mean | 14 | 42 | 53 | 72 | 88 | 96 | 99 | 7 |
|  |  |  |  |  | SD | 5 | 8 | 9 | 9 | 8 | 5 | 3 |  |

TABLE 15-continued

| ID | SiO$_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| | | 1 | 25° C./60% RH | 6 | Mean | 10 | 34 | 44 | 62 | 79 | 88 | 93 | 5 |
| | | | | | SD | 3 | 5 | 6 | 7 | 6 | 5 | 4 | |
| | | | 40° C./75% RH | 6 | Mean | 8 | 29 | 37 | 53 | 70 | 79 | 84 | 6 |
| | | | | | SD | 1 | 3 | 3 | 5 | 7 | 8 | 8 | |

Figure 14:
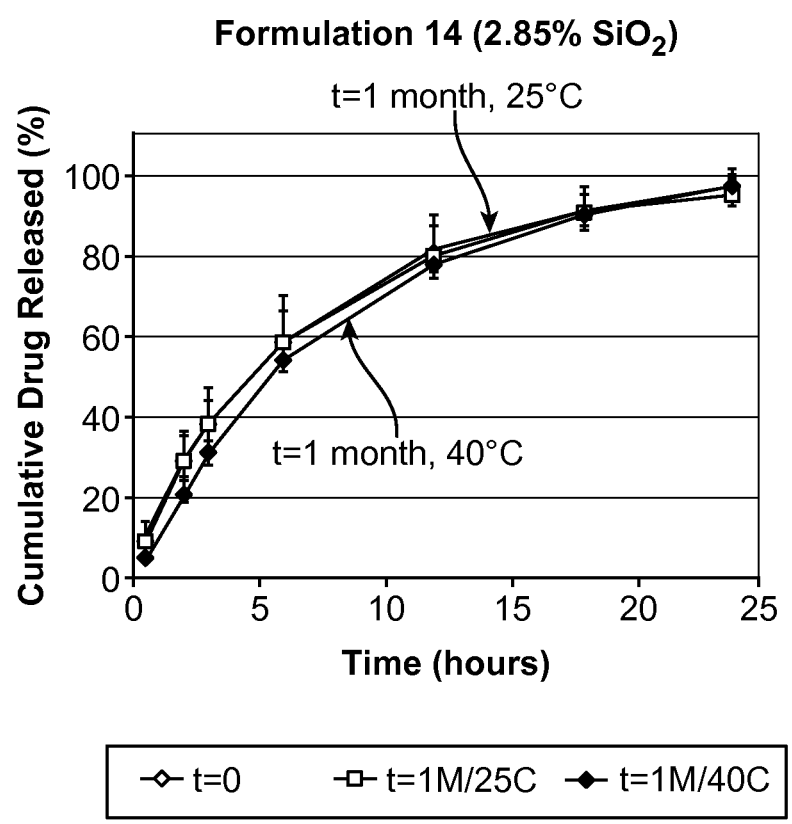
FIG. 14 is a graph showing mean release of oxycodone from Formulation 14 following storage for 1 month at 25° C. or 40° C.
Figure 15:
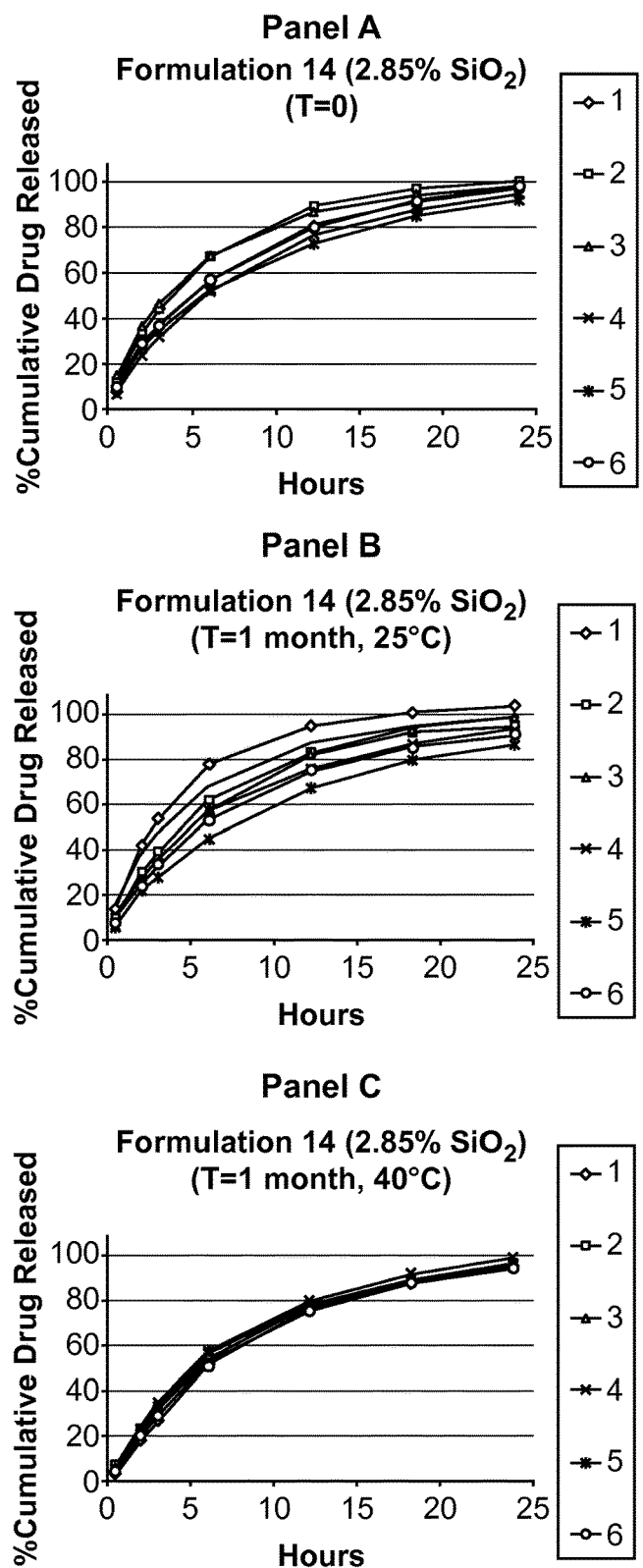
FIG. 15 provides graphs showing inter-capsule variability during dissolution testing of Formulation 14 following storage for 1 month at 25° C. or 40° C.

The results for Formulation 14 are provided in FIG. 14; FIG. 15, Panels A-C; and Table 16 below. Mean release is not significantly changed for the Formulation 14 samples relative to the T=0 samples as shown in FIG. 14. Sample variation was decreased for the Formulation 14 samples stored at 40° C./75% RH relative to the T=0 samples as shown in FIG. 15, Panels A-C and Table 16.

TABLE 16

| ID | SiO$_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| Formulation 14 | 2.85 | 0 | NA | 6 | Mean | 11 | 30 | 38 | 59 | 81 | 91 | 97 | 5 |
| | | | | | SD | 3 | 5 | 6 | 7 | 6 | 4 | 3 | |
| | | 1 | 25° C./60% RH | 6 | Mean | 9 | 29 | 38 | 59 | 80 | 90 | 95 | 8 |
| | | | | | SD | 3 | 7 | 9 | 11 | 10 | 7 | 6 | |
| | | | 40° C./75% RH | 6 | Mean | 5 | 21 | 31 | 54 | 78 | 90 | 97 | 2 |
| | | | | | SD | 1 | 2 | 3 | 3 | 2 | 2 | 2 | |

Figure 16:
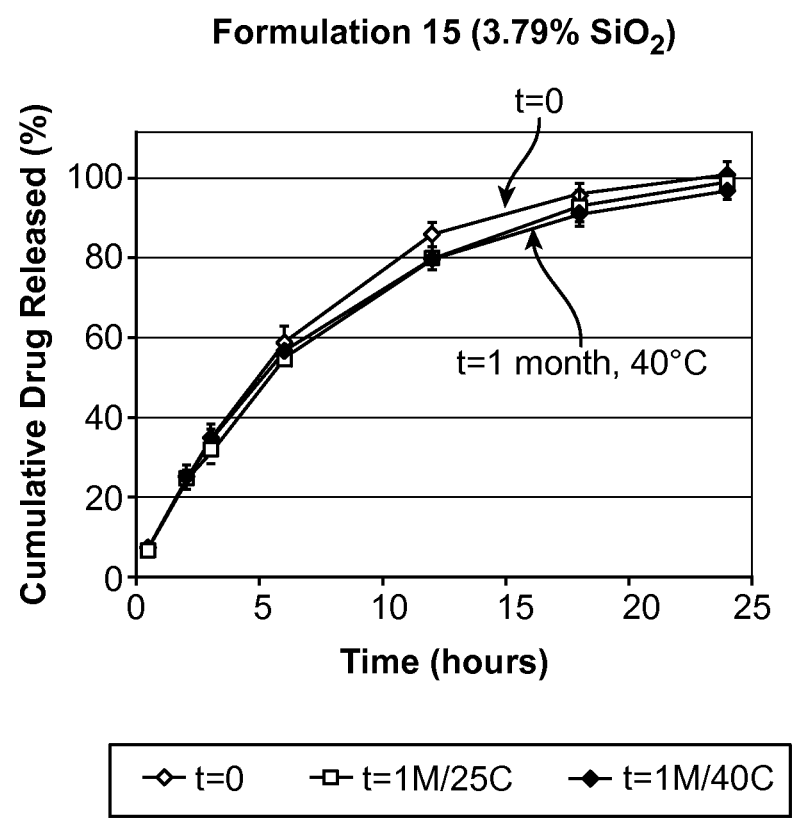
FIG. 16 is a graph showing mean release of oxycodone from Formulation 15 following storage for 1 month at 25° C. or 40° C.
Figure 17:
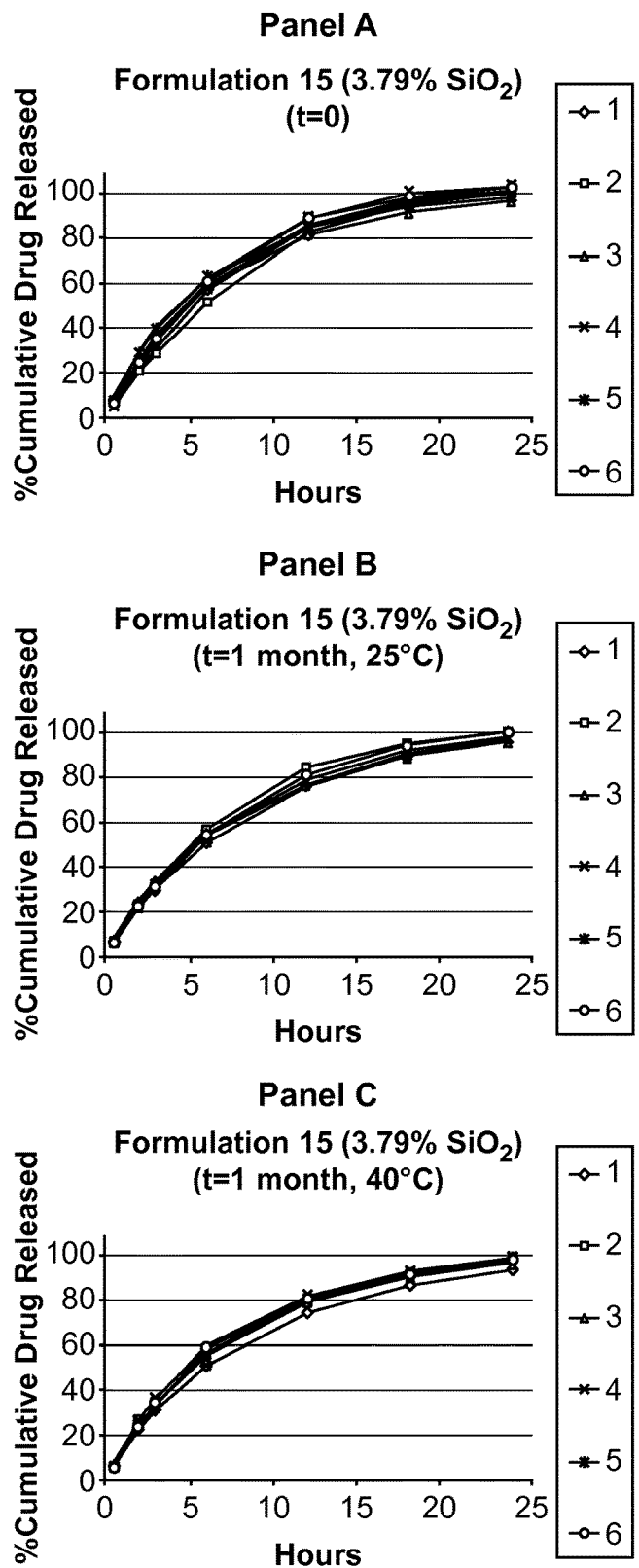
FIG. 17 provides graphs showing inter-capsule variability during dissolution testing of Formulation 15 following storage for 1 month at 25° C. or 40° C.

The results for Formulation 15 are provided in FIG. 16; FIG. 17, Panels A-C; and Table 17 below. Mean release is not significantly changed for the Formulation 15 relative to the T=0 samples as shown in FIG. 16. Sample variation was low and similar for the Formulation 15 samples stored at 25° C./60% RH and 40° C./75% RH relative to the T=0 samples as shown in FIG. 17, Panels A-C and Table 17.

TABLE 17

| ID | SiO$_2$ (%) | Time Point (Months) | Storage Condition | Sample No. | | Time Point (hrs) | | | | | | | |
|---|---|---|---|---|---|---|---|---|---|---|---|---|---|
| | | | | | | 0.5 | 2 | 3 | 6 | 12 | 18 | 24 | Sp |
| Formulation 15 | 3.79 | 0 | NA | 6 | Mean | 7 | 25 | 34 | 59 | 86 | 96 | 101 | 3 |
| | | | | | SD | 1 | 3 | 4 | 4 | 3 | 3 | 3 | |
| | | 1 | 25° C./60% RH | 6 | Mean | 7 | 24 | 32 | 55 | 80 | 93 | 99 | 2 |
| | | | | | SD | 0 | 1 | 1 | 2 | 3 | 2 | 2 | |
| | | | 40° C./75% RH | 6 | Mean | 7 | 25 | 35 | 57 | 80 | 91 | 97 | 2 |
| | | | | | SD | 1 | 2 | 2 | 3 | 2 | 2 | 2 | |

Example 11: Preparation and Analysis of Extended Release Oxycodone Compositions (Formulations 16-18)

Still additional compositions (Formulations 16-18) were prepared and characterized with respect to inter-capsule dissolution variability and abuse deterrence characteristics as indicated below.

Materials and Methods

The compositions were prepared to provide the compositions indicated in Table 18 (below). Composition components were blended and individual compositions were encapsulated in HPMC capsules as described above.

TABLE 18

| | Low-IPM Compositions | | |
|---|---|---|---|
| Composition (% w/w) | Formulation 16 | Formulation 17 | Formulation 18 |
| SAIB | 42.93 | 42.42 | 41.92 |
| TA | 37.14 | 36.7 | 36.26 |
| IPM | 2.47 | 2.47 | 2.47 |

TABLE 18-continued

Low-IPM Compositions

| Composition (% w/w) | Formulation 16 | Formulation 17 | Formulation 18 |
|---|---|---|---|
| CAB | 4.74 | 4.74 | 4.74 |
| HEC | 5.69 | 5.69 | 5.69 |
| Colloidal $SiO_2$ | 1.90 | 2.85 | 3.79 |
| Micronized oxycodone base | 5.13 | 5.13 | 5.13 |
| Capsule shell | HPMC | HPMC | HPMC |

Dissolution Testing

Six capsules from each composition lot were tested according to the testing conditions discussed above to evaluate the effect on inter-capsule dissolution variability.

Abuse Deterrence

Four capsules from each composition were tested for abuse deterrence characteristics. The release rate of oxycodone base was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5, 1, and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing Results

Figure 18:
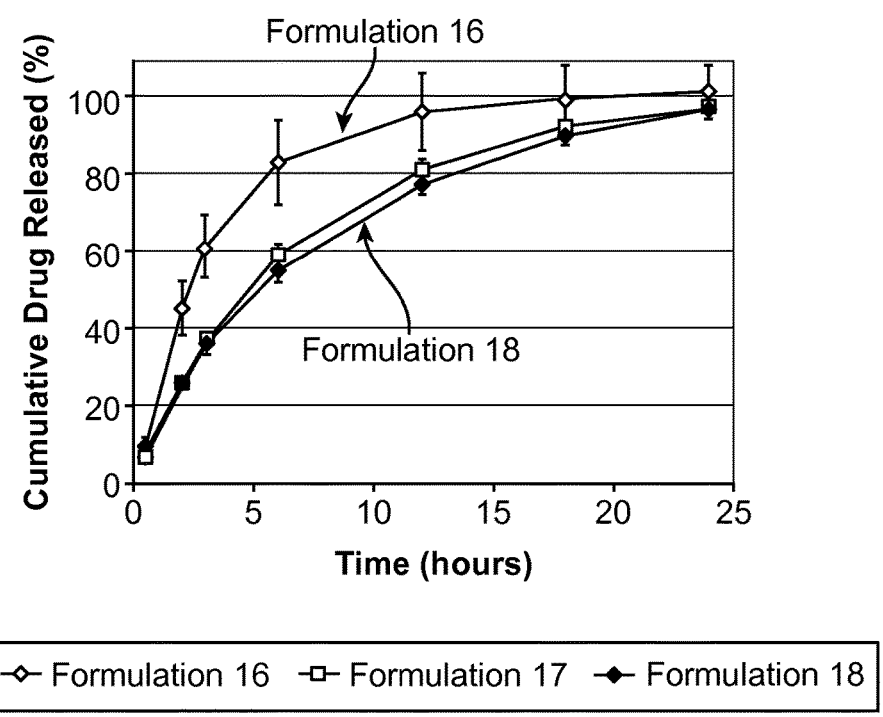
FIG. 18 is a graph showing mean release of oxycodone from Formulations 16, 17 and 18.
Figure 19:
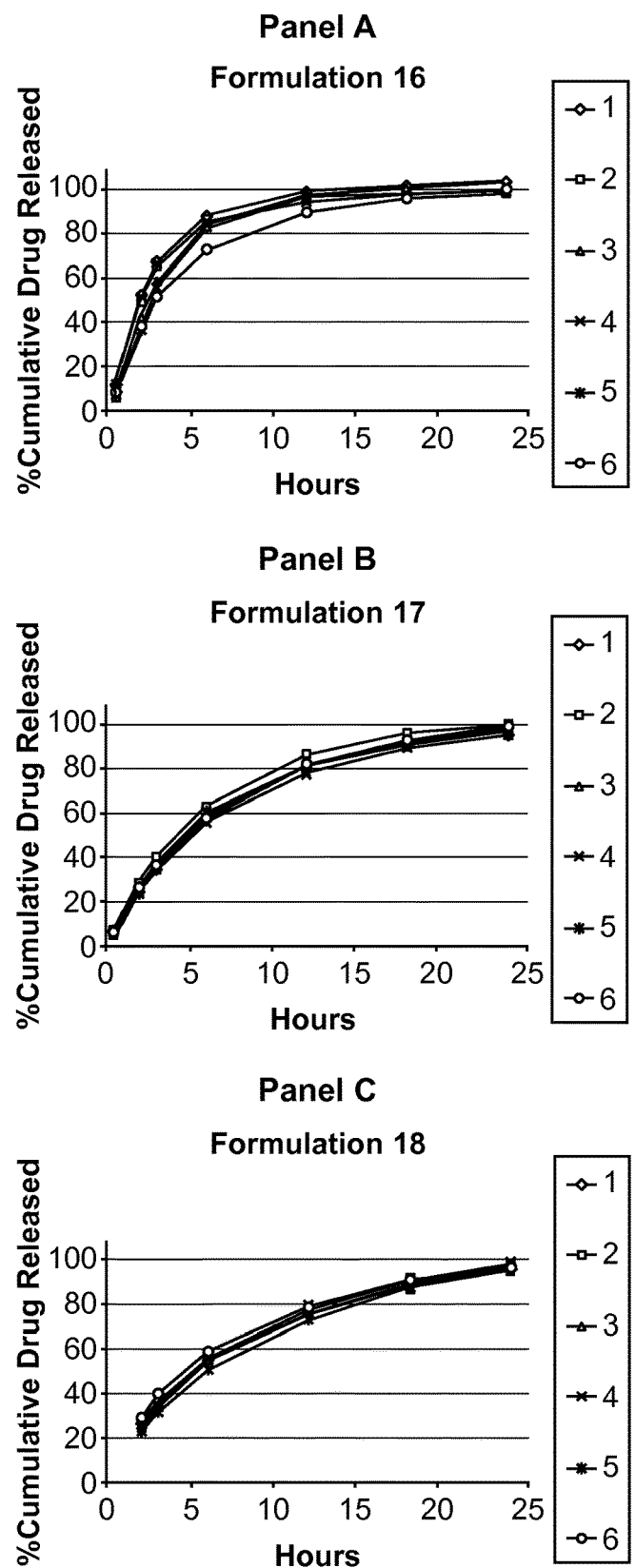
FIG. 19 provides graphs showing inter-capsule variability during dissolution testing of Formulation 16 (Panel A), Formulation 17 (Panel B) and Formulation 18 (Panel C).

The results of the dissolution experiments are provided in FIG. 18; FIG. 19, Panels A-C; and Table 19 (below). The results demonstrate a) a reduction in the mean release with increasing $SiO_2$ concentration as shown in FIG. 18, and b) a reduction in the inter-capsule variability with increasing $SiO_2$ concentration as shown in FIG. 19, Panels A-C, and Table 19.

TABLE 19

| ID | $SiO_2$ (% w/w) | Sample No. | | 0.5 | 2 | 3 | 6 | 12 | 18 | 24 | Sp |
|---|---|---|---|---|---|---|---|---|---|---|---|
| Formulation 16 | 1.90 | 6 | Mean | 10 | 45 | 61 | 83 | 96 | 99 | 101 | 4 |
| | | | SD | 2 | 7 | 6 | 5 | 3 | 2 | 2 | |
| Formulation 17 | 2.85 | 6 | Mean | 7 | 26 | 37 | 59 | 81 | 92 | 97 | 2 |
| | | | SD | 1 | 1 | 2 | 3 | 3 | 2 | 2 | |
| Formulation 18 | 3.79 | 6 | Mean | N/A | 26 | 36 | 55 | 77 | 90 | 97 | 2 |
| | | | SD | N/A | 2 | 3 | 3 | 2 | 2 | 1 | |

Abuse Deterrence Results

The % of oxycodone released from each composition at sampling time points 0.5, 1, and 3 hours as determined by reverse-phase HPLC is provided in Table 20 below.

TABLE 20

| ID | $SiO_2$ (%) | Sample # | | 0.5 | 1 | 3 |
|---|---|---|---|---|---|---|
| Formulation 16 | 1.9 | 4 | Mean | 26 | 35 | 60 |
| | | | SD | 5 | 6 | 8 |
| Formulation 17 | 2.85 | 4 | Mean | 28 | 40 | 64 |
| | | | SD | 3 | 3 | 3 |
| Formulation 18 | 3.79 | 4 | Mean | 14 | 22 | 40 |
| | | | SD | 2 | 3 | 4 |

As shown above, the % release of oxycodone was decreased for the 3.79% $SiO_2$ composition relative to the 1.9% and 2.85% $SiO_2$ compositions, suggesting an improvement in this abuse deterrence characteristic at 3.79% $SiO_2$ relative to the 1.9% and 2.85% $SiO_2$.

Example 12: One Month Stability Analysis of Extended Release Oxycodone Compositions (Formulations 16-18)

Materials and Methods

Formulations 16, 17 and 18 were stored at 25° C./60% RH or 40° C./75% RH for a one-month period of time. Six capsules from each composition lot were tested according to the testing conditions discussed above to evaluate the effect on mean release and inter-capsule dissolution variability.

Results

Figure 20:
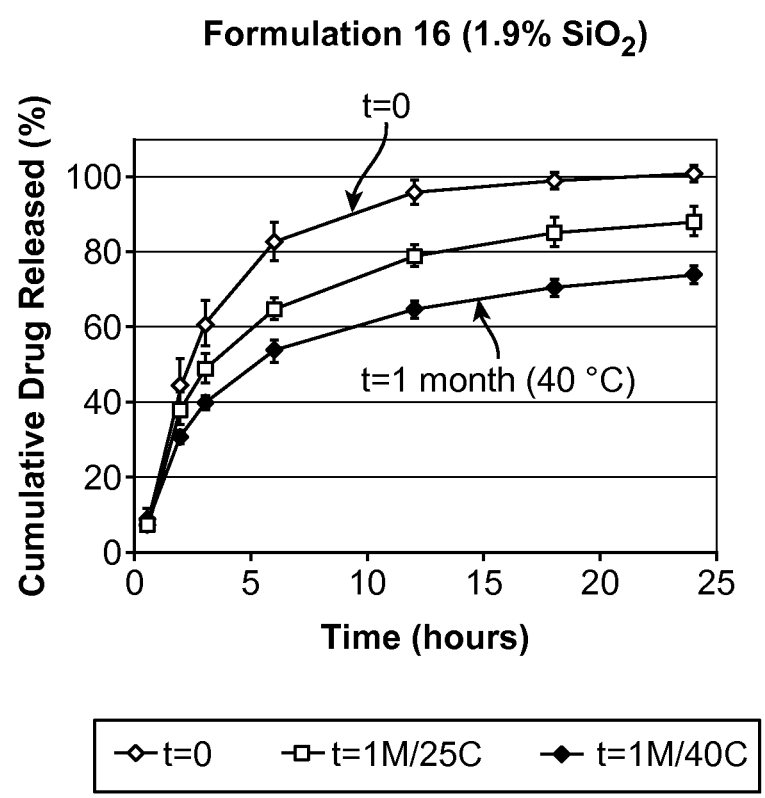
FIG. 20 is a graph showing mean release of oxycodone from Formulation 16 following storage for 1 month at 25° C. or 40° C.
Figure 21:
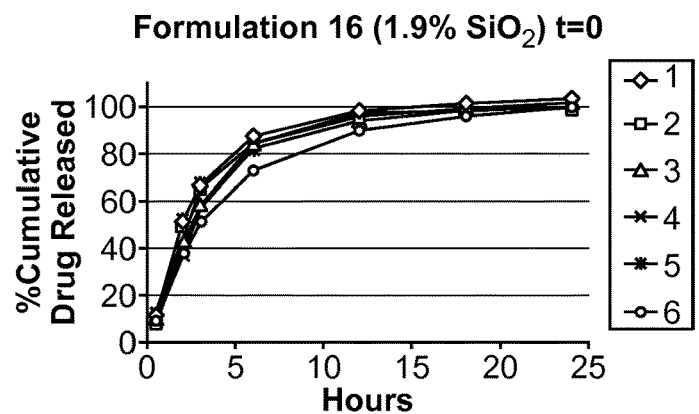
FIG. 21 provides graphs showing inter-capsule variability during dissolution testing of Formulation 16 following storage for 1 month at 25° C. or 40° C.
Figure 21:
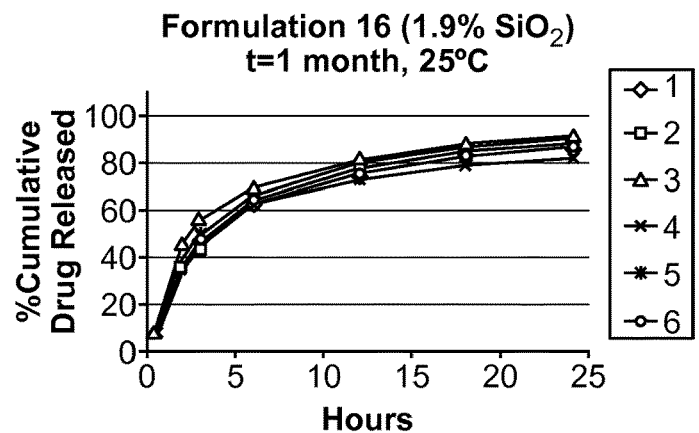
Figure 21:
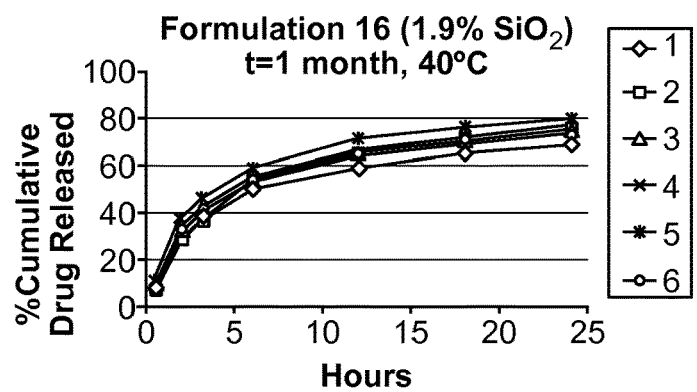

The results for Formulation 16 are provided in FIG. 20; FIG. 21, Panels A-C; and Table 21 below. Mean release decreased with increasing storage temperature for the stored Formulation 16 samples relative to the T=0 samples as shown in FIG. 20. Inter-capsule variation was similar for the stored Formulation 16 samples and the T=0 samples as shown in FIG. 21, Panels A-C and Table 21.

TABLE 21

| ID | SiO$_2$ (% w/w) | Time Point (Months) | Storage Condition | Sample No. | | 0.5 | 2 | 3 | 6 | 12 | 18 | 24 | Sp |
|---|---|---|---|---|---|---|---|---|---|---|---|---|---|
| | | | | | | \multicolumn{7}{c}{Time Point (hrs)} | |
| Formulation 16 | 1.90 | 0 | NA | 6 | Mean | 10 | 45 | 61 | 83 | 96 | 99 | 101 | 4 |
| | | | | | SD | 2 | 7 | 6 | 5 | 3 | 2 | 2 | |
| | | 1 | 25° C./60% RH | 6 | Mean | 8 | 38 | 49 | 65 | 79 | 85 | 88 | 4 |
| | | | | | SD | 1 | 5 | 4 | 3 | 3 | 4 | 4 | |
| | | | 40° C./75% RH | 6 | Mean | 9 | 31 | 40 | 54 | 65 | 71 | 74 | 3 |
| | | | | | SD | 2 | 3 | 4 | 3 | 4 | 3 | 4 | |

Figure 22:
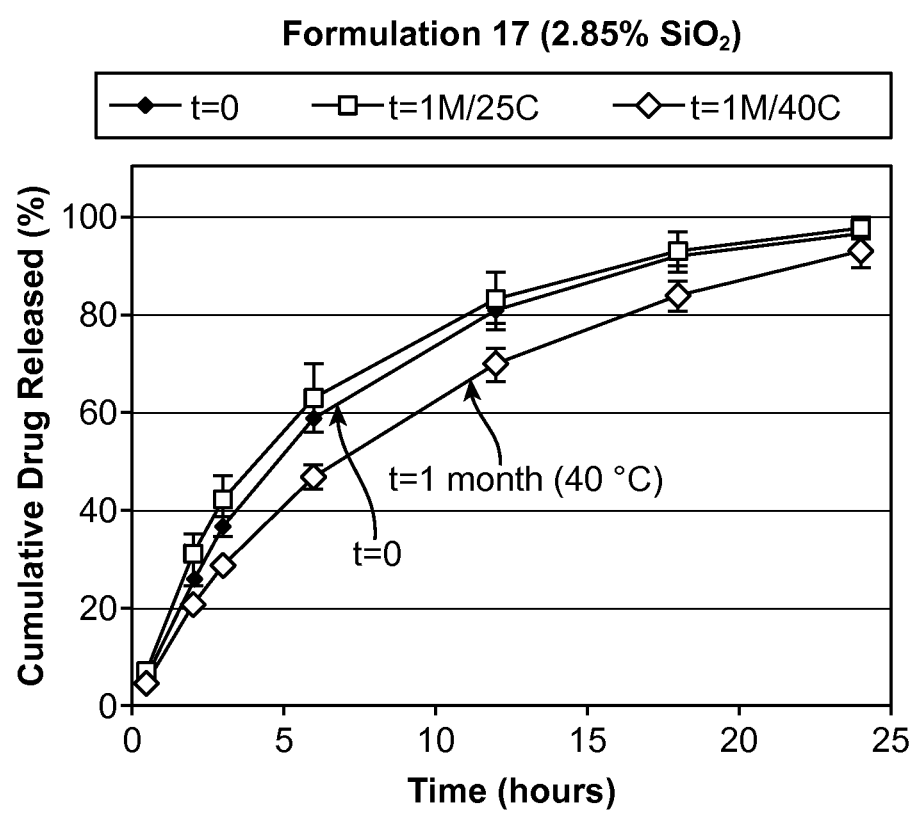
FIG. 22 is a graph showing mean release of oxycodone from Formulation 17 following storage for 1 month at 25° C. or 40° C.
Figure 23:
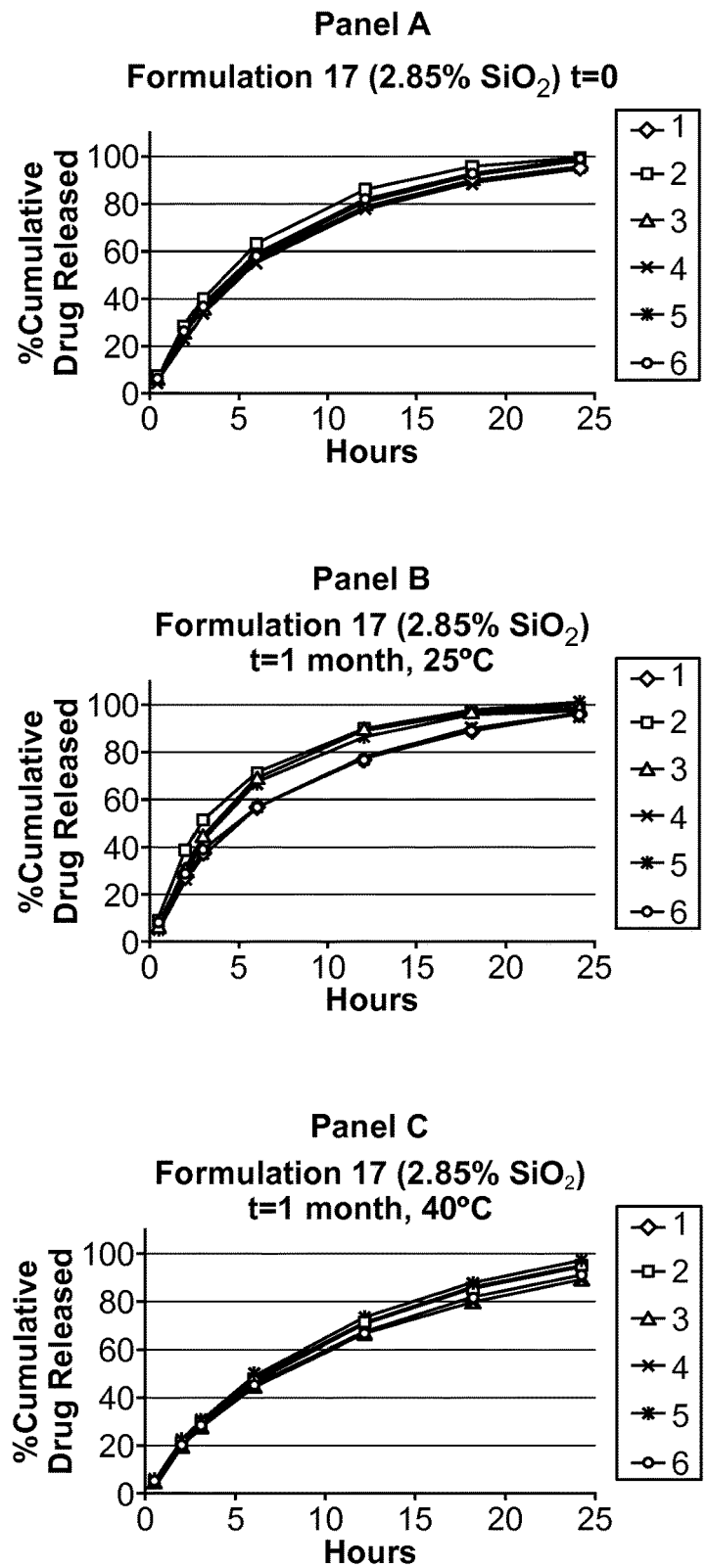
FIG. 23 provides graphs showing inter-capsule variability during dissolution testing of Formulation 17 following storage for 1 month at 25° C. or 40° C.

The results for Formulation 17 are provided in FIG. 22; FIG. 23, Panels A-C; and Table 22 below. Mean release is decreased for the Formulation 17 samples stored at 40° C./75% RH relative to the T=0 samples as shown in FIG. 22. Sample variation was increased for the Formulation 17 samples stored at 25° C./60% RH relative to the T=0 samples as shown in FIG. 23, Panels A-C and Table 22.

TABLE 22

| ID | SiO$_2$ (% w/w) | Time Point (Months) | Storage Condition | Sample No. | | 0.5 | 2 | 3 | 6 | 12 | 18 | 24 | Sp |
|---|---|---|---|---|---|---|---|---|---|---|---|---|---|
| | | | | | | \multicolumn{7}{c}{Time Point (hrs)} | |
| Formulation 17 | 3 | 0 | NA | 6 | Mean | 7 | 26 | 37 | 59 | 81 | 92 | 97 | 2 |
| | | | | | SD | 1 | 1 | 2 | 3 | 3 | 2 | 2 | |
| | | 1 | 25° C./60% RH | 6 | Mean | 7 | 31 | 42 | 63 | 83 | 93 | 98 | 5 |
| | | | | | SD | 1 | 4 | 5 | 7 | 6 | 4 | 2 | |
| | | | 40° C./75% RH | 6 | Mean | 5 | 21 | 29 | 47 | 70 | 84 | 93 | 2 |
| | | | | | SD | 0 | 1 | 1 | 2 | 3 | 3 | 3 | |

Figure 24:
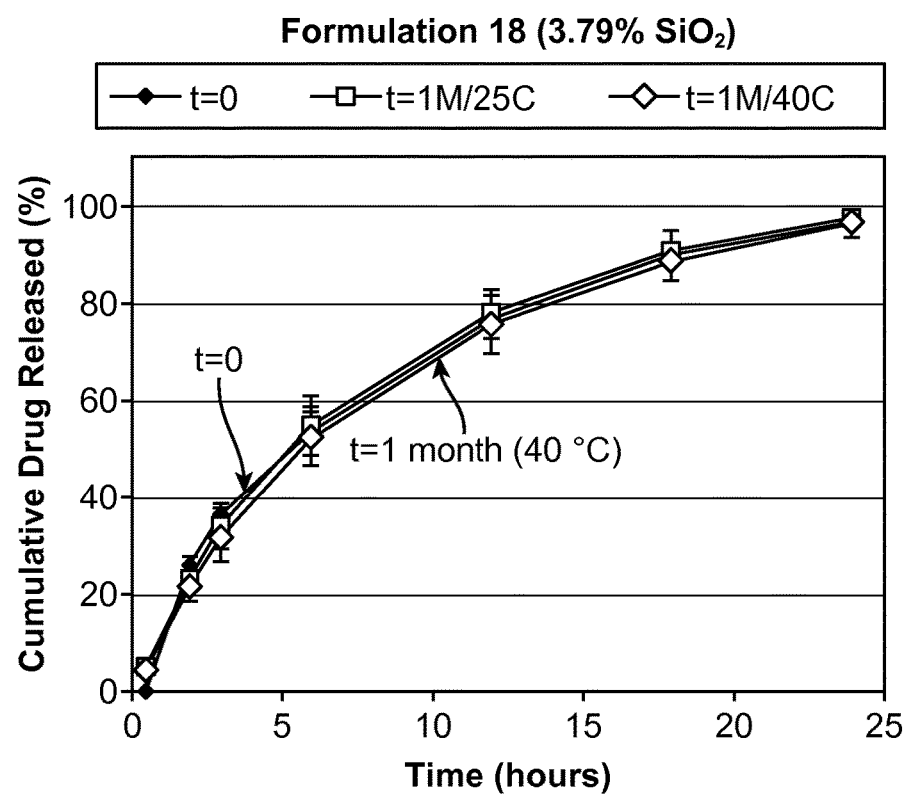
FIG. 24 is a graph showing mean release of oxycodone from Formulation 18 following storage for 1 month at 25° C. or 40° C.
Figure 25:
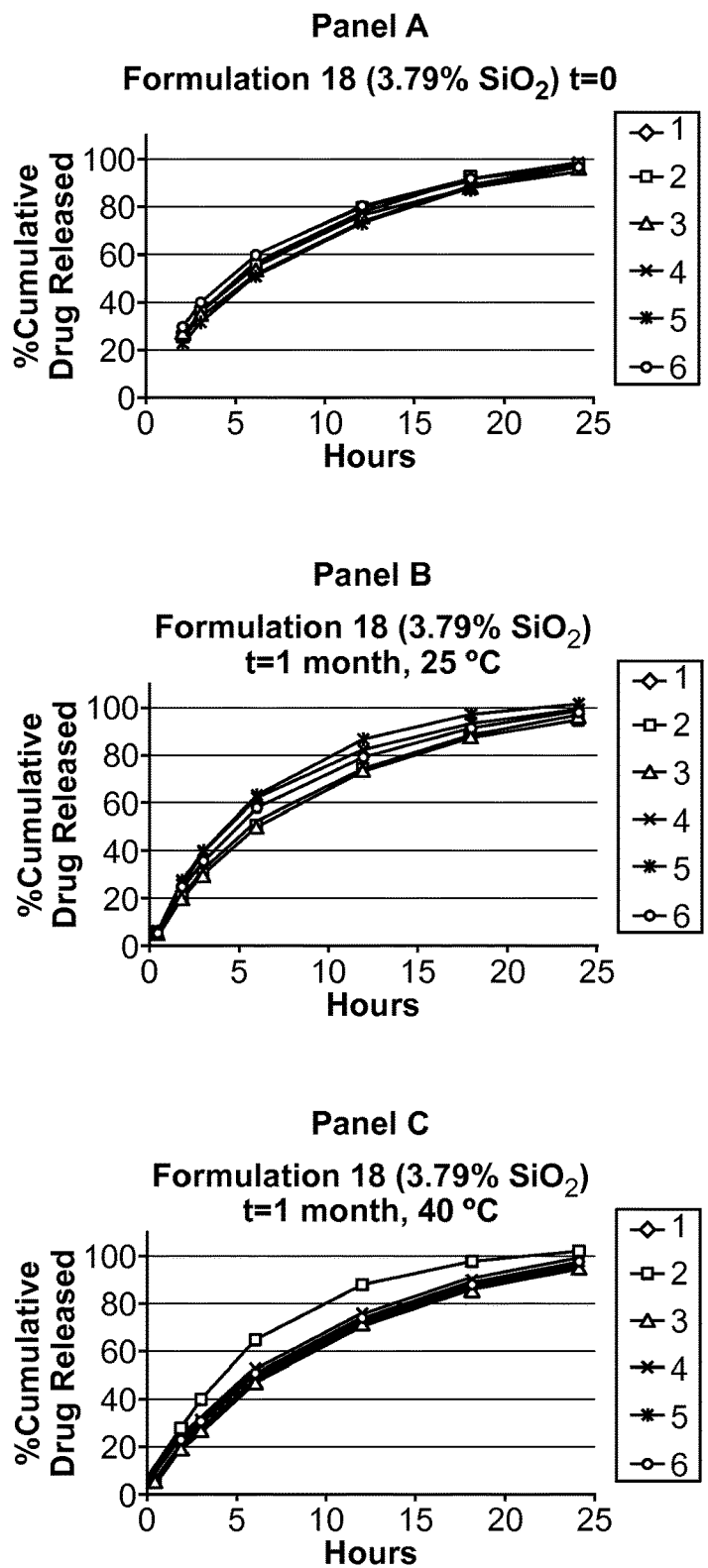
FIG. 25 provides graphs showing inter-capsule variability during dissolution testing of Formulation 18 following storage for 1 month at 25° C. or 40° C.

The results for Formulation 18 are provided in FIG. 24; FIG. 25, Panels A-C; and Table 23 below. Mean release is similar for the stored Formulation 18 samples relative to the T=0 samples as shown in FIG. 24. Sample variation was similar for the stored Formulation 18 samples as shown in FIG. 25, Panels A-C and Table 23.

TABLE 23

| ID | SiO$_2$ (% w/w) | Time Point (Months) | Storage Condition | Sample No. | | 0.5 | 2 | 3 | 6 | 12 | 18 | 24 | Sp |
|---|---|---|---|---|---|---|---|---|---|---|---|---|---|
| | | | | | | \multicolumn{7}{c}{Time Point (hrs)} | |
| Formulation 18 | 3.79 | 0 | NA | 6 | Mean | N/A | 26 | 36 | 55 | 77 | 90 | 97 | 2 |
| | | | | | SD | N/A | 2 | 3 | 3 | 2 | 2 | 1 | |
| | | 1 | 25° C./60% RH | 6 | Mean | 5 | 23 | 34 | 55 | 78 | 91 | 98 | 4 |
| | | | | | SD | 0 | 3 | 4 | 6 | 5 | 4 | 2 | |
| | | | 40° C./75% RH | 6 | Mean | 5 | 22 | 32 | 53 | 76 | 89 | 97 | 4 |
| | | | | | SD | 0 | 3 | 5 | 6 | 6 | 4 | 3 | |

Example 13: Preparation and Analysis of Extended Release Oxycodone Compositions (Formulations 5, 7, 9, 19 and 20)

Formulations 5, 7, 9, and additional compositions (Formulations 19 and 20) were prepared and characterized with respect to inter-capsule dissolution variability and rheology as indicated below.

Materials and Methods

The compositions were prepared to provide the compositions indicated in Table 24 (below). Bulk compositions for Formulations 5 and 7 were mixed to make Formulations 9, 19 and 20. Individual compositions were encapsulated generally as described above for Example 8, with the exception that HPMC capsules were used in place of gelatin capsules.

TABLE 24

| Composition (% w/w) | Formulation 5 | Formulation 19 | Formulation 9 | Formulation 20 | Formulation 7 |
|---|---|---|---|---|---|
| Triacetin (TA) | 39.08 | 39.08 | 39.08 | 39.08 | 39.08 |
| Isopropyl myristate (IPM) | 2.48 | 2.48 | 2.48 | 2.48 | 2.48 |
| Sucrose Acetate Isobutyrate (SAIB) | 40.98 | 40.48 | 39.98 | 39.48 | 38.98 |

TABLE 24-continued

| Composition (% w/w) | Formulation 5 | Formulation 19 | Formulation 9 | Formulation 20 | Formulation 7 |
|---|---|---|---|---|---|
| Hydroxyethyl cellulose (HEC) | 5.69 | 5.69 | 5.69 | 5.69 | 5.69 |
| Cellulose acetate butyrate (CAB) | 4.74 | 4.74 | 4.74 | 4.74 | 4.74 |
| Colloidal silicon dioxide (Cab-o-sil ®M-5P) | 1.90 | 2.40 | 2.90 | 3.40 | 3.90 |
| Oxycodone | 5.13 | 5.13 | 5.13 | 5.13 | 5.13 |

Dissolution Testing

Twelve capsules from each composition were tested with USP Apparatus 2 to evaluate the effect on inter-capsule dissolution variability. The release rate of oxycodone base was determined using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article and the paddle speed was set to 100 rpm. The standard sampling time points were 0.5, 2, 3, 6, 12, 18 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Rheology Testing

Samples of the above compositions were analyzed for rheological properties using an Anton Paar MCR301 Rheometer equipped with a parallel plate (25 mm diameter) and a gap setting of 1 mm. The samples were exposed to increasing temperature (20° C. to 80° C.) (at 2° C./min) at constant (0.5%) strain (oscillation mode) and 1 Hz frequency. Rheological properties for these compositions were compared with those of Reference Formulation A and Reference Formulation B, where the vehicle composition of Reference Formulation B was as follows: SAIB (39.98% w/w), Triacetin (29.62% w/w), IPM (16.00% w/w), CAB 380-20BP (5.50% w/w), HEC (5.00% w/w), Cab-O-Sil®M-5P (2.40% w/w), and Gelucire® 44/14 (1.50% w/w).

Results

Dissolution Testing Results

Figure 26:
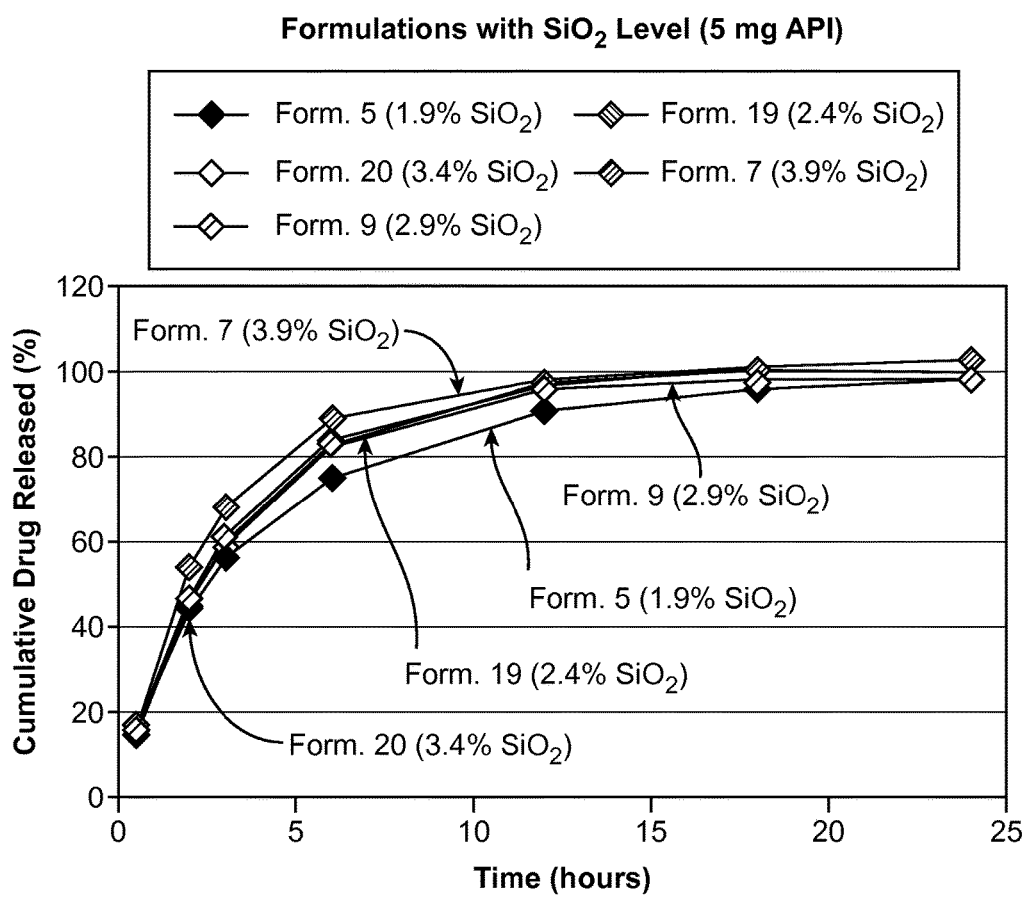
FIG. 26 is a graph showing mean release of oxycodone from Formulations 5, 7, 9, 19 and 20, with varying levels of $SiO_2$ and 5 mg oxycodone.
Figure 27:
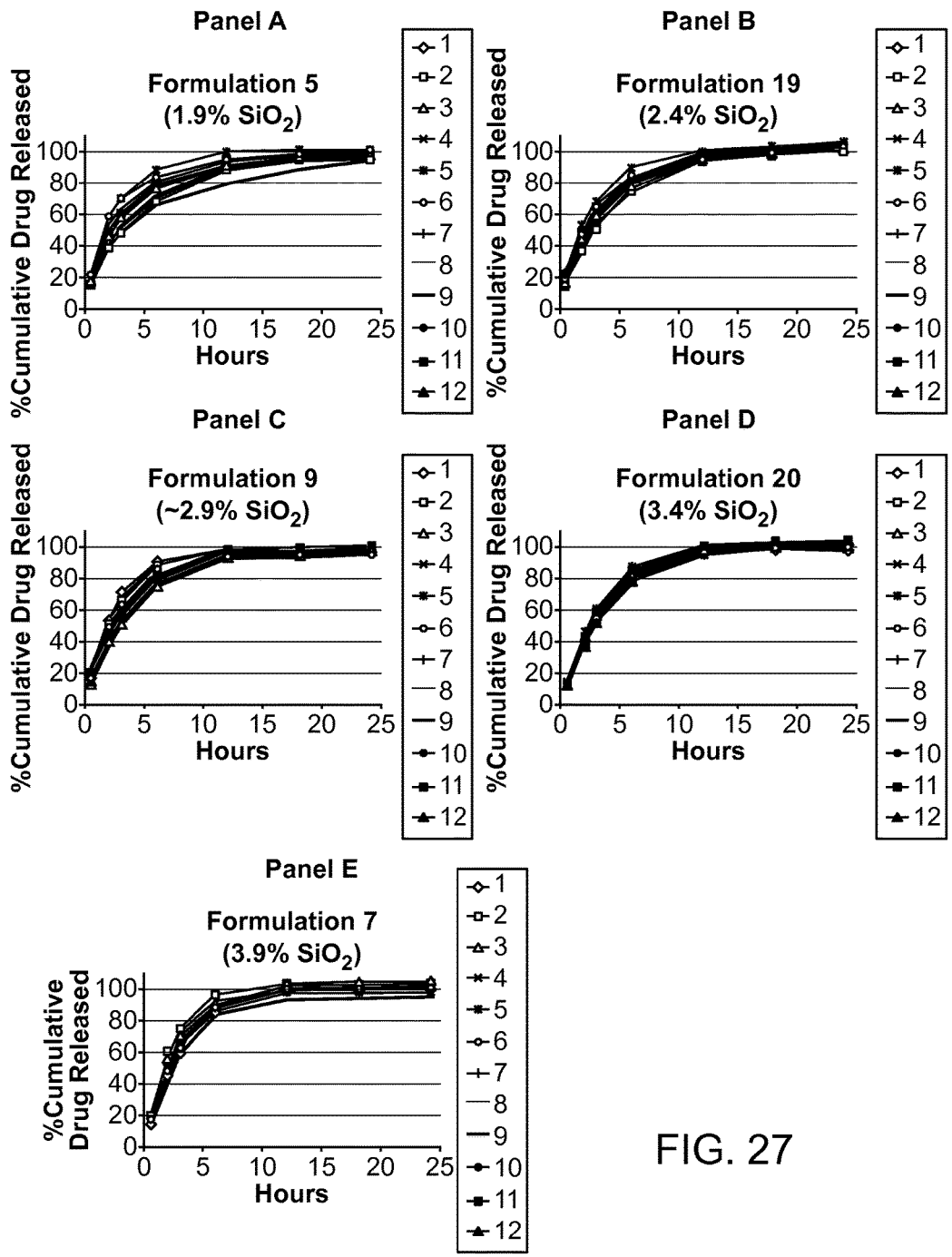
FIG. 27 provides graphs showing inter-capsule variability during dissolution testing of Formulations 5 (Panel A), 7 (Panel E), 9 (Panel C), 19 (Panel B) and 20 (Panel D), with varying levels of $SiO_2$ and 5 mg oxycodone.

The results of the dissolution experiments for the 5 mg oxycodone compositions are shown in FIG. 26; FIG. 27, Panels A-E; and Table 25 below. The in vitro dissolution results indicate an increase in mean release at earlier time points with an increase in the concentration level of $SiO_2$ in the composition (FIG. 26). Formulations 19, 9, 20 and 7, with 2.4%, 2.9%, 3.4% and 3.9% $SiO_2$ respectively, showed decreased sample variability relative to Formulation 5 (1.9% $SiO_2$), with Formulation 20 (3.4% $SiO_2$) showing the least amount of sample variability (FIG. 27, Panels A-E).

TABLE 25

| ID | $SiO_2$ (% w/w) | Sample No. | | 0.5 | 2 | 3 | 6 | 12 | 18 | 24 | Sp |
|---|---|---|---|---|---|---|---|---|---|---|---|
| Formulation 5 | 1.9 | 12 | Mean | 17 | 46 | 56 | 75 | 91 | 96 | 98 | 5 |
| | | | SD | 3 | 7 | 8 | 7 | 5 | 3 | 2 | |
| Formulation 19 | 2.4 | 12 | Mean | 18 | 47 | 60 | 82 | 97 | 100 | 103 | 3 |
| | | | SD | 3 | 5 | 5 | 4 | 2 | 1 | 1 | |
| Formulation 9 | 2.9 | 12 | Mean | 15 | 47 | 61 | 84 | 96 | 98 | 98 | 4 |
| | | | SD | 2 | 6 | 7 | 5 | 2 | 2 | 2 | |
| Formulation 20 | 3.4 | 12 | Mean | 14 | 43 | 58 | 83 | 98 | 101 | 102 | 2 |
| | | | SD | 1 | 3 | 3 | 3 | 2 | 2 | 2 | |
| Formulation 7 | 3.9 | 12 | Mean | 17 | 54 | 68 | 89 | 98 | 100 | 100 | 4 |
| | | | SD | 2 | 5 | 5 | 3 | 3 | 3 | 3 | |

(Time Point (hrs) column header spans 0.5, 2, 3, 6, 12, 18, 24)

Figure 28:
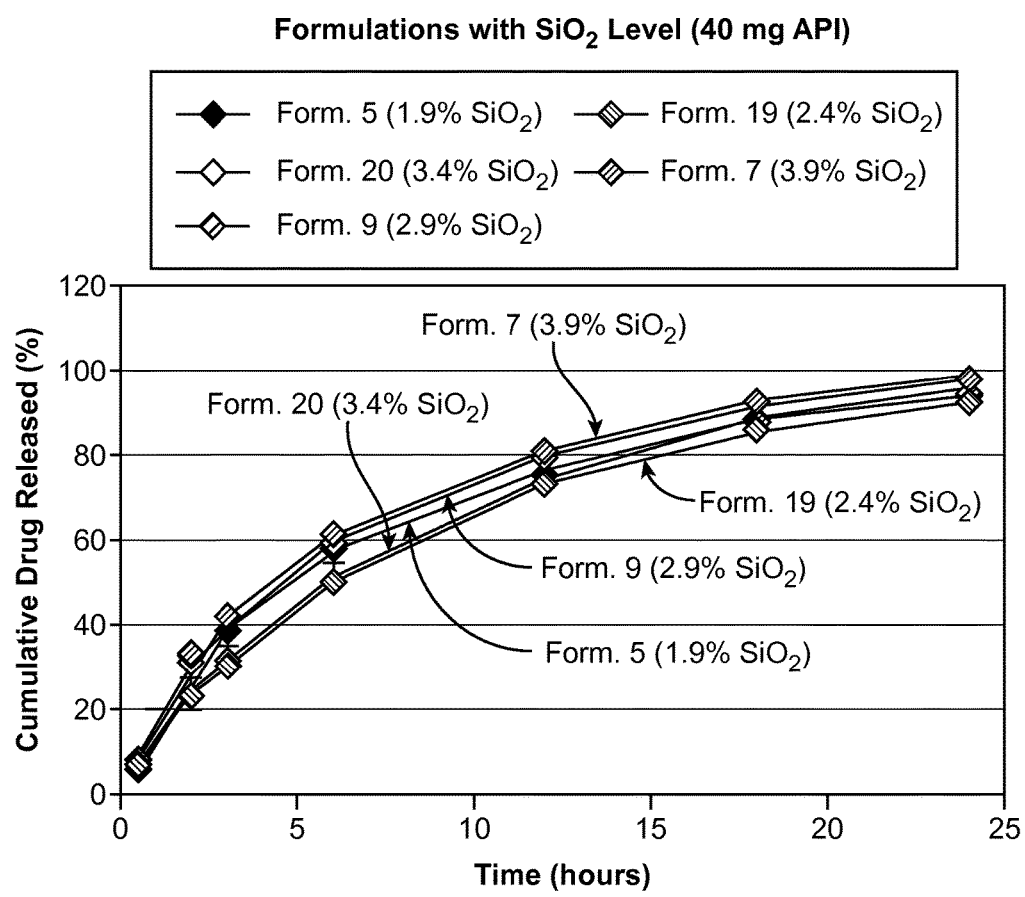
FIG. 28 is a graph showing mean release of oxycodone from Formulations 5, 7, 9, 19 and 20, with varying levels of $SiO_2$ and 40 mg oxycodone.
Figure 29:
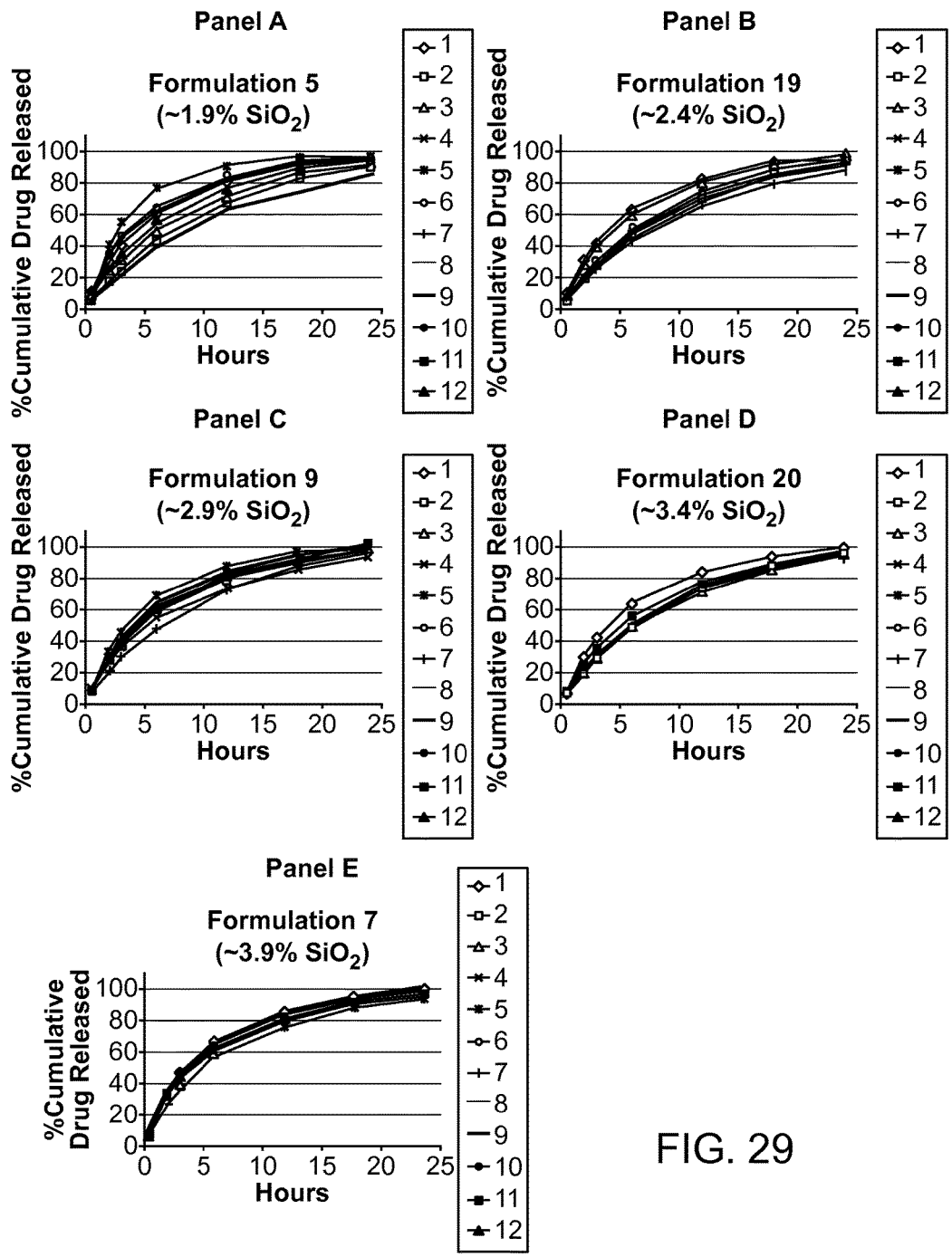
FIG. 29 provides graphs showing inter-capsule variability during dissolution testing of Formulations 5 (Panel A), 7 (Panel E), 9 (Panel C), 19 (Panel B) and 20 (Panel D), with varying levels of $SiO_2$ and 40 mg oxycodone.

The results of the dissolution experiments for the 40 mg oxycodone compositions are shown in FIG. 28; FIG. 29, Panels A-E; and Table 26 below. The in vitro dissolution results showed a decrease in sample variability with increasing $SiO_2$ concentration (FIG. 29, Panels A-E).

TABLE 26

| ID | $SiO_2$ (%) | Sample No. | | 0.5 | 2 | 3 | 6 | 12 | 18 | 24 | Sp |
|---|---|---|---|---|---|---|---|---|---|---|---|
| Formulation 5 | 1.9 | 12 | Mean | 8 | 29 | 39 | 58 | 78 | 88 | 94 | 7 |
| | | | SD | 2 | 7 | 8 | 10 | 8 | 5 | 3 | |
| Formulation 19 | 2.4 | 12 | Mean | 7 | 23 | 31 | 51 | 73 | 86 | 94 | 4 |
| | | | SD | 1 | 4 | 5 | 6 | 5 | 4 | 3 | |
| Formulation 9 | 2.9 | 12 | Mean | 7 | 28 | 39 | 60 | 81 | 93 | 99 | 4 |
| | | | SD | 1 | 3 | 4 | 5 | 5 | 3 | 2 | |
| Formulation 20 | 3.4 | 12 | Mean | 6 | 23 | 32 | 52 | 75 | 89 | 97 | 3 |
| | | | SD | 1 | 3 | 4 | 5 | 4 | 3 | 2 | |
| Formulation 7 | 3.9 | 12 | Mean | 6 | 30 | 41 | 61 | 82 | 93 | 99 | 3 |
| | | | SD | 1 | 3 | 4 | 4 | 3 | 3 | 2 | |

Rheology Testing Results

Figure 30:
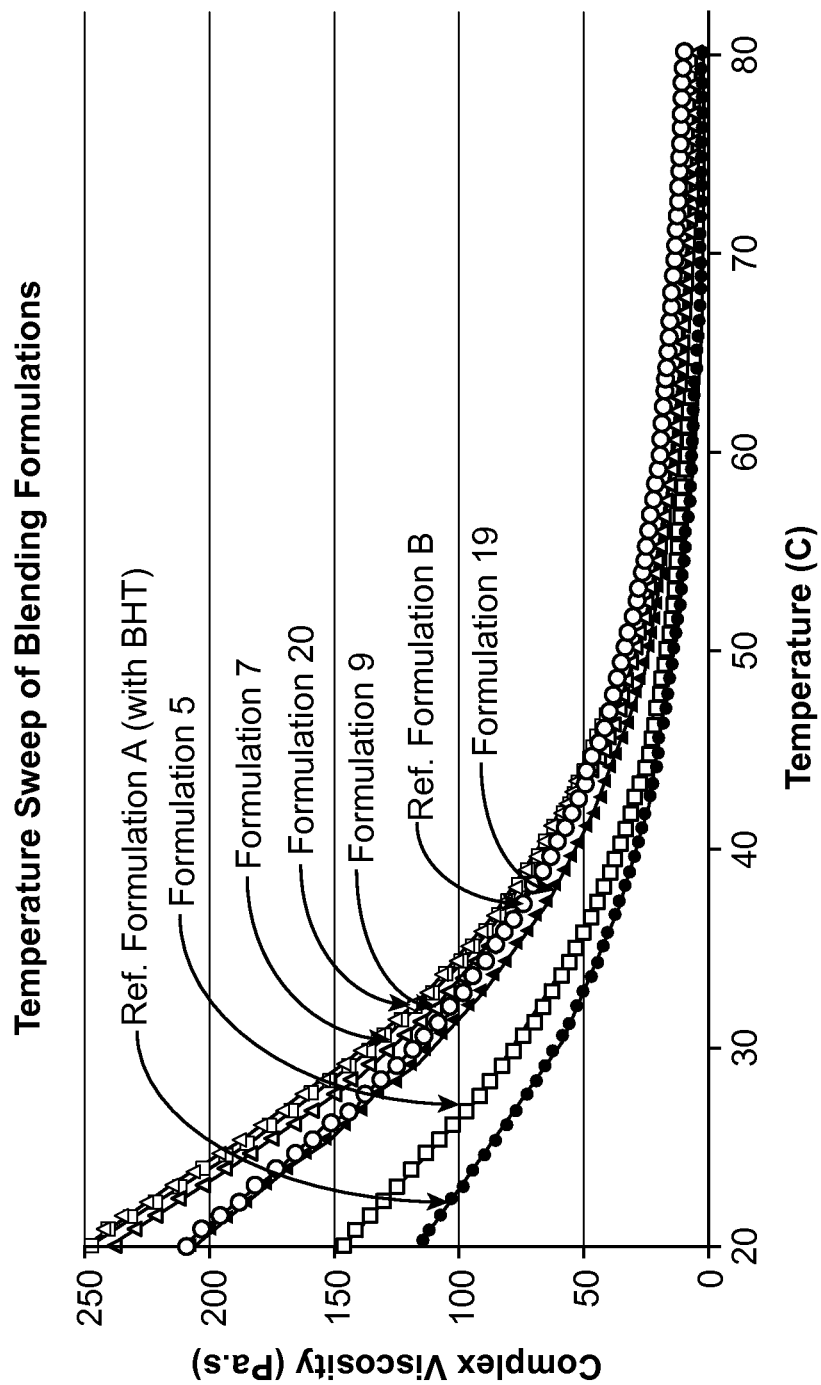
FIG. 30 is a graph showing complex viscosity as a function of temperature for Reference Formulation A and Formulations 5, 7, 9, 19 and 20.
Figure 31:
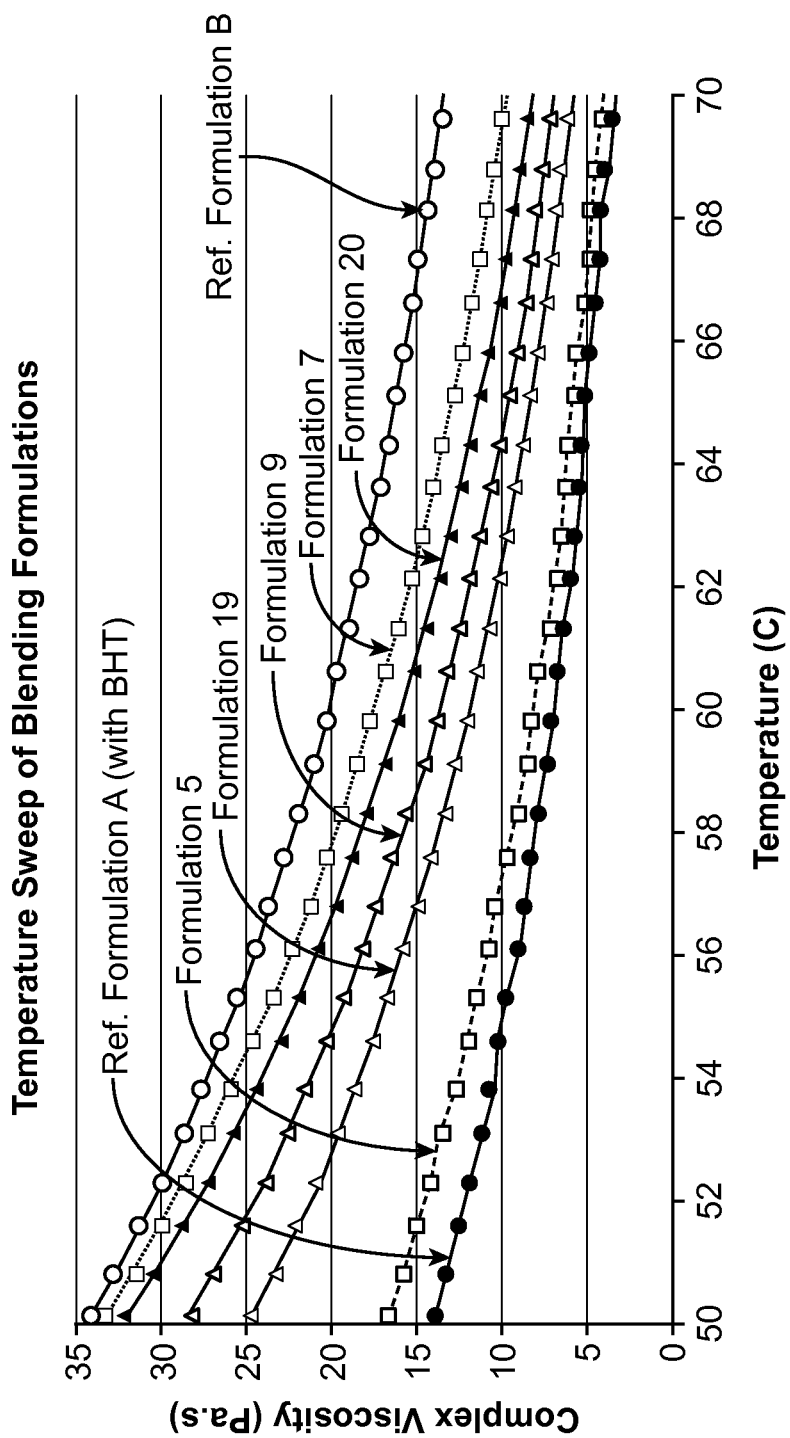
FIG. 31 is another graph showing complex viscosity as a function of temperature for Reference Formulation A and Formulations 5, 7, 9, 19 and 20. The graph in FIG. 31 provides a different temperature scale than that for FIG. 30.
Figure 32:
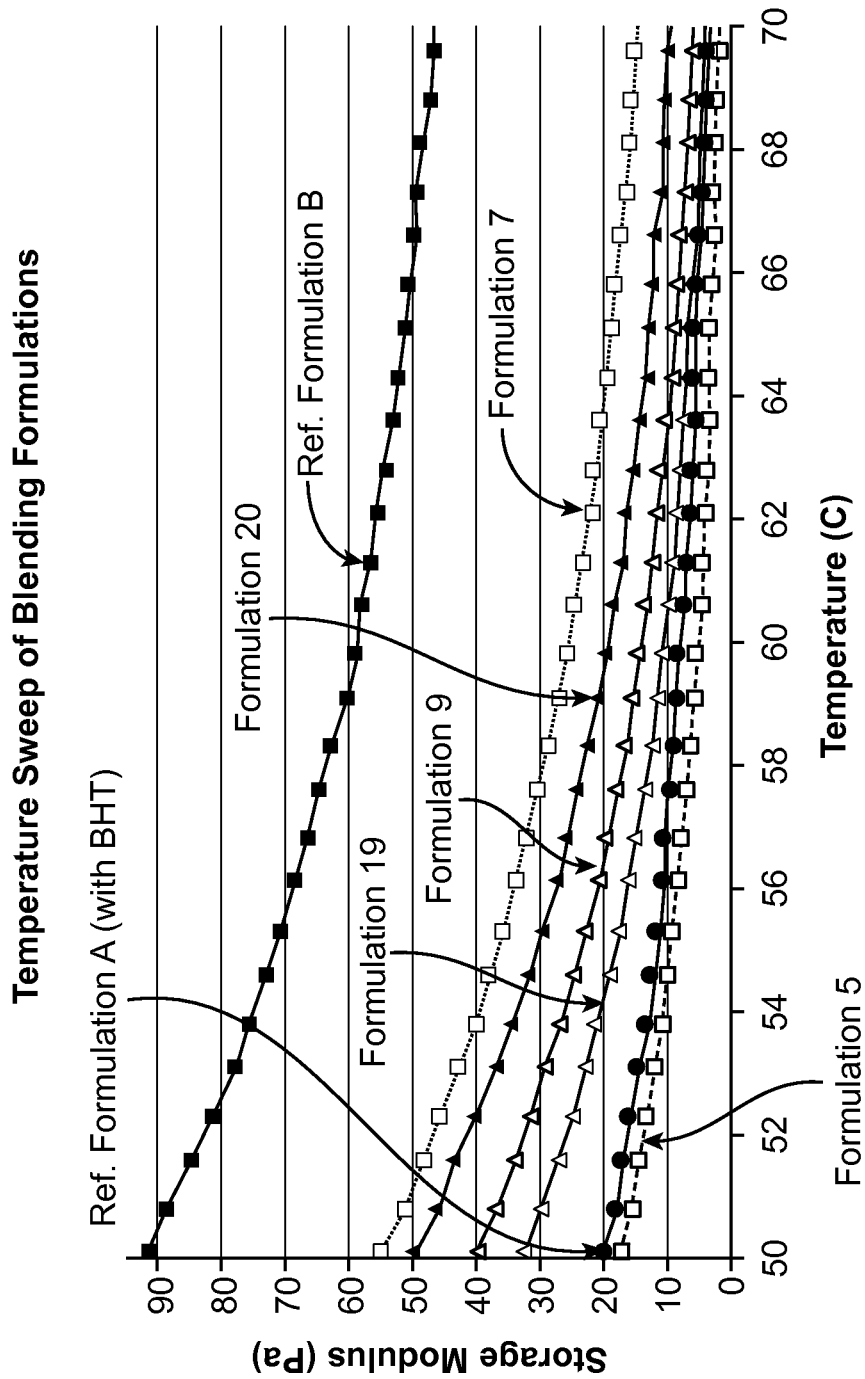
FIG. 32 is a graph showing storage modulus (G') as a function of temperature for Reference Formulation A and Formulations 5, 7, 9, 19 and 20.
Figure 33:
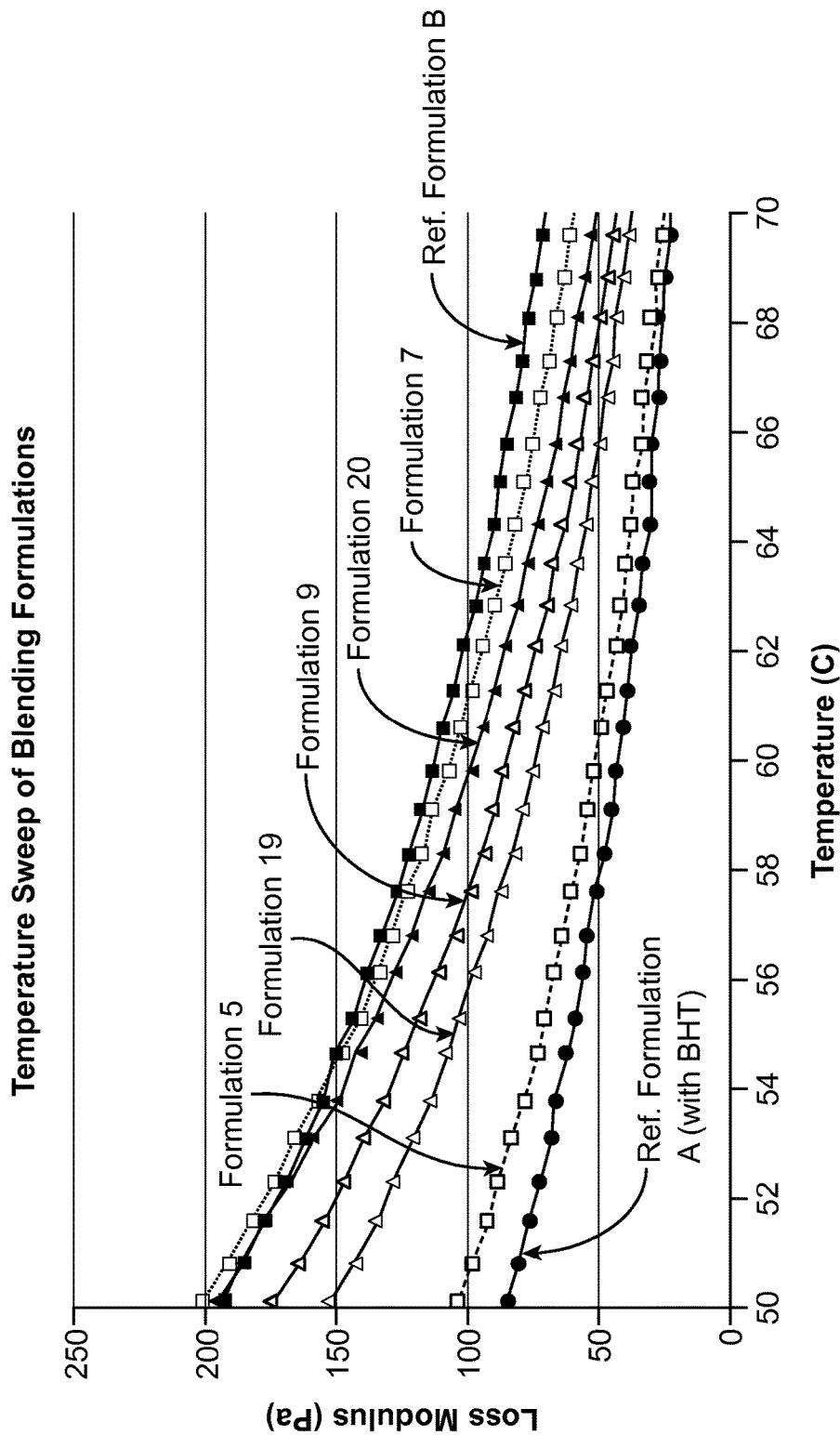
FIG. 33 is a graph showing loss modulus (G") as a function of temperature for Reference Formulation A and Formulations 5, 7, 9, 19 and 20.
Figure 34:
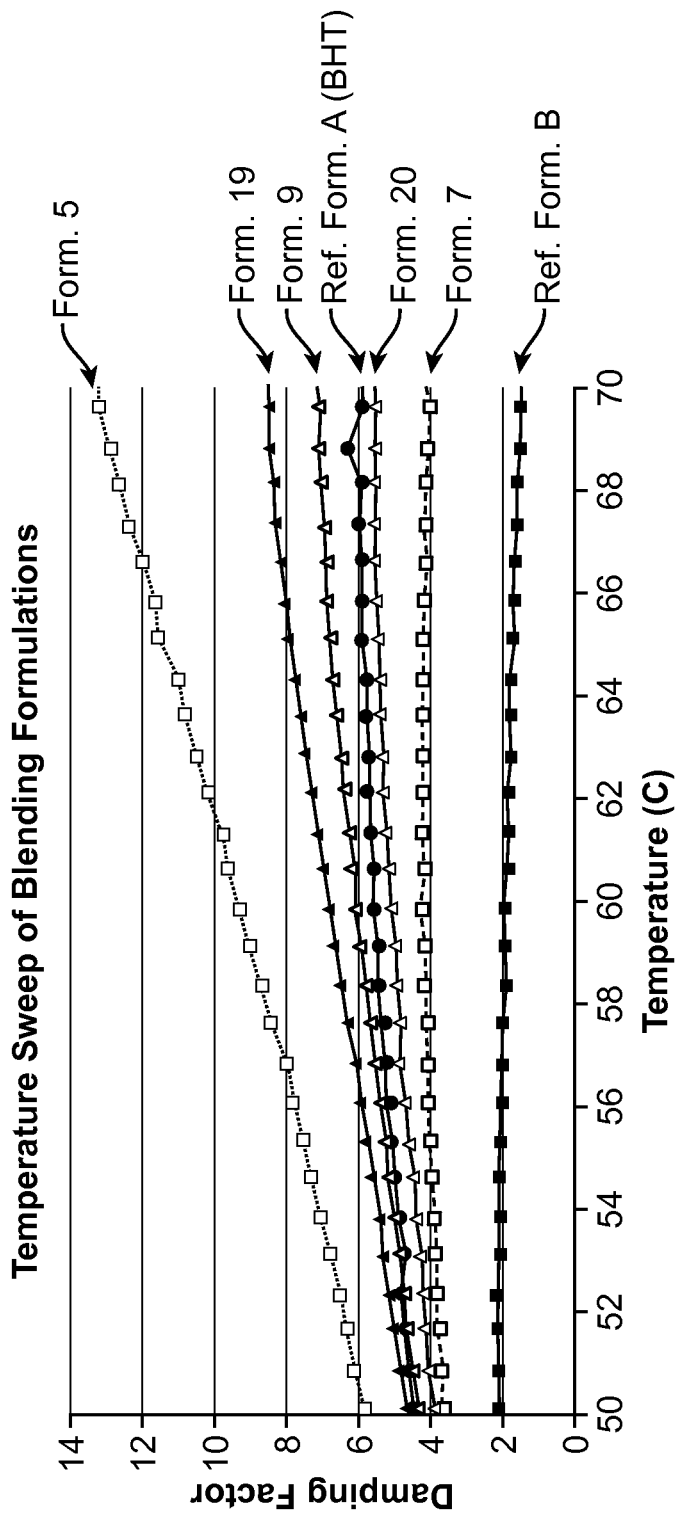
FIG. 34 is a graph showing damping factor (G"/G') as a function of temperature for Reference Formulation A and Formulations 5, 7, 9, 19 and 20.
Figure 35:
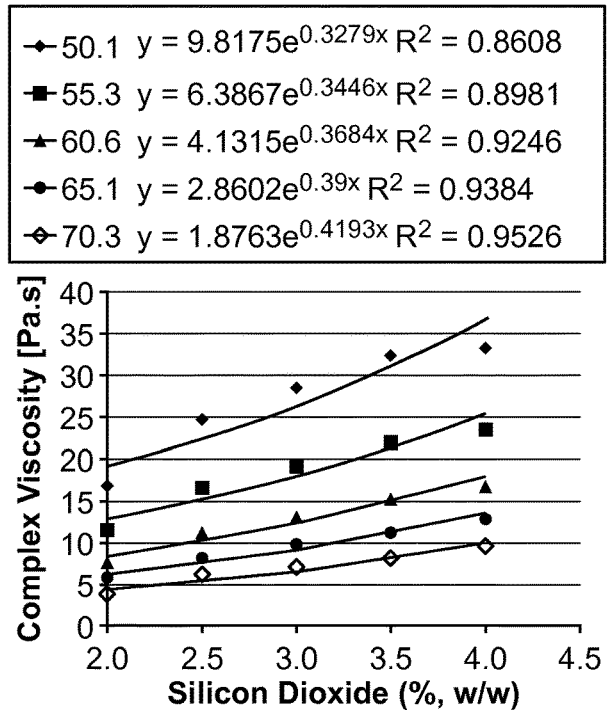
FIG. 35 provides graphs showing complex viscosity (Panel A) and storage modulus (Panel B) as a function of $SiO_2$ content at temperatures between about 50 and 70° C. based on the results for Formulations 5, 7, 9, 19 and 20.
Figure 35:
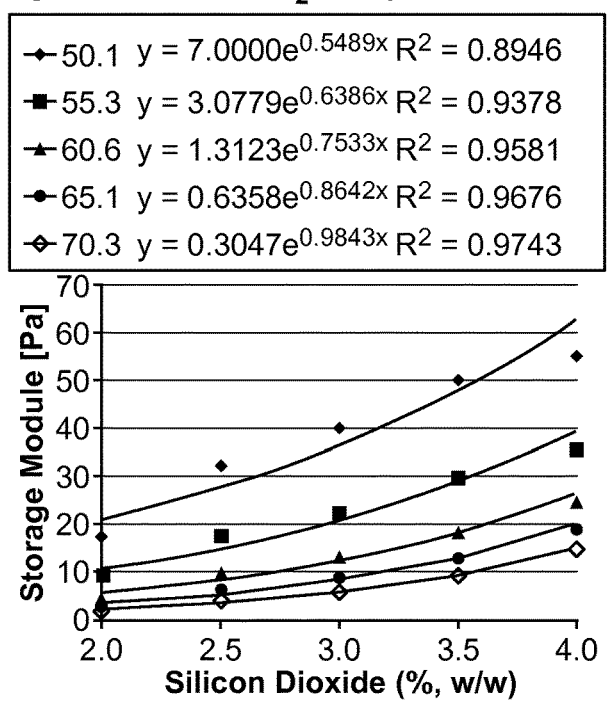
Figure 36:
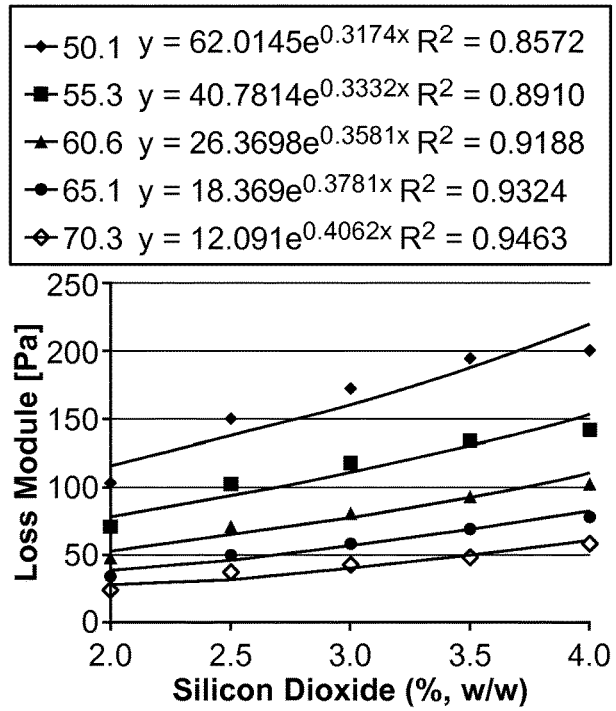
FIG. 36 provides graphs showing loss modulus (Panel A) and damping factor (Panel B) as a function of $SiO_2$ content at temperatures between about 50 and 70° C. based on the results for Formulations 5, 7, 9, 19 and 20.
Figure 36:
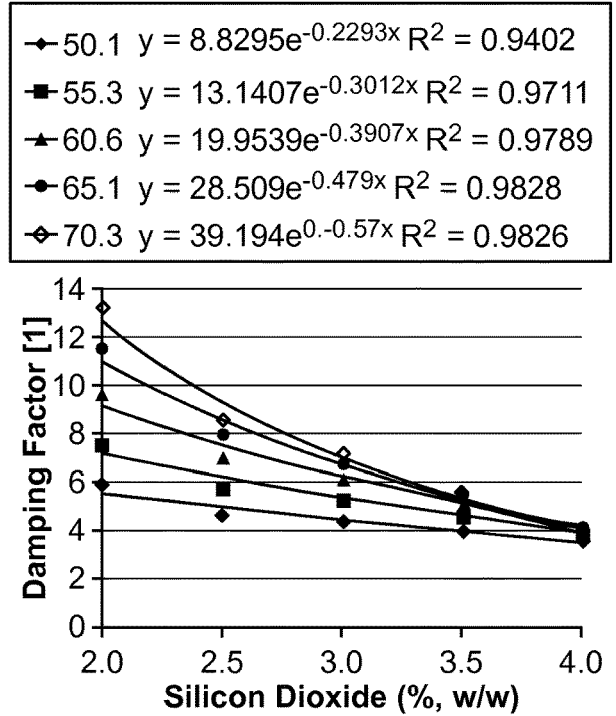

The viscoelastic outputs of the rheology testing experiments are provided in Tables 27-30 (below) and FIGS. 26-32. As shown in Table 27 and FIGS. 30 and 31, the complex viscosity range for the tested compositions narrows with an increase in temperature. In addition, there is an increase in complex viscosity with increasing concentration of $SiO_2$ for Formulations 5, 7, 9, 19 and 20 as shown in FIGS. 30, 31 and 35 (Panel A).

TABLE 27

Complex Viscosity

| Temp. (° C.) | Formulation 5 | Formulation 19 | Formulation 9 | Formulation 20 | Formulation 7 |
|---|---|---|---|---|---|
| 50 | 17 | 25 | 28 | 32 | 33 |
| 55 | 11 | 17 | 19 | 22 | 23 |
| 61 | 8 | 11 | 13 | 15 | 17 |
| 65 | 6 | 8 | 10 | 11 | 13 |
| 70 | 4 | 6 | 7 | 8 | 10 |

TABLE 28

Loss Module (G")

| Temp. (° C.) | Formulation 5 | Formulation 19 | Formulation 9 | Formulation 20 | Formulation 7 |
|---|---|---|---|---|---|
| 50 | 103 | 152 | 174 | 196 | 201 |
| 55 | 71 | 103 | 118 | 135 | 143 |
| 61 | 49 | 71 | 82 | 94 | 103 |
| 65 | 35 | 52 | 60 | 70 | 78 |
| 70 | 25 | 37 | 43 | 50 | 58 |

TABLE 29

Damping Factor (G"/G')

| Temp. (° C.) | Formulation 5 | Formulation 19 | Formulation 9 | Formulation 20 | Formulation 7 |
|---|---|---|---|---|---|
| 50 | 5.9 | 4.7 | 4.4 | 3.9 | 3.6 |
| 55 | 7.6 | 5.8 | 5.3 | 4.6 | 4.0 |
| 61 | 9.6 | 7.0 | 6.2 | 5.2 | 4.2 |
| 65 | 11.5 | 7.9 | 6.8 | 5.5 | 4.2 |
| 70 | 13.2 | 8.5 | 7.2 | 5.5 | 4.0 |

TABLE 30

Storage Module (G')

| Temp. (° C.) | Formulation 5 | Formulation 19 | Formulation 9 | Formulation 20 | Formulation 7 |
|---|---|---|---|---|---|
| 50 | 17 | 32 | 40 | 50 | 55 |
| 55 | 9 | 18 | 23 | 30 | 36 |
| 61 | 5 | 10 | 13 | 19 | 25 |
| 65 | 3 | 7 | 9 | 13 | 19 |
| 70 | 2 | 4 | 6 | 9 | 15 |

Formulations 19, 9, 20 and 7, with increased concentration of $SiO_2$ (as compared to Formulation 5), exhibited higher elastic property (lower G"/G') as shown in Tables 27-30 and FIGS. 32-36. Without intending to be bound by any particular theory, this higher elastic property may have resulted in the lower inter-capsule dissolution variability shown in FIGS. 27 and 29.

Example 14: Stability Analysis of Stored Extended Release Oxycodone Compositions (Formulations 5, 8, 9 and 7)

Formulations 5, 8, 9 and 7 were analyzed following storage for various periods of time to determine the effect on drug release and inter-capsule dissolution variability.

Materials and Methods

Formulations 5, 8, 9 and 7 (40 mg oxycodone) were stored at 25° C./60% RH and/or 40° C./75% RH for a total of 6 months, 2 months, 2 months, and 3 months respectively. Twelve capsules from each composition lot were tested according to the testing conditions discussed above to evaluate the effect on mean release and inter-capsule dissolution variability.

Results

Figure 37:
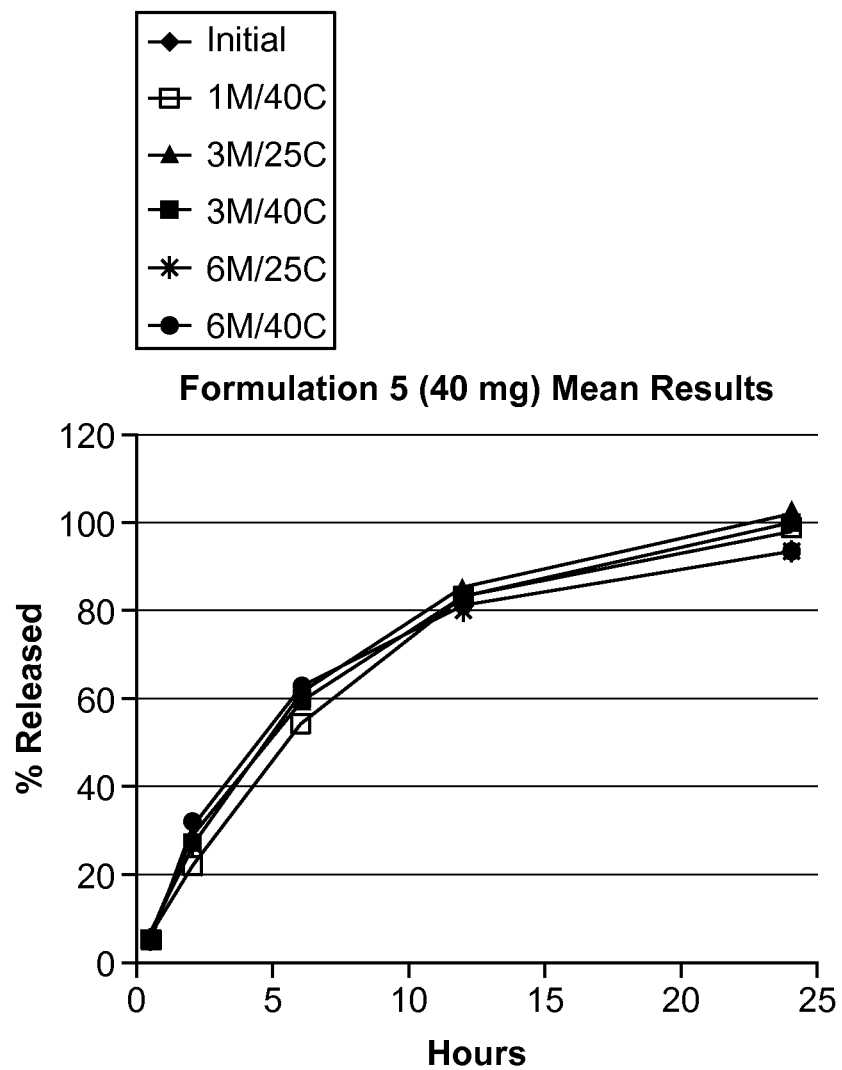
FIG. 37 is a graph showing mean release for Formulation 5 (40 mg) following storage at 25° C./60% relative humidity (RH) and 40° C./75% RH for up to 6 months.

The results for Formulation 5 are provided in FIG. 37 and Table 31 (below). No significant change in mean release was seen as a result of storage up to 6 months for Formulation 5. Formulation 5 testing resulted in a relatively higher level of dissolution sample variation than that seen for Formulations 9 and 7 (discussed below).

TABLE 31

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 7 | 29 | 61 | 83 | 98 | 5 |
| | | | SD | 1 | 4 | 7 | 6 | 3 | |
| 1 | 40° C./75% RH | 12 | Mean | 6 | 22 | 54 | 81 | 100 | 3 |
| | | | SD | 1 | 3 | 5 | 4 | 3 | |
| 3 | 25° C./60% RH | 12 | Mean | 7 | 29 | 63 | 86 | 103 | 4 |
| | | | SD | 1 | 3 | 5 | 6 | 4 | |
| | 40° C./75% RH | 12 | Mean | 6 | 27 | 60 | 84 | 100 | 4 |
| | | | SD | 1 | 3 | 6 | 6 | 4 | |
| 6 | 25° C./60% RH | 12 | Mean | 7 | 28 | 60 | 81 | 95 | 4 |
| | | | SD | 1 | 3 | 6 | 6 | 3 | |
| | 40° C./75% RH | 12 | Mean | 7 | 32 | 63 | 83 | 95 | 3 |
| | | | SD | 1 | 3 | 5 | 4 | 2 | |

Figure 38:
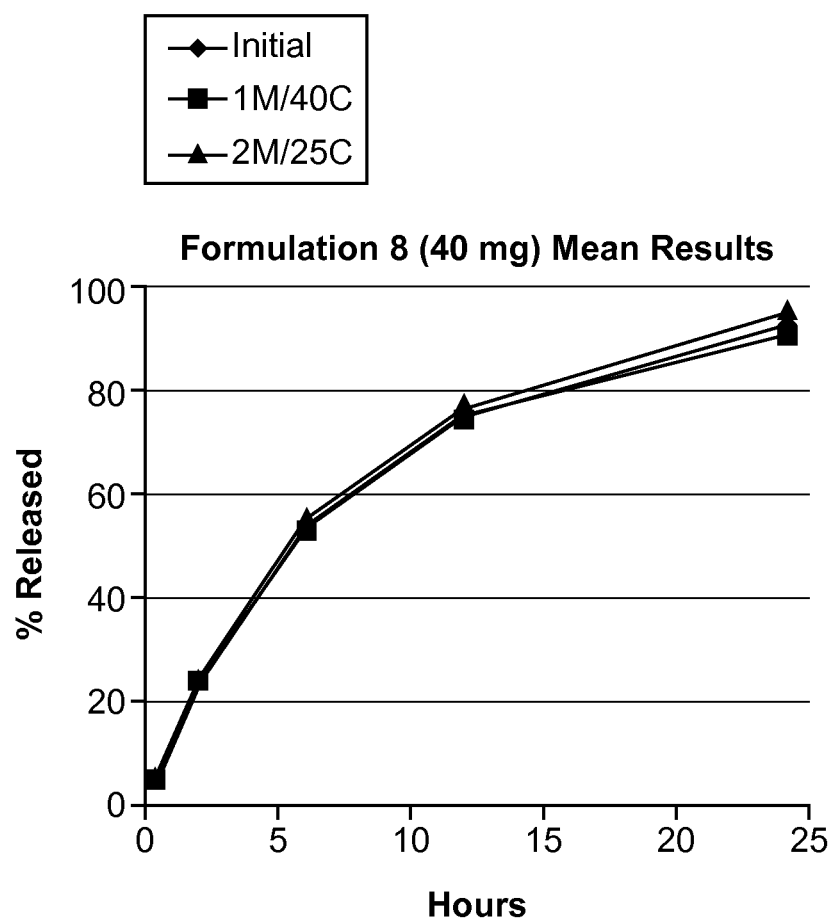
FIG. 38 is a graph showing mean release for Formulation 8 (40 mg) following storage for 1 month at 40° C./75% RH or 2 months at 25° C./60% RH.

The results for Formulation 8 are provided in FIG. 38 and Table 32 below. No significant change in mean release was seen as a result of storage up to 2 months for Formulation 8. Formulation 8 testing resulted in a relatively higher level of variation than that seen for Formulations 9 and 7 (discussed below).

TABLE 32

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 6 | 23 | 55 | 77 | 93 | 5 |
| | | | SD | 1 | 5 | 8 | 6 | 4 | |
| 1 | 40° C./75% RH | 12 | Mean | 5 | 24 | 54 | 75 | 91 | 4 |
| | | | SD | 1 | 3 | 5 | 5 | 3 | |
| 2 | 25° C./60% RH | 12 | Mean | 5 | 24 | 55 | 77 | 95 | 4 |
| | | | SD | 1 | 4 | 6 | 5 | 3 | |

Figure 39:
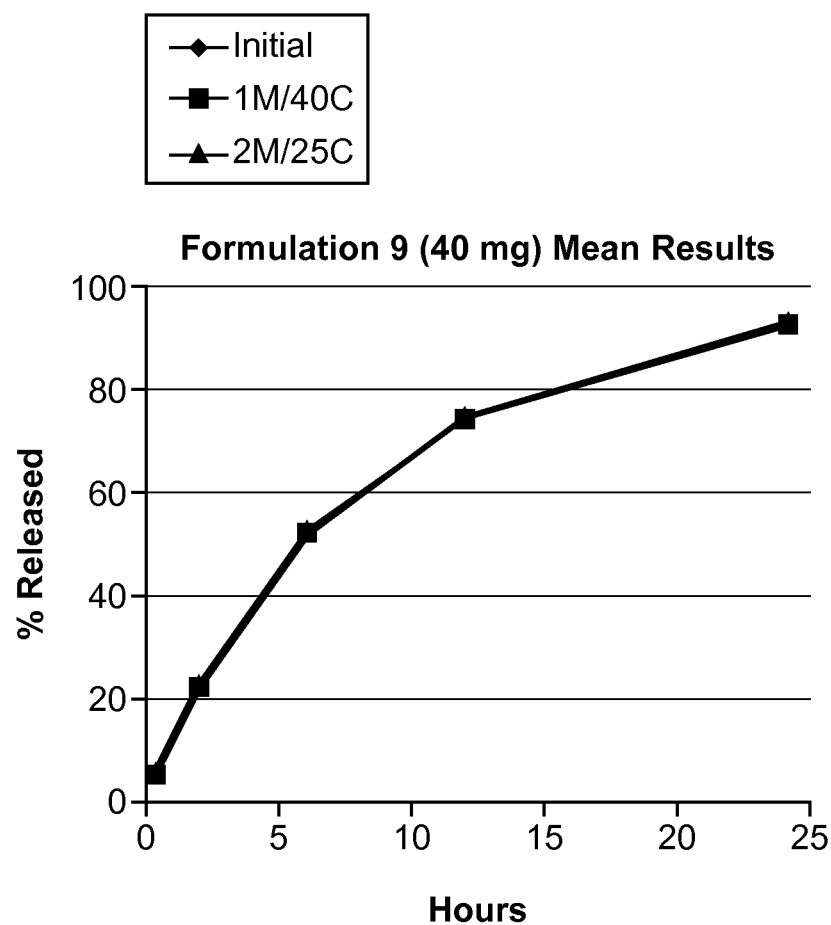
FIG. 39 is a graph showing mean release for Formulation 9 (40 mg) following storage for 1 month at 40° C./75% RH or 2 months at 25° C./60% RH.

The results for Formulation 9 are provided in FIG. 39 and Table 33 below. No significant change in mean release was seen as a result of storage for up to 2 months for Formulation 9. In addition, Formulation 9 showed a relatively low level of inter-capsule dissolution variability following storage for a 1 month period.

TABLE 33

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 5 | 22 | 53 | 75 | 93 | 2 |
| | | | SD | 1 | 1 | 2 | 2 | 2 | |
| 1 | 40° C./75% RH | 12 | Mean | 5 | 22 | 52 | 74 | 92 | 2 |
| | | | SD | 0 | 1 | 2 | 2 | 1 | |
| 2 | 25° C./60% RH | 12 | Mean | 5 | 23 | 53 | 75 | 93 | 1 |
| | | | SD | 1 | 1 | 2 | 2 | 1 | |

Figure 40:
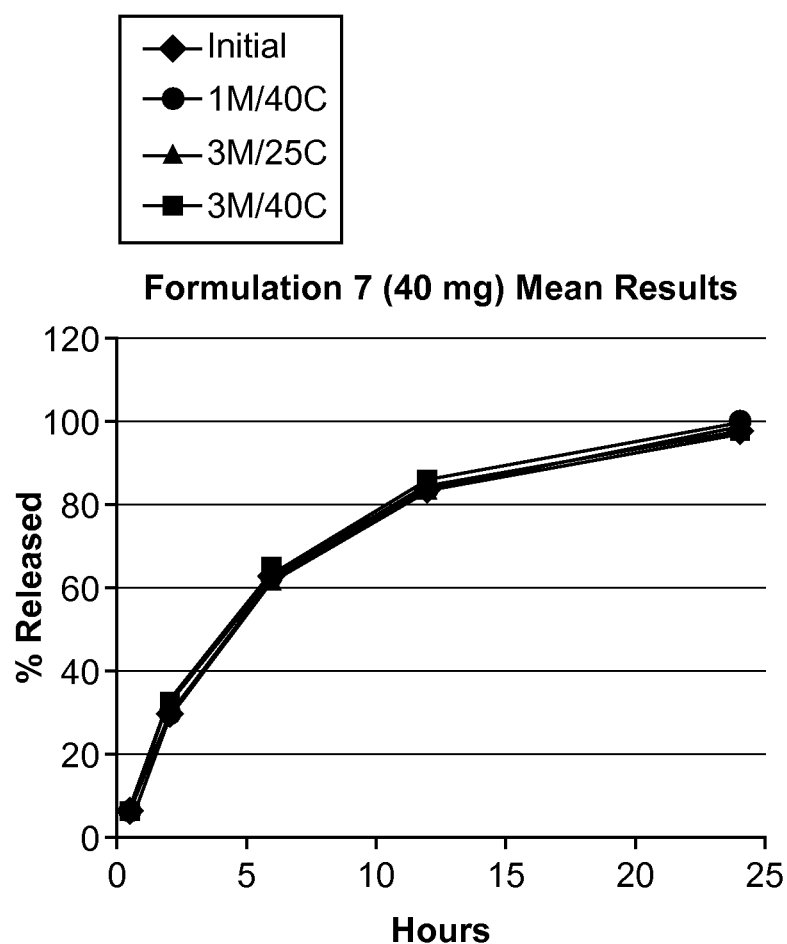
FIG. 40 is a graph showing mean release for Formulation 7 (40 mg) following storage for 1 month at 40° C./75% RH or 3 months at 25° C./60% RH or 40° C./75% RH.

The results for Formulation 7 are provided in FIG. 40 and Table 34 below. No significant change in mean release was seen as a result of storage for up to 3 months for Formulation 7. In addition, Formulation 7 showed a relatively low level of inter-capsule dissolution variability following storage for up to three months.

TABLE 34

| Time Point (Months) | Storage Condition | Sample No. | | Time Point (hrs) | | | | | |
|---|---|---|---|---|---|---|---|---|---|
| | | | | 0.5 | 2 | 6 | 12 | 24 | Sp |
| 0 | N/A | 12 | Mean | 5 | 28 | 59 | 82 | 99 | 2 |
| | | | SD | 1 | 1 | 2 | 3 | 3 | |
| 1 | 40° C./75% RH | 12 | Mean | 6 | 30 | 61 | 83 | 100 | 2 |
| | | | SD | 1 | 2 | 2 | 2 | 2 | |
| 3 | 25° C./60% RH | 12 | Mean | 6 | 32 | 64 | 85 | 98 | 2 |
| | | | SD | 0 | 1 | 2 | 3 | 3 | |
| | 40° C./75% RH | 12 | Mean | 6 | 33 | 65 | 86 | 98 | 2 |
| | | | SD | 0 | 1 | 2 | 2 | 3 | |

The initial T=0 dissolution data from Tables 31-34 was used to calculate % RSD ((SD/mean)×100) for Formulations 5, 8, 9 and 7. The results are provided below in Table 35. As shown below, Formulations 9 and 7 exhibited a % RSD of 5% or less at the 2 and 6 hour time points, while Formulations 5 exhibited a % RSD of less than 15% at the 2 and 6 hour time points. Formulation 8 exhibited a % RSD of less than 25% at the 2 and 6 hour time points.

TABLE 35

| ID | SiO$_2$ (%) | Sample # | | Time point (hrs) | | | | |
|---|---|---|---|---|---|---|---|---|
| | | | | 0.5 | 2 | 6 | 12 | 24 |
| 5 | 1.90 | 12 | Mean | 7 | 29 | 61 | 83 | 98 |
| | | | SD | 1 | 4 | 7 | 6 | 3 |
| | | | % RSD | 14 | 14 | 11 | 7 | 3 |
| 8 | 2.50 | 12 | Mean | 6 | 23 | 55 | 77 | 93 |
| | | | SD | 1 | 5 | 8 | 6 | 4 |
| | | | % RSD | 17 | 22 | 15 | 8 | 4 |
| 9 | 2.90 | 12 | Mean | 5 | 22 | 53 | 75 | 93 |
| | | | SD | 1 | 1 | 2 | 2 | 2 |
| | | | % RSD | 20 | 5 | 4 | 3 | 2 |
| 7 | 3.90 | 12 | Mean | 5 | 28 | 59 | 82 | 99 |
| | | | SD | 1 | 1 | 2 | 3 | 3 |
| | | | % RSD | 20 | 4 | 3 | 4 | 3 |

Example 15: Preparation and Analysis of Extended Release Hydrocodone Compositions (Formulations 21-26)

Hydrocodone compositions (Formulations 21-26) were prepared and characterized with respect to inter-capsule dissolution variability as indicated below.

Materials and Methods

The compositions were prepared to provide the compositions indicated in Table 36 (below). Composition components were blended and individual compositions were encapsulated in gelatin (Licaps® (GC)) or HPMC (Vcaps® (VC)) capsules as described above.

TABLE 36

| Composition (% w/w unless otherwise noted) | Formulation 21 | Formulation 22 | Formulation 23 | Formulation 24 | Formulation 25 | Formulation 26 |
|---|---|---|---|---|---|---|
| Hydrocodone Bitartrate | 13.64 | 13.64 | 13.64 | 10.00 | 10.00 | 10.00 |
| SAIB | 36.64 | 35.99 | 35.61 | 38.50 | 37.84 | 37.45 |
| Triacetin | 34.89 | 34.94 | 34.92 | 36.67 | 36.73 | 36.72 |
| IPM | 2.50 | 2.50 | 2.50 | 2.50 | 2.50 | 2.50 |
| CAB | 4.74 | 4.74 | 4.74 | 4.74 | 4.74 | 4.74 |
| HEC | 5.69 | 5.69 | 5.69 | 5.69 | 5.69 | 5.69 |
| Cab-O-Sil ®M-5P | 1.90 | 2.50 | 2.90 | 1.90 | 2.50 | 2.90 |
| Capsule Shell | GC, VC | GC, VC | GC, VC | VC | VC | VC |

Six capsules from each composition lot were tested according to the testing conditions discussed above to evaluate the effect on inter-capsule dissolution variability.

Results

The results of the dissolution experiments are provided in Table 37 (below). A clear trend with respect to inter-capsule dissolution variability and $SiO_2$ concentration was not demonstrated. However, inter-capsule dissolution variability was reduced for each composition when formulated in HPMC capsules as opposed to gelatin capsules. Formulation 23 with 2.9% $SiO_2$ showed the least amount of inter-capsule dissolution variability.

The HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 67% Mobile phase A and 33% Mobile phase B; 210 nm wavelength.

TABLE 37

| Formulation ID | SiO₂ (% w/w) | Capsule Shell | Sample # | | Time point (hrs) | | | | | | | |
|---|---|---|---|---|---|---|---|---|---|---|---|---|
| | | | | | 0.5 | 2 | 3 | 6 | 12 | 18 | 24 | Sp |
| Formulation 21 | 1.90 | GC | 6 | Mean | 15 | 60 | 75 | 95 | 101 | 102 | 102 | 6 |
| | | | | SD | 4 | 9 | 9 | 5 | 4 | 4 | 4 | |
| | | VC | 6 | Mean | 13 | 59 | 74 | 95 | 102 | 102 | 102 | 4 |
| | | | | SD | 2 | 6 | 6 | 3 | 2 | 2 | 2 | |
| Formulation 22 | 2.50 | GC | 6 | Mean | 15 | 52 | 66 | 90 | 100 | 102 | 102 | 9 |
| | | | | SD | 4 | 12 | 12 | 8 | 7 | 7 | 7 | |
| | | VC | 6 | Mean | 11 | 45 | 69 | 94 | 103 | 104 | 105 | 5 |
| | | | | SD | 2 | 5 | 7 | 6 | 4 | 4 | 4 | |
| Formulation 23 | 2.90 | GC | 6 | Mean | 16 | 52 | 67 | 91 | 101 | 103 | 103 | 5 |
| | | | | SD | 5 | 8 | 7 | 3 | 3 | 3 | 3 | |
| | | VC | 6 | Mean | 10 | 50 | 66 | 92 | 101 | 101 | 102 | 2 |
| | | | | SD | 2 | 4 | 4 | 1 | 2 | 1 | 1 | |
| Formulation 24 | 1.90 | VC | 6 | Mean | 5 | 42 | 58 | 84 | 99 | 100 | 101 | 4 |
| | | | | SD | 1 | 3 | 4 | 4 | 5 | 4 | 4 | |
| Formulation 25 | 2.50 | VC | 6 | Mean | 9 | 45 | 59 | 84 | 100 | 103 | 103 | 4 |
| | | | | SD | 2 | 5 | 5 | 3 | 3 | 3 | 3 | |
| Formulation 26 | 2.90 | VC | 6 | Mean | 13 | 53 | 66 | 88 | 101 | 103 | 103 | 5 |
| | | | | SD | 3 | 7 | 7 | 6 | 4 | 4 | 4 | |

Example 16: Preparation and Analysis of Extended Release Amphetamine Compositions (Formulations 27-30)

Amphetamine compositions (Formulations 27-30) were prepared and characterized with respect to inter-capsule dissolution variability as indicated below.

Materials and Methods

The compositions were prepared to provide the compositions indicated in Table 38 (below). Composition components were blended and individual compositions were encapsulated in HPMC (Vcaps® (VC)) capsules as described above.

Dissolution experiments were performed using 2-phase medium in a USP Apparatus 2. The capsules were placed in stainless steel (316SS) wire spiral capsule sinkers for dissolution testing. The dissolution parameters were as follows: Dissolution medium: 750 ml 0.1N HCl for the first 2 hours, add 200 ml 0.19M phosphate buffer to achieve a final pH of 6.0; Paddle speed: 50 rpm; Vessel temperature: 37 C. Sampling time points: 0.25, 0.5, 1, 1.5, 2, 3, 6, 9, 12 and 24 hours. Sampling volume: 1 mL.

TABLE 38

| Composition (% w/w) | Formulation 27 | Formulation 28 | Formulation 29 | Formulation 30 |
|---|---|---|---|---|
| D-Amphetamine Sulfate | 10.00 | 10.00 | 10.00 | 10.00 |
| SAIB | 38.50 | 37.84 | 37.45 | 36.59 |

TABLE 38-continued

| Composition (% w/w) | Formulation 27 | Formulation 28 | Formulation 29 | Formulation 30 |
|---|---|---|---|---|
| Triacetin | 36.67 | 36.73 | 36.72 | 36.59 |
| IPM | 2.50 | 2.50 | 2.50 | 2.50 |
| CAB | 4.74 | 4.74 | 4.74 | 4.74 |
| HEC | 5.69 | 5.69 | 5.69 | 5.69 |
| Cab-O-Sil ®M-5P | 1.90 | 2.50 | 2.90 | 3.90 |
| Capsule Shell | VC | VC | VC | VC |

Results

The results of the dissolution experiments are provided in Table 39 (below).

TABLE 39

| Formulation ID | SiO$_2$ (%) | Capsule Shell | Sample # | | 0.25 | 0.5 | 1 | 1.5 | 2 | 3 | 6 | 9 | 12 | 24 | Sp |
|---|---|---|---|---|---|---|---|---|---|---|---|---|---|---|---|
| Formulation 27 | 1.90 | VC | 6 | Mean | 4 | 11 | 22 | 30 | 38 | 50 | 76 | 94 | 100 | 106 | 4 |
| | | | | SD | 0 | 1 | 2 | 2 | 3 | 4 | 4 | 5 | 2 | 3 | |
| Formulation 28 | 2.50 | VC | 6 | Mean | 4 | 12 | 23 | 33 | 41 | 52 | 79 | 93 | 100 | 104 | 3 |
| | | | | SD | 1 | 1 | 1 | 1 | 1 | 2 | 2 | 2 | 2 | 5 | |
| Formulation 29 | 2.90 | VC | 6 | Mean | 4 | 12 | 25 | 36 | 46 | 58 | 84 | 99 | 105 | 108 | 2 |
| | | | | SD | 0 | 1 | 0 | 1 | 1 | 1 | 1 | 1 | 2 | 2 | |
| Formulation 30 | 3.90 | VC | 6 | Mean | 5 | 14 | 28 | 39 | 48 | 61 | 88 | 101 | 106 | 108 | 5 |
| | | | | SD | 1 | 2 | 3 | 3 | 4 | 4 | 4 | 3 | 4 | 4 | |

Example 17: Preparation and Analysis of Extended Release Methylphenidate Compositions (Formulations 31-34)

Methylphenidate compositions (Formulations 31-34) were prepared and characterized with respect to inter-capsule dissolution variability as indicated below.

Materials and Methods

The compositions were prepared to provide the compositions indicated in Table 40 (below). Composition components were blended and individual compositions were encapsulated within HPMC (Vcaps® (VC)) capsules as described above.

Dissolution experiments were performed using 2-phase medium in a USP Apparatus 2. The capsules were placed in stainless steel (316SS) wire spiral capsule sinkers for dissolution testing. The dissolution parameters were as follows:

Dissolution medium: 750 ml 0.1N HCl for the first 2 hours, add 200 ml 0.19M phosphate buffer to achieve a final pH of 6.0; Paddle speed: 50 rpm; Vessel temperature: 37 C. Sampling time points: 0.25, 0.5, 1, 1.5, 2, 3, 6, 9, 12 and 24 hours. Sampling volume: 1 mL.

The HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 71% Mobile phase A and 29% Mobile phase B; 210 nm wavelength.

TABLE 40

| Composition (% w/w) | Formulation 31 | Formulation 32 | Formulation 33 | Formulation 34 |
|---|---|---|---|---|
| Methylphenidate HCl | 20.00 | 20.00 | 20.00 | 20.00 |
| SAIB | 33.38 | 32.76 | 32.40 | 31.59 |
| Triacetin | 31.79 | 31.81 | 31.77 | 31.59 |
| IPM | 2.50 | 2.50 | 2.50 | 2.50 |
| CAB | 4.74 | 4.74 | 4.74 | 4.74 |
| HEC | 5.69 | 5.69 | 5.69 | 5.69 |
| Cab-O-Sil ®M-5P | 1.90 | 2.50 | 2.90 | 3.90 |
| Capsule Shell | VC | VC | VC | VC |

Results

The results of the dissolution experiments are provided in Table 41 (below).

TABLE 41

| Formulation ID | SiO$_2$ (%) | Capsule Shell | Sample # | | 0.25 | 0.5 | 1 | 1.5 | 2 | 3 | 6 | 9 | 12 | 24 | Sp |
|---|---|---|---|---|---|---|---|---|---|---|---|---|---|---|---|
| Formulation 31 | 1.90 | VC | 6 | Mean | 3 | 11 | 24 | 34 | 42 | 55 | 82 | 95 | 100 | 103 | 2 |
| | | | | SD | 1 | 1 | 1 | 2 | 2 | 2 | 2 | 2 | 2 | 2 | |
| Formulation 32 | 2.50 | VC | 6 | Mean | 4 | 12 | 27 | 38 | 48 | 61 | 89 | 100 | 102 | 104 | 2 |
| | | | | SD | 1 | 1 | 2 | 2 | 2 | 2 | 2 | 1 | 1 | 1 | |
| Formulation 33 | 2.90 | VC | 6 | Mean | 4 | 14 | 29 | 41 | 51 | 65 | 92 | 101 | 104 | 105 | 2 |
| | | | | SD | 1 | 2 | 1 | 1 | 1 | 1 | 1 | 2 | 2 | 3 | |
| Formulation 34 | 3.90 | VC | 6 | Mean | 4 | 14 | 30 | 42 | 52 | 66 | 92 | 99 | 102 | 103 | 2 |
| | | | | SD | 1 | 2 | 2 | 2 | 1 | 1 | 2 | 2 | 2 | 2 | |

Example 18: Preparation and Analysis of Extended Release Hydromorphone HCL Compositions (Formulations 35-45)

Hydromorphone compositions were prepared and characterized with respect to dissolution profile, inter-capsule dissolution variability, and abuse deterrence characteristics as indicated below.

Materials and Methods

The compositions were prepared to provide the compositions indicated in Table 42 (below). Composition component amounts are % w/w relative to the total weight of the formulation including hydromorphone HCl prior to encapsulation unless otherwise noted.

The formulations were prepared in 100 g scale. The temperature of the formulation compounding was maintained at 80° C.±5° C. and the mixing speed was maintained at 1500 rpm. Sucrose Acetate Isobutyrate (SAIB) was transferred into a glass container. Sieved cellulose acetate butyrate (CAB) was added to the bottle while mixing. After mixing for approximately 5 minutes, triacetin (TA) was added and mixed until the mass became clear. Butylated hydroxytoluene (BHT) was dissolved first in isopropyl myristate (IPM) and added into bottle with mixing. Hydroxyethyl cellulose (HEC) was added into the bottle and mixed well. In addition, formulations containing Labrafil M2125CS and/or sodium dodecyl sulfate (SDS) were added here and mixed well. Finally colliodal silicon dioxide (Cab-O-Sil®M-5P) was added into the bottle and were mixed to complete the formulation. Hydromorphone HCl was added into placebo formulation and dispersed well. Active formulations were then filled into size 0 gelatin capsules.

For all formulations BHT was included at a concentration of 0.02% w/w relative to the total weight of the placebo, i.e., the total weight of all components except hydromorphone HCl. The concentration of BHT is not taken into account in the % w/w calculations provided in Table 42 below.

Dissolution Testing

Dissolution experiments were performed using 2-phase medium in a USP Apparatus 2. The capsules were placed in stainless steel (316SS) wire spiral capsule sinkers for dissolution testing. The dissolution parameters were as follows:

Dissolution medium: 750 ml 0.1N HCl for the first 2 hours, add 250 ml 0.2 M phosphate buffer to achieve a final pH of 6.8; Paddle speed: 100 rpm; Vessel temperature: 37 C. Sampling time points: 0.25, 0.5, 1, 2, 3, 6, 10, 12, 18 and 24 hours. Sampling volume: 1 mL.

The HPLC parameters were as follows: Mobile phase A: 0.5% sodium dodecyl sulfate 1% glacial acetic acid, 20% acetonitrile; Mobile phase B: 100% acetonitrile; Mobile phase: 65% Mobile phase A and 35% Mobile phase B; 240 nm wavelength. Capsule number=2-4 capsules per testing.

Abuse Deterrence

Capsules from each composition were tested for abuse deterrence characteristics. The release rate of hydromorphone HCl was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof ethanol. The sample jar was placed in a shaking incubator maintained at 25° C. with 240 rpm shaking speed over the course of the 3 hour extraction test. The sampling time points were 0.5, 1, 2 and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing Results

Figure 41:
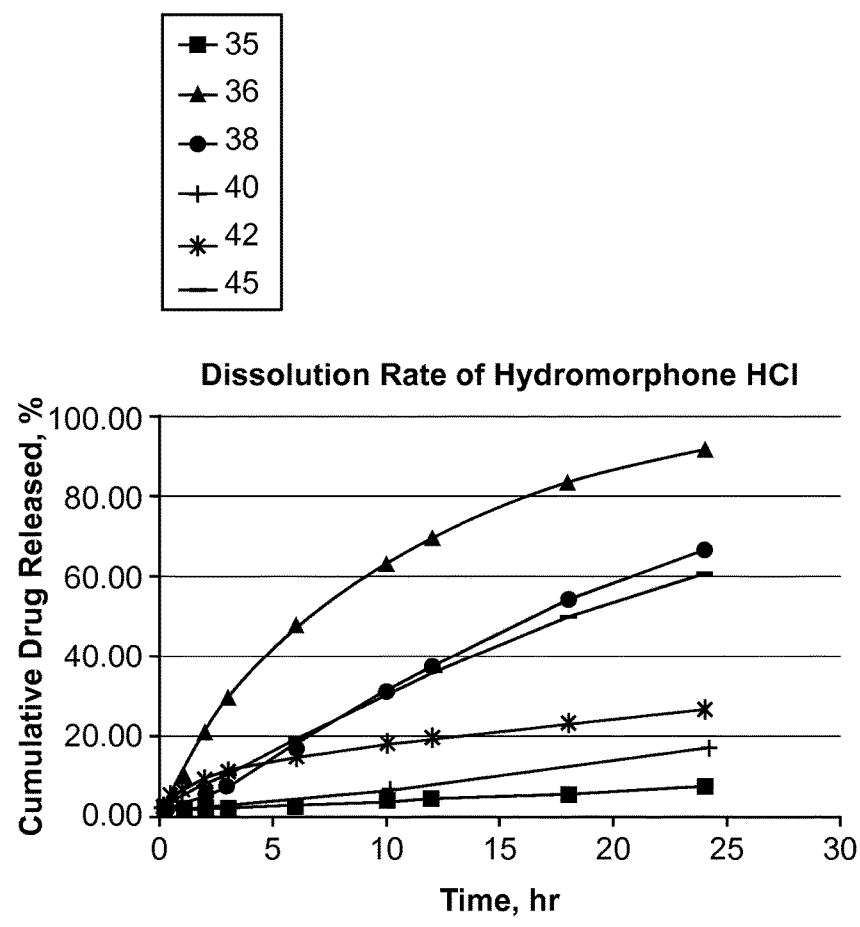
FIG. 41 is a graph showing cummulative release of hydromorphone HCl for selected formulations over time.

The results of the dissolution experiments are provided in FIG. 41 and Tables 43-44 below.

TABLE 42

| Formulation ID | SAIB/TA (ratio) | SAIB | Triacetin | IPM | CAB | SDS | Labrafil | Hydromorphone HCl | HEC | SiO2 |
|---|---|---|---|---|---|---|---|---|---|---|
| 35 | 1.8 | 41.78 | 23.21 | 16.95 | 3.77 | 0.94 | 2.83 | 5.82 | 1.88 | 2.83 |
| 36 | 1.2 | 34.60 | 28.83 | 10.72 | 3.57 | 0.89 | 2.68 | 10.67 | 7.15 | 0.89 |
| 37* | 1.8 | 41.78 | 23.21 | 11.30 | 7.53 | 0 | 0 | 5.82 | 7.53 | 2.83 |
| 38 | 1.2 | 32.65 | 27.21 | 16.08 | 3.57 | 0 | 0.00 | 10.67 | 7.15 | 2.68 |
| 39* | 1.2 | 33.39 | 27.83 | 11.30 | 7.53 | 0.94 | 2.83 | 5.82 | 7.53 | 2.83 |
| 40 | 1.8 | 43.64 | 24.25 | 10.72 | 3.57 | 0 | 2.68 | 10.67 | 1.79 | 2.68 |
| 41* | 1.2 | 33.13 | 27.61 | 16.08 | 7.15 | 0.89 | 0 | 10.67 | 1.79 | 2.68 |
| 42 | 1.2 | 41.61 | 34.68 | 11.30 | 3.77 | 0 | 0.00 | 5.82 | 1.88 | 0.94 |
| 43* | 1.6 | 41.15 | 25.72 | 11.30 | 5.65 | 0 | 0.00 | 5.82 | 7.53 | 2.83 |
| 44* | 1.2 | 34.42 | 28.68 | 11.30 | 5.65 | 0.94 | 2.83 | 5.82 | 7.53 | 2.83 |
| 45 | 1.2 | 34.11 | 28.42 | 16.08 | 5.36 | 0.89 | 0.00 | 10.67 | 1.79 | 2.68 |

*final formulation was not prepared due to high viscosity

TABLE 43

| Dissolution | HMH (mg) | Cumulative Drug Released (%) | | | | | | | | | |
|---|---|---|---|---|---|---|---|---|---|---|---|
| | | 0.25 hr | 0.5 hr | 1 hr | 2 hr | 3 hr | 6 hr | 10 hr | 12 hr | 18 hr | 24 hr |
| Formulation 35 | | | | | | | | | | | |
| #1 | 29.00 | 0.44 | 0.66 | 0.88 | 1.35 | 1.62 | 2.59 | 3.45 | 4.10 | 5.25 | 6.62 |
| #2 | 28.80 | 0.44 | 0.58 | 0.85 | 1.32 | 1.64 | 2.53 | 3.64 | 4.28 | 5.57 | 7.78 |
| #3 | 28.43 | 0.77 | 0.95 | 1.33 | 1.85 | 2.12 | 3.04 | 4.21 | 4.91 | 6.30 | 7.56 |
| #4 | 28.95 | 0.89 | 1.05 | 1.45 | 2.00 | 2.40 | 3.40 | 4.83 | 5.41 | 7.38 | 9.18 |
| Average | 28.80 | 0.6 | 0.8 | 1.1 | 1.6 | 1.9 | 2.9 | 4.0 | 4.7 | 6.1 | 7.8 |
| Std Dev | 0.26 | 0.2 | 0.2 | 0.3 | 0.3 | 0.4 | 0.4 | 0.6 | 0.6 | 0.9 | 1.1 |
| % RSD | 0.89 | 36.2 | 28.0 | 26.9 | 21.5 | 19.6 | 14.1 | 15.4 | 12.9 | 15.5 | 13.6 |
| Formulation 36 | | | | | | | | | | | |
| #1 | 28.00 | 3.28 | 5.32 | 10.02 | 20.39 | 29.00 | 47.70 | 62.22 | 67.60 | 80.14 | 88.41 |
| #2 | 28.29 | 4.24 | 7.11 | 13.27 | 26.37 | 36.62 | 56.93 | 74.39 | 80.92 | 94.43 | 100.02 |
| #3 | 28.95 | 3.41 | 5.52 | 9.87 | 20.30 | 28.18 | 45.12 | 59.34 | 65.09 | 79.34 | 88.73 |
| #4 | 28.19 | 2.70 | 4.15 | 7.86 | 16.46 | 24.46 | 42.29 | 57.86 | 64.18 | 79.15 | 89.89 |
| Average | 28.36 | 3.4 | 5.5 | 10.3 | 20.9 | 29.6 | 48.0 | 63.5 | 69.4 | 83.3 | 91.8 |
| Std Dev | 0.41 | 0.6 | 1.2 | 2.2 | 4.1 | 5.1 | 6.3 | 7.5 | 7.8 | 7.5 | 5.5 |
| % RSD | 1.45 | 18.6 | 22.0 | 21.8 | 19.6 | 17.2 | 13.2 | 11.8 | 11.2 | 9.0 | 6.0 |
| Formulation 38 | | | | | | | | | | | |
| #1 | 28.49 | 1.27 | 1.85 | 2.95 | 5.38 | 7.40 | 16.07 | 29.88 | 36.12 | 51.86 | 64.22 |
| #2 | 28.02 | 1.20 | 1.80 | 3.06 | 5.83 | 8.28 | 17.56 | 31.03 | 37.41 | 53.85 | 67.02 |
| #3 | 27.17 | 1.19 | 1.66 | 2.83 | 5.55 | 8.10 | 18.67 | 35.00 | 42.26 | 59.55 | 72.15 |
| #4 | 27.74 | 1.00 | 1.62 | 2.75 | 5.35 | 7.62 | 16.19 | 29.23 | 35.11 | 50.34 | 62.61 |
| Average | 27.85 | 1.2 | 1.7 | 2.9 | 5.5 | 7.9 | 17.1 | 31.3 | 37.7 | 53.9 | 66.5 |
| Std Dev | 0.55 | 0.1 | 0.1 | 0.1 | 0.2 | 0.4 | 1.2 | 2.6 | 3.2 | 4.0 | 4.2 |
| % RSD | 1.99 | 9.7 | 6.1 | 4.6 | 4.0 | 5.2 | 7.2 | 8.3 | 8.4 | 7.5 | 6.3 |
| Formulation 40 | | | | | | | | | | | |
| #1 | 28.99 | 0.47 | 0.63 | 0.82 | 1.21 | 1.81 | 3.02 | 4.96 | 5.94 | 9.47 | 13.25 |
| #2 | 28.61 | 0.89 | 1.15 | 1.52 | 2.23 | 2.82 | 5.06 | 8.36 | 10.33 | 16.28 | 22.85 |
| #3 | 28.80 | 0.55 | 0.67 | 0.88 | 1.33 | 1.78 | 3.19 | 5.42 | 6.81 | 10.95 | 14.97 |
| #4 | 28.70 | 0.89 | 1.01 | 1.40 | 2.14 | 2.81 | 4.64 | 7.21 | 8.77 | 13.54 | 18.32 |
| Average | 28.78 | 0.7 | 0.9 | 1.2 | 1.7 | 2.3 | 4.0 | 6.5 | 8.0 | 12.6 | 17.3 |
| Std Dev | 0.16 | 0.2 | 0.3 | 0.4 | 0.5 | 0.6 | 1.0 | 1.6 | 2.0 | 3.0 | 4.2 |
| % RSD | 0.56 | 31.8 | 29.7 | 30.7 | 30.6 | 25.6 | 25.7 | 24.4 | 24.8 | 23.9 | 24.4 |
| Formulation 42 | | | | | | | | | | | |
| #1 | 29.34 | 3.04 | 3.58 | 4.41 | 5.69 | 6.71 | 9.34 | 12.58 | 13.91 | 18.05 | 21.79 |
| #2 | 29.18 | 4.73 | 7.09 | 10.25 | 14.34 | 16.89 | 21.08 | 25.28 | 26.97 | 31.32 | 35.43 |
| #3 | 29.23 | 4.00 | 6.01 | 8.64 | 11.70 | 13.84 | 18.14 | 22.12 | 23.63 | 27.02 | 29.94 |
| #4 | 29.65 | 2.91 | 3.72 | 4.72 | 6.17 | 7.38 | 10.16 | 13.18 | 14.33 | 17.33 | 19.98 |
| Average | 29.35 | 3.7 | 5.1 | 7.0 | 9.5 | 11.2 | 14.7 | 18.3 | 19.7 | 23.4 | 26.8 |
| Std Dev | 0.21 | 0.9 | 1.7 | 2.9 | 4.2 | 5.0 | 5.8 | 6.4 | 6.6 | 6.9 | 7.2 |
| % RSD | 0.71 | 23.4 | 34.0 | 41.4 | 44.7 | 44.3 | 39.7 | 34.9 | 33.5 | 29.3 | 26.9 |

TABLE 44

Formulation 45

| Dissolution | Hydromorphone (mg) | Cumulative Drug Released (%) | | | | | | | | | |
|---|---|---|---|---|---|---|---|---|---|---|---|
| | | 0.25 hr | 0.5 hr | 1 hr | 2 hr | 3 hr | 6 hr | 10 hr | 12 hr | 18 hr | 24 hr |
| #1 | 26.92 | 2.43 | 3.28 | 4.98 | 8.26 | 11.01 | 19.59 | 31.00 | 36.15 | 49.11 | 59.43 |
| #2 | 26.92 | 1.69 | 2.73 | 4.35 | 7.70 | 10.51 | 19.50 | 30.94 | 36.08 | 49.25 | 59.65 |
| #3 | 27.86 | 1.46 | 2.24 | 3.66 | 6.86 | 9.58 | 18.59 | 30.55 | 36.06 | 49.52 | 59.63 |
| #4 | 28.33 | 1.71 | 2.48 | 3.97 | 7.29 | 10.17 | 19.51 | 32.01 | 37.51 | 52.10 | 63.88 |
| Average | 27.51 | 1.8 | 2.7 | 4.2 | 7.5 | 10.3 | 19.3 | 31.1 | 36.4 | 50.0 | 60.6 |
| Std Dev | 0.71 | 0.4 | 0.4 | 0.6 | 0.6 | 0.6 | 0.5 | 0.6 | 0.7 | 1.4 | 2.2 |
| % RSD | 2.58 | 23.2 | 16.6 | 13.4 | 7.9 | 5.8 | 2.4 | 2.0 | 1.9 | 2.8 | 3.6 |

Abuse Deterrence Results

Figure 42:
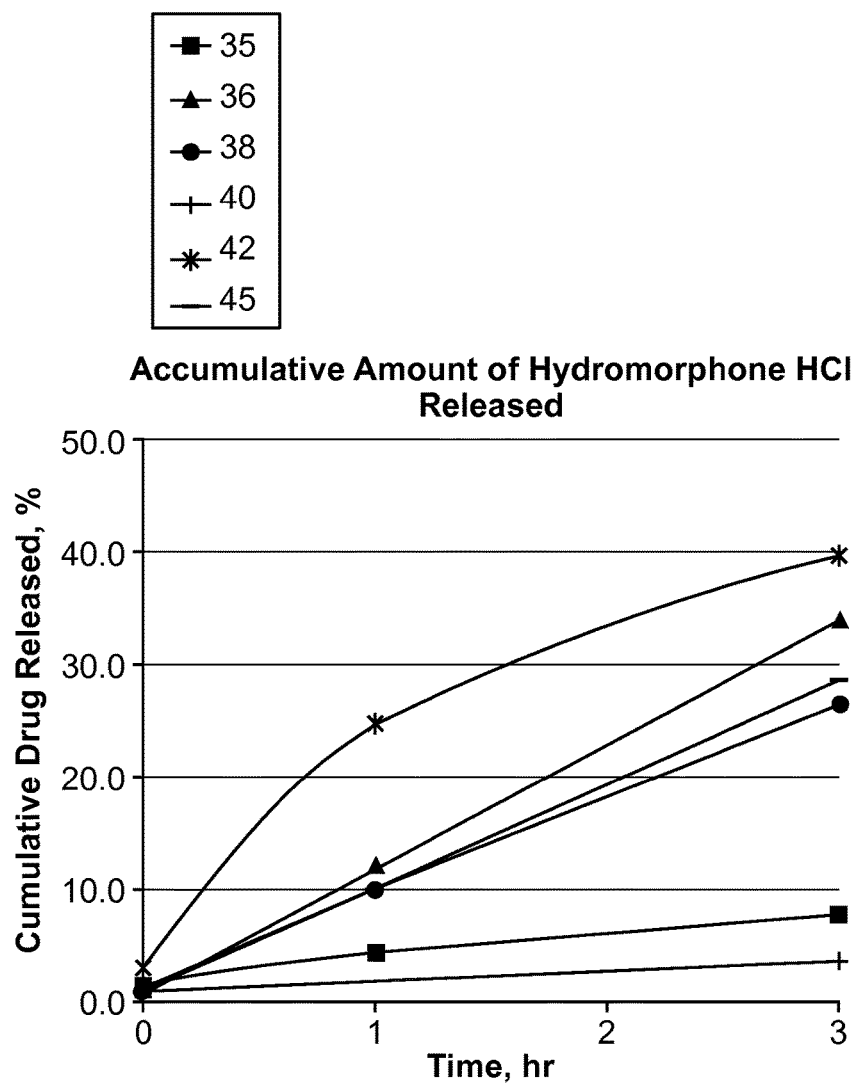
FIG. 42 is a graph showing the % cumulative amount of hydromorphone HCl released over time under abuse extraction conditions.

The results of the abuse deterrence experiments are provided in FIG. 42 and Table 45 below.

TABLE 45

| Formulation ID | % Accumulative Amount of Drug Released |
|---|---|
| Formulation 35 | 7.8 |
| Formulation 36 | 34.1 |
| Formulation 38 | 26.6 |
| Formulation 40 | 3.9 |

TABLE 45-continued

| Formulation ID | % Accumulative Amount of Drug Released |
|---|---|
| Formulation 42 | 39.7 |
| Formulation 45 | 28.6 |

Example 19: Preparation and Analysis of Additional Extended Release Hydromorphone HCL Compositions (Formulations 46-49)

Additional hydromorphone compositions were prepared and characterized with respect to dissolution profile and abuse deterrence characteristics as indicated below.

Materials and Methods

The compositions were prepared to provide the compositions indicated in Table 46 below. Composition component amounts are % w/w relative to the total weight of the formulation including hydromorphone HCl prior to encapsulation unless otherwise noted. The SAIB/triacetin ratio is noted.

The placebo formulations were prepared in 150 g scale. Three stock solutions, SAIB/TA (1.50), SAIB/TA (1.35) and 0.6% w/v BHT in IPM, were prepared before the compounding procedure started. A bottle of Gelucire® 44/14 was heated at 70° C. and homogenized at 9600 rpm prior to the starting the preparation. The temperature of the process was maintained at 60° C.±5° C. SAIB/TA stock solution was added to a jar, and then pre-heated Gelucire® 44/14 solution was added. The mixture was put into a water bath, and mixed at 500 rpm. 0.6% BHT/IPM stock solution was transferred into a vial, the vial was then rinsed with the remaining IPM and added to the formulation. The solution was mixed to ensure uniformity. Cab-O-Sil®M-5P was then added and mixed at 500 rpm. After at least 30 minutes mixing, the mixture was homogenized for 5 minutes at 9600 rpm. Sieved CAB was then added to the mixture and mixed at an initial speed of 500 rpm followed by mixing at 1500 rpm for approximately 30 total minutes or until all CAB particles were completely dissolved. Then HEC was added last, and mixed at 1500 rpm. Part of the placebo formulation was transferred into a separate bottle and hydromorphone HCl was introduced into the mixture and dispersed well to make 100 g active formulations. Active formulations were then filled into size 0 gelatin capsules.

For all formulations BHT was included at a concentration of 0.02% w/w relative to the total weight of the placebo, i.e., the total weight of all components except hydromorphone HCl. The concentration of BHT is not taken into account in the % w/w calculations provided in Table 46 below.

TABLE 46

| | | Formulation Composition | | | | | | | |
|---|---|---|---|---|---|---|---|---|---|
| Formulation ID | Dose (mg)/Fill Weight (mg)/ Conc. | SAIB/TA | SAIB | Triacetin (TA) | IPM | CAB | HEC | Cab-O-Sil ®M-5P | Gelucire ® 44/14 |
| 46 | 32/550/5.82% | 1.5 | 39.87 | 26.58 | 14.1 | 5.64 | 5.64 | 2.35 | 0 |
| 47 | 32/550/5.82% | 1.5 | 39.588 | 26.392 | 14.1 | 5.64 | 5.64 | 2.35 | 0.47 |
| 48 | 32/550/5.82% | 1.35 | 38.0654 | 28.1966 | 14.1 | 5.64 | 5.64 | 2.35 | 0.188 |
| 49 | 32/550/5.82% | 1.35 | 37.8494 | 28.0366 | 14.1 | 5.64 | 5.64 | 2.35 | 0.564 |

Dissolution Testing

Dissolution experiments were performed using 2-phase medium in a USP Apparatus 2. The capsules were placed in stainless steel (316SS) wire spiral capsule sinkers for dissolution testing. The dissolution parameters were as follows:

Dissolution medium: 750 ml 0.1N HCl for the first 2 hours; 250 ml 0.2 M phosphate buffer was added to achieve a final pH of 6.8; Paddle speed: 100 rpm; Vessel temperature: 37 C. Sampling time points: 0.25, 0.5, 1, 2, 3, 6, 10, 12, 18 and 24 hours. Sampling volume: 1 mL.

The HPLC parameters were as follows: Mobile phase A: 0.5% sodium dodecyl sulfate 1% glacial acetic acid, 20% acetonitrile; Mobile phase B: 100% acetonitrile; Mobile phase: 65% Mobile phase A and 35% Mobile phase B; 240 nm wavelength. Capsule number=2-4 capsules per testing.

Abuse Deterrence

Capsules from each composition were tested for abuse deterrence characteristics. The release rate of hydromorphone HCl was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof ethanol. The sample jar was placed in a shaking incubator maintained at 25° C. with 240 rpm shaking speed over the course of the 3 hour extraction test. The sampling time points were 0.5, 1, 2 and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing and Abuse Deterrence Results

The results of the dissolution and abuse deterrence experiments are provided in Table 47 below.

TABLE 47

| Formulation ID | Dissolution Results (% Cumulative Drug Released) | | | | | | | | | | %, Cumulative release after 3 hrs extraction |
|---|---|---|---|---|---|---|---|---|---|---|---|
|  | 0.25 hr | 1.5 hr | 1 hr | 2 hr | 3 hr | 6 hr | 10 hr | 12 hr | 18 hr | 24 hr |  |
| 46 | 0.0 | 0.0 | 0.4 | 1.3 | 1.8 | 3.1 | 4.9 | 6.0 | 9.4 | 13.5 | 7.0 |
| 47 | 0.0 | 0.7 | 1.4 | 2.7 | 3.8 | 7.2 | 11.8 | 14.3 | 21.6 | 28.9 | 7.0 |
| 48 | 0.0 | 0.0 | 0.0 | 0.6 | 0.8 | 4.2 | 6.6 | 7.9 | 12.2 | 16.8 | 5.0 |
| 49 | 0.0 | 0.2 | 1.9 | 4.0 | 5.8 | 12.7 | 23.0 | 27.8 | 40.4 | 50.6 | 8.0 |

Example 20: Preparation and Analysis of Additional Extended Release Hydromorphone HCL Compositions (Formulations 50-81)

Additional hydromorphone compositions were prepared and characterized with respect to dissolution profile and abuse deterrence characteristics as indicated below.

Materials and Methods

Figure 43:
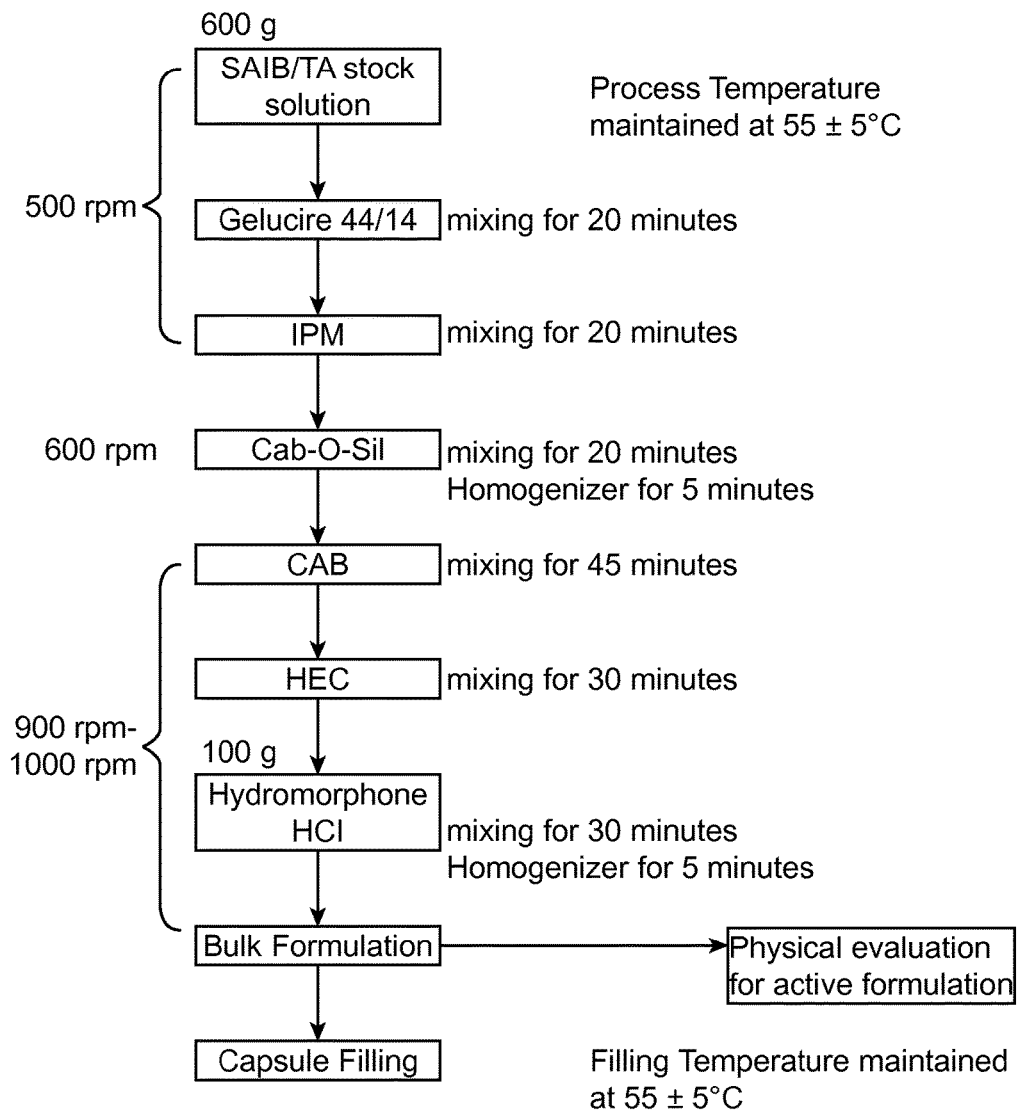
FIG. 43 is a flow chart providing materials and methods for the preparation of selected hydromorphone HCl compositions.

The compositions were prepared to provide the compositions indicated in Tables 48-50 (below). Component amounts are % w/w relative to the total weight of the formulation including hydromorphone HCl prior to encapsulation, unless otherwise indicated. The materials and methods applicable to the preparation of these formulations are provided in FIG. 43. Active formulations were filled into size 2 HPMC capsules.

TABLE 48

| Formulation ID | Hydromorphone HCl | SAIB | Triacetin | CAB | IPM | HEC | Cab-O-Sil ®M-5P | Gelucire ® 44/14 |
|---|---|---|---|---|---|---|---|---|
| 50 | 5.82% | 45.16% | 32.26% | 5.65% | 1.88% | 5.65% | 2.83% | 0.75% |
| 51 | 5.82% | 46.04% | 32.88% | 5.65% | 1.88% | 5.65% | 1.88% | 0.19% |
| 52 | 5.82% | 42.41% | 30.29% | 5.65% | 7.53% | 5.65% | 1.88% | 0.75% |
| 53 | 5.82% | 45.05% | 32.18% | 5.65% | 4.71% | 3.77% | 2.35% | 0.47% |
| 54 | 5.82% | 47.91% | 34.22% | 5.65% | 1.88% | 1.88% | 1.88% | 0.75% |
| 55 | 5.82% | 42.19% | 30.14% | 5.65% | 7.53% | 5.65% | 2.83% | 0.19% |
| 56 | 5.82% | 44.06% | 31.47% | 5.65% | 7.53% | 1.88% | 2.83% | 0.75% |
| 57 | 5.82% | 44.94% | 32.10% | 5.65% | 7.53% | 1.88% | 1.88% | 0.19% |
| 58 | 5.82% | 47.69% | 34.06% | 5.65% | 1.88% | 1.88% | 2.83% | 0.19% |

TABLE 49

| Formulation ID | Hydromorphone HCl | SAIB | Triacetin | CAB | IPM | HEC | Cab-O-Sil ®M-5P | Gelucire ® 44/14 |
|---|---|---|---|---|---|---|---|---|
| 59 | 5.82% | 41.34% | 41.34% | 5.65% | 1.88% | 1.88% | 1.88% | 0.19% |
| 60 | 5.82% | 38.05% | 38.05% | 5.65% | 7.53% | 1.88% | 2.83% | 0.19% |
| 61 | 5.82% | 38.24% | 38.24% | 5.65% | 7.53% | 1.88% | 1.88% | 0.75% |
| 62 | 5.82% | 38.61% | 38.61% | 5.65% | 4.71% | 3.77% | 2.35% | 0.47% |
| 63 | 5.82% | 36.64% | 36.64% | 5.65% | 7.53% | 5.65% | 1.88% | 0.19% |
| 64 | 5.82% | 38.99% | 38.99% | 5.65% | 1.88% | 5.65% | 2.83% | 0.19% |
| 65 | 5.82% | 39.18% | 39.18% | 5.65% | 1.88% | 5.65% | 1.88% | 0.75% |
| 66 | 5.82% | 40.59% | 40.59% | 5.65% | 1.88% | 1.88% | 2.83% | 0.75% |
| 67 | 5.82% | 35.88% | 35.88% | 5.65% | 7.53% | 5.65% | 2.83% | 0.75% |

TABLE 50

| Formulation ID | Hydromorphone HCl | SAIB | Triacetin | CAB | IPM | HEC | Cab-O-Sil ®M-5P | Gelucire ® 44/14 |
|---|---|---|---|---|---|---|---|---|
| 68 | 5.82% | 42.38% | 35.32% | 5.65% | 4.71% | 3.77% | 1.88% | 0.47% |
| 69 | 5.82% | 42.12% | 35.10% | 5.65% | 4.71% | 3.77% | 2.35% | 0.47% |
| 70 | 5.82% | 42.12% | 35.10% | 5.65% | 4.71% | 3.77% | 2.35% | 0.47% |
| 71 | 5.82% | 41.10% | 34.25% | 5.65% | 4.71% | 5.65% | 2.35% | 0.47% |
| 72 | 5.82% | 43.67% | 36.39% | 5.65% | 1.88% | 3.77% | 2.35% | 0.47% |
| 73 | 5.82% | 40.58% | 33.82% | 5.65% | 7.53% | 3.77% | 2.35% | 0.47% |
| 74 | 5.82% | 42.12% | 35.10% | 5.65% | 4.71% | 3.77% | 2.35% | 0.47% |
| 75 | 5.82% | 42.12% | 35.10% | 5.65% | 4.71% | 3.77% | 2.35% | 0.47% |
| 76 | 5.82% | 41.87% | 34.89% | 5.65% | 4.71% | 3.77% | 2.83% | 0.47% |
| 77 | 5.82% | 41.97% | 34.97% | 5.65% | 4.71% | 3.77% | 2.35% | 0.75% |
| 78 | 5.82% | 42.12% | 35.10% | 5.65% | 4.71% | 3.77% | 2.35% | 0.47% |
| 79 | 5.82% | 42.12% | 35.10% | 5.65% | 4.71% | 3.77% | 2.35% | 0.47% |
| 80 | 5.82% | 42.28% | 35.23% | 5.65% | 4.71% | 3.77% | 2.35% | 0.19% |
| 81 | 5.82% | 43.15% | 35.96% | 5.65% | 4.71% | 1.88% | 2.35% | 0.47% |

Dissolution Testing

Dissolution experiments were performed using 2-phase medium in a USP Apparatus 2. The capsules were placed in stainless steel (316SS) wire spiral capsule sinkers for dissolution testing. The dissolution parameters were as follows:

Dissolution medium: 750 ml 0.1N HCl for the first 2 hours; 250 ml 0.2 M phosphate buffer was added to achieve a final pH of 6.8; Paddle speed: 100 rpm; Vessel temperature: 37 C. Sampling time points: 0.25, 0.5, 1, 2, 3, 6, 10, 12, 18 and 24 hours. Sampling volume: 1 mL.

The HPLC parameters were as follows: Mobile phase A: 0.5% sodium dodecyl sulfate 1% glacial acetic acid, 20% acetonitrile; Mobile phase B: 100% acetonitrile; Mobile phase: 65% Mobile phase A and 35% Mobile phase B; 240 nm wavelength. Capsule number=2-4 capsules per testing.

Abuse Deterrence

Capsules from each composition were tested for abuse deterrence characteristics. The release rate of hydromorphone HCl was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof ethanol. The sample jar was placed in a shaking incubator maintained at 25° C. with 240 rpm shaking speed over the course of the 3 hour extraction test. The sampling time points were 0.5, 1, 2 and 3 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Results

Dissolution Testing and Abuse Deterrence Results

The results of the dissolution and abuse deterrence experiments are provided in Table 51 below.

TABLE 51

| Formulation ID | t = 0 | 2-phase Dissolution | | | | | | | | | | %, Abuse at 3-hour |
|---|---|---|---|---|---|---|---|---|---|---|---|---|
| | | %, 0.25 hr | %, 0.5 hr | %, 1 hr | %, 2 hrs | %, 3 hrs | %, 6 hrs | %, 10 hrs | %, 12 hrs | %, 18 hrs | %, 24 hrs | |
| 50 | Mean | 1 | 2 | 3 | 4 | 6 | 14 | 25 | 30 | 42 | 52 | 13 |
| | SD | 1 | 1 | 1 | 2 | 2 | 5 | 8 | 10 | 11 | 12 | |
| 51 | Mean | 0 | 1 | 1 | 2 | 2 | 2 | 3 | 3 | 4 | 5 | 15 |
| | SD | 0 | 1 | 0 | 1 | 0 | 1 | 1 | 1 | 1 | 1 | |
| 52 | Mean | 2 | 4 | 6 | 9 | 12 | 20 | 28 | 31 | 40 | 47 | 21 |
| | SD | 1 | 1 | 1 | 1 | 1 | 2 | 4 | 4 | 5 | 7 | |
| 53 | Mean | 0 | 1 | 1 | 1 | 2 | 2 | 3 | 3 | 4 | 5 | 16 |
| | SD | 0 | 0 | 0 | 0 | 1 | 0 | 0 | 0 | 1 | 1 | |
| 54 | Mean | 1 | 3 | 4 | 7 | 10 | 19 | 31 | 36 | 50 | 61 | 17 |
| | SD | 0 | 1 | 1 | 2 | 3 | 4 | 6 | 6 | 8 | 8 | |
| 55 | Mean | 2 | 2 | 3 | 4 | 6 | 8 | 9 | 9 | 11 | 13 | 10 |
| | SD | 0 | 1 | 0 | 1 | 2 | 1 | 1 | 2 | 2 | 3 | |
| 56 | Mean | 2 | 3 | 3 | 4 | 8 | 11 | 15 | 17 | 24 | 29 | 9 |
| | SD | 0 | 1 | 0 | 1 | 2 | 2 | 3 | 3 | 5 | 7 | |
| 57 | Mean | 2 | 2 | 2 | 3 | 4 | 5 | 5 | 6 | 6 | 6 | 5 |
| | SD | 0 | 0 | 0 | 0 | 1 | 1 | 1 | 1 | 1 | 1 | |
| 58 | Mean | 2 | 2 | 2 | 2 | 4 | 5 | 5 | 5 | 5 | 5 | 19 |
| | SD | 0 | 0 | 0 | 1 | 1 | 1 | 1 | 1 | 1 | 1 | |
| 59 | Mean | 0 | 1 | 1 | 1 | 1 | 2 | 2 | 2 | 2 | 3 | 14 |
| | SD | 0 | 0 | 0 | 0 | 0 | 1 | 0 | 0 | 1 | 1 | |
| 60 | Mean | 0 | 1 | 1 | 2 | 2 | 3 | 4 | 4 | 5 | 6 | 7 |
| | SD | 1 | 0 | 1 | 1 | 0 | 1 | 1 | 1 | 2 | 2 | |
| 61 | Mean | 1 | 3 | 4 | 7 | 9 | 18 | 28 | 32 | 44 | 54 | 14 |
| | SD | 1 | 1 | 1 | 1 | 2 | 3 | 4 | 5 | 6 | 7 | |
| 62 | Mean | 0 | 0 | 1 | 2 | 2 | 3 | 5 | 6 | 8 | 10 | 15 |
| | SD | 0 | 0 | 1 | 1 | 1 | 1 | 1 | 1 | 2 | 2 | |
| 63 | Mean | 0 | 1 | 1 | 2 | 3 | 4 | 5 | 6 | 7 | 9 | 11 |
| | SD | 0 | 0 | 0 | 1 | 1 | 1 | 1 | 1 | 2 | 1 | |
| 64 | Mean | 0 | 1 | 2 | 3 | 3 | 5 | 6 | 7 | 10 | 13 | 34 |
| | SD | 0 | 0 | 0 | 1 | 1 | 1 | 2 | 2 | 2 | 3 | |
| 65 | Mean | 1 | 5 | 10 | 18 | 25 | 45 | 62 | 68 | 83 | 93 | 30 |
| | SD | 1 | 1 | 2 | 3 | 3 | 4 | 3 | 3 | 2 | 2 | |
| 66 | Mean | 0 | 1 | 2 | 2 | 3 | 6 | 11 | 14 | 23 | 32 | 19 |
| | SD | 0 | 1 | 1 | 1 | 1 | 2 | 3 | 4 | 5 | 6 | |
| 67 | Mean | 0 | 2 | 5 | 8 | 11 | 21 | 31 | 35 | 46 | 54 | 13 |
| | SD | 0 | 1 | 1 | 2 | 3 | 4 | 6 | 6 | 7 | 7 | |
| 68 | Mean | 0 | 0 | 1 | 1 | 2 | 3 | 5 | 6 | 9 | 12 | 10 |
| | SD | 0 | 0 | 1 | 1 | 0 | 0 | 1 | 1 | 1 | 2 | |
| 69 | Mean | 0 | 0 | 1 | 2 | 2 | 4 | 5 | 6 | 8 | 10 | 12 |
| | SD | 0 | 1 | 1 | 1 | 1 | 1 | 1 | 2 | 2 | 2 | |
| 70 | Mean | 1 | 1 | 2 | 2 | 3 | 4 | 5 | 6 | 9 | 12 | 10 |
| | SD | 1 | 0 | 1 | 1 | 0 | 1 | 1 | 1 | 1 | 2 | |
| 71 | Mean | 0 | 0 | 2 | 2 | 3 | 5 | 7 | 8 | 12 | 16 | 14 |
| | SD | 0 | 0 | 1 | 1 | 0 | 1 | 1 | 2 | 1 | 2 | |
| 72 | Mean | 0 | 0 | 1 | 2 | 2 | 3 | 4 | 5 | 6 | 8 | 18 |
| | SD | 0 | 0 | 1 | 1 | 1 | 1 | 1 | 2 | 2 | 2 | |
| 73 | Mean | 0 | 1 | 1 | 2 | 2 | 4 | 6 | 7 | 10 | 12 | 9 |
| | SD | 0 | 1 | 0 | 1 | 1 | 1 | 2 | 2 | 2 | 3 | |

TABLE 51-continued

| Formulation | | 2-phase Dissolution | | | | | | | | | | | %, Abuse |
|---|---|---|---|---|---|---|---|---|---|---|---|---|---|
| ID | t = 0 | %, 0.25 hr | %, 0.5 hr | %, 1 hr | %, 2 hrs | %, 3 hrs | %, 6 hrs | %, 10 hrs | %, 12 hrs | %, 18 hrs | %, 24 hrs | | at 3-hour |
| 74 | Mean | 0 | 1 | 1 | 2 | 2 | 3 | 5 | 5 | 7 | 9 | | 13 |
|    | SD   | 0 | 1 | 1 | 1 | 1 | 1 | 1 | 2 | 2 | 2 | | |
| 75 | Mean | 1 | 1 | 1 | 2 | 2 | 3 | 5 | 5 | 8 | 9 | | 12 |
|    | SD   | 1 | 0 | 1 | 1 | 1 | 1 | 2 | 2 | 2 | 2 | | |
| 76 | Mean | 1 | 1 | 2 | 3 | 4 | 5 | 7 | 7 | 10 | 12 | | 13 |
|    | SD   | 1 | 1 | 1 | 1 | 1 | 2 | 2 | 2 | 3 | 3 | | |
| 77 | Mean | 1 | 2 | 3 | 4 | 6 | 13 | 23 | 27 | 38 | 46 | | 15 |
|    | SD   | 0 | 1 | 1 | 1 | 2 | 4 | 6 | 7 | 7 | 8 | | |
| 78 | Mean | 0 | 0 | 1 | 2 | 2 | 4 | 5 | 5 | 8 | 10 | | 11 |
|    | SD   | 0 | 0 | 1 | 0 | 1 | 1 | 1 | 1 | 1 | 1 | | |
| 79 | Mean | 0 | 0 | 1 | 1 | 2 | 2 | 4 | 4 | 6 | 7 | | 15 |
|    | SD   | 0 | 0 | 1 | 0 | 0 | 1 | 1 | 1 | 1 | 1 | | |
| 80 | Mean | 0 | 1 | 1 | 1 | 2 | 3 | 4 | 4 | 6 | 7 | | 12 |
|    | SD   | 0 | 1 | 0 | 1 | 1 | 1 | 1 | 1 | 2 | 2 | | |
| 81 | Mean | 0 | 0 | 1 | 1 | 1 | 2 | 3 | 3 | 4 | 5 | | 13 |
|    | SD   | 0 | 1 | 0 | 0 | 1 | 1 | 1 | 1 | 1 | 1 | | |

No apparent phase separation was observed for the above formulations. With respect to disolution characteristics, each of formulations 50, 52, 54, 56, 61, 66, 67 and 77 exhibited dissolution profiles similar to the initial release range of the targeted profile.

With respect to abuse deterrence, all formulations showed good resistance to 40% ethanol extraction with the exception of 64 and 65 which exhibited drug extraction of ≥30% after 3 hours.

Example 21: Preparation and Analysis of Extended Release Hydrocodone Bitartrate Compositions (Formulations 82-95)

Hydrocodone bitartrate compositions were prepared and characterized with respect to dissolution profile and abuse deterrence characteristics as indicated below.
Materials and Methods The compositions were prepared to provide the compositions indicated in Table 52 below. Component amounts are % w/w relative to the total weight of the formulation including hydrocodone bitartrate prior to encapsulation, unless otherwise indicated. The SAIB/triacetin ratio is noted.

The placebo formulations were prepared in 300 g scale. Formulations were prepared as follows: several stock solutions, SAIB/TA at different ratio and 0.6% w/v BHT in IPM, were prepared before the compounding procedure started. The preparation took place in a 60° C.±5° C. water bath, and the temperature was maintained at 60° C.±5° C. during the preparation. SAIB/TA stock solution was transferred into a jar, and 0.6% BHT in IPM solution and the remaining IPM were added to the jar while mixing at 500 rpm. This combination was then mixed uniformly. Cab-O-Sil®M-5P was added and the combination was mixed for at least 2 hours. The mixture was homogenized at 9600 rpm for 5 minutes. Sieved CAB was then added into the jar and dissolved in the content of the jar at the elevated speed. HEC was then added into the jar and dispersed. Part of the placebo was transferred into a separate jar and hydrocodone bitartrate was introduced into the mixture and dispersed well to make 100 g active formulations. The active formulations were filled into size 0 gelatin capsules.

TABLE 52

| | | Formulation (containing 0.02% BHT) | | | | | | | |
|---|---|---|---|---|---|---|---|---|---|
| Formulation ID | Dose (mg)/Fill Weight (mg)/Conc. | SAIB/TA | SAIB | Triacetin (TA) | IPM | CAB | Cab-O-Sil®M-5P | HEC | Gelucire® 50/13 |
| 82 | 75/550/13.64% | 1.5 | 37.05 | 24.70 | 11.23 | 4.75 | 3.45 | 5.18 | 0 |
| 83 | 75/550/13.64% | 1.5 | 38.08 | 25.39 | 11.23 | 3.02 | 3.45 | 5.18 | 0 |
| 84 | 75/550/13.64% | 1.5 | 35.49 | 23.66 | 13.82 | 4.75 | 3.45 | 5.18 | 0 |
| 85 | 75/550/13.64% | 1.3 | 34.66 | 26.66 | 13.82 | 3.45 | 2.59 | 5.18 | 0 |
| 86 | 75/550/13.64% | 1.3 | 36.61 | 28.16 | 11.23 | 5.18 | 2.59 | 0 | 2.59 |
| 87 | 75/550/13.64% | 1.3 | 35.14 | 27.03 | 11.23 | 5.18 | 2.59 | 5.18 | 0 |
| 88 | 75/550/13.64% | 1.3 | 33.68 | 25.91 | 13.82 | 5.18 | 2.59 | 5.18 | 0 |
| 89 | 75/550/13.64% | 1.5 | 38.34 | 25.56 | 13.82 | 3.45 | 2.59 | 0 | 2.59 |
| 90 | 75/550/13.64% | 1.5 | 38.86 | 25.91 | 11.23 | 5.18 | 2.59 | 0 | 2.59 |
| 91 | 75/550/13.64% | 1.3 | 36.61 | 28.16 | 11.23 | 3.45 | 1.73 | 5.18 | 0 |
| 92 | 75/550/13.64% | 1.5 | 39.90 | 26.60 | 11.23 | 3.45 | 2.59 | 0 | 2.59 |
| 93 | 75/550/13.64% | 1.3 | 37.10 | 28.54 | 11.23 | 5.18 | 1.73 | 0 | 2.59 |
| 94 | 75/550/13.64% | 1.5 | 38.34 | 25.56 | 11.23 | 3.45 | 2.59 | 5.18 | 0 |
| 95 | 75/550/13.64% | 1.4 | 36.77 | 26.27 | 12.52 | 4.32 | 2.59 | 2.59 | 1.30 |

Dissolution Testing

Dissolution experiments were performed using 2-phase medium in a USP Apparatus 2. The capsules were placed in stainless steel (316SS) wire spiral capsule sinkers for dissolution testing. The dissolution parameters were as follows: Dissolution medium: 750 ml 0.1N HCl for the first 2 hours; 250 ml 0.2 M phosphate buffer was added to achieve a final pH of 6.8; Paddle speed: 100 rpm; Vessel temperature: 37 C. Sampling time points: 0.5, 2, 3, 6, 12, 18 and 24 hours. Sampling volume: 1 mL.

The HPLC parameters were as follows: Mobile phase A: 0.5% sodium dodecyl sulfate1 % glacial acetic acid, 20% acetonitrile; Mobile phase B: 100% acetonitrile; Mobile phase: 65% Mobile phase A and 35% Mobile phase B; 240 nm wavelength. Capsule number=2-4 capsules per testing.

Abuse Deterrence

Capsules from each composition were tested for abuse deterrence characteristics. The release rate of hydrocodone was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof ethanol. The sample jar was placed in a shaking incubator maintained at 25° C. with 240 rpm shaking speed over the course of the 3 hour extraction test. The sampling time points were 0.5, 1 and 3 hours. A 1 mL sample was taken at each time point and assayed using reverse-phase HPLC at 240 nm wavelength. The mobile phase included 0.35% (w/v) SDS/0.7% (v/v) acetic acid/47% (v/v) acetonitrile in water.

Results

Dissolution Testing and Abuse Deterrence Results

The results of the dissolution and abuse deterrence experiments are provided in Tables 53 below.

Example 22: Preparation and Analysis of Extended Release Amphetamine Compositions (Formulations 96-100)

Amphetamine compositions were prepared and characterized with respect to dissolution profile and abuse deterrence characteristics as indicated below.

Materials and Methods

The compositions were prepared to provide the compositions indicated in Table 54 (below). Component amounts are % w/w relative to the total weight of the formulation including amphetamine sulfate prior to encapsulation, unless otherwise indicated.

The placebo formulations were prepared in 150 g scale. Formulations were prepared as follows: stock solutions, SAIB/TA at different ratio and 0.6% w/v BHT in IPM, were prepared before the compounding procedure started. The preparation took place in a 60° C.±5° C. water bath, and the temperature was maintained at 60° C.±5° C. during the preparation. SAIB/TA stock solution was transferred into a jar. Sieved CAB was added into the jar and dispersed and dissolved in the solution at an elevated speed. 0.6% BHT in IPM and IPM was added to the jar and mixed uniformly. Gelucire® 50/13 was added to the content in the jar and mixed uniformly. Cab-O-Sil®M-5P was added and mixed to disperse uniformly. Part of the placebo was transferred into a separate jar and amphetamine sulfate was introduced into the mixture and dispersed well to make 100 g active formulations. The active formulations were filled into size 0 gelatin capsules.

TABLE 53

| Formulation ID | Dissolution Results (% Cumulative Drug Released), RM-07-059 | | | | | | | %, Cumulative release after 3 hrs extraction |
|---|---|---|---|---|---|---|---|---|
| | 0.5 hr | 2 hr | 3 hr | 6 hr | 12 hr | 18 hr | 24 hr | |
| 82 | 1 | 3 | 3 | 4 | 7.8 | 11 | 14 | 15 |
| 83 | 1 | 3 | 4 | 6 | 10 | 15 | 19 | 20 |
| 84 | 1 | 2 | 3 | 5 | 9.8 | 15 | 21 | 9 |
| 85 | 0 | 3 | 4 | 7 | 16 | 24 | 30 | 18 |
| 86 | 27 | 54 | 62 | 78 | 94 | 97 | 98 | 38 |
| 87 | 0 | 3 | 3 | 6 | 11 | 17 | 20 | 12 |
| 88 | 0 | 3 | 4 | 7 | 15 | 23 | 31 | 11 |
| 89 | 25 | 43 | 51 | 70 | 91 | 97 | 99 | 49 |
| 90 | 22 | 46 | 55 | 71 | 90 | 96 | 98 | 34 |
| 91 | 2 | 4 | 4 | 8 | 16 | 23 | 30 | 17 |
| 92 | 24 | 45 | 53 | 70 | 87 | 93 | 95 | 38 |
| 93 | 22 | 48 | 57 | 71 | 87 | 92 | 95 | 65 |
| 94 | 1 | 3 | 4 | 7 | 14 | 19 | 22 | 15 |
| 95 | 18 | 42 | 49 | 63 | 81 | 89 | 93 | 37 |

TABLE 54

| Formulation ID | API | D-Amp Conc. % | SAIB/ Triacetin | Formulation (containing 0.02% BHT) |||||||
|---|---|---|---|---|---|---|---|---|---|---|
| | | | | SAIB % | Triacetin % | IPM % | CAB % | HEC % | Cab-O-Sil ®M-5P % | Gelucire ® 50/13, % |
| 96 | D-Amphetamine Sulfate | 5.45 | 1.35 | 38.97 | 28.87 | 9.46 | 4.96 | 5.67 | 1.89 | 4.73 |
| 97 | D-Amphetamine Sulfate | 5.45 | 1.35 | 38.43 | 28.47 | 9.46 | 5.91 | 5.67 | 1.89 | 4.73 |
| 98 | D-Amphetamine Sulfate | 5.45 | 1.35 | 42.77 | 31.68 | 9.46 | 5.91 | 0.00 | 0.00 | 4.73 |
| 99 | D-Amphetamine Sulfate | 5.45 | 1.35 | 38.16 | 28.26 | 16.07 | 4.96 | 0.00 | 2.36 | 4.73 |
| 100 | D-Amphetamine Sulfate | 5.45 | 1.35 | 37.89 | 28.06 | 16.07 | 4.96 | 0.00 | 2.84 | 4.73 |

Dissolution Testing 2-phase dissolution medium was utilized in a USP Apparatus 2. Capsules were placed in stainless steel (316SS) wire spiral capsule sinkers for dissolution testing. The dissolution parameters were as follows: Dissolution medium: 750 ml 0.1N HCl for the first 2 hours, followed by the addition of 200 ml 0.19M phosphate buffer to achieve a final pH of 6.0; Paddle speed: 50 rpm; Vessel temperature: 37° C. Sampling time points: 0.25, 0.5, 1, 1.5, 2, 3, 6, 9, 12 and 24 hours. Sampling volume: 1 mL. HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 67% Mobile phase A and 33% Mobile phase B; 210 nm wavelength. Capsule number=4 capsules per test.

Abuse Deterrence

Capsules from each composition were tested for abuse deterrence characteristics. The release rate of dextroamphetamine was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5 and 3 hours. A 1 mL sample was taken at each time point and assayed using reverse-phase HPLC at 210 nm wavelength. The mobile phase included and 33% (v/v) acetonitrile in 67% (v/v) 5 mM 1-Decanesulfonic Acid, Na salt, 5 mM sodium phosphate, pH 2.5.

Results

Dissolution Testing and Abuse Deterrence Results

The results of the dissolution and abuse deterrence experiments are provided in Tables 55-59 and 60 respectively below.

TABLE 55

Formulation 96

| Dissolution | D-Amphetamine Sulfate (mg) | % Cumulative drug released (%) |||||||||
|---|---|---|---|---|---|---|---|---|---|---|
| | | 1 hr | 2 hr | 3 hr | 6 hr | 8 hr | 10 hr | 12 hr | 18 hr | 24 hr |
| #1 | 15.18 | 44.45 | 63.27 | 73.77 | 90.63 | 96.43 | 99.14 | 100.27 | 100.65 | 100.71 |
| #2 | 14.91 | 42.75 | 59.03 | 67.82 | 84.87 | 91.81 | 95.78 | 97.92 | 98.54 | 98.79 |
| #3 | 15.89 | 46.80 | 64.48 | 73.97 | 91.33 | 97.95 | 101.67 | 103.18 | 104.06 | 103.87 |
| #4 | 15.34 | 44.40 | 60.43 | 70.29 | 87.97 | 94.09 | 98.12 | 99.82 | 100.64 | 101.14 |
| Average | 15.3 | 44.6 | 61.8 | 71.5 | 88.7 | 95.1 | 98.7 | 100.3 | 101.0 | 101.1 |
| Std Dev | 0.4 | 1.7 | 2.5 | 3.0 | 2.9 | 2.7 | 2.4 | 2.2 | 2.3 | 2.1 |
| % RSD | 2.7 | 3.7 | 4.1 | 4.1 | 3.3 | 2.8 | 2.5 | 2.2 | 2.3 | 2.1 |

TABLE 56

Formulation 97

| Dissolution | D-Amphetamine Sulfate (mg) | % Cumulative drug released (%) |||||||||
|---|---|---|---|---|---|---|---|---|---|---|
| | | 1 hr | 2 hr | 3 hr | 6 hr | 8 hr | 10 hr | 12 hr | 18 hr | 24 hr |
| #1 | 14.68 | 39.40 | 55.03 | 64.15 | 81.19 | 88.38 | 92.48 | 94.74 | 96.19 | 97.32 |
| #2 | 15.99 | 42.85 | 59.48 | 69.28 | 86.95 | 94.59 | 98.55 | 101.07 | 102.71 | 103.71 |
| #3 | 15.88 | 39.95 | 57.18 | 67.37 | 85.81 | 93.44 | 97.85 | 100.81 | 102.57 | 103.57 |
| #4 | 15.82 | 35.45 | 51.68 | 61.80 | 80.80 | 88.94 | 94.23 | 98.01 | 101.78 | 102.59 |
| Average | 15.6 | 39.4 | 55.8 | 65.6 | 83.7 | 91.3 | 95.8 | 98.7 | 100.8 | 101.8 |
| Std Dev | 0.6 | 3.0 | 3.3 | 3.3 | 3.1 | 3.1 | 2.9 | 3.0 | 3.1 | 3.0 |
| % RSD | 3.9 | 7.7 | 5.9 | 5.1 | 3.8 | 3.4 | 3.0 | 3.0 | 3.1 | 3.0 |

TABLE 57

Formulation 98

| Dissolution | D-Amphetamine Sulfate (mg) | % Cumulative drug released (%) | | | | | | | | |
|---|---|---|---|---|---|---|---|---|---|---|
| | | 1 hr | 2 hr | 3 hr | 6 hr | 8 hr | 10 hr | 12 hr | 18 hr | 24 hr |
| #1 | 14.73 | 0.00 | 2.35 | 2.97 | 4.87 | 6.00 | 7.20 | 8.65 | 13.36 | 17.88 |
| #2 | 14.78 | 0.00 | 0.00 | 2.53 | 4.11 | 5.87 | 7.07 | 7.57 | 10.97 | 14.74 |
| #3 | 14.73 | 0.00 | 3.05 | 3.23 | 4.68 | 5.94 | 7.01 | 8.33 | 12.11 | 15.75 |
| #4 | 14.84 | 0.00 | 0.00 | 2.78 | 4.67 | 6.06 | 7.70 | 9.40 | 14.43 | 19.33 |
| Average | 14.8 | 0.0 | 1.3 | 2.9 | 4.6 | 6.0 | 7.2 | 8.5 | 12.7 | 16.9 |
| Std Dev | 0.1 | 0.0 | 1.6 | 0.3 | 0.3 | 0.1 | 0.3 | 0.8 | 1.5 | 2.1 |
| % RSD | 0.4 | NA | 117.4 | 10.3 | 7.2 | 1.4 | 4.3 | 8.9 | 11.8 | 12.2 |

TABLE 58

Formulation 99

| Dissolution | D-Amphetamine Sulfate (mg) | % Cumulative drug released (%) | | | | | | | | |
|---|---|---|---|---|---|---|---|---|---|---|
| | | 0.25 hr | 0.5 hr | 1 hr | 1.5 hr | 2 hr | 3 hr | 6 hr | 9 hr | 12 hr | 24 hr |
| #1 | 14.62 | 20.00 | 33.13 | 50.74 | 63.09 | 71.94 | 82.41 | 94.37 | 96.06 | 96.63 | 97.99 |
| #2 | 15.00 | 19.40 | 34.33 | 50.89 | 61.84 | 70.15 | 80.64 | 94.93 | 97.44 | 97.88 | 99.05 |
| #3 | 15.44 | 21.60 | 38.23 | 55.18 | 66.19 | 74.39 | 84.95 | 98.67 | 100.81 | 101.37 | 102.42 |
| #4 | 14.84 | 23.45 | 38.28 | 54.24 | 64.65 | 72.35 | 82.30 | 95.33 | 97.65 | 98.03 | 99.39 |
| Average | 15.0 | 20.3 | 35.2 | 52.3 | 63.7 | 72.2 | 82.7 | 96.0 | 98.1 | 98.6 | 99.8 |
| Std Dev | 0.3 | 1.1 | 2.7 | 2.5 | 2.2 | 2.1 | 2.2 | 2.3 | 2.4 | 2.5 | 2.3 |
| % RSD | 2.3 | 5.6 | 7.6 | 4.8 | 3.5 | 3.0 | 2.6 | 2.4 | 2.5 | 2.5 | 2.3 |

TABLE 59

Formulation 100

| Dissolution | D-Amphetamine Sulfate (mg) | % Cumulative drug released (%) | | | | | | | | |
|---|---|---|---|---|---|---|---|---|---|---|
| | | 0.25 hr | 0.5 hr | 1 hr | 1.5 hr | 2 hr | 3 hr | 6 hr | 9 hr | 12 hr | 24 hr |
| #1 | 14.68 | 18.75 | 34.93 | 51.33 | 62.09 | 69.55 | 79.51 | 93.86 | 96.62 | 97.44 | 99.11 |
| #2 | 15.34 | 20.50 | 38.18 | 56.28 | 67.53 | 75.64 | 85.33 | 97.92 | 100.06 | 100.94 | 102.23 |
| #3 | 14.79 | 21.50 | 35.08 | 51.39 | 62.15 | 70.55 | 80.21 | 94.43 | 96.82 | 97.26 | 98.93 |
| #4 | 14.36 | 18.80 | 32.08 | 49.34 | 60.74 | 69.05 | 78.49 | 91.27 | 93.28 | 93.78 | 95.39 |
| Average | 14.8 | 20.3 | 36.1 | 53.0 | 63.9 | 71.9 | 81.7 | 95.4 | 97.8 | 98.5 | 100.1 |
| Std Dev | 0.4 | 1.4 | 1.8 | 2.8 | 3.1 | 3.3 | 3.2 | 2.2 | 1.9 | 2.1 | 1.9 |
| % RSD | 2.8 | 6.9 | 5.1 | 5.4 | 4.9 | 4.5 | 3.9 | 2.3 | 2.0 | 2.1 | 1.9 |

TABLE 60

| Formulation ID | %, Cumulative release after 3 hrs extraction |
|---|---|
| 96 | 55 |
| 97 | 55 |
| 98 | 44 |
| 99 | 54 |
| 100 | 52 |

Example 23: Preparation and Analysis of Additional Extended Release Oxycodone Compositions (Formulations 101-104)

Oxycodone compositions were prepared and characterized with respect to appearance as indicated below.

Materials and Methods

The compositions were prepared to provide the compositions indicated in Table 61 (below). Formulation 103 was prepared as follows: SAIB/IPM/Ethyl Lactate (EL)=65/3/27 stock solution was prepared. Approximately 19 g of SAIB/IPM/EL solution was weighed and mix with 0.1 g of Tween 20 and 1 g of SiO₂ to make placebo Formulation 103. 1.147 g of oxycodone base was added to placebo Formulation 103 to produce 54.06 mg/g Formulation 103. Formulation 103 was then filled into hard gelatin capsule size 00 with approximately 780 mg fill weight for testing.

Stock solution C, SAIB/IPM=65/3, was prepared to make Formulation 104. Stock solution C was made by weighing out approximately 260 grams of SAIB and mixing with 12 grams of IPM. To make formulation 104, CA/SAIB/IPM/SiO₂, 5/65/3/2.5, placebo 101 (Formulation 101 without oxycodone) and placebo 102 (Formulation 102 without oxycodone) were made separately. Placebo 101 was prepared by mixing 13.6 grams of stock solution C with 2 gram of SiO₂ and placebo 102 was prepared by mixing 13.6 grams of stock solution C and 2 grams of cellulose acetate (CA). 3.16 grams of placebo 101 SiO₂/SAIB/IPM, 5/65/3 and 3.16 grams of placebo 102 CA/SAIB/IPM, 10/65/3 were mixed at a 50:50 ratio to make placebo 104. 0.351 grams of oxycodone base was added to placebo 104 to produce 52.29 mg/g formulation 104. Formulations were then filled into gelatin capsule size 00 with approximately 780 mg fill weight and observed with respect to appearance.

Results

The results with respect to appearance are provided in Table 61 below.

TABLE 61

| Formulation ID | Polymer | Solvent | SAIB | Rheology Modifier | Other excipients | Appearance of Polymer in Solvent 1 (or of initial mixture) | Appearnance after addition of SAIB (& rheology (or modifier) of final mixture) | Appearance of Mass in EtOH/water |
|---|---|---|---|---|---|---|---|---|
| 101 | 6.85% Cabosil M-5 | — | 89.04% | 4.11% IPM | oxycodone | NA | viscous gel -> suspension after compounding | oil-like drops and sand-like particles in milky soln after 3.5 hours |
| 102 | 12.82% CA-398-10NF | — | 83.33% | 3.85% IPM | oxycodone | NA | viscous suspension | oil-like drops and sand-like particles in milky soln after 3.5 hours |
| 103 | 4.98% Cabosil M-5 | 26.87% EL | 64.68% | 2.99% IPM | 0.5% Tween-20 + oxycodone | oxycodone in all solvents/ SAIB -> suspension | add Cabosil -> viscous paste | oil-like droplets in opaque solution after 3.5 hours |
| 104 | 3.42% Cabosil/ 3.42% CA-398-10NF | — | 89.04% | 4.11% IPM | oxycodone | mix 101 and 102 placebos -> viscous suspension | add oxycodone -> viscous pasty suspension | oil-like droplets in opaque solution after 3.5 hours |

Example 24: Preparation and Analysis of Additional Extended Release Oxycodone Composition (Formulations 105)

Oxycodone compositions were prepared and characterized with respect to dissolution and abuse deterrence characteristics as indicated below.

Materials and Methods

The compositions were prepared to provide the compositions indicated in Table 62 below. Component amounts are % w/w relative to the total weight of the formulation including oxycodone base prior to encapsulation, unless otherwise indicated.

The placebo formulations were prepared in 500 g scale. A stock solution, SAIB/TA (1.35), was prepared before the compounding procedure started. The preparation took place in a 60° C.±5° C. water bath. SAIB/TA (1.35) was transferred into a jar, and BHT was added to the solution while mixing at 500 rpm. Then CAB was added to the solution, and mixed @1500 RPM until all the particles were dissolved. IPM was added to the mixture and dispersed uniformly, and then HEC was added into the jar and mixed for 30 minutes. Cab-O-Sil®M-5P particles were added to the mixture and were dispersed uniformly. Part of the placebo formulation was transferred into a separate jar and oxycodone base was introduced into the mixture and dispersed well to make 100 g active formulations. Active formulations were filled into size 00 gelatin capsules.

Dissolution Testing

Dissolution experiments were performed using 2-phase medium in a USP Apparatus 2. The capsules were placed in stainless steel (316SS) wire spiral capsule sinkers for dissolution testing. The dissolution parameters were as follows: Dissolution medium: 750 ml 0.1N HCl for the first 2 hours, add 250 ml 0.2 M phosphate buffer to achieve a final pH of 6.8; Paddle speed: 100 rpm; Vessel temperature: 37 C. Sampling time points: 0.25, 0.5, 1, 2, 3, 6, 10, 12, 18 and 24 hours. Sampling volume: 1 mL.

The HPLC parameters were as follows: Mobile phase A: 0.5% sodium dodecyl sulfate1 % glacial acetic acid, 20% acetonitrile; Mobile phase B: 100% acetonitrile; Mobile phase: 65% Mobile phase A and 35% Mobile phase B; 240 nm wavelength. Capsule number=2-4 capsules per testing.

Abuse Deterrence

Capsules from each composition were tested for abuse deterrence characteristics. The release rate of oxycodone was determined using an isocratic HPLC method at defined time points. The capsules were subjected to 60 mL of acidified 80-proof ethanol with vigorous shaking. Each capsule was placed in a wide mouth round jar containing 36 mL of 0.1 N HCl and 24 mL 200-proof of ethanol. The sample jar was placed in a shaking incubator maintained at 25° C. with 240 rpm shaking speed over the course of the 3 hour extraction test. The sampling time points were 0.5, 1, and 3 hours. A 1 mL sample was taken at each time point and assayed using reverse-phase HPLC at 240 nm wavelength.

TABLE 62

| Formulation ID # | Dose/ Fill Wt (mg/mg) | SAIB/TA Ratio | Formulation Composition (with 0.02% BHT) | | | | | | |
|---|---|---|---|---|---|---|---|---|---|
| | | | Oxycodone % | SAIB % | Triacetin (TA) % | IPM % | CAB % | HEC % | Cab-O-Sil ®M-5P % |
| 105 | 80/780 | 1.35 | 10.26 | 35.44 | 26.26 | 15.26 | 4.71 | 5.38 | 2.69 |

The mobile phase included 0.35% (w/v) SDS/0.7% (v/v) acetic acid/44% (v/v) acetonitrile in water.

Results

Dissolution Testing and Abuse Deterrence Results

The results of the dissolution and abuse deterrence experiments are provided in Table 63 below.

TABLE 63

| Formulation ID # | Dose/Fill Wt (mg/mg) | Dissolution (TM-254B) | | | | | | %, Cumulative release after 3 hrs extraction (TM-256) |
|---|---|---|---|---|---|---|---|---|
| | | % 0.5 hr | % 3 hr | % 6 hr | % 10 hr | % 12 hr | % 24 hr | |
| 105 | 80/780 | 7 | 24 | 40 | 68 | 85 | 95 | 44 |

Example 25: Capsule Shell Interaction Study

The formulations indicated in Table 64 were prepared and filled into either hard gelatin or HPMC capsules to evaluate the effect of capsule choice on dissolution and storage time dependent change in mean release of active agent. The Formulation 106 placebo was prepared at 1 kg scale using an overhead mixer. A Sucrose Acetate Isobutyrate (SAIB)/Triacetin(TA)=1.5 stock solution was prepared prior to the compounding process, and the temperature of the process was maintained at 60° C.±5° C. throughout. SAIB/TA (1.50) stock solution was added to a glass jar, and placed into the water bath. Isopropyl Myristate (IPM) was added, and mixed at 600 rpm. Colliodal silicon dioxide (Cab-O-Sil) was added to the solution mixed for 20 minutes. The mixture was homogenized using Fisher PowerGen 500 with a setting of 9600 rpm for 5 minutes. Sieved cellulose acetate butyrate (CAB) was added to the jar while mixing at 1000 rpm followed by 1430 rpm for 35 minutes. Finally, sieved hydroxyethyl cellulose (HEC) was added into the jar and mixed for 30 minutes to complete the formulation. The active formulation was prepared in 250 g scale. For Formulation 106, approximately 13 grams of oxycodone base was weighed out and mixed with 240 gram of placebo formulation in a separate bottle until uniform. The Formulation 107 placebo was prepared similarly to the above with the exception of adding Gelucire 44/14 in the formulation. For Formulation 107, approximately 27 grams of oxycodone base was weighed out and mixed with 236 gram of placebo formulation in a separate bottle until uniform.

Placebo and active formulations were manually filled into white opaque hard gelatin capsules (Capsugel Licap size 0) with filling weight of 585 mg. The same fill weight was filled into white HPMC capsules (Qualicaps Quali-V size 0). For Formulation 106, 30 mg capsules were made. For Formulation 107, 60 mg capsules were made.

TABLE 64

| Component | Formulation 106 30 mg % Weight | Formulation 107 60 mg % Weight |
|---|---|---|
| Oxycodone Base | 5.13 | 10.26 |
| SAIB | 40.98 | 35.87 |
| Triacetin | 27.32 | 26.57 |
| IPM | 14.23 | 14.36 |
| CAB | 4.74 | 4.94 |
| HEC | 5.69 | 4.49 |
| Cab-O-Sil | 1.90 | 2.15 |
| BHT | 0.02 | 0.02 |
| Gelucire 44/14 | — | 1.35 |

In addition, the water content of the empty capsules was determined by Karl Fischer titration generally as set forth in USP <921> Method 1C using an AquaStar C3000 Karl Fischer Coulometric Titrator. The results of the Karl Fischer titration showing the difference in water content between the empty gelatin and HPMC capsules are provided below in Table 65.

TABLE 65

| Sample | W. (mg) | Ave. | Stdev | % CV |
|---|---|---|---|---|
| Licaps ® Gelatin Capsules | 94.44 | 15.28 | 0.02 | 0.1 |
| | 95.30 | 14.86 | 0.07 | 0.5 |
| | 97.91 | 15.44 | 0.11 | 0.7 |
| | Grand= | 15.19 | 0.30 | 2.0 |
| Quali-V ® HPMC Capules | 92.30 | 4.72 | 0.03 | 0.6 |
| | 96.60 | 4.72 | 0.15 | 3.2 |
| | Grand= | 4.72 | 0.00 | 0.1 |

The release rate of oxycodone base was determined from six capsules using a USP Apparatus 2 dissolution tester. Dissolution medium containing 1000 ml 0.1 N HCl with 0.5% (w/w) SDS was maintained at 37° C. with 100 rpm paddle speed over the course of the 24 hour dissolution test. A 20 mesh screen hanging basket was incorporated to hold the test article. The standard sampling time points were 0.5, 2, 3, 6, 12, 18 and 24 hours. A 1 mL sample was taken at each time point and assayed using reverse-phase HPLC at 240 nm wavelength. The mobile phase included 0.35% (w/v) SDS/0.7% (v/v) acetic acid/44% (v/v) acetonitrile in water.

Figure 44:
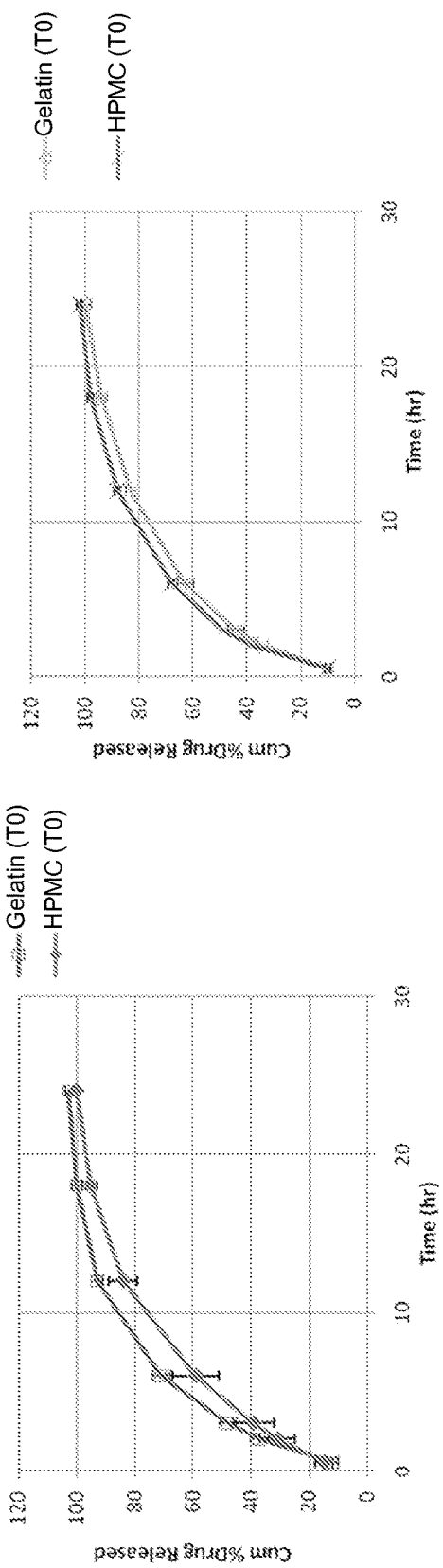
FIG. 44 is a graph showing initial dissolution results (TO) for select formulations in gelatin and HPMC capsules.
Figure 45:
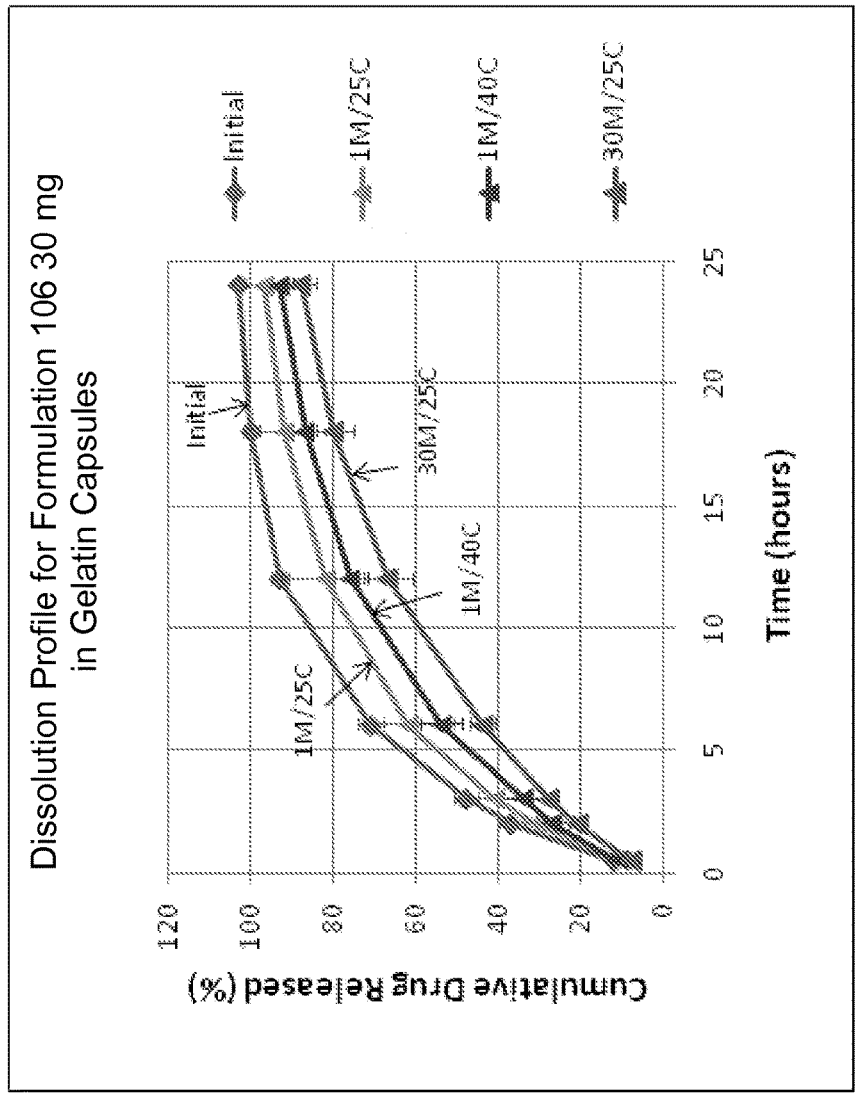
FIG. 45 is a graph showing cumulative % drug release over time for a formulation in hard gelatin capsules with storage conditions of 1 month at 25° C. and 40° C., or 30 months at 25° C.
Figure 46:
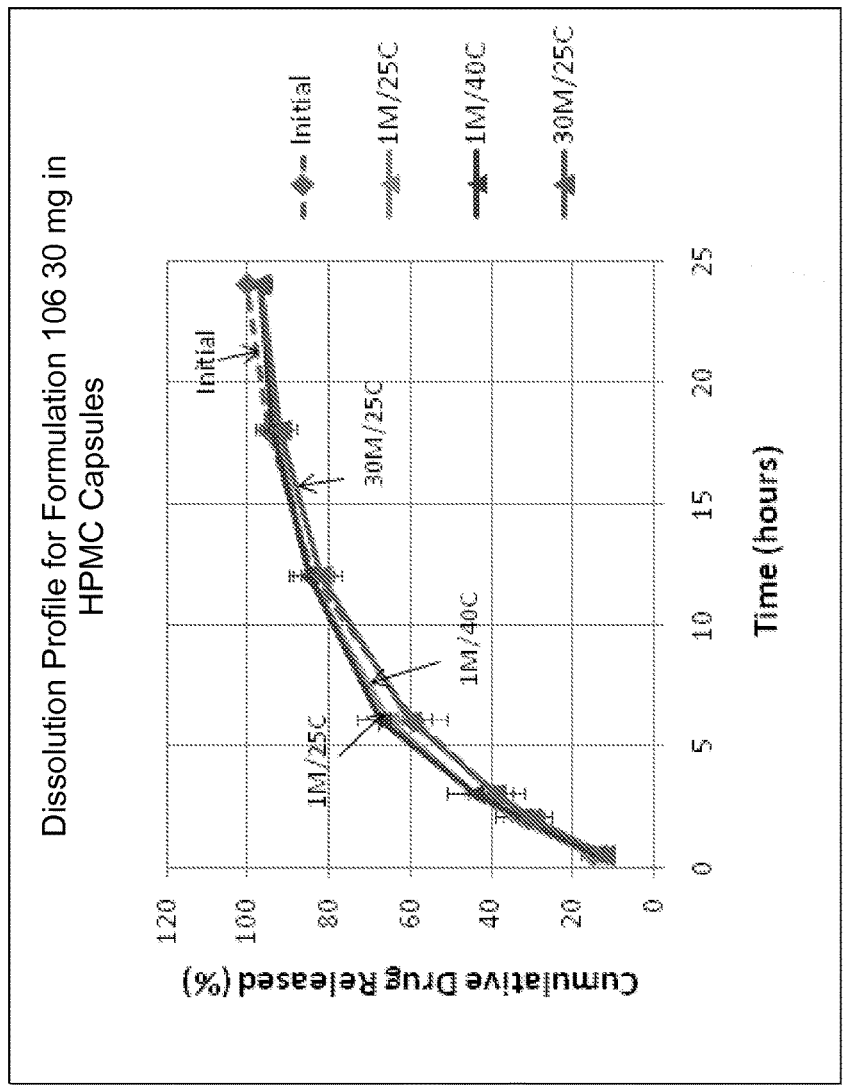
FIG. 46 is a graph showing cumulative % drug release over time for the formulation of FIG. 45 in HPMC capsules with storage conditions of 1 month at 25° C. and 40° C., or 30 months at 25° C.
Figure 47:
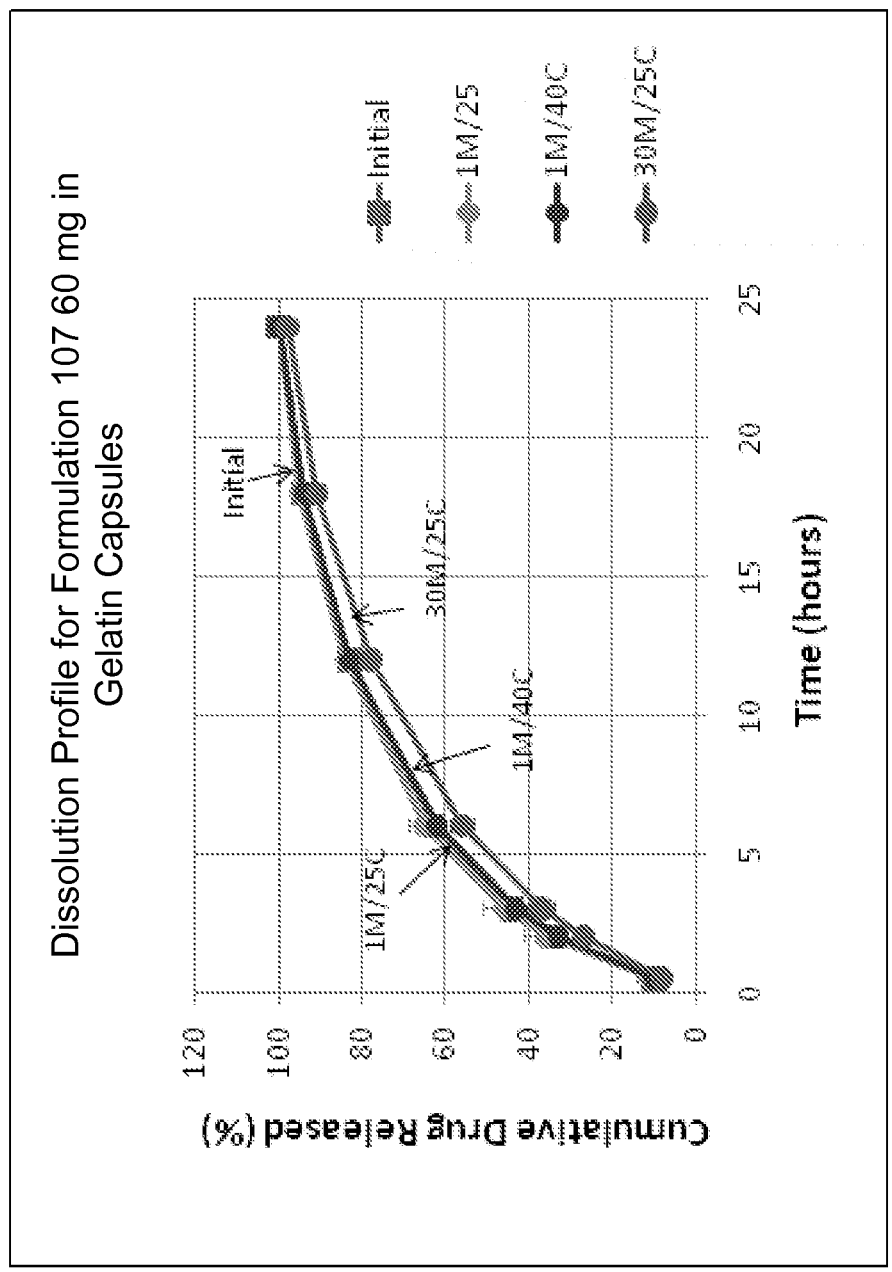
FIG. 47 is a graph showing cumulative % drug release over time for a formulation in hard gelatin capsules with storage conditions of 1 month at 25° C. and 40° C., or 30 months at 25° C.
Figure 48:
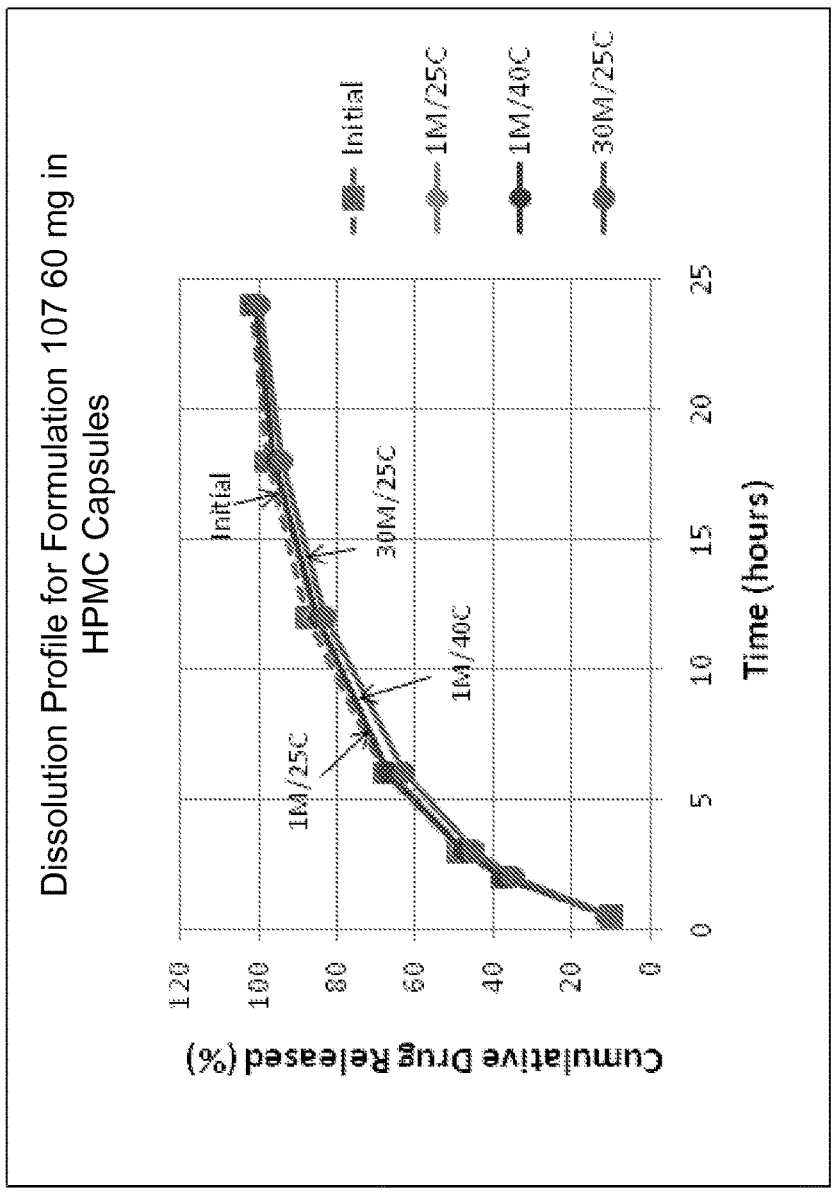
FIG. 48 is a graph showing cumulative % drug release over time for the formulation of FIG. 47 in HPMC capsules with storage conditions of 1 month at 25° C. and 40° C., or 30 months at 25° C.

The initial dissolution results at T=0 for Formulations 106 and 107 in gelatin and HPMC capsules are provided in FIG. 44. FIG. 45 shows a storage time-dependent change in mean release of the active agent for Formulation 106 in gelatin capsules when stored for 1 month at 25° C. and 40° C., or for 30 months at 25° C. As shown in FIG. 46, Formulation 106 exhibited greater stability in HPMC capsules as evidenced by a decrease in the storage time-dependent change in mean release of the active agent. FIG. 47 shows dissolution results for Formulation 107 in gelatin capsules when stored for 1 month at 25° C. and 40° C., or for 30 months at 25° C. FIG. 48 shows dissolution results for Formulation 107 in HPMC capsules when stored for 1 month at 25° C. and 40° C., or for 30 months at 25° C. Formulation 107 exhibited good stability in both gelatin and HPMC capsules as evidenced by the absence of a significant storage time-dependent change in mean release of the active agent. Without intending to be bound by any particular theory, it appears that Formulation 106 filled in hard gelatin capsules showed dissolution changes due to potential interaction between the capsule and the formulation. Formulation 107 showed good product stability without dissolution change in both types of capsule shell.

What is claimed is:

1. A composition comprising:
    a pharmacologically active agent;
    a high viscosity liquid carrier material (HVLCM) having a viscosity of at least 5000 cP at 37° C. that does not crystallize neat at 25° C. and 1 atmosphere, wherein the HVLCM is present in an amount ranging from about 35% by weight to about 45% by weight relative to the total weight of the composition;

a solvent, wherein the solvent is present in an amount ranging from about 31% by weight to about 45% by weight relative to the total weight of the composition;

a network former, wherein the network former is present in an amount ranging from about 2% by weight to about 10% by weight relative to the total weight of the composition;

water, wherein the composition does not comprise more than 2.0% water by weight, based on total weight of the composition; and a mineral particle, wherein the mineral particle is present in the composition in an amount ranging from 2.4% by weight to about 5.4% by weight relative to the total weight of the composition.

2. The composition of claim 1, wherein the pharmacologically active agent comprises an opioid.

3. The composition of claim 1, wherein the pharmacologically active agent is selected from oxycodone, oxymorphone, hydrocodone, and hydromorphone, either in the free base form or a pharmaceutically acceptable salt form thereof.

4. The composition of claim 1, wherein the pharmacologically active agent is oxycodone.

5. The composition of claim 1, wherein the HVLCM is sucrose acetate isobutyrate (SAIB).

6. The composition of claim 1, wherein the solvent comprises triacetin.

7. The composition of claim 1, wherein the network former comprises cellulose acetate butyrate (CAB).

8. The composition of claim 1, wherein the network former comprises CAB having a number average molecular weight ranging from 50,000 Daltons to 100,000 Daltons.

9. The composition of claim 1, wherein the network former comprises CAB having at least one feature selected from a butyryl content ranging from about 17% to about 41%, an acetyl content ranging from about 13% to about 30%, and a hydroxyl content ranging from about 0.5% to about 1.7%.

10. The composition of claim 1, wherein the composition comprises water at from about 1.0 to 2.0% by weight, based on total weight of the composition.

11. The composition of claim 1, wherein the composition does not comprise more than 2.0% water by weight, based on total weight of the composition, following storage of the composition for a period of 12 months at 25° C. and 60% relative humidity.

12. The composition of claim 1, wherein the mineral particle comprises silicon dioxide.

13. The composition of claim 1, further comprising a hydrophilic agent.

14. The composition of claim 13, wherein the hydrophilic agent comprises HEC.

15. The composition of claim 1, further comprising a rheology modifier.

16. The composition of claim 15, wherein the rheology modifier is isopropyl myristate (IPM).

17. The composition of claim 1, wherein the composition is contained within a capsule.

18. The composition of claim 1, wherein the composition is contained within a capsule having a water content of less than about 10% by weight.

19. The composition of claim 1, wherein the composition is contained within a capsule comprising hydroxypropyl methylcellulose.

20. A method for treating pain in a subject, the method comprising orally administering to the subject a composition as defined in claim 1, wherein the pharmacologically active agent comprises an opioid.

* * * * *